(12) United States Patent
Tew et al.

(10) Patent No.: US 8,445,611 B2
(45) Date of Patent: May 21, 2013

(54) ANTIMICROBIAL POLYMERS

(75) Inventors: Gregory N. Tew, South Deerfield, MA (US); Ahmad E. Madkour, Leverett, MA (US); Karen Lienkamp, Ware, MA (US); Ashlan Marie Musante, Mainz (DE)

(73) Assignee: University of Massachusetts, Boston, MA (US)

( * ) Notice: Subject to any disclaimer, the term of this patent is extended or adjusted under 35 U.S.C. 154(b) by 0 days.

(21) Appl. No.: 13/441,114

(22) Filed: Apr. 6, 2012

(65) Prior Publication Data

US 2012/0195849 A1 Aug. 2, 2012

Related U.S. Application Data

(63) Continuation of application No. 12/795,892, filed on Jun. 8, 2010, now Pat. No. 8,153,739.

(60) Provisional application No. 61/185,035, filed on Jun. 8, 2009.

(51) Int. Cl.
*C08F 28/06* (2006.01)

(52) U.S. Cl.
USPC ........ 526/256; 424/78.32; 526/270; 526/308; 549/29; 549/79

(58) Field of Classification Search
USPC .......... 424/78.32; 526/256, 720, 308; 549/79, 549/29
See application file for complete search history.

(56) References Cited

U.S. PATENT DOCUMENTS

2008/0251460 A1* 10/2008 Gstrein et al. ................ 210/660

* cited by examiner

*Primary Examiner* — Robert Jones, Jr.
(74) *Attorney, Agent, or Firm* — Milstein Zhang & Wu LLC

(57) ABSTRACT

The invention generally relates to novel polymers (SMAMPs) and their syntheses and use. The polymers exhibit promising properties of AMPs. In particularly, for example, a ring-opening metathesis polymerization (ROMP) platform was developed that allows syntheses of SMAMPs that employ a minimum number of norbornene-based building blocks and/or enable easy and independent variation of hydrophobic and hydrophilic groups in the monomer units and/or along the polymeric backbone to finetune and select desirable properties of the polymers.

15 Claims, 47 Drawing Sheets

FIG. 1: 'Construction kit' approach to obtain facially amphiphilic monomers and polymers. Just as with a Lego construction kit, the synthetic approach presented here allows the independent combination of a hydrophilic, a hydrophobic and a polymerizable part of the monomer to yield a whole set of antimicrobial polymers with tunable activity and selectivity.

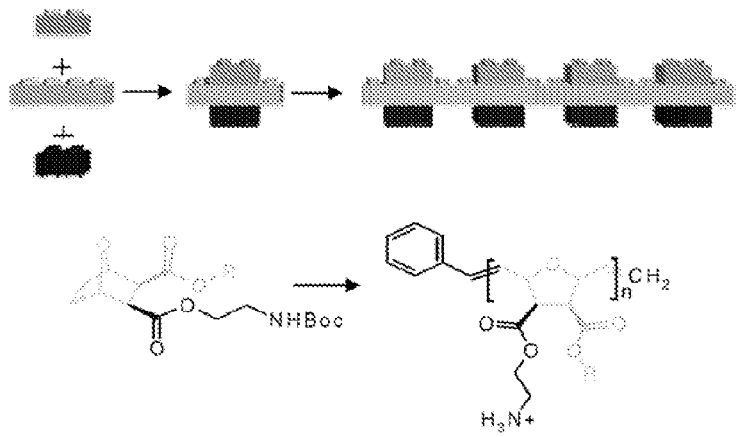

FIG. 2: Biological data ($MIC_{90}$ for *E. coli* and *S. aureus*, and $HC_{50}$ for red blood cells) for the homopolymers. a) 3000 g/mol series, b) 10000 g/mol series.

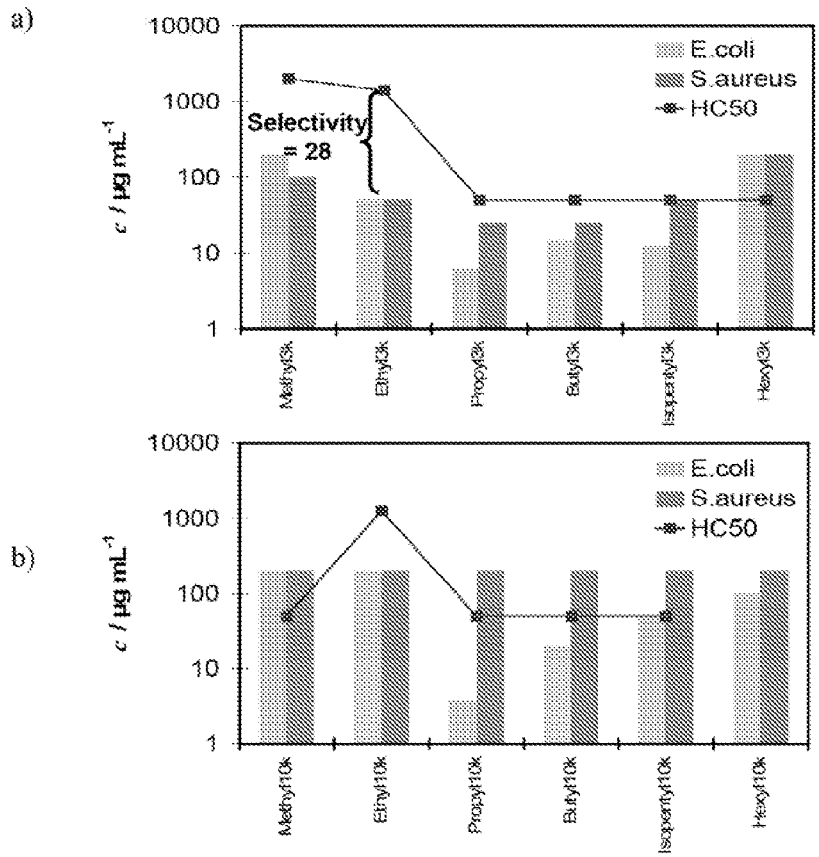

FIG. 3: Characterization of propyl oligomers. a) GPC traces, b) MALDI-TOF MS peaks and distributions
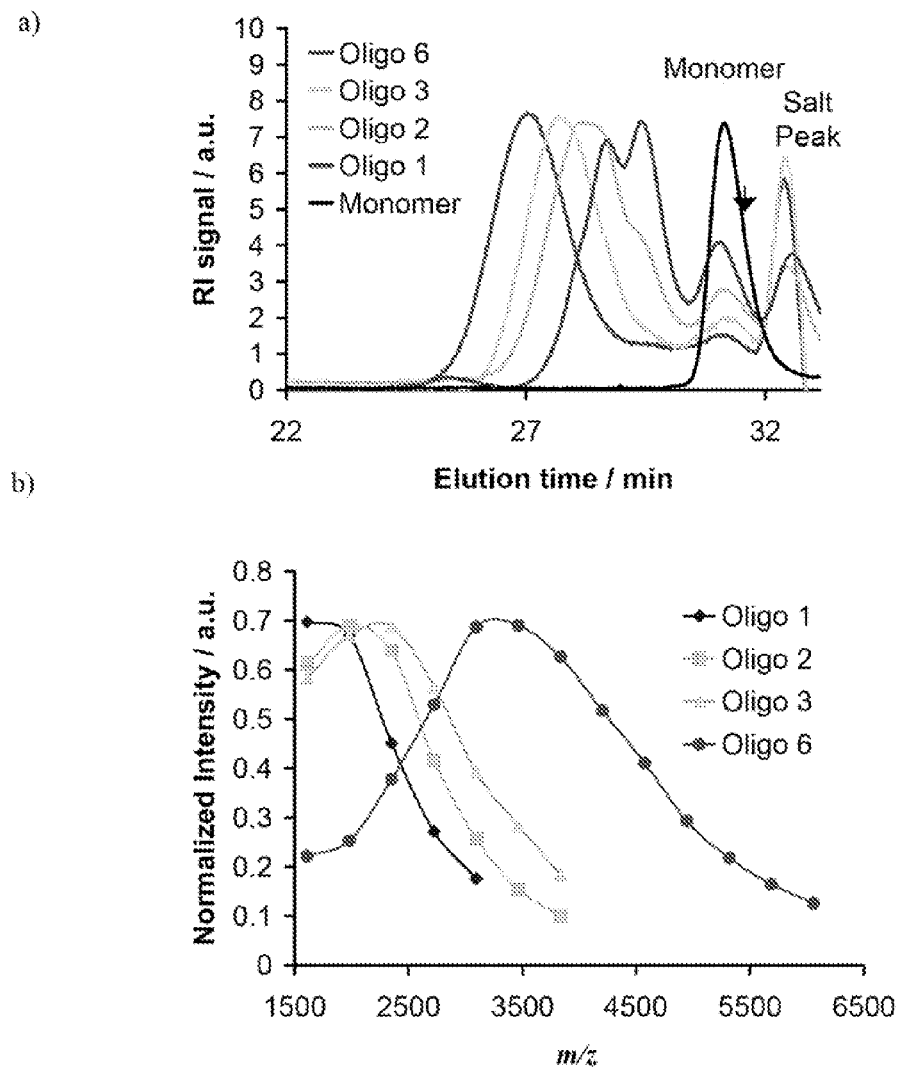

FIG. 4: Biological data ($MIC_{90}$ for *E. coli* and *S. aureus*, and $HC_{50}$ for red blood cells) for the propyl oligomer series.
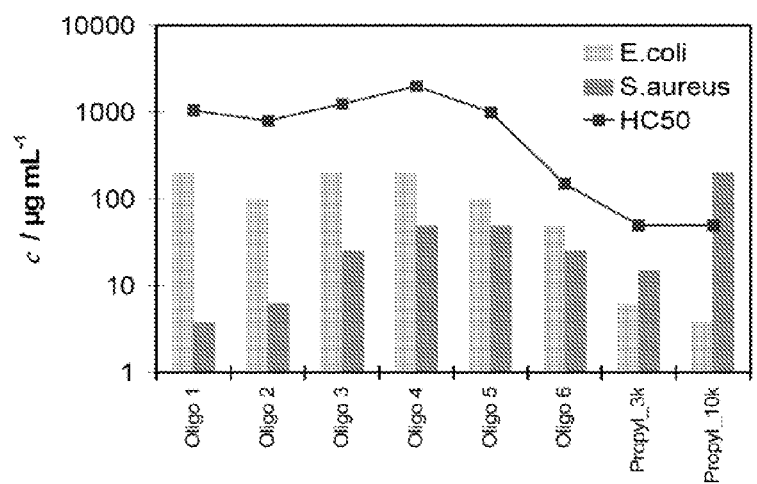
FIG. 5: Biological data ($MIC_{90}$ for *E. coli* and *S. aureus*, and $HC_{50}$ for red blood cells) for the copolymers. a) ethyl-propyl series, b) methyl-ethyl series, c) methyl-propyl series. Sample labeling: e.g. E1:P9 is a copolymer with 10 mol% ethyl and 90 mol% propyl monomer.
a)
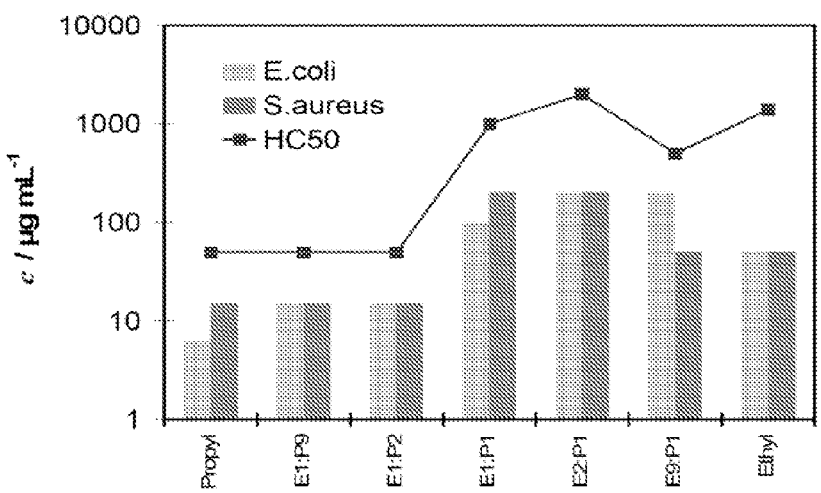

b)
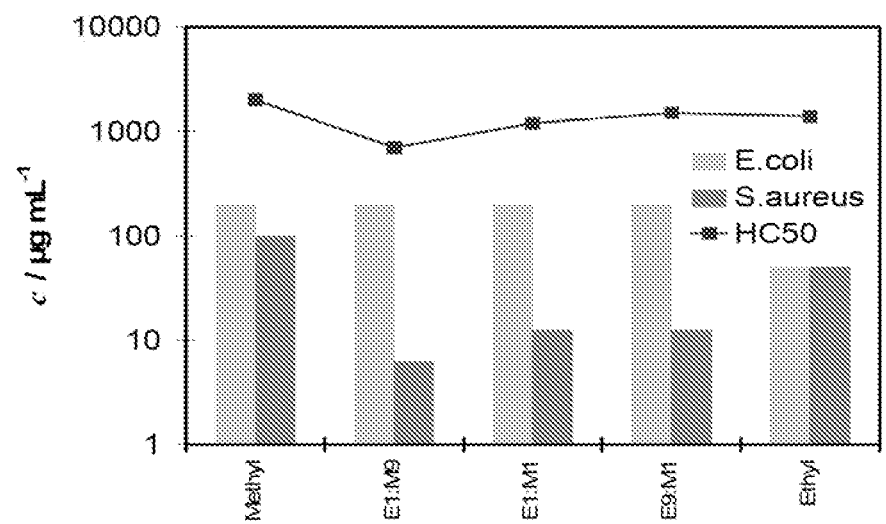
c)
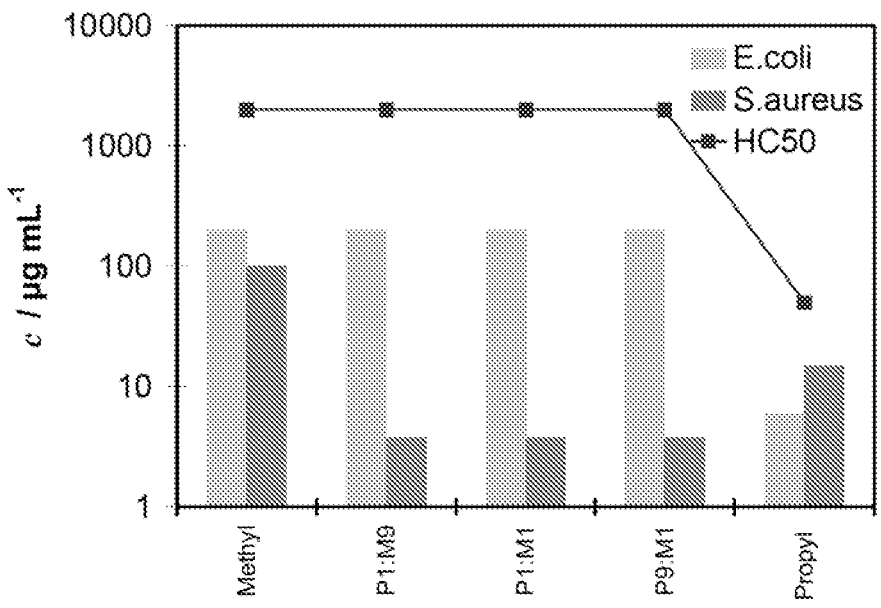

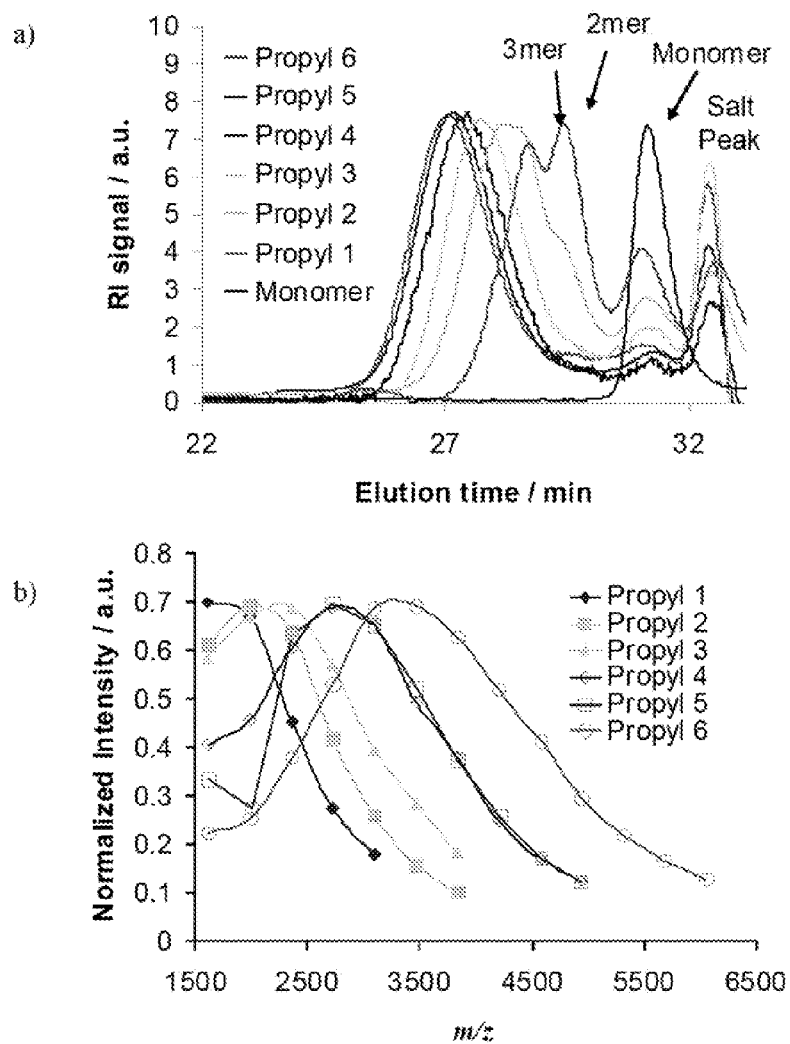
FIG. 6: Characterization of ALL propyl oligomers. a) GPC traces, b) MALDI-TOF MS peaks and distributions

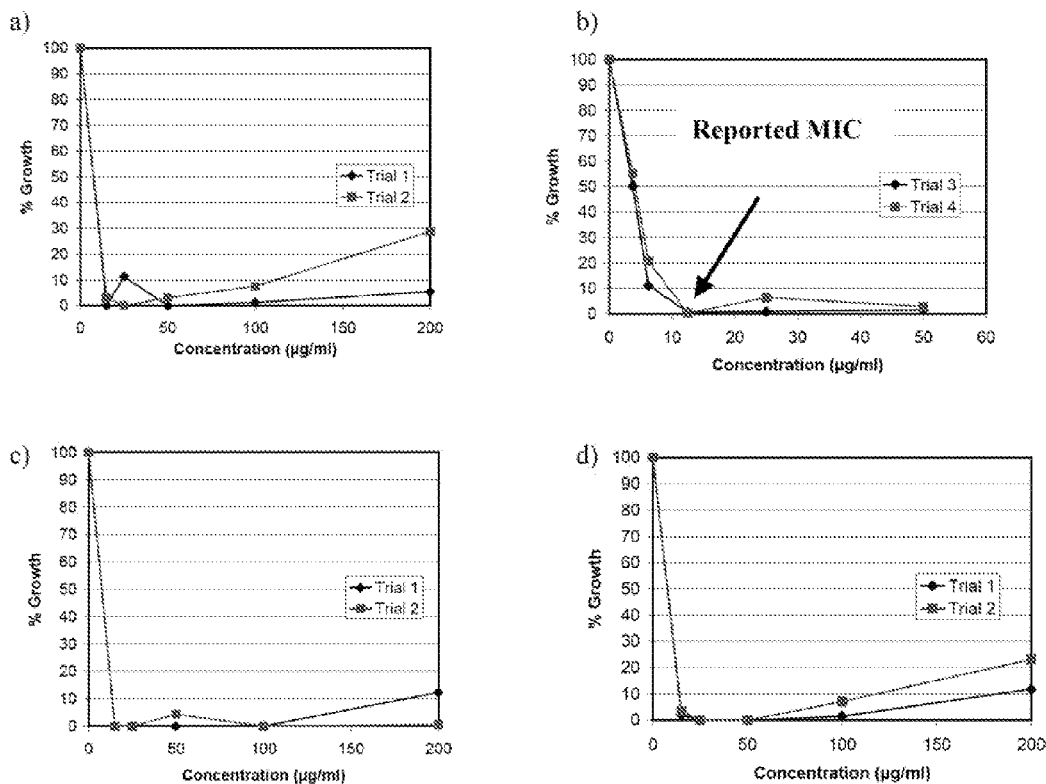

FIG. 7: Examples of a highly active polymer: a) E1:M1 copolymer, MIC testing against *S. aureus*, $MIC_{90}$ = 12.5 µg/mL, Trial 1 and 2, b) same system, Trial 3 and 4, c) Proyl_3k, MIC testing against *E. coli*, d) Proyl_3k, MIC testing against *S. aureus*.

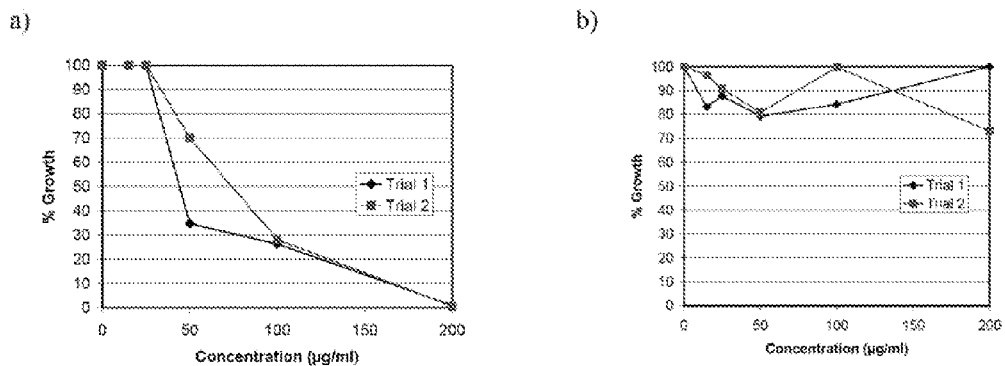

FIG. 8: Example of a) a moderately active polymer: Propyl_10k, MIC testing against *S. aureus*, $MIC_{90}$ = 200 µg/mL, and b) an inactive polymer: Propyl_10k, MIC testing against *E. coli*, $MIC_{90}$ >200 µg/mL

FIG. 9: $HC_{50}$ curve of a) a very hemolytic polymer: Oligo 6, $HC_{50}$ = 150 μg/mL; b) a moderately hemolytic polymer: E1:M9, $HC_{50}$ = 700 μg/mL; and c) a non-hemolytic polymer: M9:P1, $HC_{50}$ > 2000 μg/mL
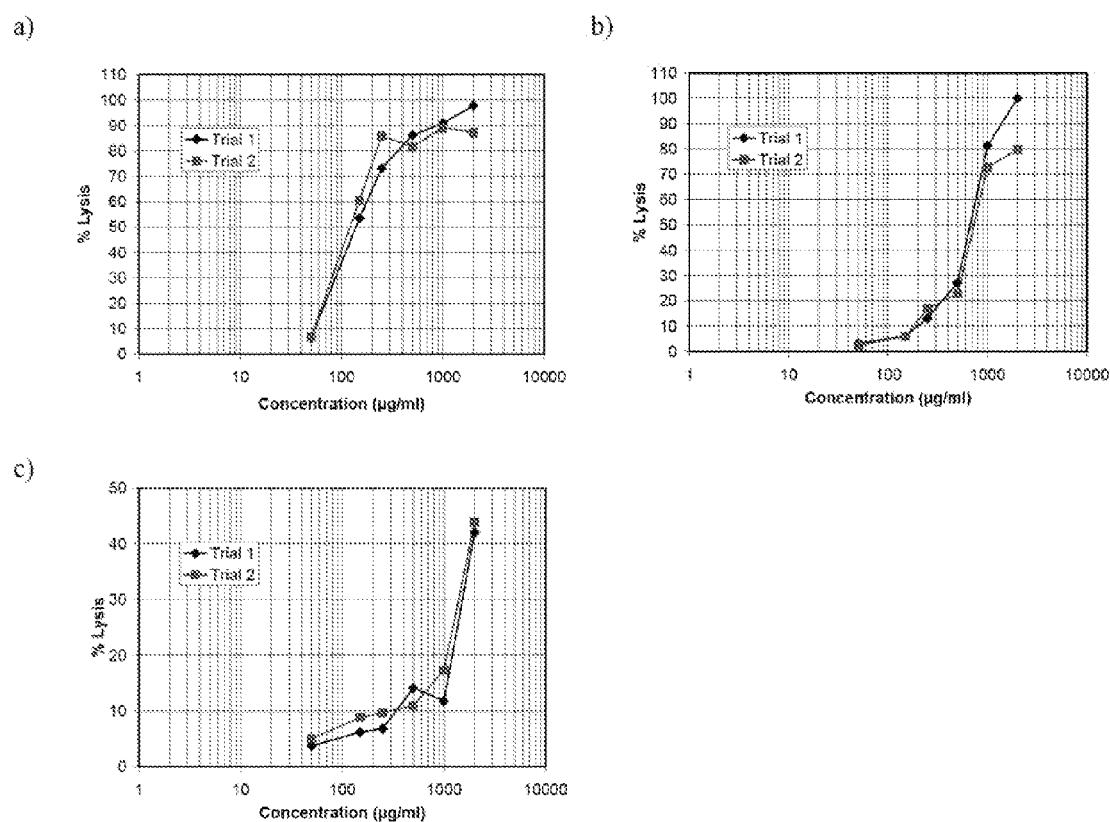

FIG. 10: Cartoon representation of the cell membrane and cell wall morphology of a) *E. coli* (Gram-negative) and b) *S. aureus* (Gram-positive), and their interactions with SMAMPs; details like ion channels, LPS, and membrane proteins are omitted for clarity.

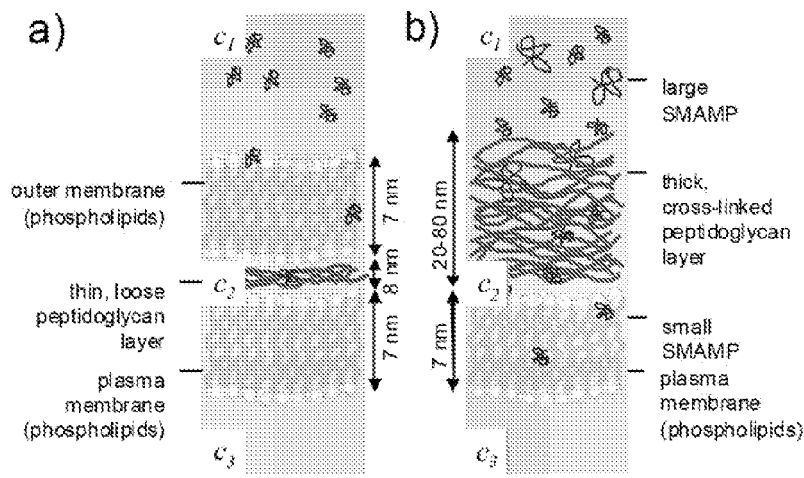

FIG. 11: Structure and antimicrobial properties (MIC$_{90}$ against *E. coli* and *S. aureus* and HC$_{50}$ of human red blood cells) for different molecular weights of the SMAMP

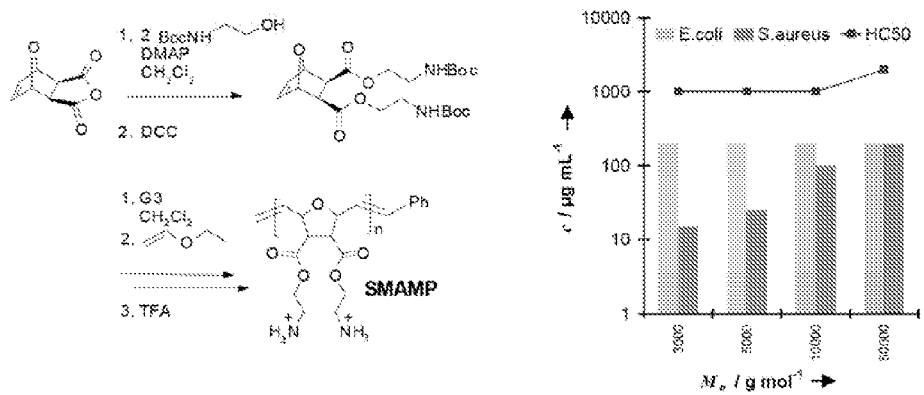

FIG. 12: Dye-leakage experiments on model membranes: a) $EC_{50}$ curves for the 3000 g/mol SMAMP (*E. coli* mimics and *S. aureus* mimics); b) Effect of increasing peptidoglycan concentration at constant polymer concentration (diamonds); peptidoglycan only (triangle); c) membrane-active SMAMPS in the presence of peptidoglycan: Leakage is significantly reduced as compared to the control sample.

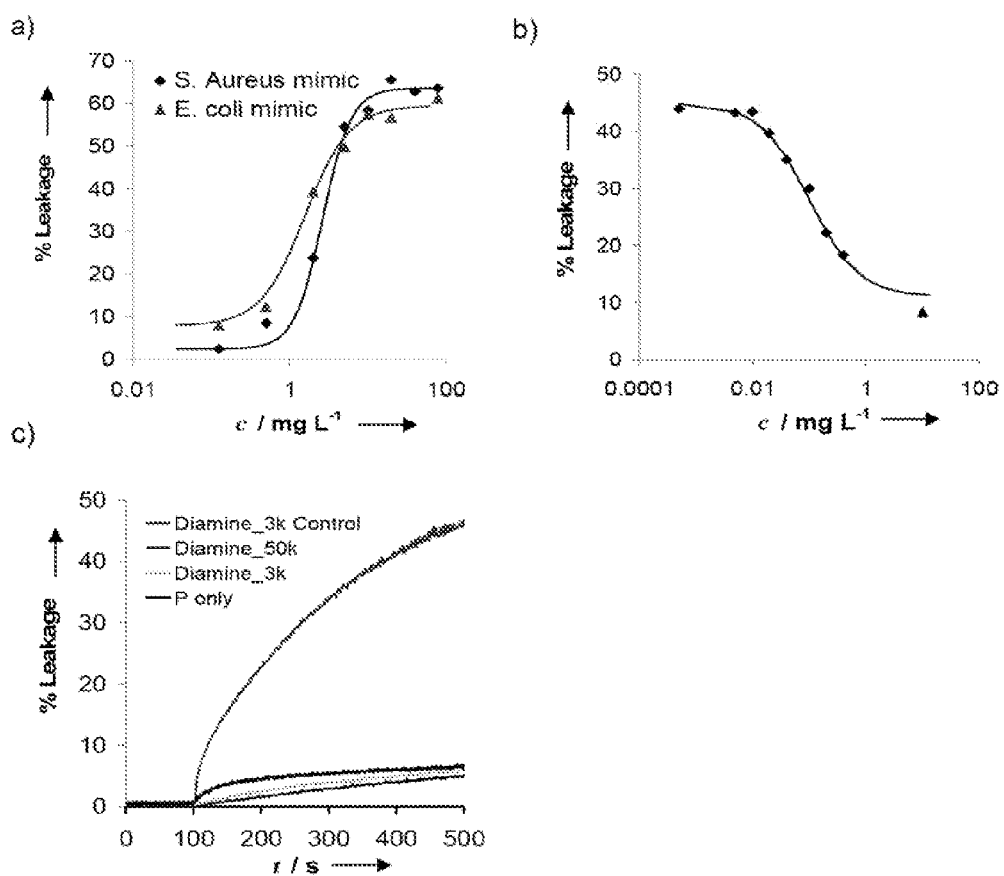

FIG. 13: Rationalization of the results of the dye-leakage experiments in the presence of peptidoglycan: a) When first adding the peptidoglycan extract, and then the SMAMP, membrane activity is observed; b) When incubating the SMAMP with the peptidoglycan extract for 10 min, the polymers are still membrane active; c) Incubation for 24 hours quenches the membrane activity.
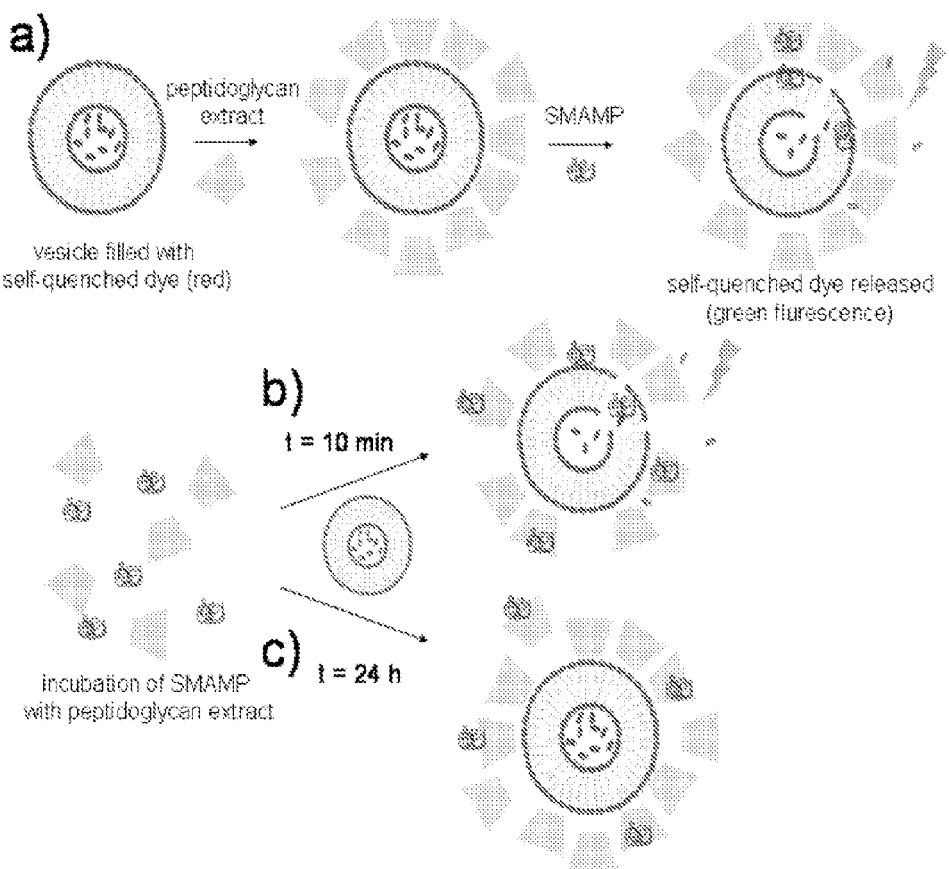

FIG. 14: Dye-leakage experiments on model membranes: a) cartoon illustration: model vesicles were filled with a self-quenching fluorescent dye. When adding a membrane-active SMAMP, dye-leakage occurs, leading to fluorescence. By plotting fluorescence versus time and normalizing the data (using the surfactant Triton-X to indicate 100 % dye-leakage), a curve that can be used to qualitatively and quantitatively assess membrane activity is obtained; b) PE:PG (75/25) membranes (*E. coli* mimics); c) CL membranes (*S. aureus* mimics); d) CL membranes (*S. aureus* mimics), with peptidoglycan, t = 10 min.

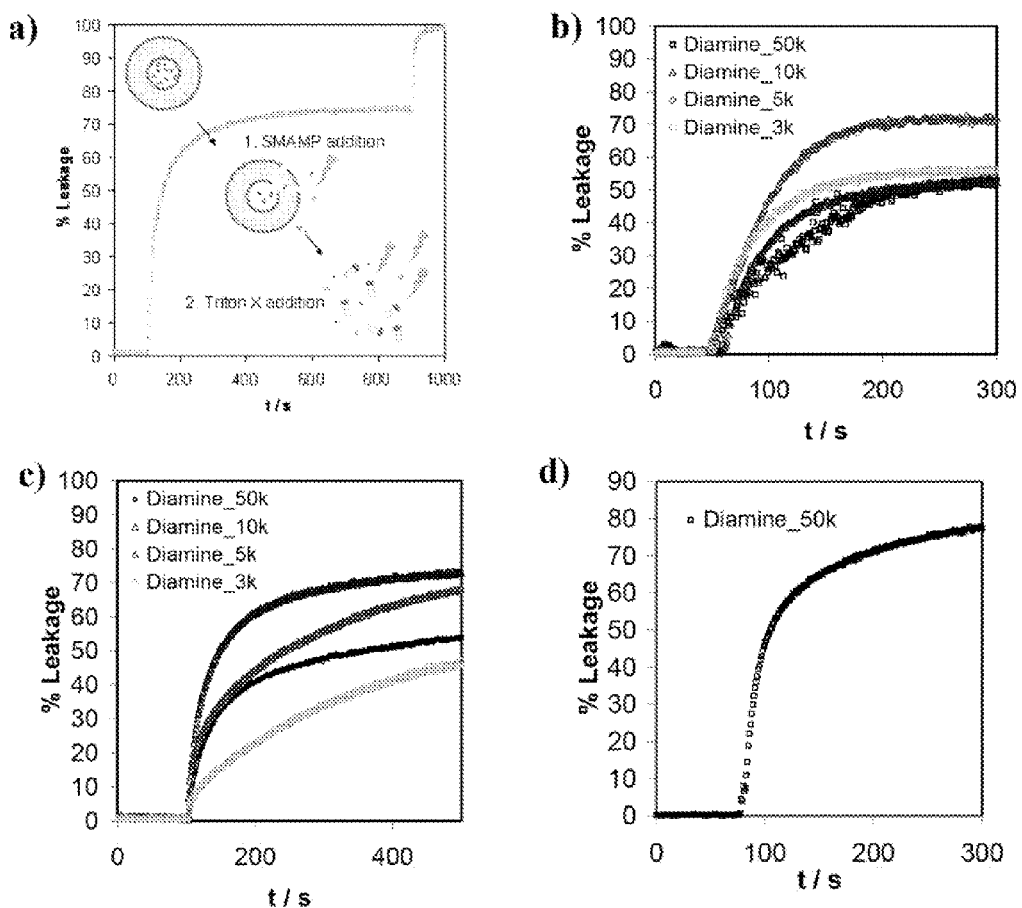

FIG. 15: GPC data for the SMAMP homopolymer 4 series. Target molecular weight is plotted versus number average molecular weight from Gel permeation Chromatography (in DMF/0.01 M LiCl, calibrated with poly(styrene standards).

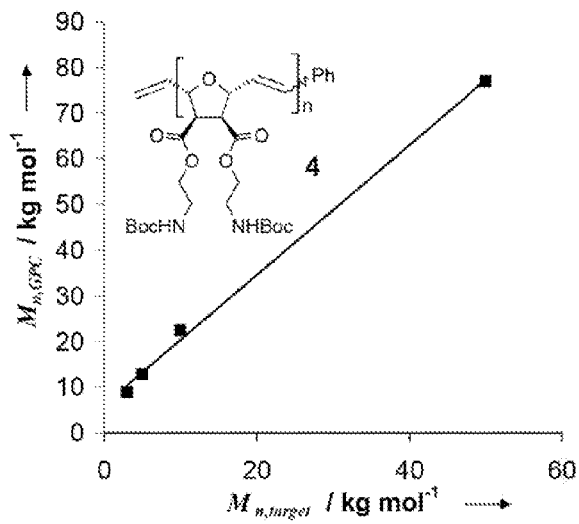

FIG. 16: Dye-leakage curves obtained upon adding SMAMP solutions to cardiolipin model vesicles (*S. aureus* mimics). The polymer solutions were added at t = 100 sec ($c_{final}$ = 20 µg/mL). All leakage curves were standardized using Triton X-100 (added at t = 800 sec), which gave 100 % leakage.

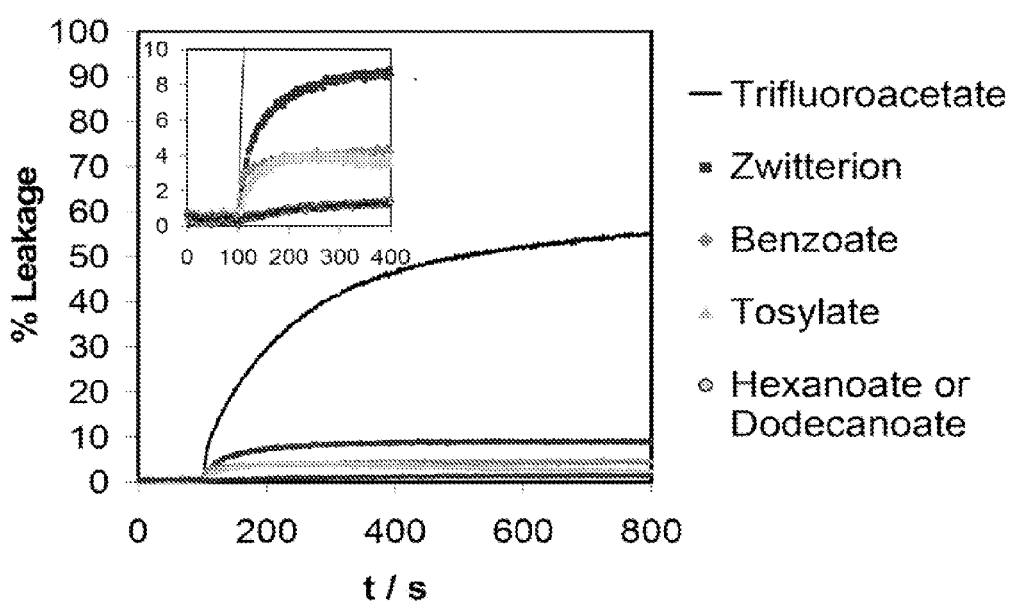

FIG. 17: Structural comparison between Hexanoate_3k (a) and Hexyl_3k (b)
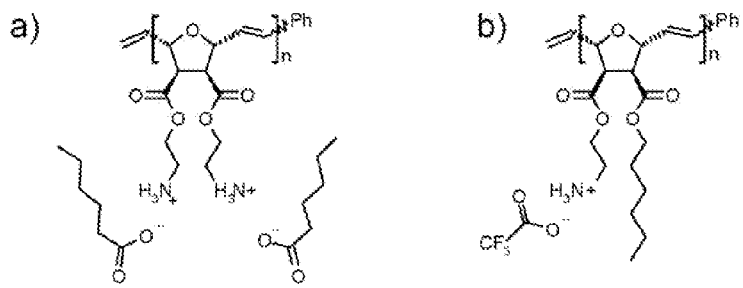
FIG. 18: Cartoon representation of local charge surplus for Zwitterion_3k. Parentheses show the neutral ion pairs.
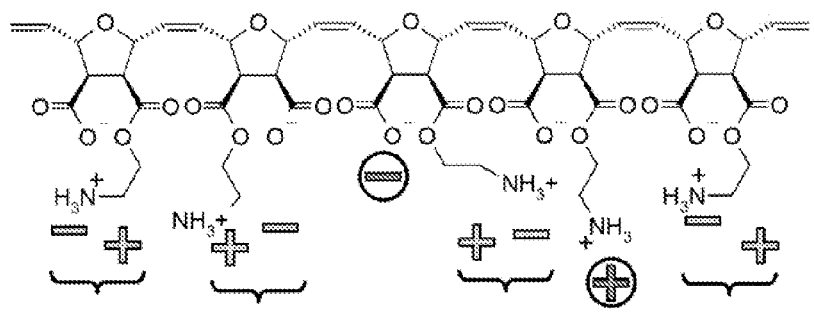
FIG. 19: Structure of model polymers with gradually decreasing molecular charge; R = methyl to butyl. For R = methyl, these polymers have constant hydrophobicity.
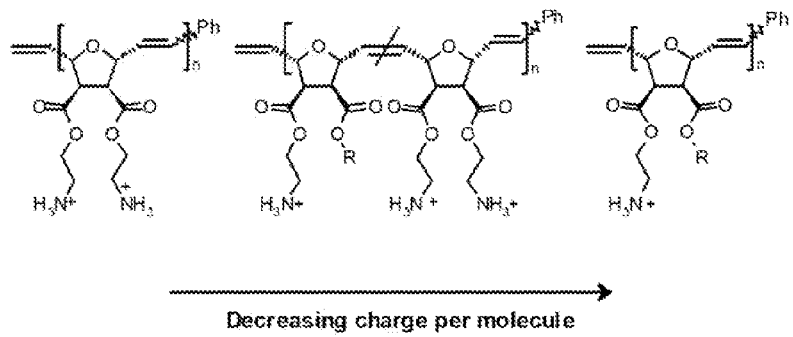
Decreasing charge per molecule FIG. 20. Antimicrobial and hemolytic properties ($MIC_{90}$ in µg $mL^{-1}$ against *Escherichia coli* and *Staphylococcus aureus* and $HC_{50}$ in µg $mL^{-1}$ of human red blood cells) of diamine-monoamine copolymers: a) diamine-methyl, b) diamine-ethyl, c) diamine-propyl, and d) diamine-butyl. M9:D1 refers to a copolymer with a molar ratio of methyl:diamine = 9:1. The 3000 g/mol monoamine homopolymers of each monomer are included for comparison.

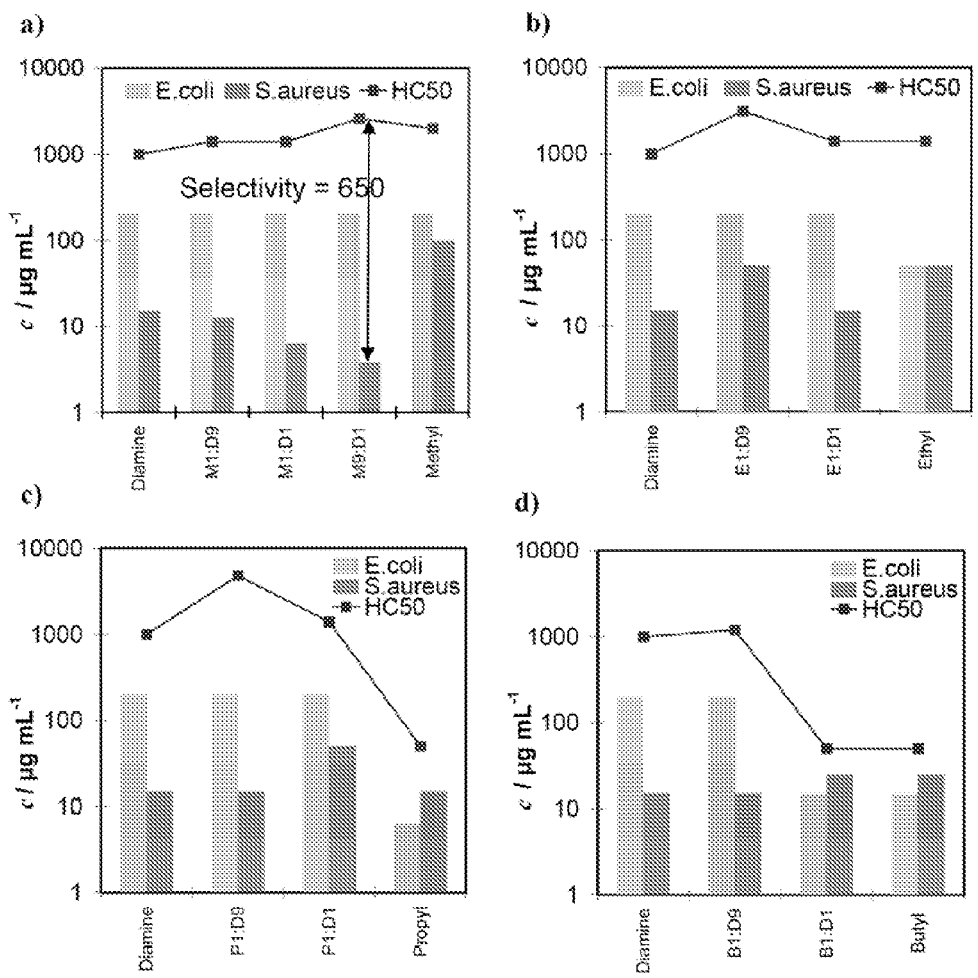

FIG. 21: Illustration of the dye-leakage experiment. SMAMP solution is added to the dye-loaded vesicles at t = 100 sec, causing leakage. At t=900 sec (in this case), Triton X is added to standardize the experiment, leading to 100% leakage.

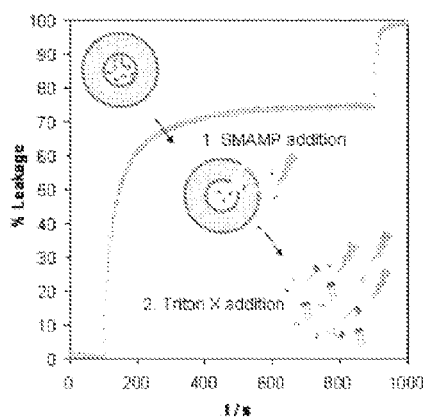

FIG. 22: Dye-Leakage data for the Hexyl_3k polymer. % Leakage is plotted as a function of polymer concentration. As can be seen from this data, a polymer concentration of 20 µg/ml causes 38% leakage.

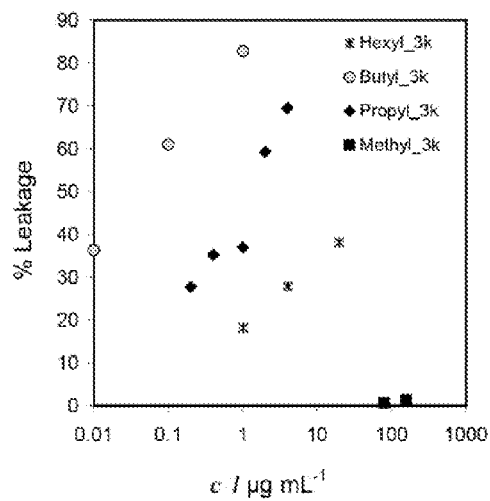

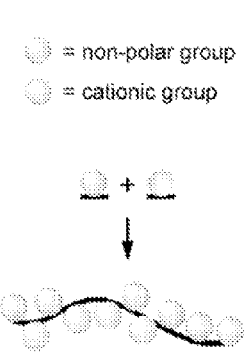

FIG. 23. Representative cartoon and polymer structures illustrating methods using "segregated" monomers and "facially amphiphilic" monomers to create antimicrobial polymers. In the above cases, a series of polymers were synthesized and the best selectivities as defined by HC/MIC are noted above (HC = hemolytic concentration, MIC = minimum inhibitory concentration). The bacteria strain tested leading to these values is also shown (*Ec* = *Escherichia coli*, *Bs* = *Bacillus subtilis*, *Sa* = *Staphylococcus aureus*). (See supporting info. for more details on MIC and HC assays.)

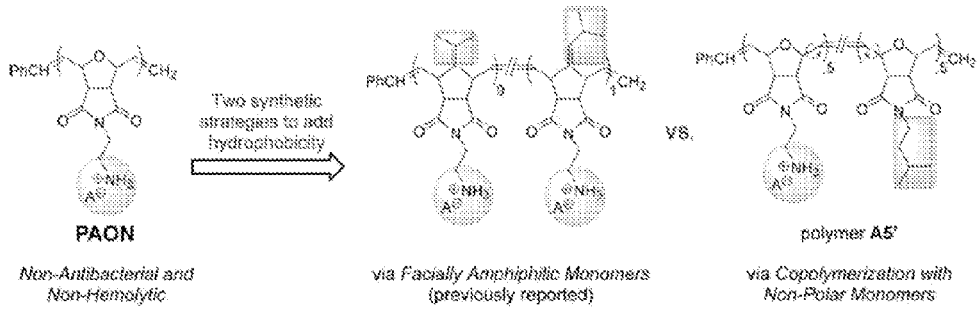

FIG. 24. Two methods to endow polynorbornenes, based on polyamine oxanorbornene, PAON, with antibacterial properties. The center structure was previously reported. The right structure, polymer A5', synthesized for this study, shows a five-carbon branched chain as the non-polar moiety (one out of eleven alkyl chains tested). Presumably, rotation about the single bonds (red curved arrows) in the polymer backbone allows for the orientation of these random copolymers into a globally amphiphilic conformation.

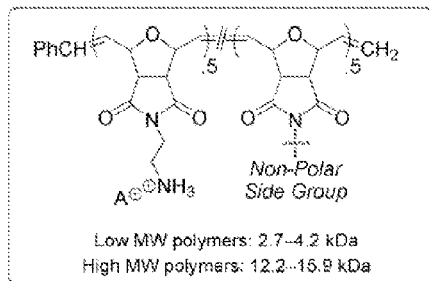

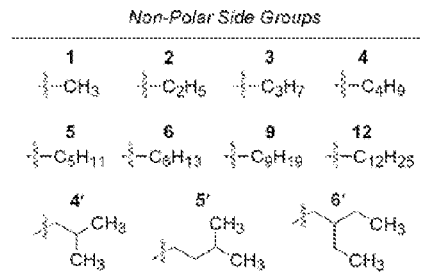

FIG. 25. 50/50 random copolymers synthesized at two different molecular weights. PAON and several non-50/50 compositions were also synthesized for a total of thirty-two polymers examined. A = $^-O_2CCF_3$. Notation examples: PAON = the homo-amine polymer, A5' = 50/50 random copolymer of the amine and the 5' non-polar monomer, $A_8 5'_2$ = random copolymer with an approximately 80/20 molar ratio of monomers.

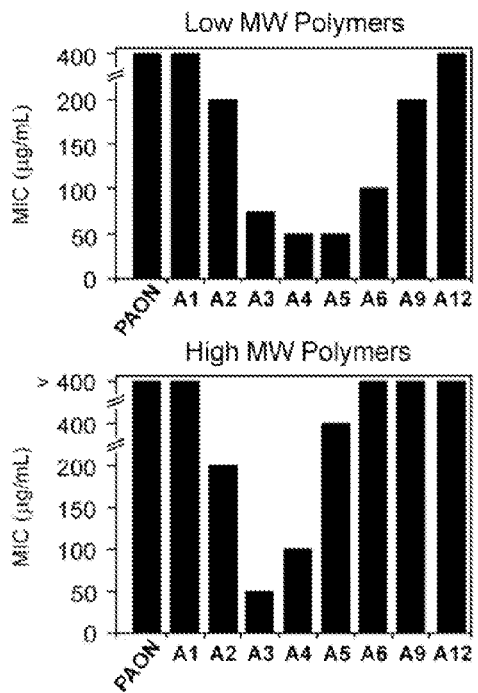

FIG. 26. MICs of selected polymers illustrating optimal hydrophobicity for the most active ones A4, A5 (Low MW) and A3 (High MW).

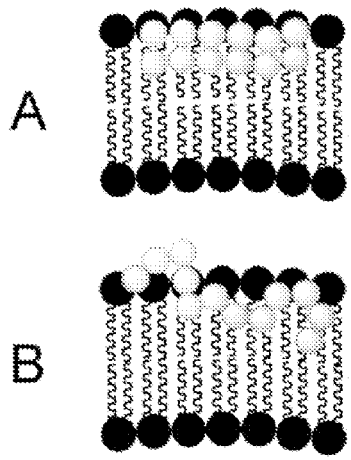

FIG. 27. Cartoon proposing that polymer interactions with the polar head group (black circles) and the non-polar lipid tails (squiggly lines) of the membrane are significantly different for polymers from FA monomers (A) versus that of polymers from segregated monomers (B).

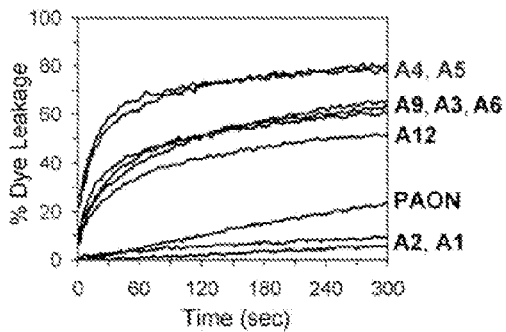

FIG. 28. Graph of polymer-induce dye leakage with the most antimicrobial polymers highlighted in red.

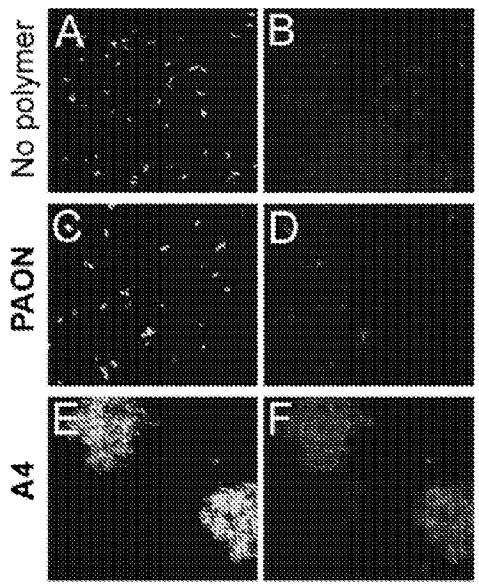

FIG. 29. Fluorescence microscopy of stained *E. coli* in the absence and presence of polymer. Each sample consists of $10^8$ bacteria cells incubated for 30 min with polymer (75 μg/ml final concentration) or buffer. Left panels were visualized with a green filter to display SYTO9 emission and the right panels show the same fields visualized with a red filter to display propidium iodide emission.

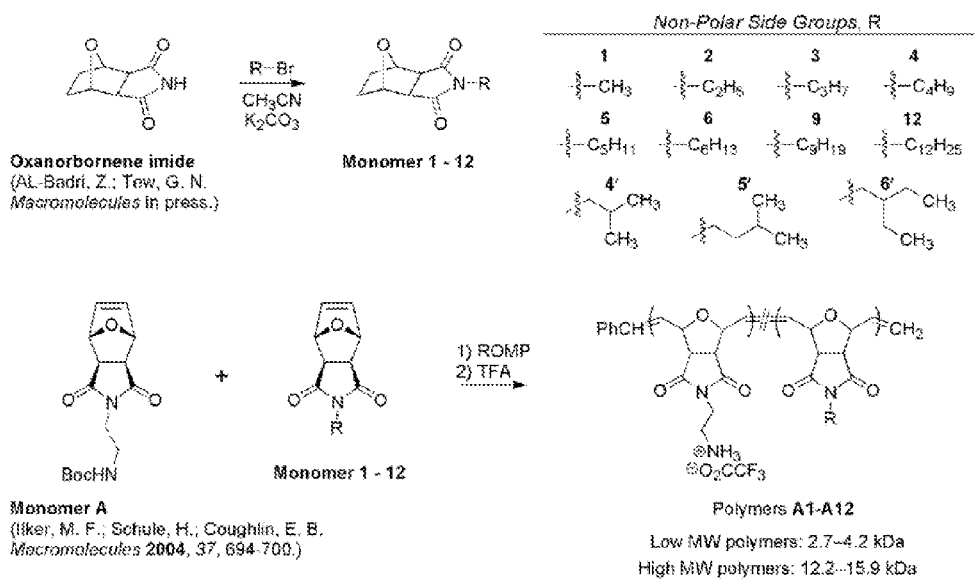
FIG. 30. Synthetic scheme of the synthesis of Monomer 1-12 (from Oxanorbornene imide) and the copolymerization with Monomer A and subsequent Boc deprotection.
FIG. 31
Molecular evolution of antibacterials: from natural AMPs (left: magainin) via synthetic foldamers to ROMP-based SMAMPs (right: poly3 from FIG. e-4).
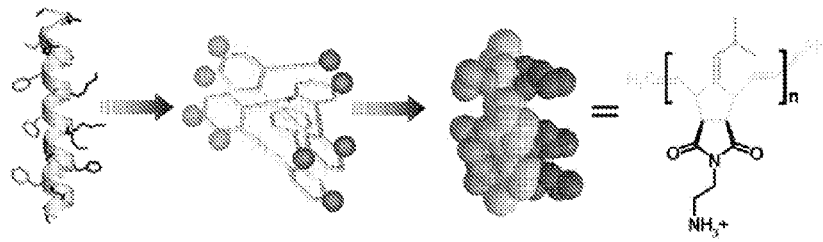

FIG. 32

MIC and HC curves. Red squares = MIC curve ($MIC_{100}$, $MIC_{90}$ and $MIC_{50}$ = 100, 50 and 25 µg/mL, respectively); blue diamonds = HC curve ($HC_{100}$, $HC_{50}$ and $HC_0$ = 2000, 650 and 10 µg/mL, respectively; light blue triangles = HC curve ($HC_{100}$, $HC_{50}$ and $HC_0$ = >4000, 2000 and 10 µg/mL, respectively). The blue curves illustrate that two polymers with identical $HC_0$ may have drastically different $HC_{50}$s and $HC_{100}$s. The shaded region represents the therapeutic width of the compound, i.e. the concentration range in which the compound is active yet not too toxic for the host organism.

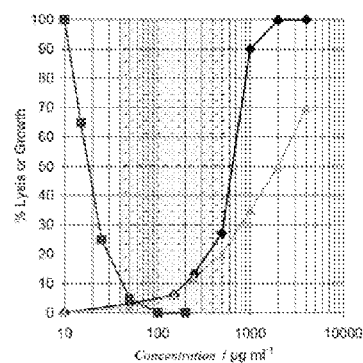

FIG. 33

Monomer and polymer synthesis. R1 and R2 denote hydrophobic groups, R3 is the hydrophilic group.

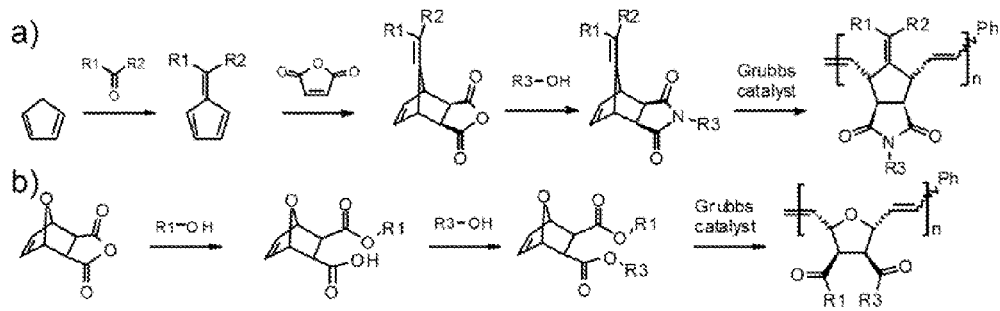

Library of ROMP-based SMAMP polymers. Top: norbornene-imide platform, Bottom: ester platform. The parent series are marked in red and underwent hydrophobic (green) and hydrophilic or charge related (blue) modifications. In one case, counterion variations were investigated (khaki), and one SMAMP was modified with guanidinium groups (grey).

FIG. 35
Biological data for three series of SMAMP homopolymers, made from facially amphiphilic monomers, plotted as concentration (MIC$_{90}$ or HC$_{50}$, respectively) versus increasing hydrophobicity; light gray columns = MIC$_{90}$, *E. coli*, dark gray columns = MIC$_{90}$, *S. aureus*; red squares = HC$_{50}$, human erythorocytes; a) Series 1, b) Series 3, where PE refers to R = phenylethyl and is not strictly a homologue of the series, c) Series 2.

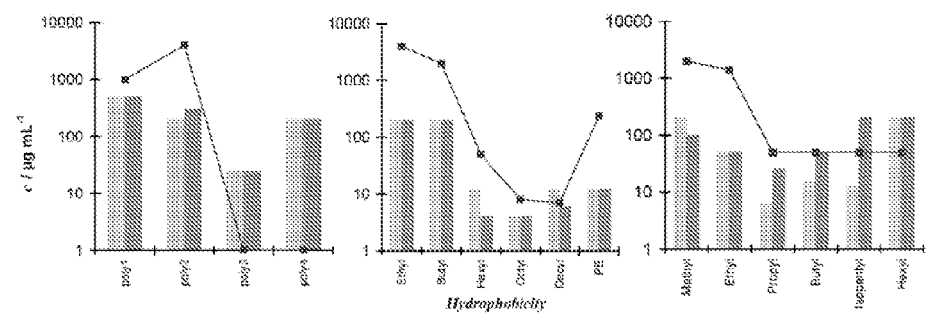

FIG. 36

Biological data for series of SMAMP copolymers, made from facially amphiphilic monomers, plotted as concentration (MIC$_{90}$ or HC$_{50}$, respectively) versus increasing hydrophobicity; light gray columns = MIC$_{90}$, *E. coli*, dark gray columns = MIC$_{90}$, *S. aureus*; red squares = HC$_{50}$, human erythorocytes; a) **poly2-*co*-poly3, b) Series 4 (FIG. e-4), R1 = methyl, R2 = ethyl; c) Series 4, R1 = methyl, R2 = propyl, d) Series 4**, R1 = ethyl, R2 = propyl.

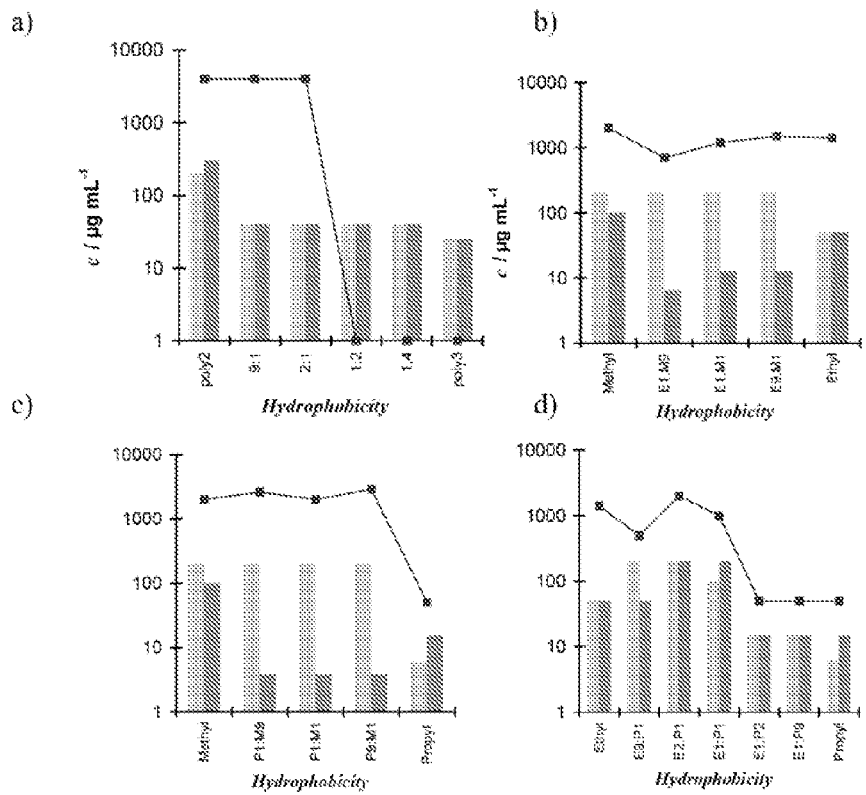

FIG. 37 a) Biological data for for series of SMAMP copolymers, made from segregated monomers, plotted as concentration (MIC$_{90}$ or HC$_{50}$, respectively) versus increasing hydrophobicity; light gray columns = MIC$_{90}$, *E. coli*, dark gray columns = MIC$_{90}$, *S. aureus*; red squares = HC$_{50}$, human erythorocytes; b) Illustration of SMAMP-membrane interactions: top: segregated SMAMPs, bottom: facially amphiphilic SMAMPs.

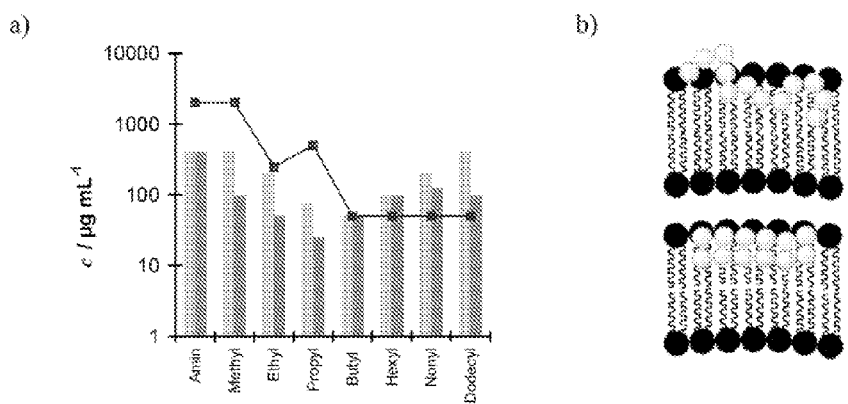

FIG. 38.

Biological data for three series of SMAMP copolymers, made from facially amphiphilic and hydrophilic moieties, plotted as concentration (MIC$_{90}$ or HC$_{50}$, respectively) versus increasing hydrophilicity; light gray columns = MIC$_{90}$, *E. coli*, dark gray columns = MIC$_{90}$, *S. aureus*; red squares = HC$_{50}$, human erythrocytes; a) Series 4, R = Sugar, b) Series 4, R = zwitterion, Series 4, R = PEG.

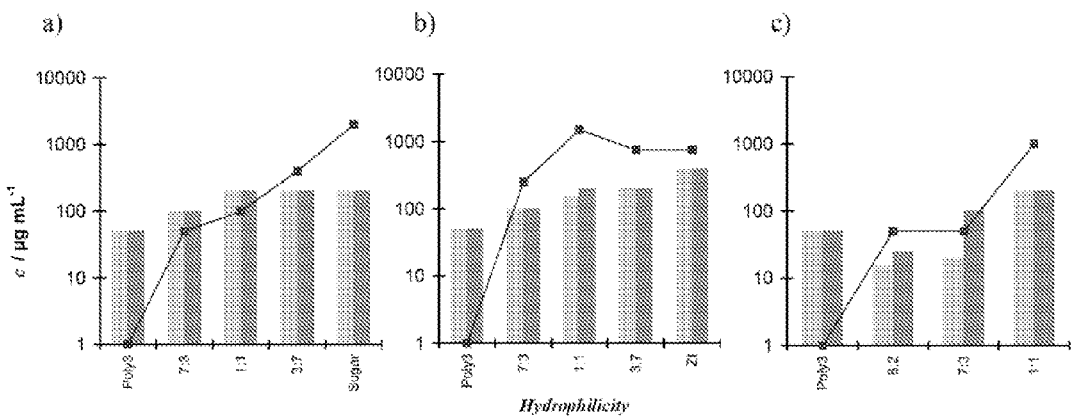

FIG. 39. Biological data for imid-based SMAMP polymers with increasing charge per repeat unit (Series 7 in FIG. 34), plotted as concentration ($MIC_{90}$ or $HC_{50}$, respectively) versus increasing nominal charge per repeat unit; light gray columns = $MIC_{90}$, *E. coli*, dark gray columns = $MIC_{90}$, *S. aureus*; red squares = $HC_{50}$, human erythrocytes; left: poly1 derivatives, right: poly3 derivatives

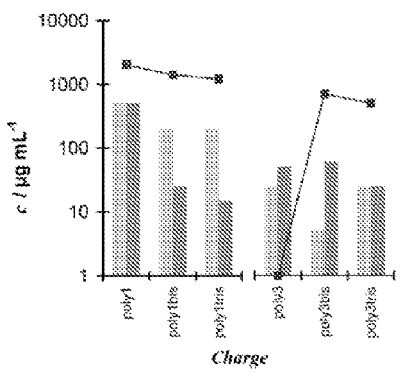

FIG. 40 Biological data for ester-based SMAMP copolymers with increasing charge density (Series 8 in FIG. 34), plotted as concentration ($MIC_{90}$ or $HC_{50}$, respectively) versus increasing nominal charge; light gray columns = $MIC_{90}$, *E. coli*, dark gray columns = $MIC_{90}$, *S. aureus*; red squares = $HC_{50}$, human erythorocytes; a) methyl copolymers, b) ethyl copolymers, c) propyl copolymers, d) butyl copolymers.

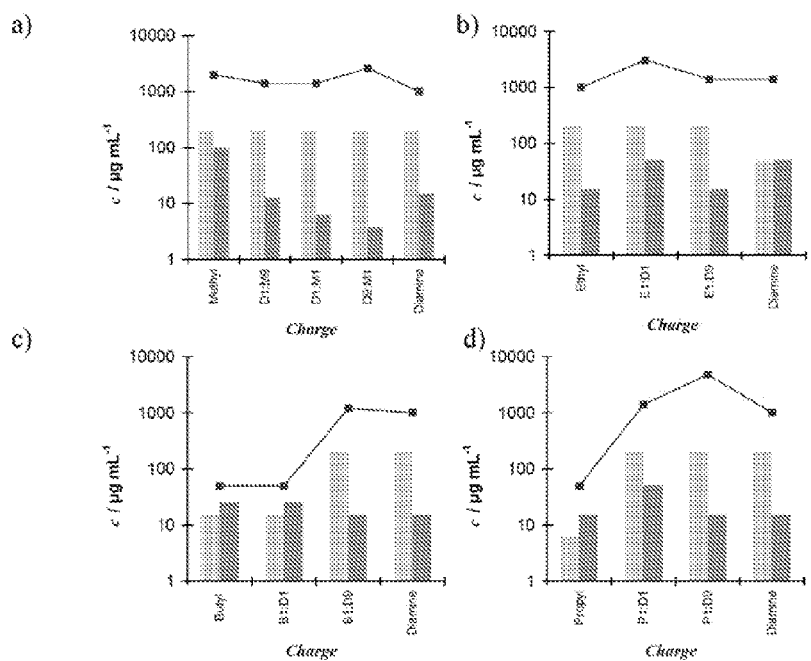

FIG. 41

MIC$_{90}$ data (against *S. aureus*) for ion-exchanged SMAMPs (polymer 9 in FIG. 34), plotted as concentration versus hydrophobicity. The x-axis labels denote the respective counterion, where TFA = trifluoroacetate.

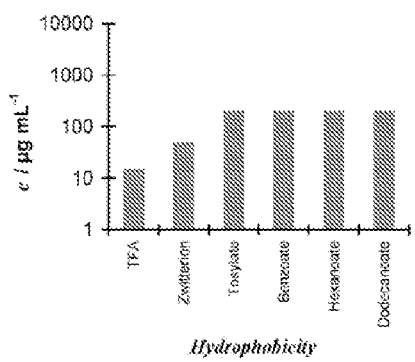

FIG. 42

Molecular weight dependence of biological properties for various SMAMPs, plotted as concentration (MIC$_{90}$ or HC$_{50}$, respectively) versus increasing nominal charge; light gray columns = MIC$_{90}$, *E. coli*, dark gray columns = MIC$_{90}$, *S. aureus*; red squares = HC$_{50}$, human erythorocytes; a) different molecular weights of poly3, b) 10 000 g/mol polymers of series 2 (FIG. 34), c) different molecular weights of 9, d) different molecular weights of the propyl polymer from series 2.

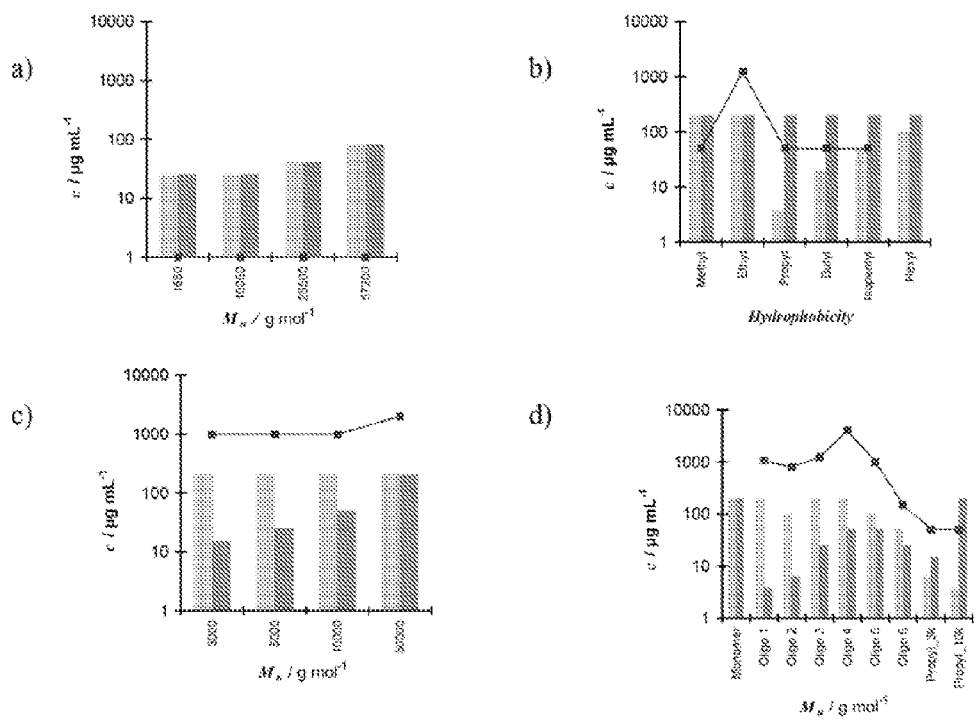

FIG. 43

Dye-leakage percentage versus SMAMP concentration of *E. coli* and *S. aureus* mimicking vesicles

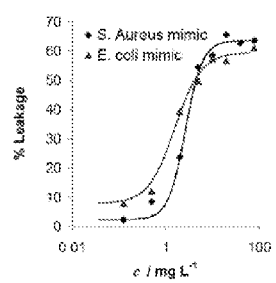

FIG. 44

Fluorescence microscopy image of *E. coli* cells treated with live-dead stain. The images of the left column were taken using a green filter (SYTO 9 emission), the ones in the right column were taken using a red filter (propidium iodide emission). A/B: Control, no polymer; C/D: poly1, E/F: butyl polymer from series 5.

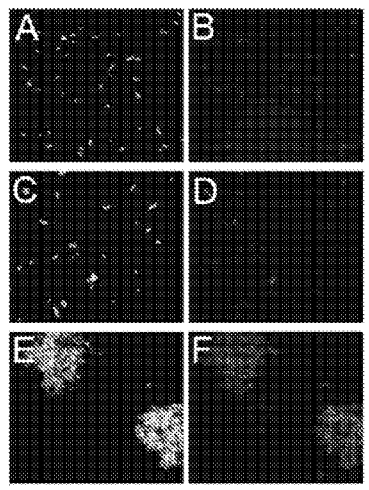

FIG. 45

Dynamic light scattering studies on vesicles exposed to a series of SMAMPs (poly1 to poly3).

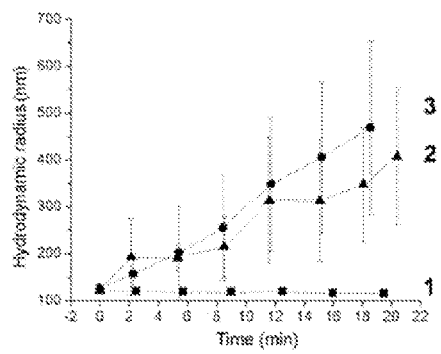

FIG. 46 a) Dye-leakage curves for the active poly3, the inactive poly1, and the membrane-permeating polymer 10; b) Fluorescence microscopy images of *S. aureus* cells treated with live-dead stain. The images of the top row were taken using a green filter (SYTO 9 emission), the ones in the bottom row were taken using a red filter (propidium iodide emission). A/B: poly1; C/D: poly3, E/F: polymer 10.

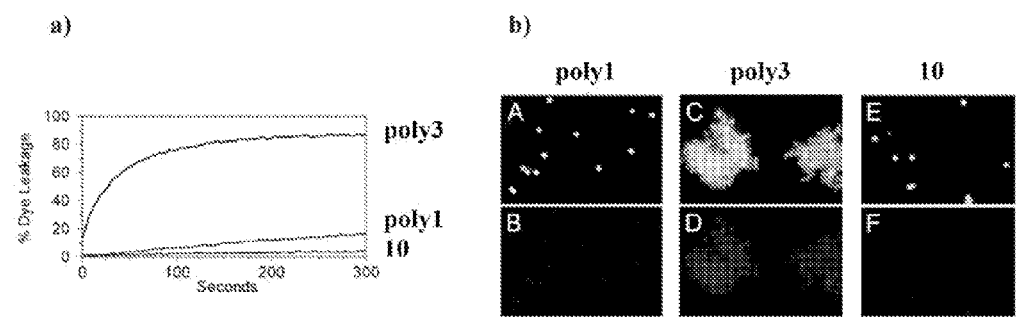

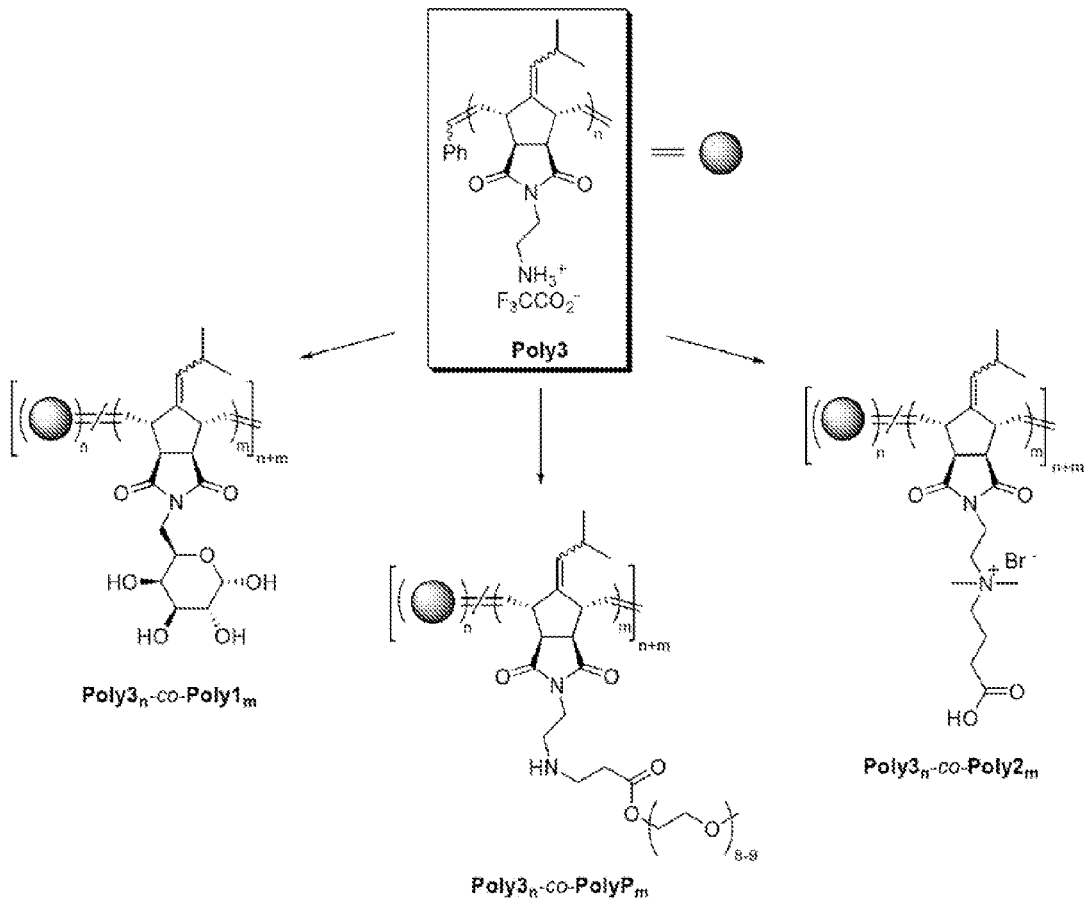
FIG. 47. Schematic representation of modifications to Poly3 via incorporation of hydrophilic groups. Explanation of nomenclature: Poly3$_n$-co-Poly1$_m$ : n indicates the mol fraction of M3 and m indicates the mol fraction of M1 in the copolymer composition.

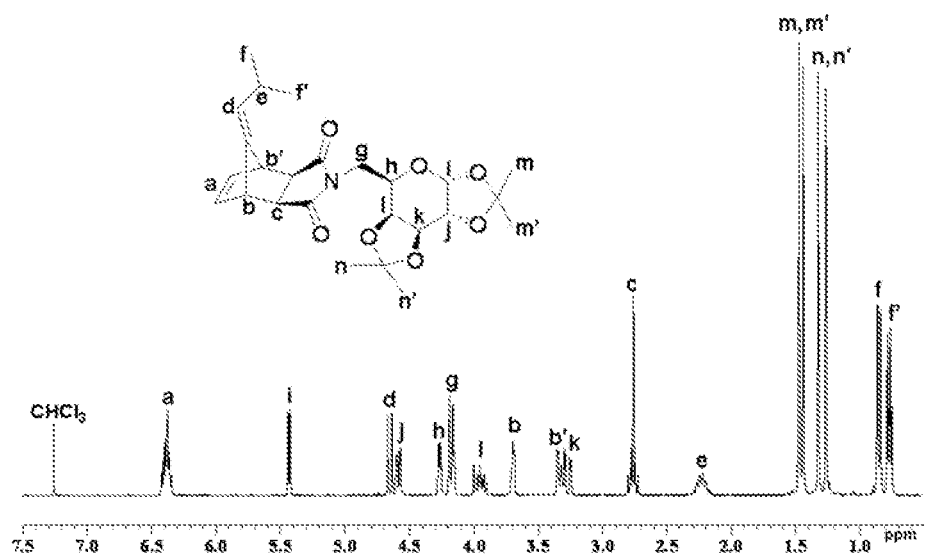
FIG. 48. $^1$H NMR of M1, in CDCl$_3$.
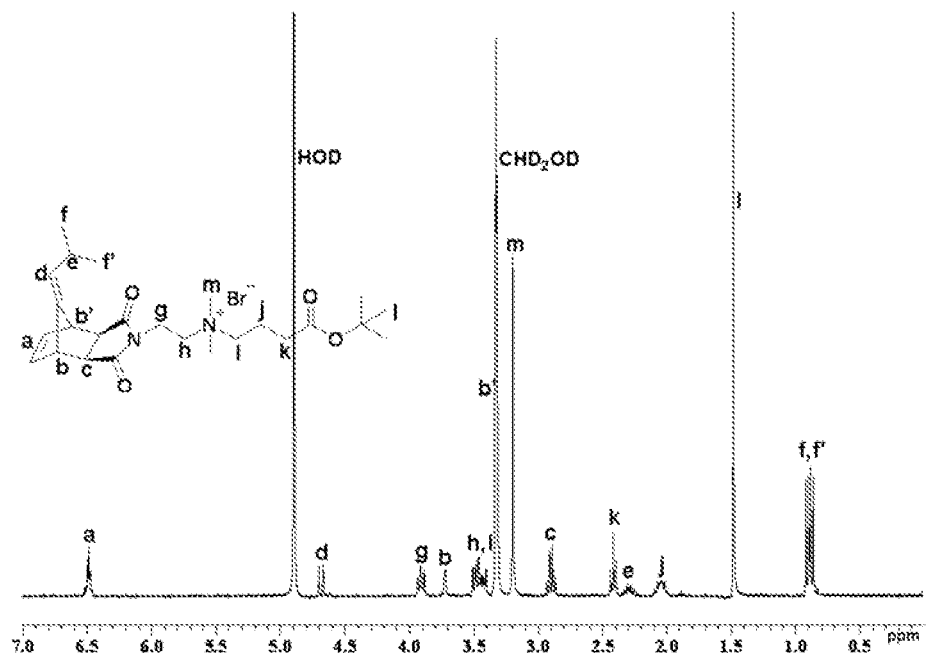
FIG. 49. $^1$H NMR of M2, in CD$_3$OD.

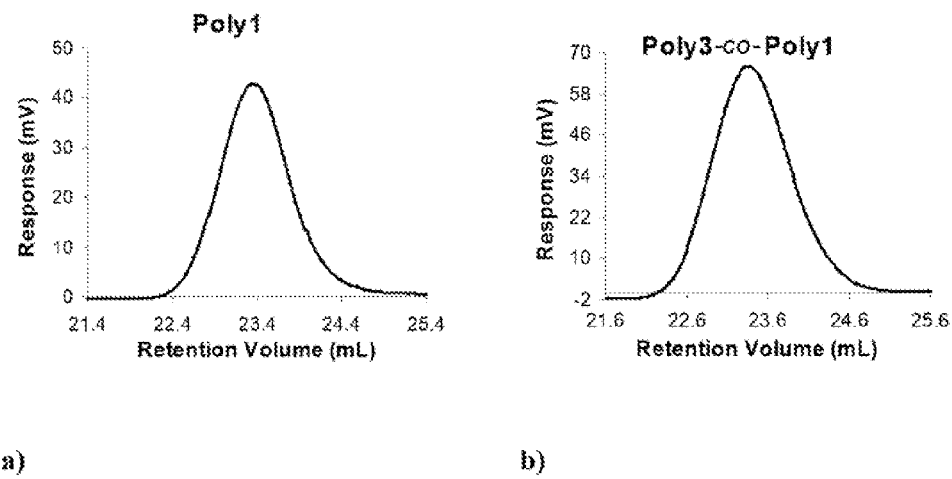
FIG. 50. GPC traces of (a) Poly1 ($M_n$ = 2.8 kDa) and (b) Poly3$_{0.5}$-co-Poly1$_{0.5}$ ($M_n$ = 2.9 kDa).
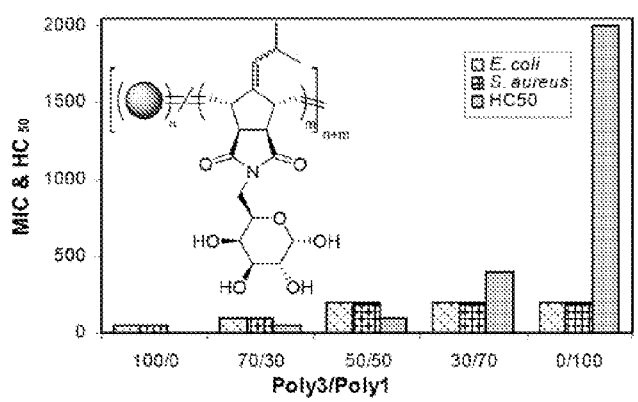
FIG. 51. MIC and HC$_{50}$ data of Poly3$_n$-co-Poly1$_m$.

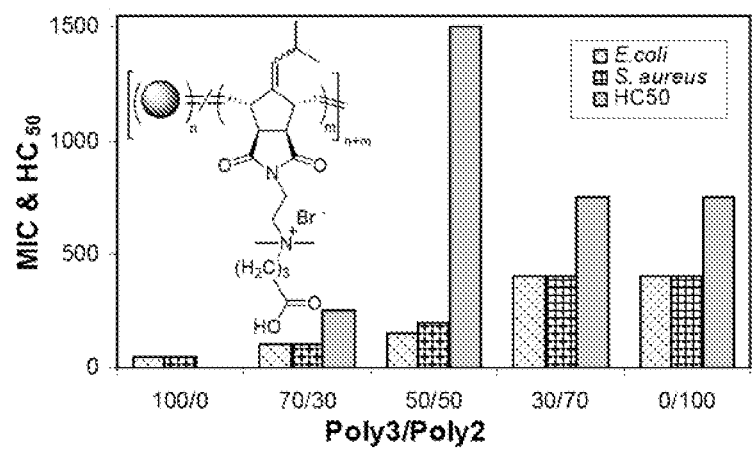
FIG. 52. MIC and HC$_{50}$ data of Poly3$_n$-co-Poly2$_m$.
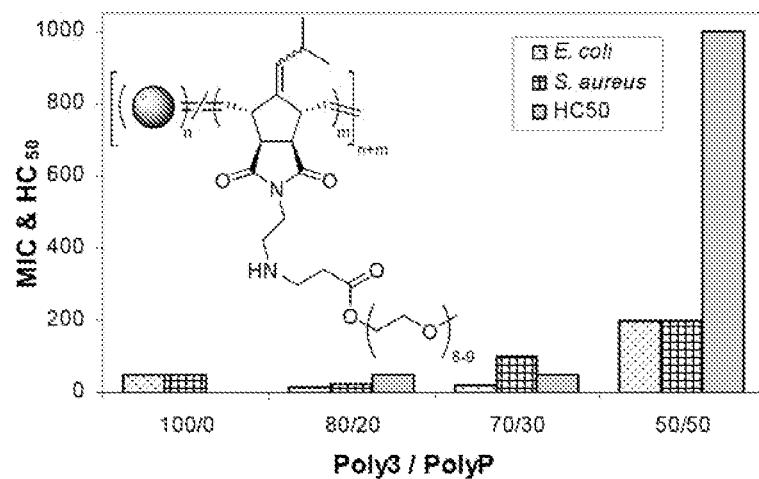
FIG. 53. MIC and HC$_{50}$ data of Poly3$_n$-co-PolyP$_m$.

FIG. 54. GPC traces of (a) Poly1 ($M_n = 2.8$ kDa) and (b) Poly3$_{0.5}$-co-Poly1$_{0.5}$ ($M_n = 2.9$ kDa).
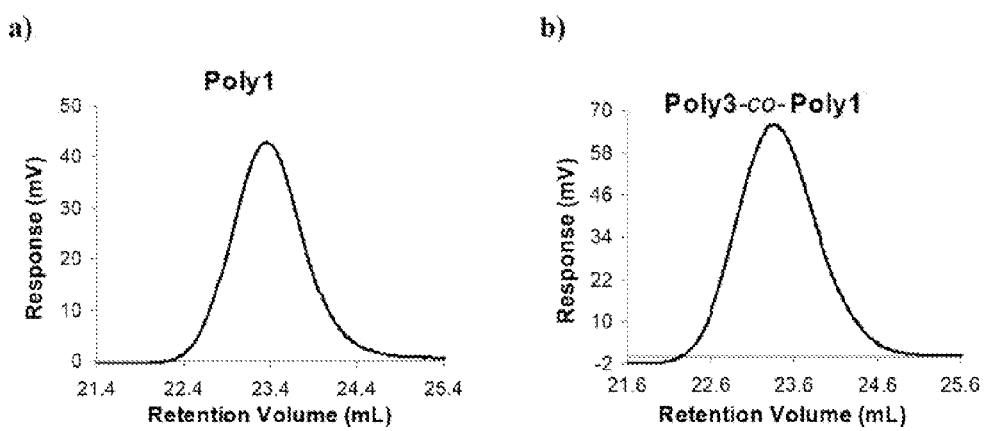
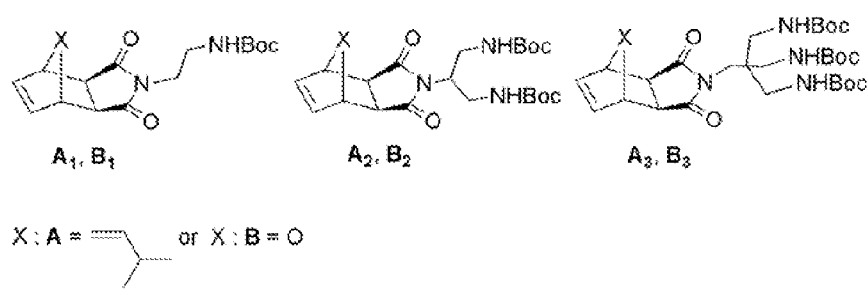
FIG. 55. Chemical structures of norbornene monomers with multiple amine functionalities.

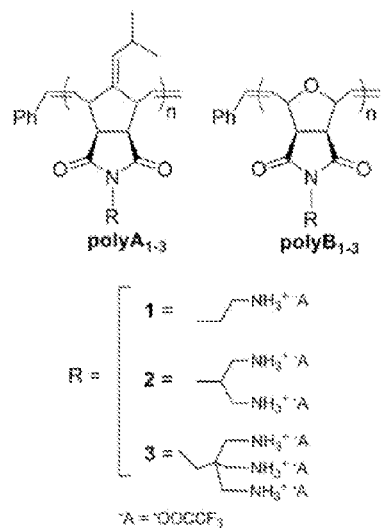

FIG. 56. Antimicrobial polynorbornene derivatives.

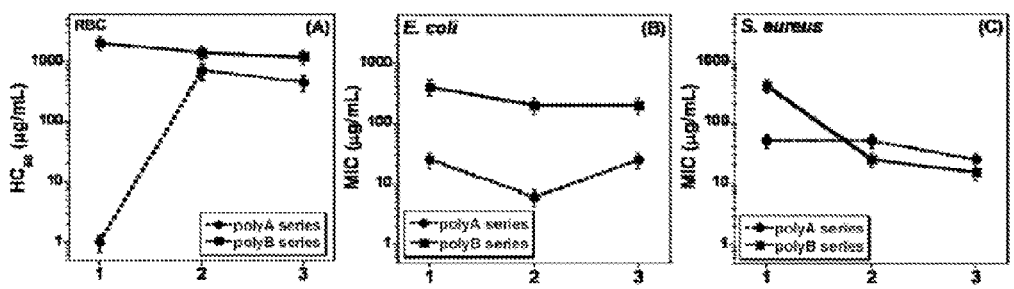

FIG. 57. Hemolytic activity ($HC_{50}$) of polyA$_{1-3}$ and polyB$_{1-3}$ series against human RBCs (A). Antibacterial activity ($MIC_{90}$) of polyA$_{1-3}$ and polyB$_{1-3}$ series against Gram-negative bacteria *E. coli* (B); against Gram-positive bacteria *S. aureus* (C). X-axis = number of cationically charged amines per monomer repeat unit; 1 = mono-amine; 2 = bis-amine; 3 = tris-amine.

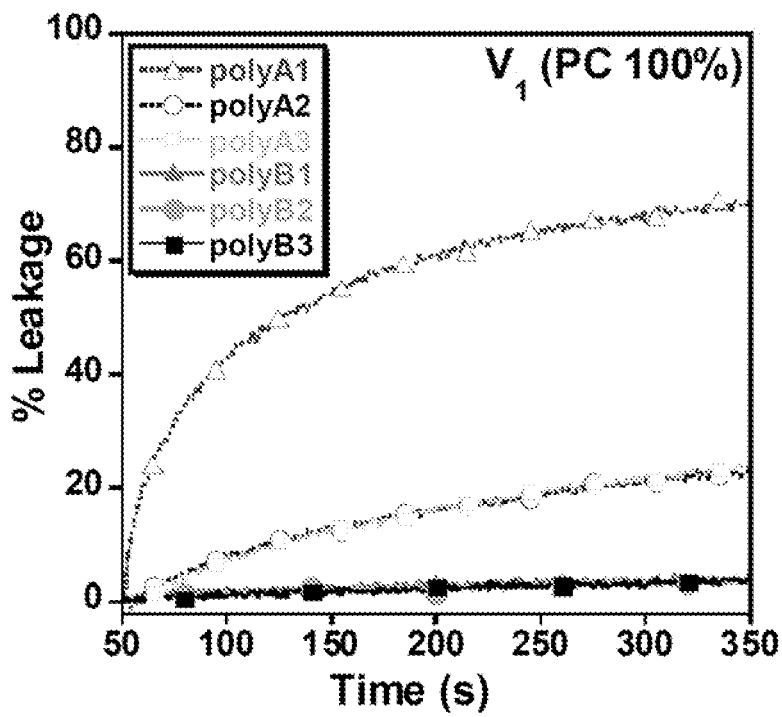
FIG. 58. Percentage of calcein dye leakage from PC liposomes $V_1$, final lipid concentration is 5.0 μM. The dye leakage experiments were performed in 10 mM phosphate, 90 mM NaCl buffer pH 7.0; at t = 50 s, 0.2 μg/mL polymer sample (in DMSO) was added, and at t = 350 s, 20% Triton-X was added to provide 100% leakage.

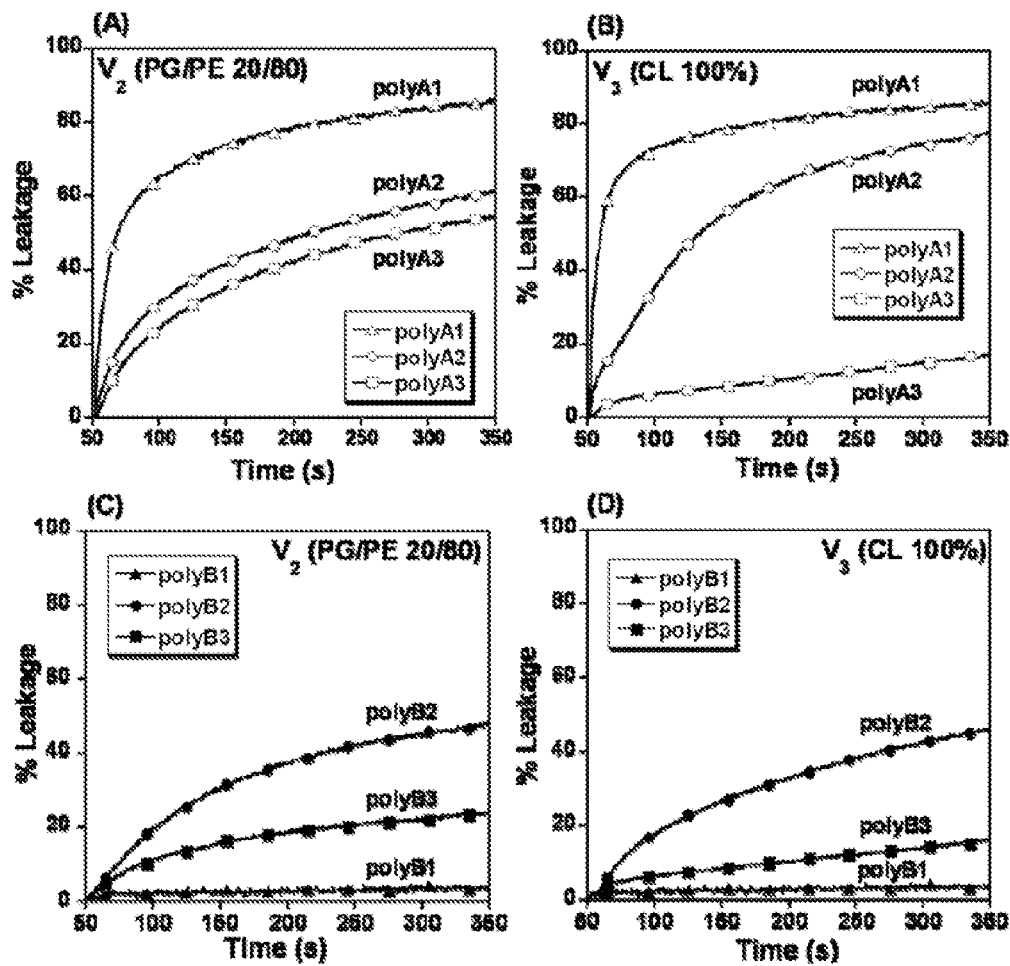
FIG. 59. Percentage of calcein dye leakage from 20/80 PG/PE vesicles $V_2$ (A and C) and CL vesicles $V_3$ (B and D), final lipid concentration is 5.0 μM. The dye leakage experiments were performed in 10 mM phosphate, 90 mM NaCl buffer pH 7.0; at t = 50 s, 0.2 μg/mL (for A and C) and 1.0 μg/mL (for A and D) polymer sample (in DMSO) was added, and at t = 350 s, 20% Triton-X was added to provide 100% leakage.

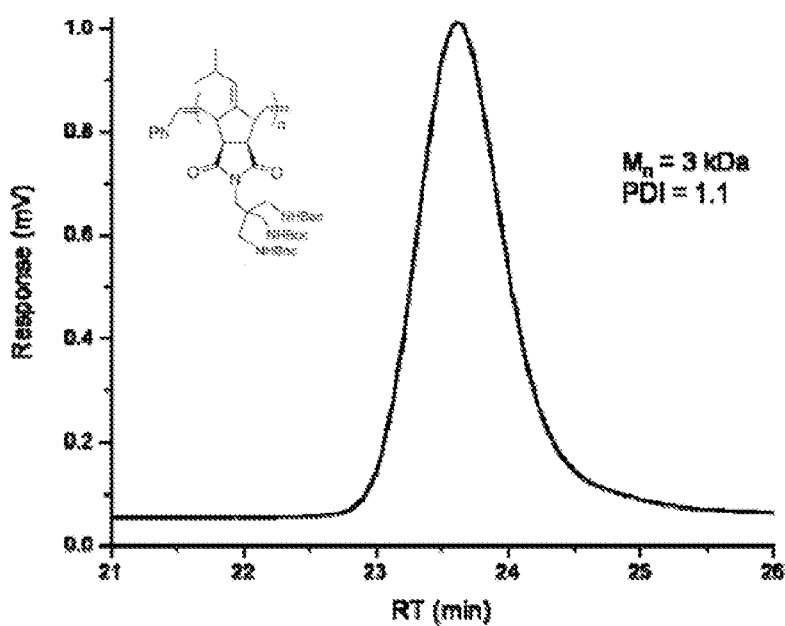
FIG. 60. GPC analysis of polyA₃.
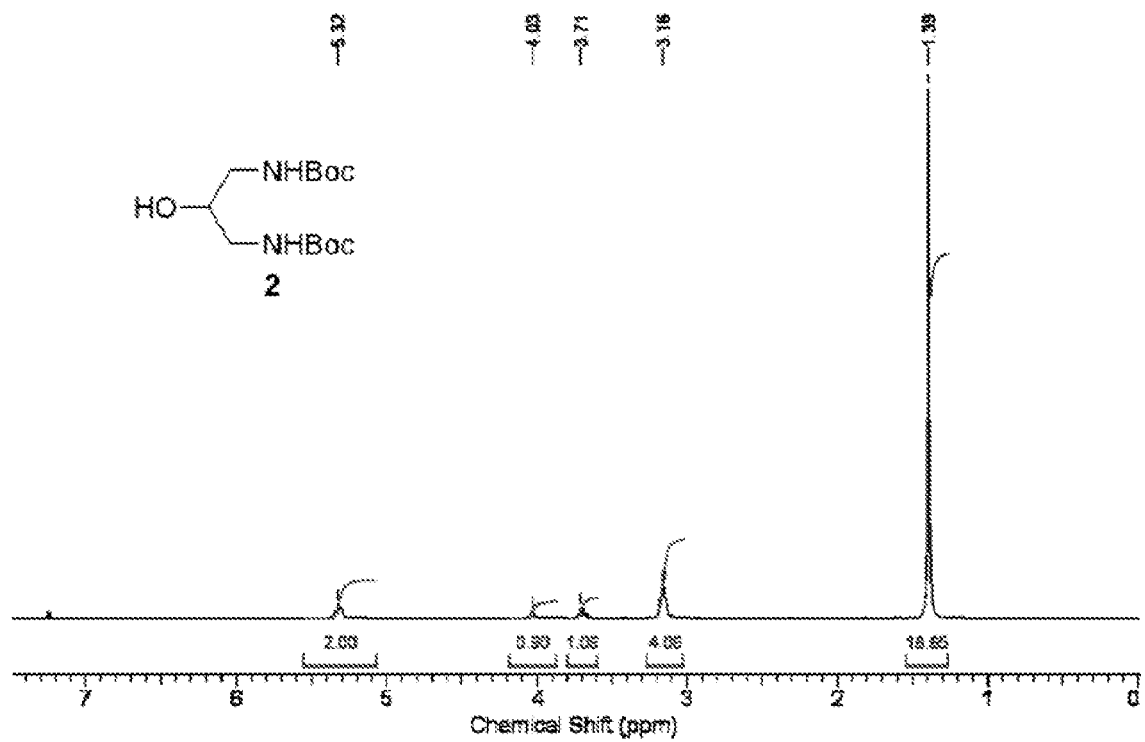
FIG. 61. ¹H NMR spectrum in CDCl₃ of compound 2.

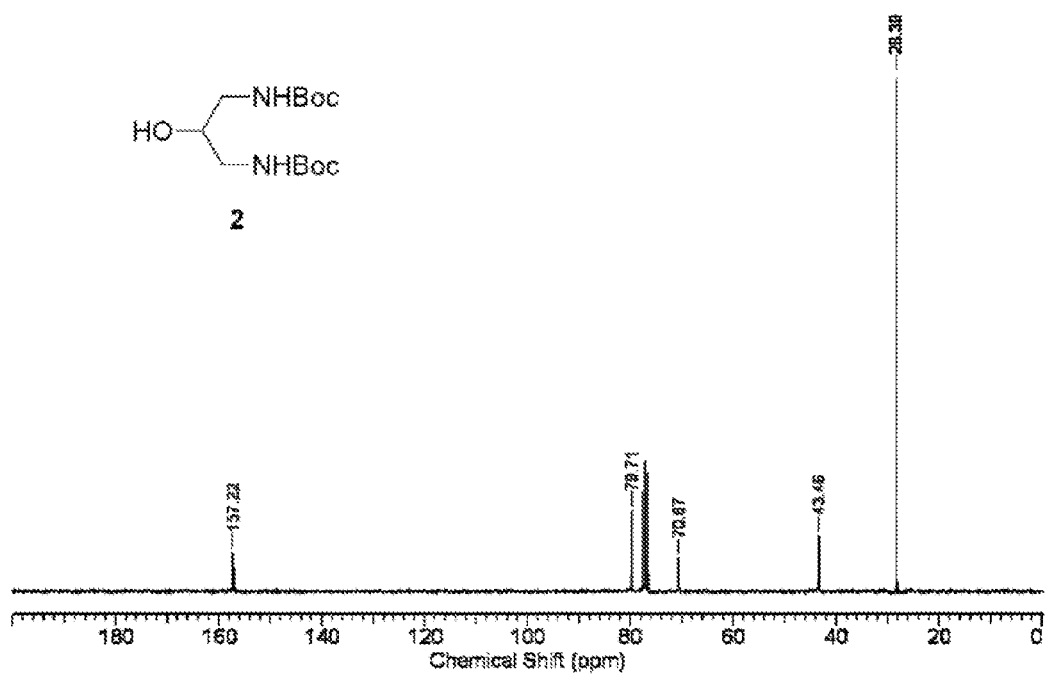
FIG. 62. $^{13}$C NMR spectrum in CDCl$_3$ of compound 2.

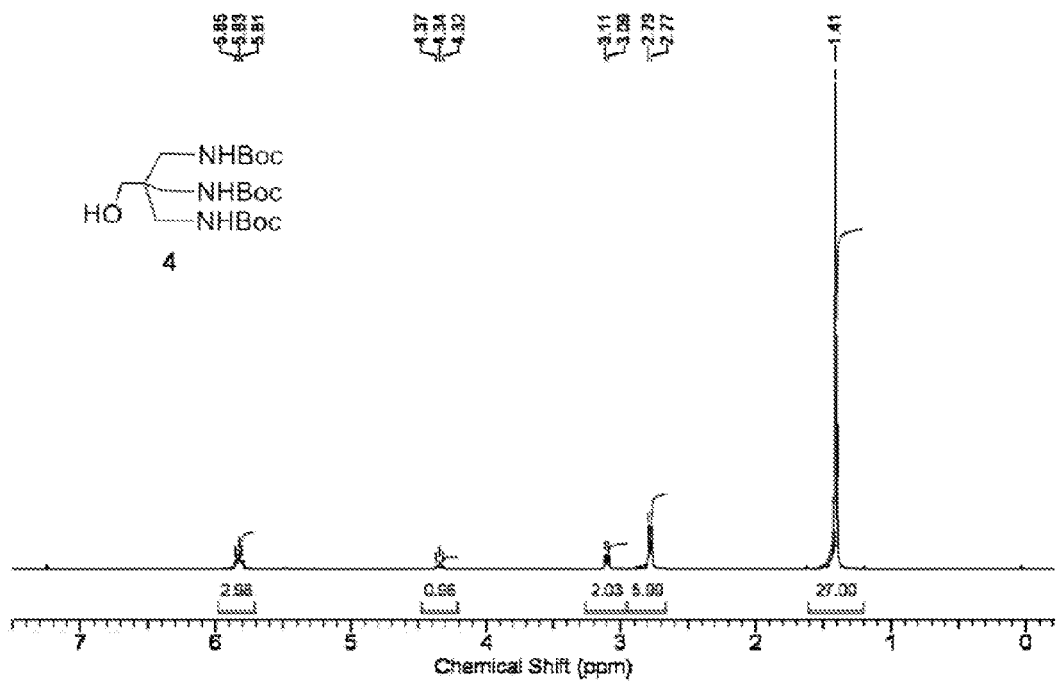
FIG. 63. $^1$H NMR spectrum in CDCl$_3$ of compound 4.
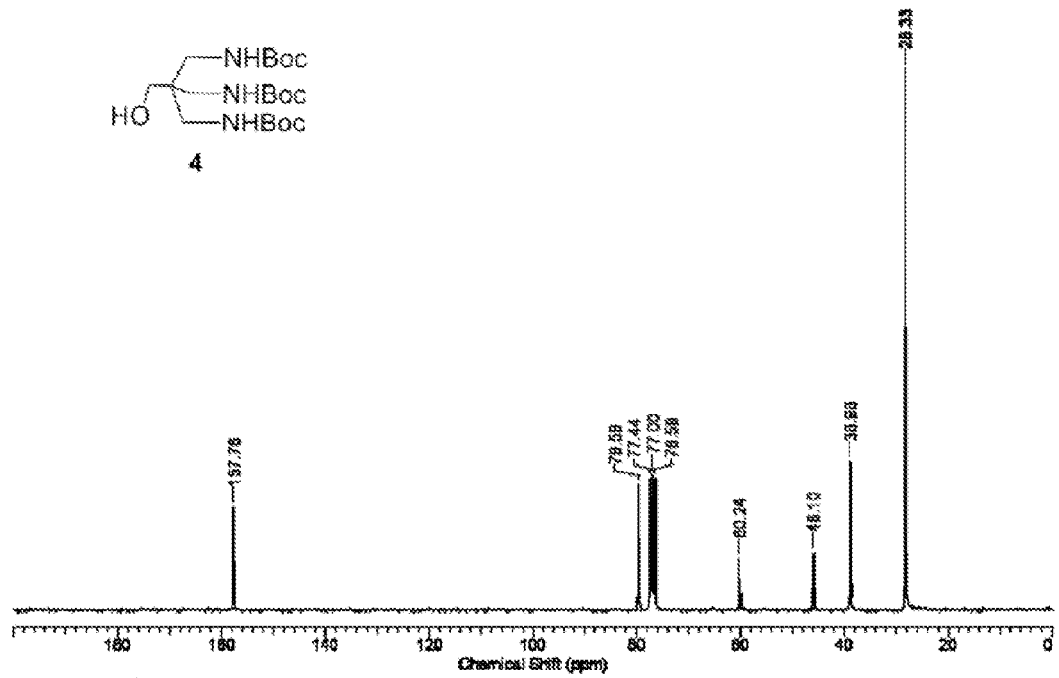
FIG. 64. $^{13}$C NMR spectrum in CDCl$_3$ of compound 4.

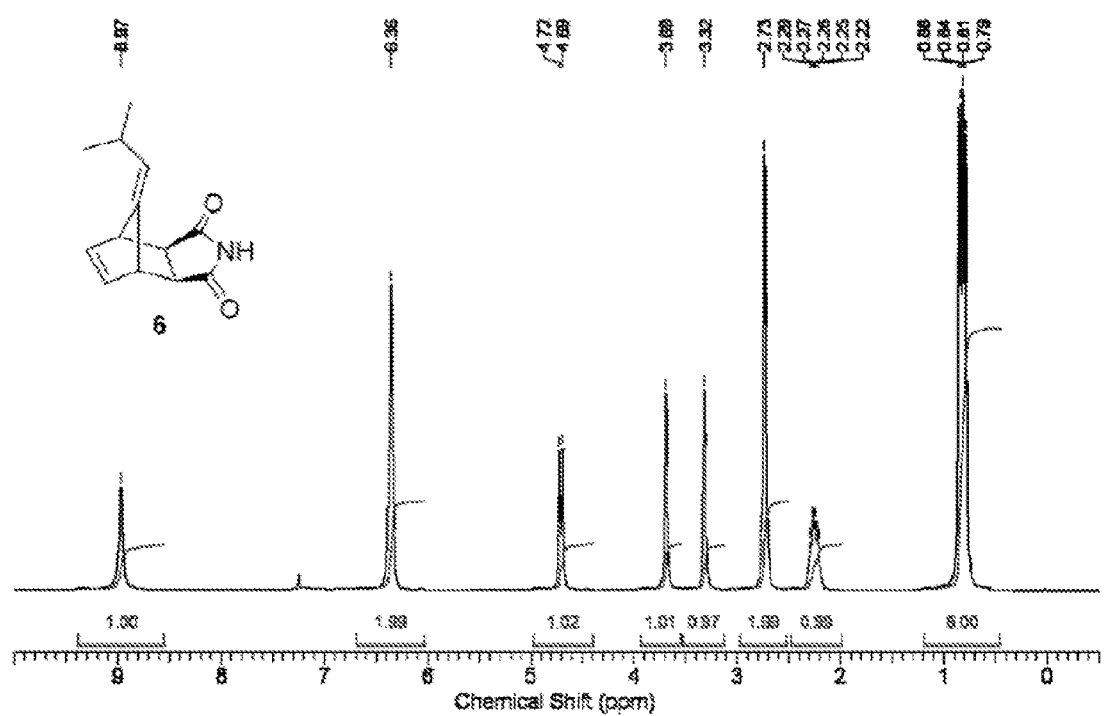
FIG. 65. $^1$H NMR spectrum in $CDCl_3$ of compound 6.

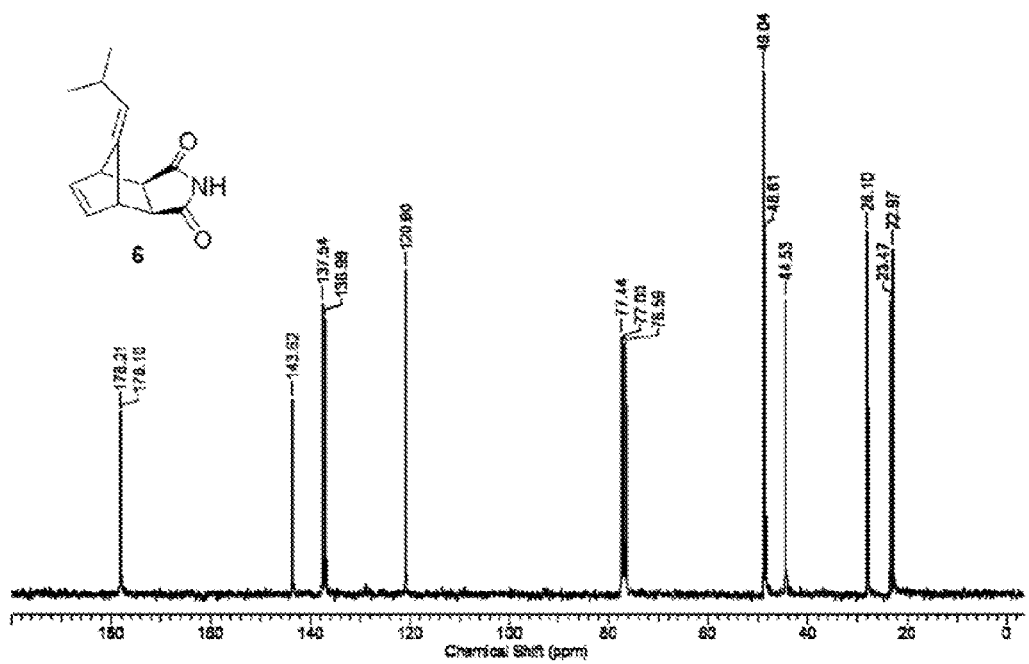
FIG. 66. $^{13}$C NMR spectrum in CDCl$_3$ of compound 6.
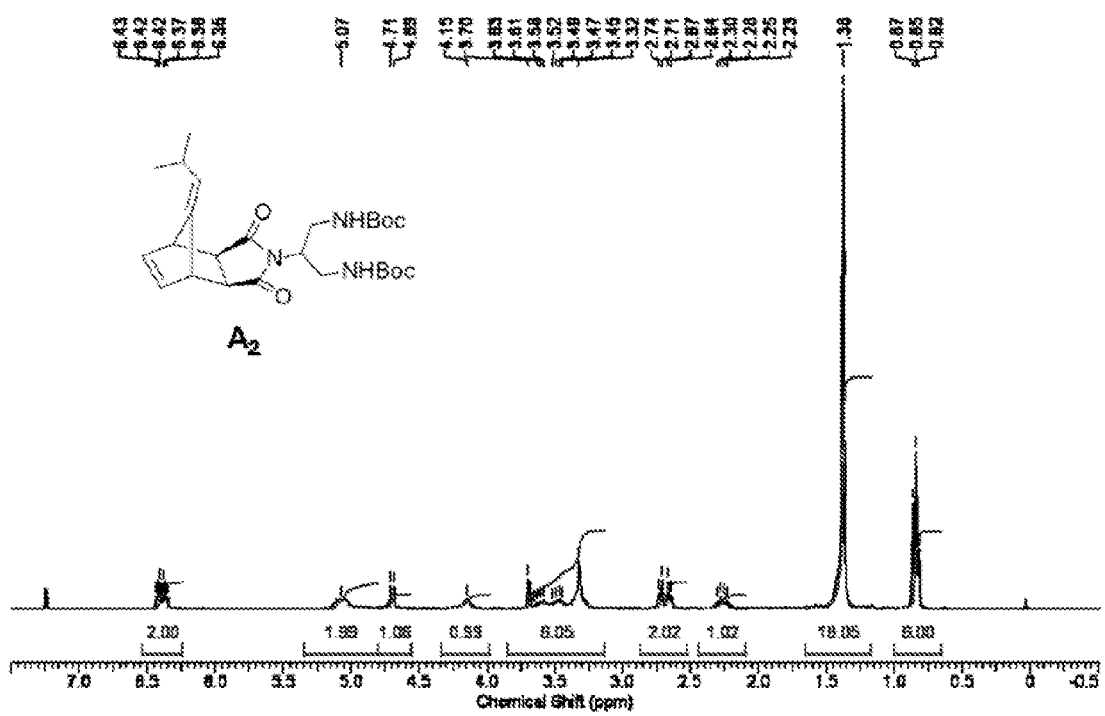
FIG. 67. $^1$H NMR spectrum in CDCl$_3$ of monomer A$_2$.

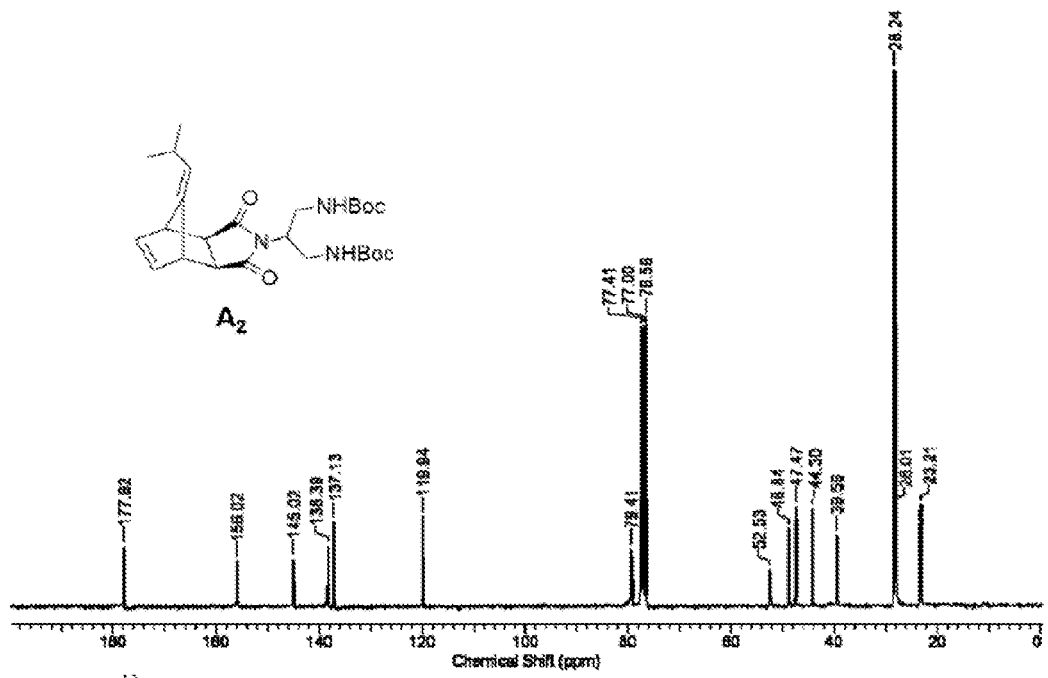
FIG. 68. $^{13}$C NMR spectrum in CDCl$_3$ of monomer A$_2$.
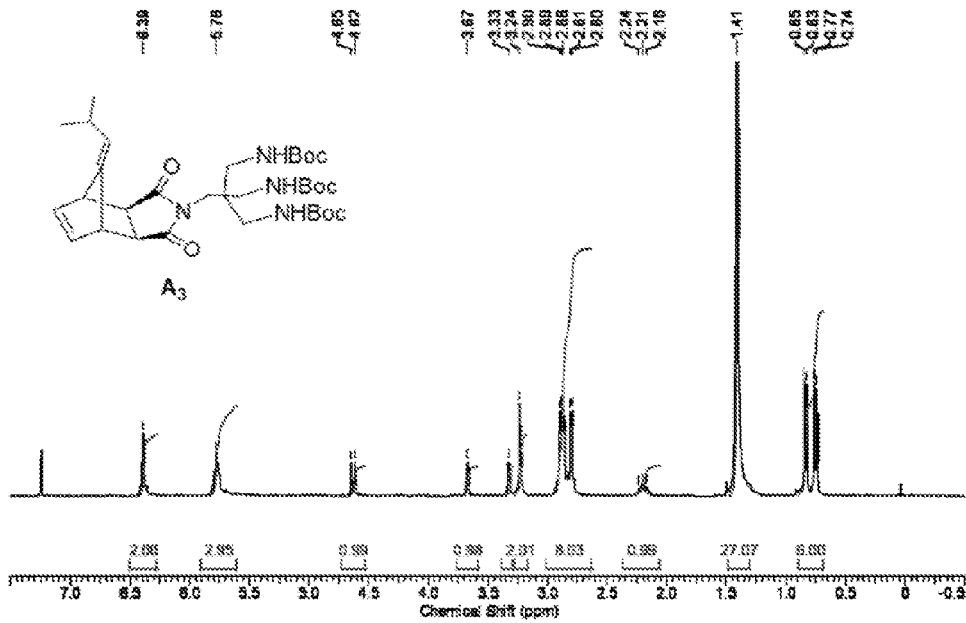
FIG. 69. $^1$H NMR spectrum in CDCl$_3$ of monomer A$_3$.

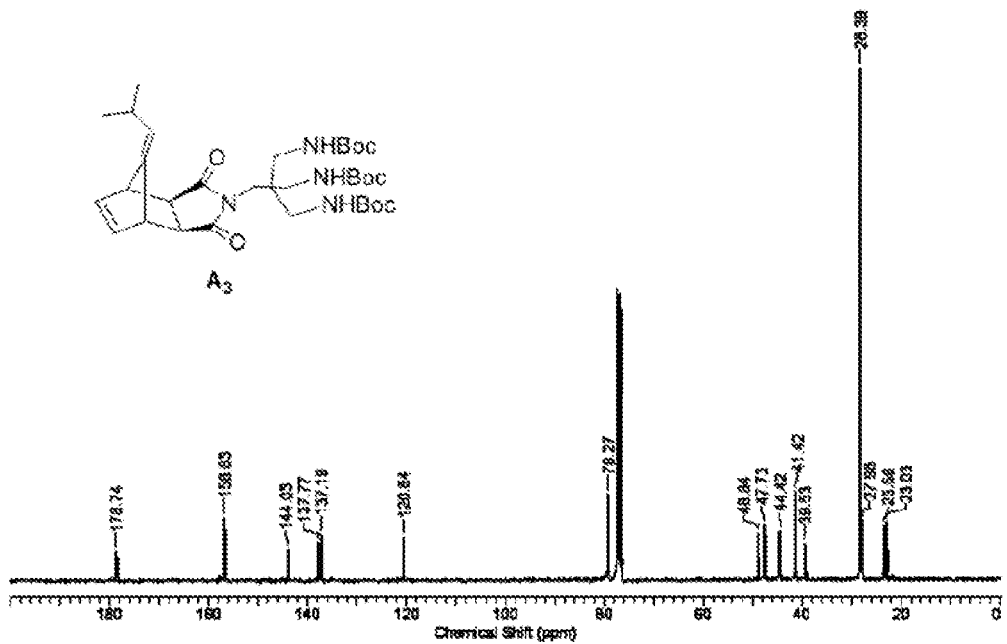
FIG. 70. $^{13}$C NMR spectrum in CDCl$_3$ of monomer A$_3$.
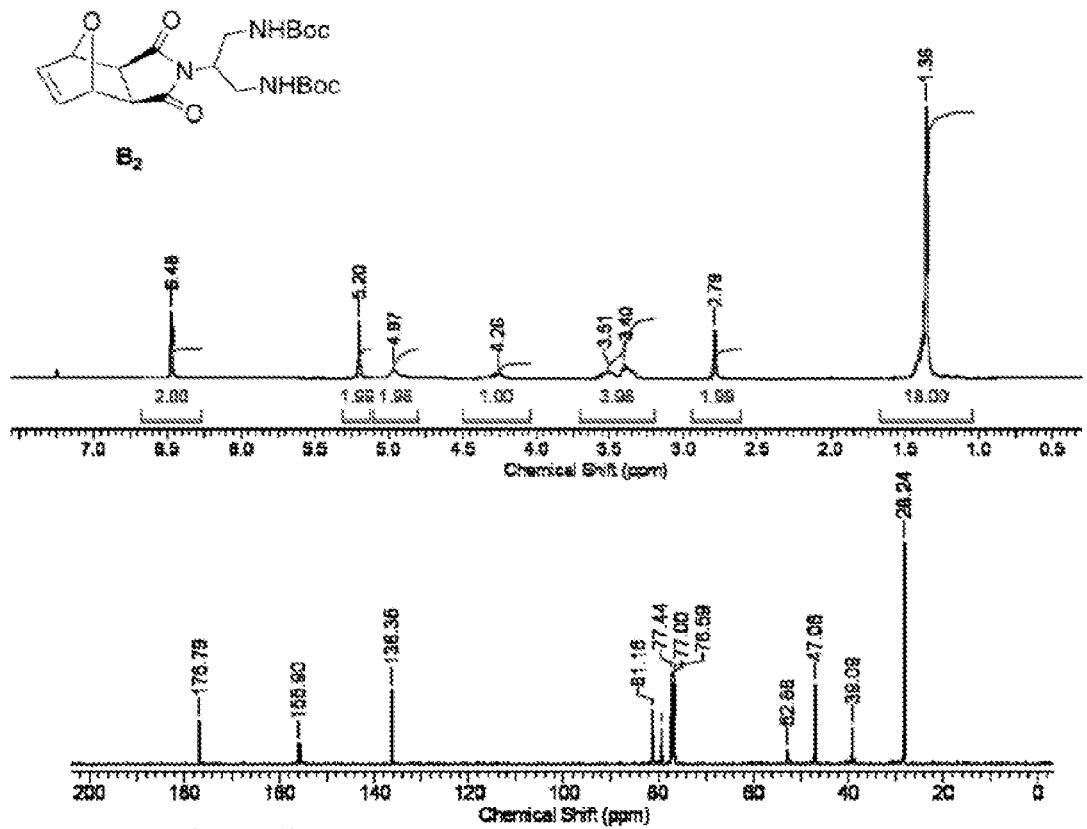
FIG. 71. $^1$H and $^{13}$C NMR spectra in CDCl$_3$ of monomer B$_2$.

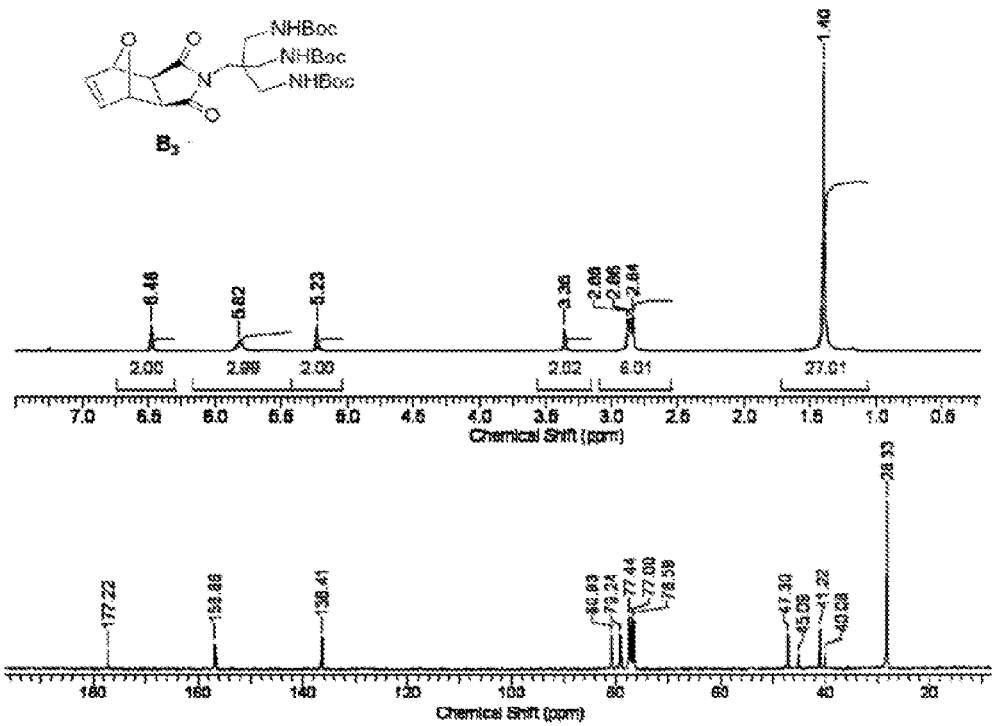
FIG. 72. $^1$H and $^{13}$C NMR spectra in CDCl$_3$ of monomer B$_3$.
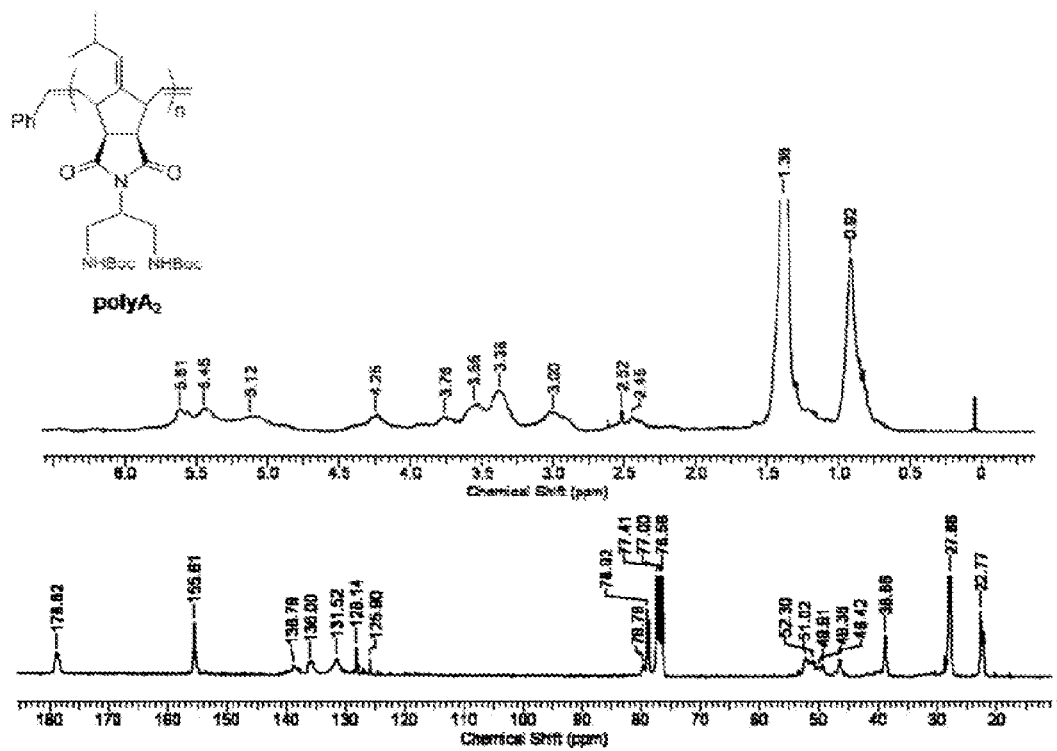
FIG. 73. $^1$H and $^{13}$C NMR spectra in CDCl$_3$ of polyA$_2$.

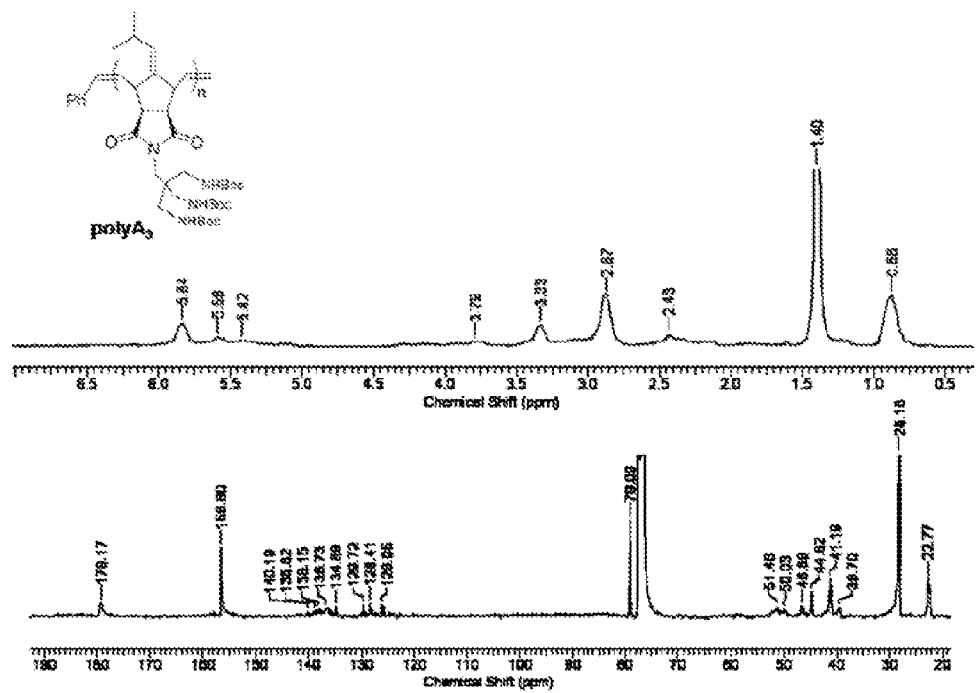
FIG. 74. $^1$H and $^{13}$C NMR spectra in CDCl$_3$ of polyA$_3$.
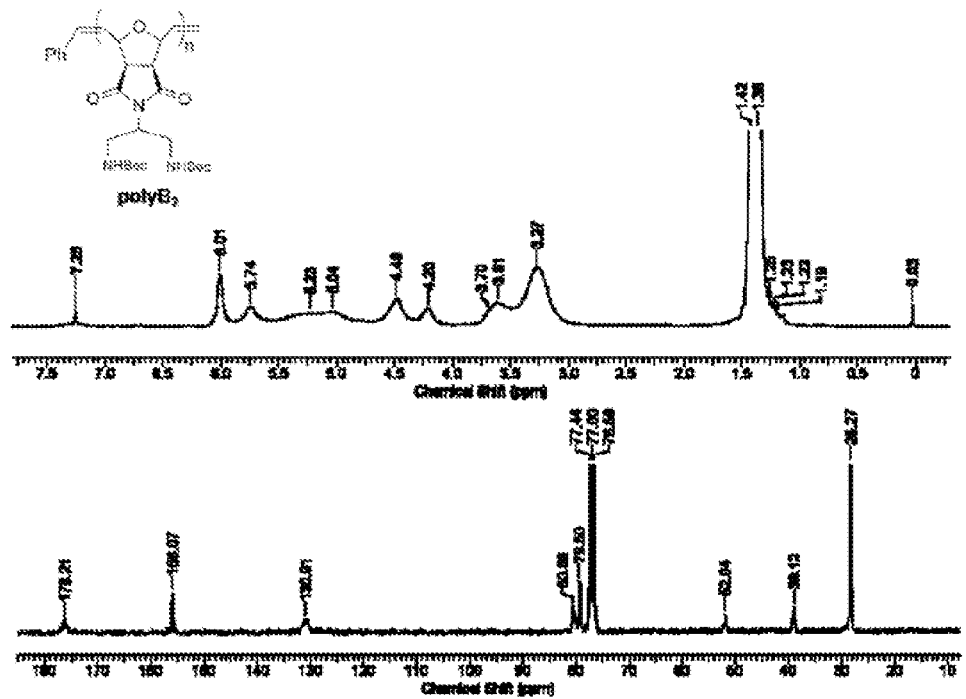
FIG. 75. $^1$H and $^{13}$C NMR spectra in CDCl$_3$ of polyB$_2$.

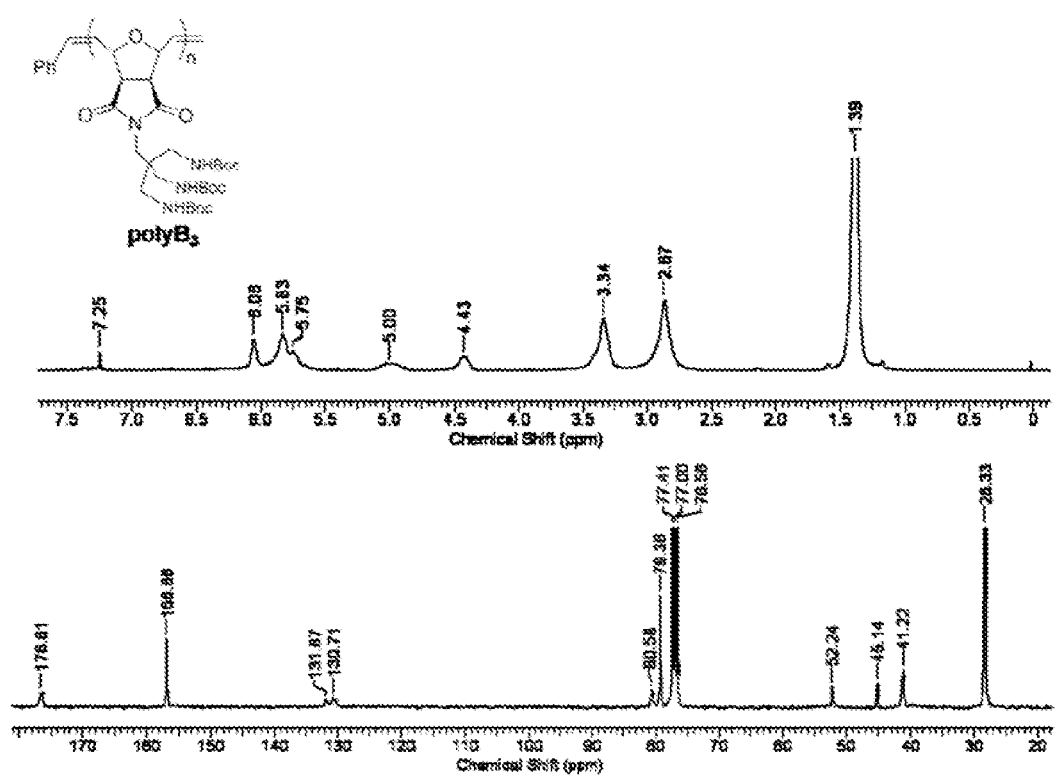
FIG. 76. $^1$H and $^{13}$C NMR spectra in CDCl$_3$ of polyB$_3$.

ANTIMICROBIAL POLYMERS

CROSS REFERENCE TO RELATED APPLICATIONS

This application is a continuation of and claims the benefit of priority from U.S. application Ser. No. 12/795,892, filed Jun. 8, 2010, which claims the benefit of U.S. Provisional Application Ser. No. 61/185,035, filed Jun. 8, 2009, the entire content of each of which is incorporated herein by reference in its entirety.

FIELD OF THE INVENTION

The invention relates to novel antimicrobial polymers. More particularly, the invention relates to antimicrobial polymers that are synthetic mimics of antimicrobial peptides, and related preparation, methods and uses thereof.

BACKGROUND OF THE INVENTION

Natural antimicrobial peptides (AMPs) are among the first line of defense when organisms are under attack by bacterial pathogens. These host-defense peptides have shown broad-spectrum antimicrobial activity. (Brodgen, *Nature Rev. Microbiol.* 2005, 3, 238-250.) Because their production in the organism is much faster than that of specific antibodies, the AMPs are a vital component of innate immunity. AMPs are found in many species, including humans, animals, plants and invertebrates. Different from common antibiotics that target specific cell structures, AMPs use non-receptor interactions, including in many cases direct action against the bacteria's membranes. (Yang, et al, *J. Am. Chem. Soc.* 2007, 129, 12141.) The cells of the host organism are less affected. Thus, AMPs can selectively attack bacteria within a host organism. Bacteria could become immune to AMPs only when they change their entire membrane chemistry or other targets—thus resistance to AMPs is retarded as compared to other antibiotics. (Zasloff, *Nature* 2002, 415, 389-395.) Due to this promising feature, there has been increasing interest in synthetic mimics of antimicrobial peptides (SMAMPs). These include the SMAMPs made of α- and β-amino acids, peptoids, aromatic oligomers, and synthetic polymers. (Zasloff, *Proc. Natl. Acad. Sci. USA* 1987, 84, 5449; Castro, et al., *Curr. Protein Peptide Sci.* 2006, 7, 473; Chen, et al., *J. Biol. Chem.* 2005, 280, 12316; Won, et al., *J. of Biol. Chem.* 2004, 279, 14784; Hamuro, et al., *J. Am. Chem. Soc.* 1999, 121, 12200; Porter, et al., *Nature* 2000, 404, 565; Liu, et al., *J. Am. Chem. Soc.* 2001, 123, 7553; Epand, et al., *Biochemistry* 2004, 43, 9527; Patch, et al., *J. Am. Chem. Soc.* 2003, 125, 12092; Brouwer, et al., *Peptides* 2006, 27, 2585; Haynie, et al., *Antimicrob. Agents Chemother.* 1995, 39, 301; Tew, et al., *Proc. Natl. Acad. Sci. USA* 2002, 99, 5110; Liu, et al., *Angew. Chem. Internat. Ed.* 2004, 43, 1158; Tang, et al., *Chem. Commun.* 2005, 12, 1537; Kuroda, et al., *J. Am. Chem. Soc.* 2005, 127, 4128; Ilker, et al., *J. Am. Chem. Soc.* 2004, 126, 15870; Arnt, et al., *J. Am. Chem. Soc.* 2002, 124, 7664; Arnt, et al., *Langmuir* 2003, 19, 2404; Arm, et al., *J. Polymer Sci. A, Polymer Chem.* 2004, 42, 3860; Mowery, et al. *J. Am. Chem. Soc.* 2007, 129, 15474.)

One common feature of most AMPs is their positive charge and facial amphiphilicity. Regardless of the secondary structures, these peptides generally display one hydrophobic and one hydrophilic face along their backbone. (Brodgen, *Nature Rev. Microbial.* 2005, 3, 238-250; Boman, *Immunol. Rev.* 2000, 173, 5; Hancock, et al., *Trends Biotech.* 1998, 16, 82.) Due to positive charges in the hydrophilic part, AMPs bind preferentially to the anionic outer membranes of bacterial pathogens or other anionic targets including proteins and DNA. (Zasloff, *Nature* 2002, 415, 389-395; Yeaman, et al., *Pharmacol. Rev.* 2003, 55, 27.) In many cases, their facial amphiphilicity allows them to insert into the bacterial membrane and to locally change the membrane's lipid organization in such a way that trans-membrane pores are formed, although other mechanisms of action are also known. This interaction may lead to a breakdown of the membrane potential, the leaking of the cytoplasm and eventually the death of the pathogen cell. (Yount, et al., *Biopolymers (Peptide Sci.)* 2006, 84, 435.)

There is an unmet need for novel SMAMPs that possess desirable and tunable antimicrobial properties while at the same time are easy to prepare.

SUMMARY OF THE INVENTION

The invention is based in part on certain novel polymers (SMAMPs) obtained through advanced polymer design and synthetics methods, which polymers exhibit promising properties of AMPs. In particularly, for example, a ring-opening metathesis polymerization (ROMP) platform was developed that allow syntheses of SMAMPs. The platform employs a minimum number of norbornene-based building blocks and enables easy and independent variation of hydrophobic and hydrophilic groups in the monomer units and/or along the polymeric backbone, thereby allowing one to finetune and select desirable properties of the polymers, e.g., potency and selectivity.

In one aspect, the invention generally relates to a monomer unit having the structure of:

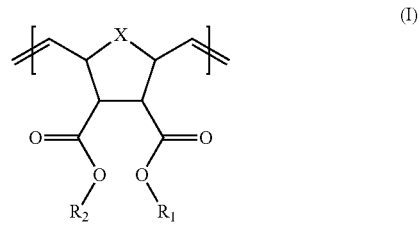

(I)

wherein one of $R_1$ and $R_2$ comprises a hydrophobic group and the other one of $R_1$ and $R_2$ comprises a hydrophilic group; and X is C—$R_3$, O or S, wherein $R_3$ is a hydrogen or a $C_1$-$C_{12}$ alkyl or alkoxy group (e.g., a $C_1$-$C_6$ alkyl or alkoxy group).

The hydrophobic group may include a substituted or unsubstituted alkry group, e.g., a substituted or unsubstituted $C_1$-$C_{10}$ alkyl group (e.g., a $C_1$-$C_6$ alkyl group). The hydrophilic group may include a group selected from ammonium ions, sulfonium ions, guanidinium ions, phosphonium ions, and mono- and di-alkyl substituted amino groups, for example.

In certain embodiments, X is O; $R_1$ is a linear or branched $C_1$-$C_{12}$ alkyl group (e.g., a $C_1$-$C_6$ alkyl group); and $R_2$ is

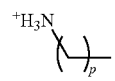

or a guanidinium ion

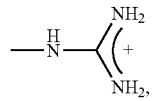

wherein p is an integer from 1-10 (i.e, 1, 2, 3, 4, 5, 6, 7, 8, 9, 10).

In certain embodiments, X is C—$R_3$; $R_1$ is a linear or branched $C_1$-$C_{12}$ alkyl group (e.g., a $C_1$-$C_6$ alkyl group); and $R_2$ is

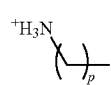

or a guanidinium ion

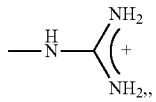

wherein p is an integer from 1-10. In some embodiments, $R_3$ is hydrogen.

In another aspect, the invention generally relates to a polymer comprising a monomer unit

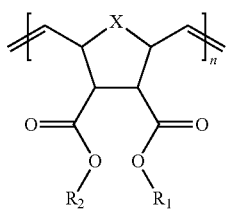

(II)

wherein one of $R_1$ and $R_2$ comprises a hydrophobic group and the other one of $R_1$ and $R_2$ comprises a hydrophilic group; and X is C—$R_3$, O or S, wherein $R_3$ is a hydrogen or a $C_1$-$C_{12}$ alkyl or alkoxy group.

The hydrophobic group may include a substituted or unsubstituted alkry group, e.g., a substituted or unsubstituted $C_1$-$C_{10}$ alkyl group (e.g., a $C_1$-$C_6$ alkyl group). The hydrophilic group may include a group selected from ammonium ions, sulfonium ions, guanidinium ions, phosphonium ions, and mono- and di-alkyl substituted amino groups, for example.

In certain embodiments, X is O; $R_1$ is a linear or branched $C_1$-$C_{12}$ alkyl group (e.g., a $C_1$-$C_6$ alkyl group); and $R_2$ is

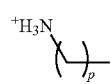

or a guanidinium ion

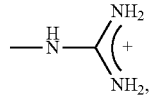

wherein p is an integer from 1-10 (i.e, 1, 2, 3, 4, 5, 6, 7, 8, 9, 10).

In certain embodiments, X is C—$R_3$; $R_1$ is a linear or branched $C_1$-$C_{12}$ alkyl group (e.g., a $C_1$-$C_6$ alkyl group); and $R_2$ is

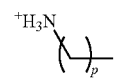

or a guanidinium ion

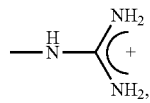

wherein p is an integer from 1-10. In some embodiments, $R_3$ is hydrogen.

For example, n is an integer from about 1 to about 1,000, for example, from about 1 to about 100; from about 1 to about 20; from about 1 to about 10; from about 1 to about 5; from about 3 to about 50; from about 3 to about 20; from about 3 to about 10; from about 3 to about 5.

In some applications, the polymer may preferably be a co-polymer. In certain embodiments, the co-polymer may include structural monomer units of:

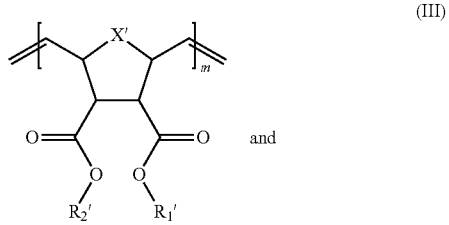

(III)

and

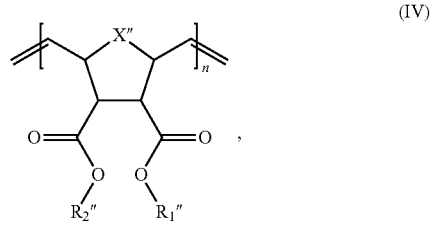

(IV)

wherein each of X' and X" is C—$R_3$, O or S, wherein $R_3$ is a hydrogen or a $C_1$-$C_{12}$ alkyl or alkoxy group (e.g., a $C_1$-$C_6$ alkyl or alkoxy group); each of $R_1'$ and $R_1''$ is a hydrophobic group and each of $R_2'$ and $R_2''$ is a hydrophilic group, provided that $R_1'$ and $R_1''$ are not the same, $R_2'$ and $R_2''$ are not the same, or X' and X" are not the same; and each of m and n is an integer from about 1 to about 1,000.

Each of m and n is an integer from about 1 to about 1,000, for example, from about 1 to about 100; from about 1 to about 20; from about 1 to about 10; from about 1 to about 5; from about 3 to about 50; from about 3 to about 20; from about 3 to about 10; from about 3 to about 5.

In some embodiments, each of $R_1'$ and $R_1''$ is independently a linear or branched $C_1$-$C_{12}$ alkyl group (e.g., a $C_1$-$C_6$ alkyl group); and each of $R_2'$ and $R_2''$ is independently

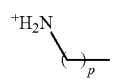

or a guanidinium ion

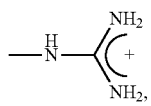

wherein p is an integer from 1-10 (i.e, 1, 2, 3, 4, 5, 6, 7, 8, 9, 10).

In some embodiments, each of X' and X" is O. In some other embodiments, each of X' and X" is independently C—$R_3$. In some other embodiments, one of X' and X" is O and the other is C—$R_3$.

In certain embodiments, one or more (e.g., all) of —C(=O)O— groups in (I), (II), (III) or (IV) occupy the exo-stereo position.

In another aspect, the invention generally relates to a polymer prepared by ring-opening metathesis polymerization, the polymer comprising hydrophobic and hydrophilic groups attached to the polymeric backbone such that, within a monomeric structural unit, the hydrophobic and hydrophilic groups are attached to the polymeric backbond at adjacent atoms. For example, in the polymer the hydrophobic and hydrophilic groups are attached to the polymeric backbond via ester linkages. The polymers of the invention may have a molecular weight of $M_n$ between about 1,000 and about 100,000, between 1,000 and 50,000, between 1,000 and 10,000, for example.

The invention also relates to a product comprising a polymer of the invention and methods for preparing polymers of the invention, for example, by ring-opening metathesis polymerization.

BRIEF DESCRIPTION OF THE DRAWINGS

FIG. 1 illustrates an embodiment of a 'construction kit' approach to obtain facially amphiphilic monomers and polymers.

FIG. 2 shows certain exemplary biological data.

FIG. 3 shows certain characterization data of exemplary propyl oligomers.

FIG. 4 shows certain exemplary biological data.

FIG. 5 shows certain exemplary biological data.

FIG. 6 shows certain characterization of propyl oligomers.

FIG. 7 shows exemplary highly active polymer.

FIG. 8 shows exemplary moderately active polymer and inactive polymer.

FIG. 9 shows exemplary $HC_{50}$ curve of certain polymer.

FIG. 10 shows an illustrative representation of certain cell membrane and cell wall morphology.

FIG. 11 shows certain exemplary structure and antimicrobial properties for different molecular weights of the SMAMP.

FIG. 12 shows certain exemplary dye-leakage experiments on model membranes.

FIG. 13 schematically illustrates certain rationalization of the results of the dye-leakage experiments in the presence of peptidoglycan.

FIG. 14: shows certain exemplary dye-leakage experiments on model membranes.

FIG. 15: shows certain exemplary GPC data for the SMAMP homopolymer series.

FIG. 16: shows certain exemplary dye-leakage curves.

FIG. 17: shows certain exemplary structural comparison.

FIG. 18: shows certain exemplary cartoon representation of local charge surplus.

FIG. 19: shows certain exemplary structure of model polymers.

FIG. 20. shows certain exemplary antimicrobial and hemolytic properties of certain copolymers.

FIG. 21 shows certain exemplary illustration of a dye-leakage experiment.

FIG. 22 shows certain exemplary dye-leakage data.

FIG. 23 shows certain exemplary representative cartoon and polymer structures.

FIG. 24 shows certain exemplary methods to endow polynorbornenes.

FIG. 25 shows certain exemplary 50/50 random copolymers.

FIG. 26 shows certain exemplary MICs of selected polymers.

FIG. 27 shows certain exemplary cartoon regarding polymer interactions.

FIG. 28 shows certain exemplary graph of polymer-induce dye leakage.

FIG. 29 shows certain exemplary fluorescence microscopy of stained E. coli in the absence and presence of polymer.

FIG. 30 shows certain exemplary synthetic scheme.

FIG. 31 shows certain exemplary molecular evolution of antibacterials.

FIG. 32 shows certain exemplary MIC and HC curves.

FIG. 33 shows certain exemplary monomer and polymer synthesis.

FIG. 35 shows certain exemplary biological data for three exemplary series of SMAMP homopolymers.

FIG. 36 shows certain exemplary biological data for exemplary series of SMAMP copolymers.

FIG. 37 shows certain exemplary biological data for exemplary series of SMAMP copolymers, and illustration of SMAMP-membrane interactions.

FIG. 38 shows certain exemplary biological data for three exemplary series of SMAMP copolymers.

FIG. 39 shows certain exemplary biological data for exemplary imid-based SMAMP polymers.

FIG. 40 shows certain exemplary biological data for exemplary ester-based SMAMP copolymers.

FIG. 41 shows certain exemplary $MIC_{90}$ data.

FIG. 42 shows certain exemplary molecular weight dependence of biological properties for various SMAMPs.

FIG. 43 shows certain exemplary dye-leakage percentage versus SMAMP concentration.

FIG. 44 shows certain exemplary fluorescence microscopy image.

FIG. 45 shows certain exemplary dynamic light scattering studies.

FIG. 46 shows certain exemplary dye-leakage curves and fluorescence microscopy images.

FIG. 47 shows certain exemplary schematic representation of modifications of polymers.

FIG. 48 shows certain exemplary NMR data.
FIG. 49 shows certain exemplary NMR data.
FIG. 50 shows certain exemplary GPC traces.
FIG. 51 shows certain exemplary MIC and $HC_{50}$ data.
FIG. 52 shows certain exemplary MIC and $HC_{50}$ data.
FIG. 53 shows certain exemplary MIC and $HC_{50}$ data.
FIG. 54 shows certain exemplary GPC traces.
FIG. 55 shows certain exemplary chemical structures of norbornene monomers with multiple amine functionalities.
FIG. 56 shows certain exemplary antimicrobial polynorbornene derivatives.
FIG. 57 shows certain exemplary hemolytic activity ($HC_{50}$).
FIG. 58 shows certain exemplary percentage of calcein dye leakage data.
FIG. 59 shows certain exemplary percentage of calcein dye leakage data.
FIG. 60 shows certain exemplary GPC analysis.
FIG. 61 shows certain exemplary NMR data.
FIG. 62 shows certain exemplary NMR data.
FIG. 63 shows certain exemplary NMR data.
FIG. 64 shows certain exemplary NMR data.
FIG. 65 shows certain exemplary NMR data.
FIG. 66 shows certain exemplary NMR data.
FIG. 67 shows certain exemplary NMR data.
FIG. 68 shows certain exemplary NMR data.
FIG. 69 shows certain exemplary NMR data.
FIG. 70 shows certain exemplary NMR data.
FIG. 71 shows certain exemplary NMR data.
FIG. 72 shows certain exemplary NMR data.
FIG. 73 shows certain exemplary NMR data.
FIG. 74 shows certain exemplary NMR data.
FIG. 75 shows certain exemplary NMR data.
FIG. 76 shows certain exemplary NMR data.

DEFINITIONS

Figure 34:
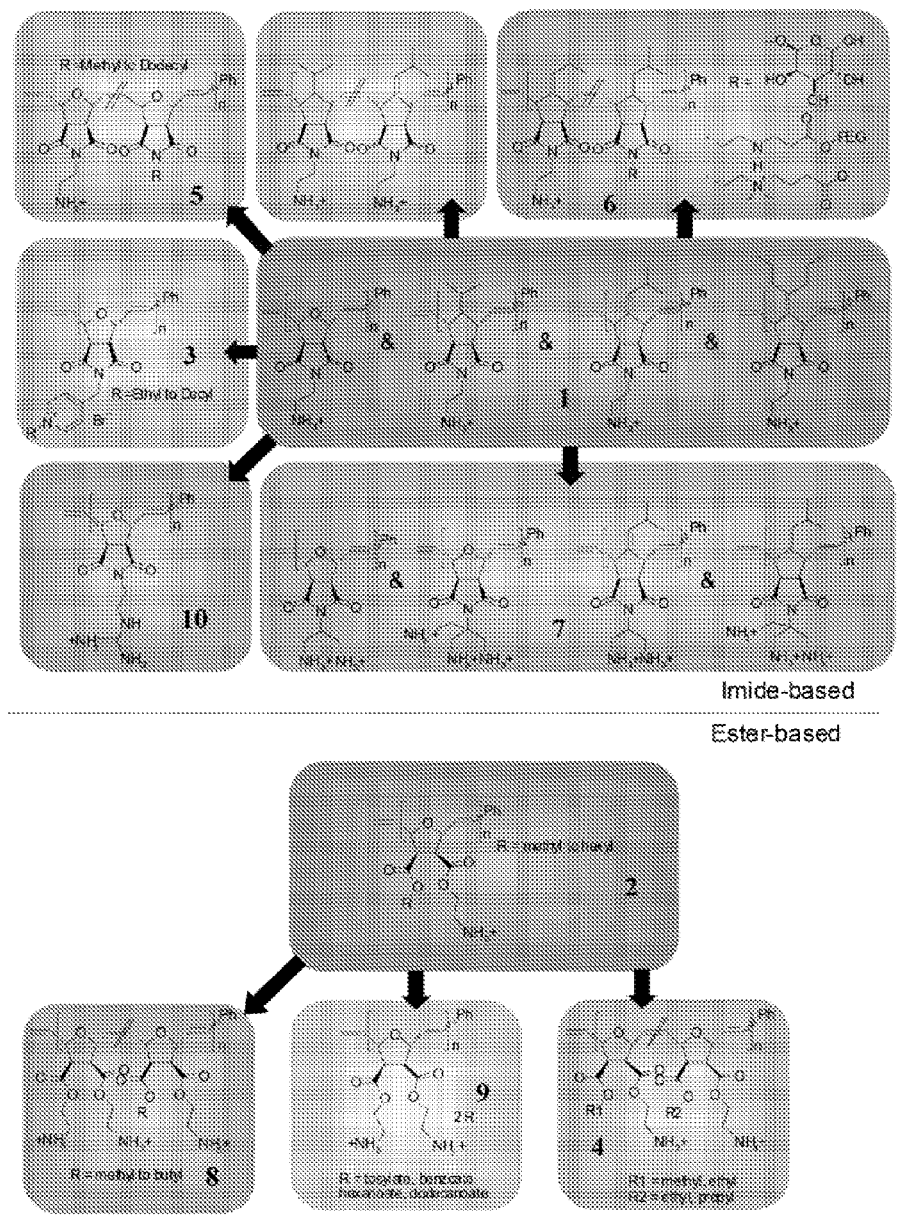
FIG. 34 shows certain exemplary library of ROMP-based SMAMP polymers.

Definitions of specific functional groups and chemical terms are described in more detail below. General principles of organic chemistry, as well as specific functional moieties and reactivity, are described in "Organic Chemistry", Thomas Sorrell, University Science Books, Sausalito: 1999.

Certain compounds of the present invention may exist in particular geometric or stereoisomeric forms. The present invention contemplates all such compounds, including cis- and trans-isomers, R- and S-enantiomers, diastereomers, (D)-isomers, (L)-isomers, the racemic mixtures thereof, and other mixtures thereof, as falling within the scope of the invention. Additional asymmetric carbon atoms may be present in a substituent such as an alkyl group. All such isomers, as well as mixtures thereof, are intended to be included in this invention.

Given the benefit of this disclosure, one of ordinary skill in the art will appreciate that synthetic methods, as described herein, utilize a variety of protecting groups. By the term "protecting group", as used herein, it is meant that a particular functional moiety, e.g., O, S, or N, is temporarily blocked so that a reaction can be carried out selectively at another reactive site in a multifunctional compound. In preferred embodiments, a protecting group reacts selectively in good yield to give a protected substrate that is stable to the projected reactions; the protecting group should be selectively removable in good yield by readily available, preferably non-toxic reagents that do not attack the other functional groups; the protecting group forms an easily separable derivative (more preferably without the generation of new stereogenic centers); and the protecting group has a minimum of additional functionality to avoid further sites of reaction. Oxygen, sulfur, nitrogen, and carbon protecting groups may be utilized. Examples of a variety of protecting groups can be found in *Protective Groups in Organic Synthesis*, Third Ed. Greene, T. W. and Wuts, P. G., Eds., John Wiley & Sons, New York: 1999.

It will be appreciated that the compounds, as described herein, may be substituted with any number of substituents or functional moieties.

The term "alkyl", as used herein, refers to a saturated linear or branched (including cyclic) hydrocarbon free radical, unsubstituted (i.e., with corresponding number of carbon and hydrogen atoms), or optionally substituted with substituents known to those skilled in the art. For example, alkyl groups include ($C_1$-$C_6$) alkyl (or $C_1$-$C_6$ alkyl), which refers to a saturated linear or branched free radical consisting essentially of 1 to 6 carbon atoms (i.e., 1, 2, 3, 4, 5, or 6 carbon atoms) and a corresponding number of hydrogen atoms. Exemplary ($C_1$-$C_6$) alkyl groups include methyl, ethyl, n-propyl, isopropyl, n-butyl, isobutyl, etc. Of course, other ($C_1$-$C_6$) alkyl groups will be readily apparent to those of skill in the art given the benefit of the present disclosure.

The terms "hydrophobic group" or "hydrophobic moiety", as used herein, refer to a group having a property such that an affinity of the group for water is low (e.g., low polarity). Non-limiting examples of hydrophobic groups or moieties include substituted and unsubstituted alkyl groups (e.g., lower alkyl groups having 6, 7, 8, 9, 10, 11, 12, or 13-30 or more carbon atoms, linear, branched or cyclic), alkenyl groups, alkynyl groups, aryl groups, saturated or unsaturated cyclic hydrocarbons, heteroaryl, heteroarylalkyl, heterocyclic, and corresponding substituted groups. A hydrophobic group may contain some hydrophilic groups or substituents insofar as the hydrophobic character of the group is not outweighed. In further variations, a hydrophobic group may include substituted silicon atoms, and may include fluorine atoms. The hydrophobic moieties may be linear, branched, or cyclic.

The terms "hydrophilic group" or "hydrophilic moiety" as used herein, refer to a group having a property such that an affinity of the group for water is high (e.g., high polarity). Non-limiting examples of hydrophilic groups or moieties include hydroxyl, methoxy, phenyl, carboxylic acids and ions and salts thereof, methyl, ethyl, and vinyl esters of carboxylic acids, amides, amino, cyano, isocyano, nitrile, ammonium ions or salts, sulfonium ions or salts, phosphonium ions or salts, mono- and di-alkyl substituted amino groups, polypropyleneglycols, polyethylene glycols, glycosyl groups, sugars, epoxy groups, acrylates, sulfonamides, nitro, —OP(O)(OCH$_2$CH$_2$N$^+$RRR)O$^-$, guanidinium, aminate, acrylamide, pyridinium, piperidine, and combinations thereof, wherein each R is independently selected from H or alkyl. Further examples include polymethylene chains substituted with alcohol, carboxylate, acrylate, or methacrylate. Hydrophilic moieties may also include alkyl chains having internal amino or substituted amino groups, for example, internal —NH—, —NC(O)R—, or —NC(O)CH=CH$_2$— groups, wherein R is H or alkyl. Hydrophilic moieties may also include polycaprolactones, polycaprolactone diols, poly(acetic acid)s, poly(vinyl acetates)s, poly(2-vinyl pyridine)s, cellulose esters, cellulose hydroxylethers, poly(L-lysine hydrobromide)s, poly(itaconic acid)s, poly(maleic acid)s, poly(styrenesulfonic acid)s, poly(aniline)s, or poly(vinyl phosphonic acid)s. A hydrophilic group may contain some hydrophobic groups or substituents insofar as the hydrophilic character of the group is not outweighed.

As used herein, MIC$_{90}$=minimum inhibitory concentration that will reduce the growth of a certain bacteria by 90% as compared to an untreated control. Low MIC$_{90}$ values indicate a high antibacterial activity. HC$_{50}$=hemolytic concentration at which 50% of human red blood cells are lysed. Samples that yield high HC$_{50}$ values have a low toxicity. Selectivity=HC$_{50}$/MIC$_{90}$. High selectivity values imply a good tolerance by the host organism, combined with a high toxicity towards the target organism.

DETAILED DESCRIPTION OF THE INVENTION

The invention generally relates to certain novel polymers (SMAMPs) developed through advanced polymer design and synthetics methods. In particular, for example, a ring-opening metathesis polymerization (ROMP) platform was developed that allow syntheses of SMAMPs that employ a minimum number of norbornene-based building, blocks and enable easy and independent variation of hydrophobic and hydrophilic groups in the monomer units and/or along the polymeric backbone to finetune and select desirable properties (e.g., potency and selectivity) of the polymers. The polymers exhibit promising properties of AMPs.

In one aspect, the invention generally relates to a monomer unit having the structure of:

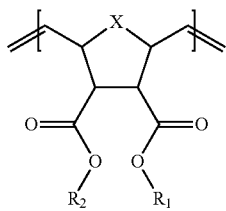

(I)

wherein one of R$_1$ and R$_2$ comprises a hydrophobic group and the other one of R$_1$ and R$_2$ comprises a hydrophilic group; and X is C—R$_3$, O or S, wherein R$_3$ is a hydrogen or a C$_1$-C$_{12}$ alkyl or alkoxy group (e.g., a C$_1$-C$_6$ alkyl or alkoxy group).

The hydrophobic group may include a substituted or unsubstituted alkry group, e.g., a' substituted or unsubstituted C$_1$-C$_{10}$ alkyl group (e.g., a C$_1$-C$_6$ alkyl group). The hydrophilic group may include a cationic group, which may be selected from ammonium ions, sulfonium ions, guanidinium ions, phosphonium ions, and mono- and di-alkyl substituted amino groups, for example.

In certain embodiments, X is O; R$_1$ is a linear or branched C$_1$-C$_{12}$ alkyl group (e.g., a C$_1$-C$_6$ alkyl group); and R$_2$ is

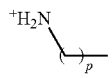

or a guanidinium ion

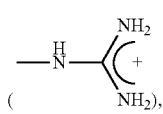

wherein p is an integer from 1-10 (i.e, 1, 2, 3, 4, 5, 6, 7, 8, 9, 10).

In certain embodiments, X is C—R$_3$; R$_1$ is a linear or branched C$_1$-C$_{12}$ alkyl group (e.g., a C$_1$-C$_6$ alkyl group); and R$_2$ is

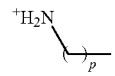

or a guanidinium ion, wherein p is an integer from 1-10. In some embodiments, R$_3$ is hydrogen.

In another aspect, the invention generally relates to a polymer comprising a monomer unit having the structure of:

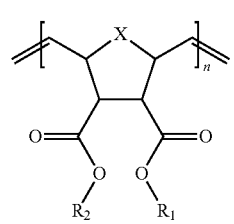

(II)

wherein one of R$_1$ and R$_2$ comprises a hydrophobic group and the other one of R$_1$ and R$_2$ comprises a hydrophilic group; and X is C—R$_3$, O or S, wherein R$_3$ is a hydrogen or a C$_1$-C$_{12}$ alkyl or alkoxy group.

The hydrophobic group may include a substituted or unsubstituted alkry group, e.g., a substituted or unsubstituted C$_1$-C$_{10}$ alkyl group (e.g., a C$_1$-C$_6$ alkyl group). The hydrophilic group may include a cationic group, which may be selected from ammonium ions, sulfonium ions, guanidinium ions, phosphonium ions, and mono- and di-alkyl substituted amino groups, for example.

In certain embodiments, X is O; R$_1$ is a linear or branched C$_1$-C$_{12}$ alkyl group (e.g., a C$_1$-C$_6$ alkyl group); and R$_2$ is

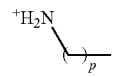

or a guanidinium ion, wherein p is an integer from 1-10 (i.e, 1, 2, 3, 4, 5, 6, 7, 8, 9, 10).

In certain embodiments, X is C—R$_3$; R$_1$ is a linear or branched C$_1$-C$_{12}$ alkyl group (e.g., a C$_1$-C$_6$ alkyl group); and R$_2$ is

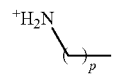

or a guanidinium ion, wherein p is an integer from 1-10. In some embodiments, R$_3$ is hydrogen.

For example, n is an integer from about 1 to about 1,000, for example, from about 1 to about 100; from about 1 to about 20; from about 1 to about 10; from about 1 to about 5; from about 3 to about 50; from about 3 to about 20; from about 3 to about 10; from about 3 to about 5.

In some applications, the polymer may preferably be a co-polymer. In certain embodiments, the co-polymer may include structural monomer units of:

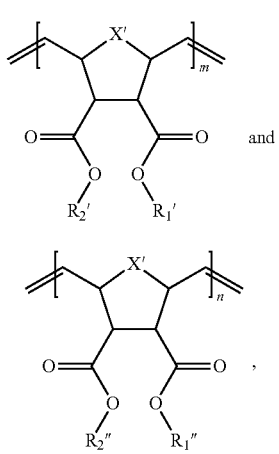

wherein each of X' and X" is C—R$_3$, O or S, wherein R$_3$ is a hydrogen or a C$_1$-C$_{12}$ alkyl or alkoxy group (e.g., a C$_1$-C$_6$ alkyl or alkoxy group); each of R$_1$' and R$_1$" is a hydrophobic group and each of R$_2$' and R$_2$" is a hydrophilic group, provided that R$_1$' and R$_1$" are not the same, R$_2$' and R$_2$" are not the same, or X' and X" are not the same; and each of m and n is an integer from about 1 to about 1,000.

Each of m and n is an integer from about 1 to about 1,000, for example, from about 1 to about 100; from about 1 to about 20; from about 1 to about 10; from about 1 to about 5; from about 3 to about 50; from about 3 to about 20; from about 3 to about 10; from about 3 to about 5.

In some embodiments, each of R$_1$' and R$_1$" is independently a linear or branched C$_1$-C$_{12}$ alkyl group (e.g., a C$_1$-C$_6$ alkyl group); and each of R$_2$' and R$_2$" is independently

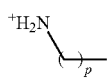

or a guanidinium ion, wherein p is an integer from 1-10 (i.e, 1, 2, 3, 4, 5, 6, 7, 8, 9, 10).

In some embodiments, each of X' and X" is O. In some other embodiments, each of X' and X" is independently C—R$_3$. In some other embodiments, one of X' and X" is O and the other is C—R$_3$.

In certain embodiments, one or more (e.g., all) of —C(=O)O— groups in (I), (II), (III) or (IV) occupy the exo-stereo position.

In another aspect, the invention generally relates to a polymer prepared by ring-opening metathesis polymerization, the polymer comprising hydrophobic and hydrophilic groups attached to the polymeric backbone such that, within a monomeric structural unit, the hydrophobic and hydrophilic groups are attached to the polymeric backbond at adjacent atoms. For example, in the polymer the hydrophobic and hydrophilic groups are attached to the polymeric backbond via ester linkages.

The polymers of the invention may have a molecular weight of M$_n$ between about 1,000 and about 100,000, between 1,000 and 50,000, between 1,000 and 10,000, for example The invention also relates to a product comprising a polymer of the invention and methods for preparing polymers of the invention by ring-opening metathesis polymerization.

a. Highly Selective Antimicrobial Polymers

Access to synthetic AMP polymers may open up new applications, for example in the materials area, where bacterial infections from medical plastics are a current critical problem in our hospitals. Synthetic polymers can be obtained easily and in large quantities while still presenting facial amphiphilicity and positive charge, the important features of AMPs. Although there have been several recent reports of polymeric SMAMPs, their overall activities and selectivities remain far from optimal. Examples include: DeGrado and coworkers reported SMAMPs based on poly(ammonium methylmethacrylate) salts copolymerized with poly(butylmethacrylate) to tune the amphiphilicity; Klajnert et al. produced dendritic SMAMPs; Liu et al. synthesized SMAMPs from poly(maleic acid) linked to peptide tetramers; Makovitzki et al. recently made SMAMPs based on lipopeptides; and Gellman and coworkers presented a poly(amide) based polymer with good activities (12.5 μg/mL against E. coli and 3.1 μg/mL against S. aureus) and selectivities up to 32 for bacterial over mammalian cells. (Kuroda, et al., *Polymer Prepr.* 2004, 45, 610; Klajnert, et al., *Int. J. Pharm.* 2006, 309, 208; Liu, et al., *J. Med. Chem.* 2006, 49, 3436; Makovitzki, et al., *Proc. Natl. Acad. Sci. USA* 2006, 103, 15997; Mowery, et al. *J. Am. Chem. Soc.* 2007, 129, 15474.) Tew and coworkers synthesized facially amphiphilic antibacterial polymers based on arylamides, urea, and poly(phenylene ethynylene). (Tew, et al., *Proc. Natl. Acad. Sci. USA* 2002, 99, 5110; Tang, et al., *Chem. Commun.* 2005, 12, 1537; Arnt, et al., *J. Am. Chem. Soc.* 2002, 124, 7664; Arnt, et al., *Langmuir* 2003, 19, 2404.)

SMAMPs based on poly(norbornene) derivatives were previously described by Tew and Coughlin: they reported polymers with facially amphiphilic repeat units that had tunable antimicrobial activity depending on a defined ratio of hydrophobic and hydrophilic moieties in the repeat unit. Their most selective polymer had a hundred times higher activity towards bacteria than against human red blood cells. (Ilker, et al., *J. Am. Chem. Soc.* 2004, 126, 15870.) They also very recently reported poly(norbornenes) with quaternary pyridinium groups (selectivities up to 20 against E. coli). (Eren, et al., *Macromol. Chem. Phys.* 2008, 209, 516-524.)

Previously reported poly(norbornene) based SMAMPs required extensive synthetic effort to tune the amphiphilicity of the repeat units, or did not allow copolymer synthesis. Although previous work has shown that antimicrobial activity can also be achieved with random copolymers of hydrophilic and hydrophobic monomers, having facially amphiphilic monomers, i.e. monomers with a hydrophilic cationic and a hydrophobic part on the same polymerizable unit, allows for more precise tuning of the antibacterial activity. (Kuroda, et al., *J. Am. Chem. Soc.* 2005, 127, 4128; Mowery, et al. *J. Am. Chem. Soc.* 2007, 129, 15474.)

Disclosed herein is a novel and unique approach based on a ring-opening metathesis polymerization (ROMP) platform that (i) uses a minimum number of building blocks and (ii) allows the easy and independent variation of the hydrophobic and hydrophilic residues on the monomer. The important components of our molecular construction kit are highlighted in FIG. 1. The hydrophilic and hydrophobic components are attached to the polymerizable oxanorbornene group and can be varied independently.

The molecular construction kit approach described here allows the synthesis of a whole library of synthetic facially amphiphilic antibacterial homopolymers and copolymers with tunable activity and selectivity. The hydrophilic and hydrophobic components can be varied independently, allowing future synthesis of an even more extensive library of antibacterial polymers. Homopolymers of the 3k series thus obtained show a remarkable antibacterial activity against *E. coli* and *S. aureus*, which could be tuned over two orders of magnitude by variation of the hydrophobic residue R. Some of the homopolymers of the 10k series showed a double selectivity of *E. coli* over mammalian cells as well as over *S. aureus*. It was further demonstrated that molecular weight can be used as a parameter to tune the antibacterial activity. The optimum activity against *S. aureus* was found to be at 750 g/mol to 1,100 g/mol and against *E. coli* at 3,000 g/mol and 10,000 g/mol. Selectivities of *S. aureus* over red blood cells as high as >533 were obtained by copolymerizing an inactive/non-hemolytic monomer with an active/hemolytic monomer. These polymers were also doubly selective with >533 times higher selectivity of *S. aureus* over red blood cells, and with >53 times more selective for *S. aureus* over *E. coli*. Such a high selectivity against *S. aureus* is particularly exciting as the Methicillin-resistant form of *S. aureus*, MRSA, is an antibiotic-resistant 'superbug' and one of today's most serious health threats for hospital patients.

This is a clear example thus far of how the biological properties of cationic amphiphilic polymers can be tuned to first increase the selectivity of bacteria over mammalian cells, and second increase the selectivity towards one bacteria family over another. This discrimination is important for antimicrobial agents since many bacterial types are in fact beneficial to the body.

EXAMPLES

Monomer Synthesis.

To obtain new synthetic antimicrobial polymers via ROMP, the first task was to design an easy and modular synthetic pathway towards facially amphiphilic monomers (FIG. 1). The three-step approach taken to obtain these monomers is presented in Scheme 1. In the first step, furan and maleic anhydride underwent a Diels-Alder reaction, yielding exclusively the exo-adduct in accordance with the literature. (Mantovani, et al., *J. Am. Chem. Soc.* 2005, 127, 2966.) This facile step provided compound 1 containing a polymerizable oxanorbornene group and a cyclic anhydride that allowed twofold and unsymmetrical functionalization. The anhydride 1 was ring-opened with an alcohol to introduce the desired hydrophobic moiety R, which was varied from methyl to hexyl, yielding a series of half-monomers 2a-f with different hydrophobicities. All compounds were crystallizable and thus easy to purify. In the last step, the designated cationic group was attached. As ROMP usually does not tolerate the presence of unprotected amines due to their ligating properties, the desired hydrophilic group ($NH_3^+$) was introduced in its protected tert-butyl carbamate (NHBoc) form. (Slugovc, et al., *Macromol. Rapid Commun.* 2004, 25, 1283.) The half-monomers 2a-f were reacted with the Boc-protected 2-amino ethanol by DCC coupling, yielding a series of masked amphiphilic monomers 3a-f (Scheme 1). This last step required purification by column chromatography to yield pure products. The overall yield of all three reaction steps was ~40%.

Scheme 1:

Monomer Synthesis. The hydrophobic component of the facially amphiphilic monomer is introduced in the second reaction step (R=methyl, ethyl, propyl, butyl, isopentyl or hexyl), and the protected hydrophilic moiety is attached in the last step.

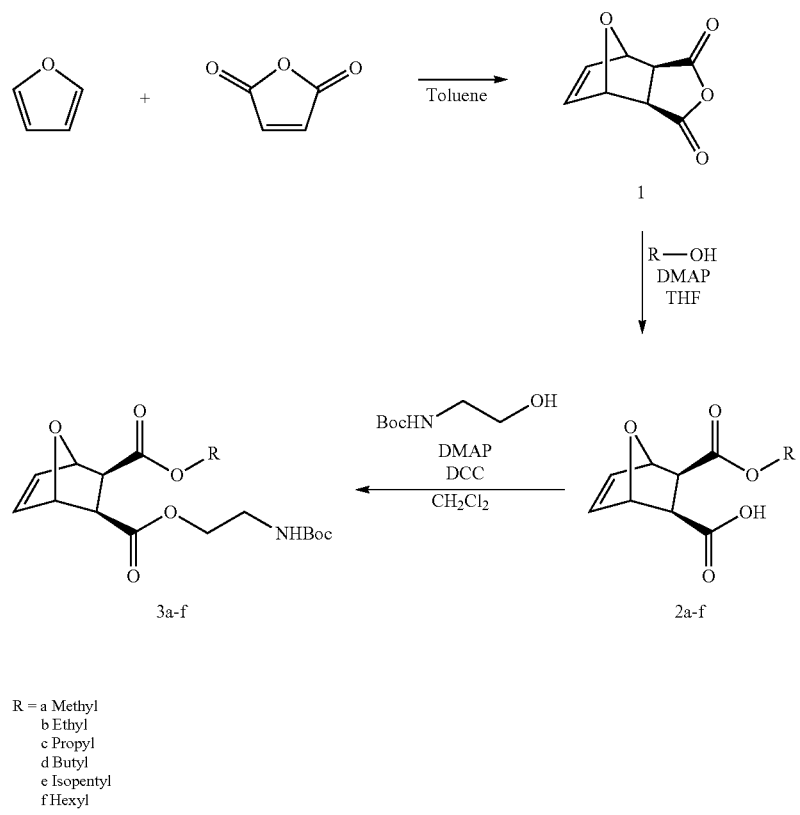

R = a Methyl
b Ethyl
c Propyl
d Butyl
e Isopentyl
f Hexyl

Scheme 2:

Polymer Synthesis. ROMP polymerization is followed by polymer analogous hydrolysis with trifluoroacetic acid to yield the facially amphiphilic polymer.

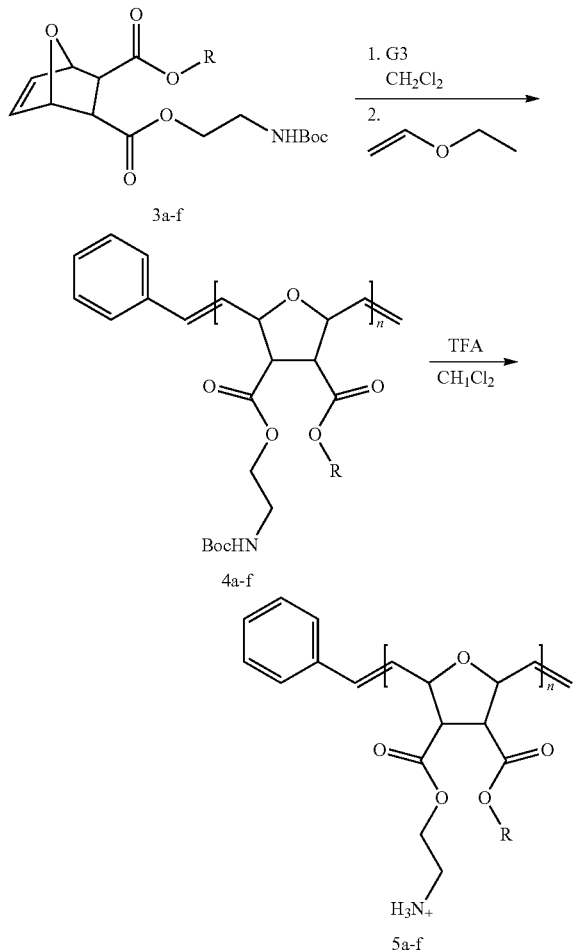

R = a Methyl
b Ethyl
c Propyl
d Butyl
e Isopentyl
f Hexyl

Homopolymer Synthesis and Molecular Weight Characterization.

From the monomers 3a-f, two series of homopolymers with molecular weights of about 3,000 g/mol (the "3k" series) and abut 10,000 g/mol (the "10 k" series) were synthesized. The polymerization of the monomers shown in Scheme 2 was carried out using the third generation Grubbs catalyst (G3) and yielded the precursor polymers 4a-f. (Dichloro-di(3-bromopyridino)-N,N'-Dimesitylenoimidazolino-Ru=CHPh, c.f. Love, et al., *Angew. Chem. Internal. Ed.* 2002, 41, 4035.) The facially amphiphilic SMAMPs 5a-f were obtained by polymer analogous deprotection: the Boc protecting group was completely removed with trifluoroacetic acid according to NMR. Depending on the alkyl residue, the resulting polymers were water-soluble or dispersible after work up. For convenience, instead of referring to these polymers here by compound numbers, for example 5a-f, a polymer with R=propyl and a molecular weight of 3000 g/mol will be referred to as Propyl_3k. The organosoluble precursor polymers were analyzed by gel permeation chromatography (GPC) in DMF (Table 1a). The molecular weights obtained from GPC using polystyrene standards as a calibration are significantly larger than the ones expected from the reaction stoichiometry. It is well known from the literature that the G3 catalyst initiates quantitatively, so incomplete initiation is unlikely to be responsible for this disparity. (Slugovc, et al., *Macromol. Rapid Commun.* 2004, 25, 1283.) Analysis of the Boc-protected Propyl_3k sample ($M_{n, GPC}$=9200 g/mol) by MALDI-TOF MS (Matrix Assisted Laser Ionization and Desorption Time Of Flight Mass Spectrometry) yields a distribution with a maximum intensity at m/z=3095, which is in excellent agreement with the targeted molecular weight. This means that GPC overestimates the molecular weight for these structures, which is further supported by additional oligomer data discussed.

Table 1:

Homopolymers: a) Precursor polymer characterization by GPC (DMF, 0.01 mol LiCl, PS standards). b) Characterization of the antimicrobial homopolymers by biological assays: Inhibitory activity towards bacterial growth of *E. coli* and *S. aureus* bacteria. ($MIC_{90}$=minimal inhibitory concentration preventing 90% bacterial growth) and hemolytic activity towards red blood cells ($HC_{50}$=concentration lysing 50% of blood cells).

TABLE 1a

| Sample | Monomer | $M_{n, Target}$ g mol$^{-1}$ | GPC $M_n$ g mol$^{-1}$ | $M_w/M_n$ |
|---|---|---|---|---|
| Methyl_3k | Methyl | 3000 | 11200 | 1.08 |
| Ethyl_3k | Ethyl | 3000 | 9200 | 1.10 |
| Propyl_3k | Propyl | 3000 | 9200 | 1.10 |
| Butyl_3k | Butyl | 3000 | 11500 | 1.08 |
| Isopentyl_3k | Isopentyl | 3000 | 11400 | 1.11 |
| Hexyl_3k | Hexyl | 3000 | 11000 | 1.08 |
| Methyl_10k | Methyl | 10000 | 49000 | 1.05 |
| Ethyl_10k | Ethyl | 10000 | 11300 | 1.10 |
| Propyl_10k | Propyl | 10000 | 28200 | 1.07 |
| Butyl_10k | Butyl | 10000 | 26700 | 1.07 |
| Isopentyl_8k | Isopentyl | 8000 | 22600 | 1.06 |
| Isopentyl_10k | Isopentyl | 10000 | 51500 | 1.16 |
| Hexyl_10k | Hexyl | 10000 | 27600 | 1.04 |

TABLE 1b

| | $MIC_{90}$ µg mL$^{-1}$ | | $HC_{50}$ | Selectivty | |
|---|---|---|---|---|---|
| Sample | *E. coli* | *S. aureus* | µg mL$^{-1}$ | *E. coli* | *S. aureus* |
| Methyl_3k | >200 | 100 | 2000 | <10 | 20 |
| Ethyl_3k | 50 | 50 | 1400 | 28 | 28 |
| Propyl_3k | 6.25 | 15 | 50 | 8.3 | 3.3 |
| Butyl_3k | 15 | 25 | <50 | <3.3 | <2.0 |
| Isopentyl_3k | 12.5 | 50 | <50 | <4.0 | <1.0 |
| Hexyl_3k | >200 | >200 | <50 | <0.3 | <0.3 |
| Methyl_10k | >200 | >200 | 50 | <10 | <10 |
| Ethyl_10k | >200 | >200 | 1250 | <6.3 | <6.3 |
| Propyl_10k | 3.75 | 200 | <50 | 13 | <0.25 |
| Butyl_10k | 20 | >200 | <50 | <2.5 | <0.3 |
| Isopentyl_8k | 50 | >200 | <50 | <0.3 | <0.3 |
| Isopentyl_10k | 50 | 200 | <50 | <0.3 | <0.3 |
| Hexyl_10k | 100 | >200 | n.d. | n.d. | n.d. |

Biological Activity of Homopolymers.

The biological properties of the homopolymers, i.e. their antibacterial activity, $MIC_{90}$, towards growth of *Escherichia coli* and *Staphylococcus aureus* bacteria, and their hemolytic activity, $HC_{50}$, towards red blood cells, were tested as described previously. ($MIC_{90}$=minimal inhibitory concentration preventing 90% bacterial growth, $HC_{1-50}$=hemolytic concentration lysing 50% of blood cells, c.f. Rennie, et al., *J. Industrial Microbiol. Biotechnol.* 2005, 32, 296.) $HC_{50}/MIC_{90}$ quantifies the antimicrobial selectivity. The biological data obtained for these homopolymers are included in Table 2. The $MIC_{90}$ and $HC_{50}$ values are also plotted in FIGS. 2a and 2b. As can be seen, the polymer with the highest selectivity for bacterial over mammalian cells is Ethyl_3k, with a good selectivity of 28 for both *E. coli* and *S. aureus*.

For comparison, MSI-78, a derivative of the natural host-defense peptide magainin, has a selectivity of 10. (Gabriel, et al., *Materials Sci. Engineering Rev.* 2007, 57, 28) For the 3k series shown in FIG. 2a, the following trend is observed: starting with the non-toxic ($HC_{50}$=2000 μg/mL) and inactive ($MIC_{90}$>200 μg/mL) Methyl_3k, the antibacterial activity peaks for the Propyl_3k ($MIC_{90}$=6.25 μg/mL for *E. coli*), and there the polymers also start becoming more hemolytic ($HC_{50}$≦50 μg/mL). From Butyl_3k to Hexyl_3k the activity decreases again until the polymers become inactive ($MIC_{90}$>200 μg/mL), but this time strongly hemolytic. The $MIC_{90}$s for *S. aureus* show the same trend, but the activities are generally lower. The data for the 10k series are compiled in FIG. 2b. The $MIC_{90}$s for the 10k polymers are similar to the ones for the 3k series, with a maximum activity at Propyl_10k, but these samples are generally less active against *E. coli* than the 3k polymers, and inactive against *S. aureus*.

These observations can be rationalized by taking the different compositions of mammalian and bacterial membranes into account. Human red blood cells (RBC) are predominantly composed of cholesterol and phosphatidylcholine (outer leaflet). In contrast, the membranes of Gram-negative bacteria like *E. coli* consist mostly of phosphatidylethanolamine and anionically charged phosphatidylglycerol (PG) while Gram-positive bacteria like *S. aureus* have membranes that consist mainly of anionically charged PG and cardiolipin. Thus, bacterial membranes are more negatively charged than RBC membranes. (Som, et al., *Journal of Physical Chemistry B* 2008 3495-3502.) Just as observed for natural AMPs, the anionic surface charge may attract the positively charged SMAMP. Due to their hydrophobic component they can subsequently penetrate the lipid bilayer if the SMAMP's facial amphiphilicity is rightly balanced. An overly hydrophilic SMAMP, like Methyl_3k, is not able to penetrate the hydrophobic core of the lipid bilayer and is therefore inactive. Alternatively, such a hydrophilic molecule may prefer to remain in solution as opposed to being adsorbed to the membrane. Their high hydrophilicity also prevents Methyl_3k and Ethyl_3k from lysing RBCs—only the more hydrophobic homologues (Propyl_3k onwards) cause significant hemolysis (FIG. 2a). An overly hydrophobic SMAMP like Hexyl_3k has strong membrane activity and as a result is very hemolytic. The maximum activity against *E. coli* and *S. aureus* for the 3k series was from the Propyl_3k polymer, which seems to have the optimal facial amphiphilicity to penetrate the bacterial membrane.

While Propyl_3k was also found to be the most toxic polymer of the 3k series against *S. aureus*, the 10k polymers were all inactive against this pathogen (FIG. 2b). This may be rationalized as follows: Gram-positive bacteria have a 15-80 nm thick negatively charged murein layer around the cell membrane. As is well known from the polyelectrolyte literature, complexation of one polyion with an oppositely charged polyion (symplex formation) is essentially irreversible, while complexes of a polyion with a less charged species are reversible. (Dautzenberg, et al., *Polyelectrolytes*. Hanser/Gardner: Munich, 1994.) Thus, assuming that the negatively charged murein layer forms a polyion-polyion complex with the positively charged SMAMPs, the dissociation of such a complex becomes increasingly more difficult with increasing molecular weight (more charges on the SMAMP). The higher molecular weight SMAMPs get stuck in the murein layer of Gram-positive bacteria before reaching the plasma membrane and as a result do not kill *S. aureus* cells irrespective of their amphiphilicity. The appropriately hydrophobic polymers may be active against Gram-negative bacteria because they have a much thinner (2 nm) murein layer which is located between the outer and cytoplasmic membranes, consistant with the data shown in FIG. 2b. For example, Propyl_10k has an $MIC_{90}$ of 3.75 μg/mL against *E. coli* while its $MIC_{90}$ against *S. aureus* is 200 μg/mL, resulting in a polymer that is doubly selective, which is >50 times more active against *E. coli* than against *S. aureus*, and 13 times more active against *E. coli* than against RBCs.

Oligomer Synthesis and Molecular Weight Impact on Biological Activity.

All monomers were deprotected (with trifluoroacetic acid as described for the polymers), subjected to $MIC_{90}$ testing, and found to be inactive ($MIC_{90}$s>200 μg/mL). This shows that a minimum chain length is necessary to obtain any antibacterial activity. Consequently, choosing the propyl monomer as an example, small molecular weight oligomers were synthesized and analyzed (see Table 3a). The GPC traces for the oligomers (selected samples for clarity), along with the monomer, are shown in FIG. 3a. The peak maxima of all samples are in the expected order: the higher molecular weight oligomers elute before the lower molecular weight ones. MALDI-TOF MS was used to determine the actual oligomer molecular weight. The peaks of the MALDI-TOF mass spectra are shown in FIG. 3b as a distribution function (normalized intensity vs. m/z). From the relative peak intensities and m/z ratio of each peak, the number average molecular weight, $M_n$, and the polydispersity of the samples were calculated. Those distributions were monomodal, unlike some the GPC traces which appear to be multimodal due to the column resolution. These data are included in Table 3a. The results show once more that GPC curves calibrated with poly(styrene) standards heavily overestimates the molecular weight, while the average number of repeat units $n_{MALDI}$ is in much better agreement with the calculated number of repeat units. However, the smallest oligomer obtained had a degree of polymerization of 3.7 instead of the target of 2 due to the reaction kinetics of this particular solvent/catalyst system.

Table 3:

Oligomers: a) Precursor oligomer characterization by GPC (DMF, 0.01 mol L$^{-1}$ LiCl, PS standards). b) Characterization of the antimicrobial oligomers by biological assays: Inhibitory activity towards bacterial growth of *E. coli* and *S. aureus* bacteria. ($MIC_{90}$=minimal inhibitory concentration preventing 90% bacterial growth) and hemolytic activity towards red blood cells ($HC_{50}$=concentration lysing 50% of blood cells).

TABLE 3a)

| Sample | $M_{n\ Target}$ g mol$^{-1}$ | GPC $M_n$ g mol$^{-1}$ | $n_{GPC}$ | GPC $M_w/M_n$ | MALDI $M_n$ g mol$^{-1}$ | MALDI $M_w/M_n$ | $n_{MALDI}$ |
|---|---|---|---|---|---|---|---|
| Monomer (3c, hydrolyzed) | 370 | 1080 | 2.9 | 1.04 | — | — | — |
| Oligo 1 | 740 | 3300 | 8.9 | 1.08 | 1529 | 1.11 | 3.7 |
| Oligo 2 | 1110 | 4300 | 11.6 | 1.09 | 2151 | 1.09 | 5.3 |
| Oligo 3 | 1480 | 5800 | 15.7 | 1.07 | 2642 | 1.07 | 6.7 |
| Oligo 4 | 1850 | 5900 | 16.0 | 1.09 | 2873 | 1.11 | 7.0 |
| Oligo 5 | 2220 | 6900 | 18.6 | 1.10 | 3260 | 1.08 | 8.2 |
| Oligo 6 | 2590 | 7400 | 20 | 1.08 | 3935 | 1.09 | 9.7 |

TABLE 3b

| Sample | MIC$_{90}$ μg mL$^{-1}$ | | HC$_{50}$ | Selectivty | |
|---|---|---|---|---|---|
| | E. coli | S. aureus | μg mL$^{-1}$ | E. coli | S. aureus |
| Monomer (3c, hydrolyzed) | >200 | >200 | n.d. | n.d. | n.d. |
| Oligo 1 | 200 | <3.75 | 1050 | 5.25 | 280 |
| Oligo 2 | 100 | 6.25 | 800 | 8.0 | 128 |
| Oligo 3 | 200 | 25 | 1250 | 6.3 | 50 |
| Oligo 4 | >200 | 50 | >2000 | >10 | 40 |
| Oligo 5 | 100 | 50 | 1000 | 10 | 20 |
| Oligo 6 | 50 | 25 | 150 | 3.0 | 6.0 |
| Propyl_3k | 6.25 | 15 | 50 | 8.3 | 3.3 |
| Propyl_10k | 3.75 | 200 | <50 | <13 | <0.25 |

The biological data for the propyl series are summarized in FIG. 4 and Table 3b. Within the error limits of the method, all oligomers are equally non-hemolytic up to Oligo 5. Hemolytic activity increases by one order of magnitude with Oligo 6 (HC$_{50}$)=150 μg/mL) and increases further for Propyl_3k (HC$_{50}$=50 μg/mL) and Propyl_10k (HC$_{50}$<50 μg/mL). FIG. 4 shows that the small molecular weight oligomers are inactive against E. coli. Starting with Oligo 5, a marked increase in activity against E. coli (MIC$_{90}$=100 μg/mL) is observed, which reaches a maximum for Propyl_10k with an MIC$_{90}$ of 3.75 μg/mL. For S. aureus, the opposite trend is observed (FIG. 4). The best activities were found for the small oligomers (MIC$_{90}$s=6.25 μg/mL and <3.75 μg/mL for Oligo 1 and Oligo 2, respectively). Activity is progressively lost as the molecular weight increases up to Propyl_10k (MIC$_{90}$=200 μg/mL). The results of the molecular weight dependent propyl series show that molecular weight can be used as a parameter to selectively target either E. coli or S. aureus, and possibly Gram-negative or Gram-positive bacteria in general.

Previous research indicated that some SMAMPs have slight molecular weight dependent activity. Ilker et al. concluded for their system that the biological activity is independent of molecular weight (for M$_n$=1600 to 137000 g/mol). Poly2 and poly4 (MIC$_{90}$s of 200 μg/mL against E. coli) did not show a molecular weight dependence. Poly3 was reported with M$_n$ ranging from 1,650 g/mol to 57,200 g/mol and MIC$_{90}$s of 25 μg/mL to 80 μg/mL, respectively. (Ilker, et al., J. Am. Chem. Soc. 2004, 126, 15870.) DeGrado reported poly(methacrylate) copolymers with M$_n$ around 1600 g/mol having an MIC$_{90}$ of 16 μg/mL while polymers above 7900 g/moL exhibited an MIC$_{90}$ of 80 μg/mL against E. coli. (Kuroda, et al., J. Am. Chem. Soc. 2005, 127, 4128.) In contrast, Oligo 1 has an M$_n$ equal to 740 g/mol and MIC$_{90}$s<3.75 μg/mL against S. aureus and 200 μg/mL against E. coli while Propyl_10k has MIC$_{90}$s of 200 μg/mL against S. aureus and 3.75 μg/mL against E. coli. Thus, antimicrobial activity is molecular weight dependent for these SMAMPs.

Tuning the Selectivities by Copolymer Synthesis:

The incorporation of highly active but hemolytic repeat units into an otherwise non-active and non-hemolytic polymer can dramatically increase the selectivity. (Ilker, et al., J. Am. Chem. Soc. 2004, 126, 15870.) Here, the Methyl_3k homopolymer qualifies as inactive and non-toxic, whereas the Propyl_3k homopolymer is active and hemolytic. The Ethyl_3k homopolymer is neither most active nor toxic, but has the highest selectivity. Thus, methyl, ethyl and propyl monomers were chosen for copolymerization. Three series of copolymers with a target molecular weight around 3000 g/mol and a varying monomer feed ratio were synthesized and studied (Table 4a). The copolymer composition was checked by NMR spectroscopy, which revealed that the polymer composition matched with the monomer feed ratio.

Table 4:

Copolymers: a) Precursor polymer characterization by GPC (DMF, 0.01 mol L$^{-1}$ LiCl, PS standards). b) Characterization of the antimicrobial copolymers by biological assays: Inhibitory activity towards bacterial growth of E. coli and S. aureus bacteria. Sample labeling: e.g. E1:P9 is a copolymer with 10 mol % ethyl and 90 mol % propyl monomer.

TABLE 43a

| Sample | Monomers | M$_{n\ Target}$ g mol$^{-1}$ | GPC M$_n$ g mol$^{-1}$ | M$_w$/M$_n$ |
|---|---|---|---|---|
| E1:P9 | Ethyl-Propyl | 3500 | 11600 | 1.08 |
| E1:P2 | Ethyl-Propyl | 3400 | 7000 | 1.34 |
| E1:P1 | Ethyl-Propyl | 3000 | 11000 | 1.08 |
| E2:P1 | Ethyl-Propyl | 3500 | 10200 | 1.15 |
| E9:P1 | Ethyl-Propyl | 3400 | 7600 | 1.30 |
| M9:E1 | Methyl-Ethyl | 3400 | 13600 | 1.10 |
| M1:E1 | Methyl-Ethyl | 3500 | 14400 | 1.08 |
| M1:E9 | Methyl-Ethyl | 3500 | 14500 | 1.08 |
| M9:P1 | Methyl-Propyl | 3400 | 15300 | 1.07 |
| M1:P1 | Methyl-Propyl | 3600 | 15900 | 1.07 |
| M1:P9 | Methyl-Propyl | 3700 | 14700 | 1.07 |

TABLE 4b)

| Sample | Monomer | M$_{n.\ Target}$ g mol$^{-1}$ | MIC$_{90}$ μg mL$^{-1}$ | | HC$_{50}$ μg mL$^{-1}$ | Selectivty | |
|---|---|---|---|---|---|---|---|
| | | | E. coli | S. aureus | | E. coli | S. aureus |
| Propyl_3k | Propyl | 3000 | 6.25 | 15 | 50 | 8.0 | 3.3 |
| E1:P9 | Ethyl:Propyl | 3500 | 15 | 15 | <50 | <3.3 | <3.3 |
| E1:P2 | Ethyl:Propyl | 3400 | 15 | 15 | <50 | <3.3 | <3.3 |
| E1:P1 | Ethyl:Propyl | 3000 | 100 | 200 | 1000 | 10 | 5.0 |
| E2:P1 | Ethyl:Propyl | 3500 | >200 | 200 | >2000 | 10 | >10 |
| E9:P1 | Ethyl:Propyl | 3400 | >200 | 50 | 500 | <2.5 | 10 |
| Ethyl_3k | Ethyl | 3000 | 50 | 50 | 1400 | 28 | 28 |
| Methyl_3k | Methyl | 3000 | >200 | 100 | 2000 | <10 | 20 |
| M9:E1 | Methyl-Ethyl | 3400 | >200 | 6.25 | 700 | <3.5 | 112 |
| M1:E1 | Methyl-Ethyl | 3500 | >200 | 12.5 | 1200 | <6.0 | 96 |
| M1:E9 | Methyl-Ethyl | 3500 | >200 | 12.5 | 1500 | <7 | 120 |
| Ethyl_3k | Ethyl | 3000 | 50 | 50 | 1400 | 28 | 28 |
| Methyl_3k | Methyl | 3000 | >200 | 100 | 2000 | 10 | 20 |
| M9:P1 | Methyl-Propyl | 3400 | >200 | <3.75 | >2000 | 10 | >533 |
| M1:P1 | Methyl-Propyl | 3600 | >200 | <3.75 | >2000 | 10 | >533 |
| M1:P9 | Methyl-Propyl | 3700 | >200 | <3.75 | >2000 | 10 | >533 |
| Propyl_3k | Propyl | 3000 | 6.25 | 15 | 50 | 8.3 | 3.3 |

The biological data are compiled in Table 4b, and in FIGS. 5a to 5c. For the ethyl-propyl series, none of the copolymers reached the high selectivity of the parent Ethyl_3k polymer: with increasing propyl content, the ethyl-propyl copolymers become more active, but also more toxic. Both series of methyl copolymers showed the expected trend: they become extremely active even with little amount (10 mol %) of the more active monomer but stay non-hemolytic. They are potently active against S. aureus ($MIC_{90}$, <3.75 µg/mL) and remain totally inactive against E. coli ($MIC_{90}$>200 µg/mL). These copolymers are again doubly selective: >533 for bacterial over mammalian cells, and >53 for S. aureus over E. coli. This double selectivity is inverse to the one described earlier.

resolution mass spectra were obtained from a JEOL JMS 700 instrument (JEOL, Peabody, Mass.); Matrix Assisted Laser Desorption and Ionization Time of Flight Mass Spectra (MALDI-TOF MS) were measured on a Bruker Daltonics Reflex III (Bruker, Madison, Wis.). The biological activity of the polymer samples (the minimal concentration inhibiting 90% of bacterial growth ($MIC_{90}$) for Escherichia coli (D31) and Staphylococcus aureus (ATCC25923), and the concentration that lyses 50% of red blood cells ($HC_{50}$) were determined as reported previously. (Rennie, et al., J. Industr. Microbio. Biotech. 2005, 32, 7, 296.)

Monomer Synthesis

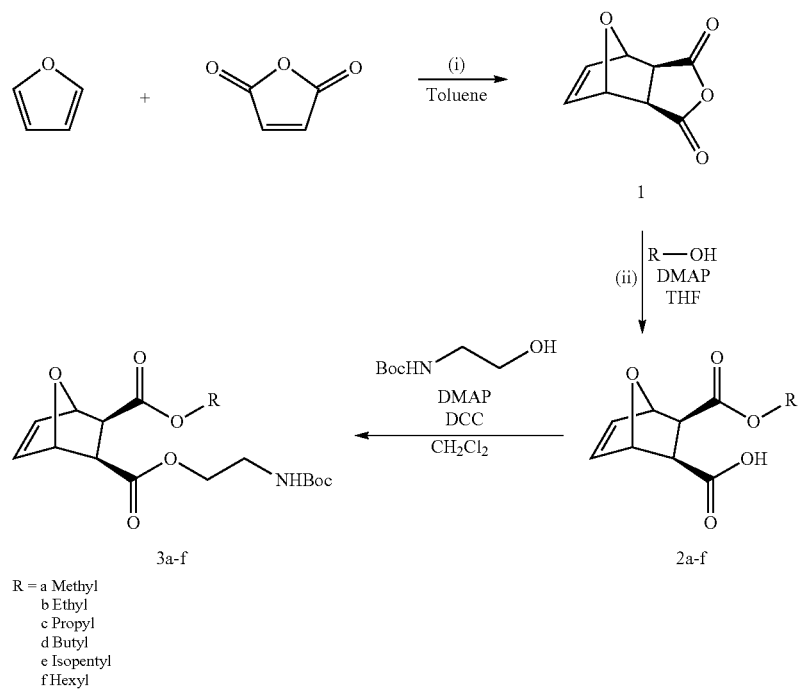

R = a Methyl
b Ethyl
c Propyl
d Butyl
e Isopentyl
f Hexyl

Experimental Details

General:

Maleic anhydride, furane, 4-dimethyl aminopyridine (DMAP), 1,3-dicyclohexylcarbodiimide (DCC), methanol, ethanol, 1-propanol, 1-butanol, isopentanol, 1-hexanol, ethylvinyl ether and trifluoroacetic acid (TFA) were obtained as reagent grade from Aldrich, Fluka or Acros and used as received.

Third generation Grubbs catalyst (Dichloro-di(3-bromopyridino)-N,N'-Dimesitylenoimidazolino-Ru=CHPh; G3) was synthesized as described previously by Grubbs et al. (Love, et al., Angew. Chem. Int. Ed. 2002, 41, 4035.) The HPLC grade solvents N,N-dimethylformamide (DMF), toluene, ethyl acetate and hexane were purchased from Aldrich, Fisher Scientific or Acros and used as received. THF (HPLC grade, Fisher Scientific) was distilled from sodium/benzophenone under nitrogen. Dichloromethane (HPLC grade, Fisher Scientific) was distilled from $CaH_2$ under nitrogen.

Gel permeation chromatography (DMF/0.01 M LiCl, calibrated with polystyrene standards, toluene as flow marker, 50° C.) was measured on a PL50 GPC setup (Polymer Laboratories, Amherst, Mass.) with a PL Gel 5 µm pre-column and two 10 µm analytical Mixed-D columns (Polymer Laboratories, Amherst, Mass.). NMR spectra were recorded on a Bruker DPX300 spectrometer (Bruker, Madison, Wis.). High (i) Maleic anhydride (100 g, 1.02 mol) was dissolved in 1 L toluene. 150 mL (140.7 g, 2.05 mmol) furan were added. The solution was stirred for 3 days. The product (1) was then filtered, washed with toluene and dried under vacuum. A colorless powder was obtained. Yields and spectroscopic data matched those reported previously. (Mantovani, et al., J. Am. Chem. Soc. 2005, 127, 2966.)

(ii) 1 (5 g, 30.0 mmol) was dissolved in THF. Two equivalents of the respective alcohol (e.g. 5.26 g (60 mmol) isopentanol for R=isopentyl) and 10 mol % DMAP were added. After stirring over night, the solvent was removed by vacuum evaporation at room temperature. The unreacted alcohol was removed by dynamic vacuum ($5 \cdot 10^{-2}$ mbar). Crystallization from dichloromethane/hexane yielded, e.g. for R=isopentyl, 4.7 g (18.5 mmol, 62%) of the product (2).

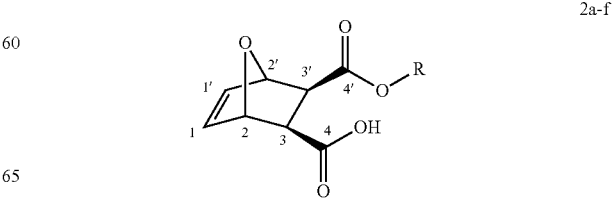

2a-f

2a: R=Methyl: colorless solid, $^1$H-NMR (300 MHz, CDCl$_3$): 2.86 (m, 2H, H3 & H3'), 3.71 (s, 3H, CH$_3$), 5.27 & 5.32 (m, 2H, H2 & H2'), 6.47 (m, 2H, H1 & H1').

2b: R=Ethyl: colorless solid, $^1$H-NMR (300 MHz, CDCl$_3$): 1.25 (t, J=7.2 Hz, 3H, CH$_2$—CH$_3$), 2.83 (m, 2H, H3 & H3'), 4.16 (q, J=7.1 Hz, 2H, CH$_2$—CH$_3$), 5.25 & 5.31 (s, 2H, H2 & H2'), 6.46 (m, 2H, H1 & H1'), 7.53-8.21 (br s, 1H, OH).

2c: R=Propyl: colorless solid, $^1$H-NMR (300 MHz, CDCl$_3$): 0.92 (t, J=7.3 Hz, 3H, CH$_2$—CH$_3$), 1.63 (m, 2H, β-CH$_2$), 2.84 (m, 2H, H3 & H3'), 4.05 (m, 2H, α-CH$_2$), 5.23 & 5.29 (m, 2H, H2 & H2'), 6.46 (m, 2H, H1 & H1'), 9.12-9.68 (br s, 1H, OH).

2d: R=Butyl: colorless oil, $^1$H-NMR (300 MHz, CDCl$_3$): 0.85 (t, J=7.1 Hz, 3H, CH$_2$—CH$_3$), 1.30 (m, 2H, γ-CH$_2$), 1.54 (m, 2H, β-CH$_2$), 2.78 (m, 2H, H3 & H3'), 4.04 (m, 2H, α-CH$_2$) 5.21 & 5.27 (m, 2H, H2 & H2'), 6.39 (m, 2H, H1 & H1').

2e: R=iso-Pentyl: colorless oil, $^1$H-NMR (300 MHz, CDCl$_3$): 0.90 (d, J=6.6 Hz, 6H, CH$_2$—CH$_3$), 1.53 (m, 1H, CH—CH$_3$), 1.68 (m, 2H, β-CH$_2$), 2.84 (m, 2H, H3 & H3'), 4.08 (m, 2H, α-CH$_2$) 5.25 & 5.31 (m, 2I-1, H2 & H2'), 6.45 (m, 2H, H1 & H1'), 8.70-9.68 (br s, 1H, OH).

2f: R=Hexyl: colorless solid, $^1$H-NMR (300 MHz, CDCl$_3$): 0.88 (t, J=6.4 Hz, 3H, CH$_2$—CH$_3$), 1.28 (m, 6H, γ- to ε-CH$_2$), 1.61 (m, 2H, β-CH$_2$), 2.85 (m, 2H, H3 & H3'), 4.13 (m, 2H, α-CH$_2$) 5.25 & 5.29 (m, 2H, H2 & H2'), 6.47 (m, 2H, H1 & H1').

(iii) 1 eq 2a-f (e.g. 2 g (7.88 mmol) for R=isopentyl) was dissolved in 25 mL dichloromethane. 1 eq (1.27 g, 7.88 mmol) boc-protected 2-amino ethanol and 10 mol % of DMAP were added. The solution was cooled to 0° C. 1 eq (206.3 g, 7.88 mmol) DCC was added, and the suspension was stirred over night. It was then filtered through a short alumina column (5 cm neutral Al$_2$O$_3$/dichlormethane). The solvent was removed by vacuum evaporation and the crude product was chromatographed (15 cm silica gel, ethyl acetate: hexane 9:1 to 1:1). Evaporation of the solvent yielded the pure monomer. The yield ranged from 70-80%.

3a-f

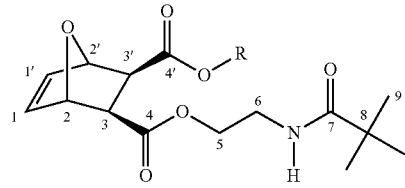

3a: R=Methyl: colorless solid, $^1$H-NMR (300 MHz, CDCl$_3$): 1.43 (s, 9H, H9), 2.82 (m, 2H, H3 & H3'), 3.40 (m, 2H, H6), 3.73 (s, 3H, C$_{1-13}$), 4.16 (m, 2H, H5), 5.03 (br s, 1H, NH), 5.25 & 5.29 (m, 2H, H2 & H2'), 6.46 (m, 2H, H1 & H1'). $^{13}$C-NMR (75 MHz, CDCl$_3$): 28.4 (C9), 39.5 (C6), 46.9 & 47.1 (C3, C3'), 52.4 (R, CH$_3$), 64.8 (C5), 79.3 (C8), 80.4 & 80.6 (C2, C2'), 136.6 & 136.7 (C1, C1'), 171.6 (C4, C4').
HR-MS (FAB): calc. 341.36. found 342.15.

3b: R=Ethyl: colorless solid, $^1$H-NMR (300 MHz, CDCl$_3$): 1.27 (t, J=7.2 Hz, 3H, CH$_2$—CH$_3$), 1.44 (s, 9H, H9), 2.81 (m, 2H, H3 & H3'), 3.39 (m, 2H, H6), 4.16 (m, 4H, CH$_2$—CH$_3$ and H5), 5.05 (br s, 1H, NH), 5.25 & 5.31 (m, 2H, H2 & H2'), 6.46 (m, 2H, H1 & H1'). $^{13}$C-NMR (75 MHz, CDCl$_3$): 14.4 (R, CH$_3$), 28.4 (C9), 39.4 (C6), 46.8 & 47.1 (C3, C3'), 61.3 (R, CH$_2$), 64.8 (C5), 79.3 (C8), 80.4 & 80.7 (C2, C2'), 136.6 & 136.7 (C1, C1'), 155.9 (C7), 171.6 & 171.7 (C4, C4').
HR-MS (FAB): calc. 355.39. found 356.17.

3c: R=Propyl: colorless solid, $^1$H-NMR (300 MHz, CDCl$_3$): 1.25 (m, 3H, CH$_2$—CH$_3$), 1.43 (s, 9H, H9), 1.67 (m, 2H, β-CH$_2$), 2.81 (q, 2H, H3 & H3'), 3.40 (m, 2H, H6), 4.12 (m, 4H, α-CH$_2$ and H5), 5.07 (br s, 1H, NH), 5.24 & 5.30 (m, 2H, H2 & H2'), 6.46 (m, 2H, H1 & H1'). $^{13}$C-NMR (75 MHz, CDCl$_3$): 10.4 (R, CH$_3$), 21.9 (R, β-CH$_2$), 28.4 (C9), 39.5 (C6), 46.8 & 47.2 (C3, C3'), 64.8 (C5), 66.9 (R, α-CH$_2$), 79.3 (C8), 80.4 & 80.7 (C2, C2'), 136.6 & 136.7 (C1, C1'), 155.9 (C7), 171.6 & 171.8 (C4, C4'). HR-MS (FAB): calc. 369.42. found 370.19

3d: R=Butyl: colorless oil, $^1$H-NMR (300 MHz, CDCl$_3$): 0.93 (m, 3H, CH$_2$—CH$_3$), 1.37 (m, 2H, γ-CH$_2$), 1.44 (s, 9H, H9), 1.62 (m, 2I-1, β-CH$_2$), 2.82 (q, 2H, H3 & H3'), 3.39 (m, 2I-1, H6), 4.12 (m, 4H, α-CH$_2$ and H5), 5.06 (br s, 1H, NH), 5.23 & 5.29 (m, 2H, H2 & H2'), 6.46 (m, 2H, H1 & H1'). $^{13}$C-NMR (75 MHz, CDCl$_3$): 13.7 (R, CH$_3$), 19.0 (R, γ-CH$_2$), 28.3 (C9), 30.4 (R, β-CH$_2$), 39.4 (C6), 46.7 & 47.1 (C3, C3'), 64.7 (C5), 65.1 (R, α-CH$_2$), 79.2 (C8), 80.4 & 80.6 (C2, C2'), 136.5 & 136.6 (C1, C1'), 155.9 (C7), 171.5 & 171.8 (C4, C4').
HR-MS (FAB): calc. 383.45. found 384.21.

3e: R=iso-Pentyl: colorless oil, $^1$H-NMR (300 MHz, CDCl$_3$): 0.92 (d, J=6.4 Hz, 6H, CH—CH$_3$), 1.44 (s, 9H, H9), 1.53 (m, 1H, CH—CH$_3$), 1.69 (m, 2H, β-CH$_2$), 2.82 (q, 2H, H3 & H3'), 3.41 (m, 2H, H6), 4.18 (m, 4H, α-CH$_2$ and H5), 5.07 (br s, 1H, NH), 5.23 & 5.29 (m, 2H, H2 & H2'), 6.46 (m, 2H, H1 & H1'). $^{13}$C-NMR: n.d., HR-MS (FAB): n.d.

3f: R=Hexyl: colorless oil, $^1$H-NMR (300 MHz, CDCl$_3$): 0.88 (t, J=6.6 Hz, 3H, CH$_2$—CH$_3$), 1.43 (s, 9H, t-butyl), 1.37 (m, 6H, γ-ε-CH$_2$) 1.62 (m, 2H, β-CH$_2$), 2.82 (m, 2H, H3 & H3'), 3.42 (m, 2H, H6), 4.14 (m, 4H, α-CH$_2$ and H5), 5.07 (br s, 1H, NH), 5.23 & 5.29 (m, 2H, H2 & H2'), 6.46 (m, 2H, H1 & H1'). $^{13}$C-NMR (75 MHz, CDCl$_3$): 10.9 (R, CH$_3$), 22.5 (R, δ-CH$_2$), 15.4 (R, γ-CH$_2$), 28.3 (C9), 28.5 (R, β-CH$_2$), 39.3 (C6), 46.6 & 46.9 (C3, C3'), 64.4 (C5), 65.2 (R, α-CH$_2$), 78.9 (C8), 80.3 & 80.5 (C2, C2'), 136.4 & 136.6 (C1, C1'), 155.8 (C7), 171.5 & 171.7 (C4, C4'). HR-MS (FAB): calc. 411.50. found 412.24.

Polymer Synthesis:

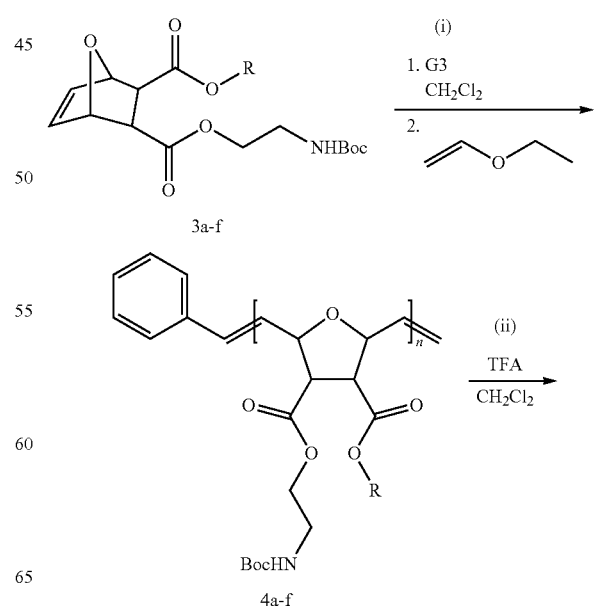

-continued

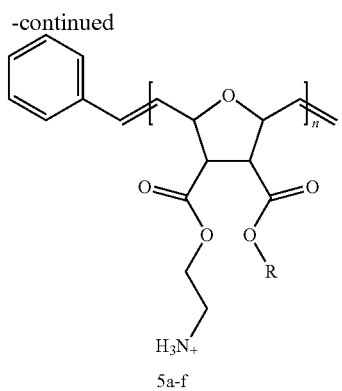

R = a Methyl
b Ethyl
c Propyl
d Butyl
e Isopentyl
f Hexyl (i) The monomer 3a-f and G3-catalyst amounts (see Table 5 for details) were dissolved in 1 mL dichloromethane each and subject to three freeze-thaw cycles. The catalyst was added in one shot to the vigorously stirring monomer solution at room temperature under argon. After 30 min, the living polymer chain was end-capped with an excess of ethylvinyl ether (1 mL, 754 mg, 10.5 mmol). The solution was allowed to stir over night. After evaporation of the solvent and drying, an aliquot of each polymer was taken for GPC and NMR analysis. The product was a brown solid.

4a: R=Methyl: $^1$H-NMR (300 MHz, CDCl$_3$): 1.43 (s, 9H, H9), 3.12 (br m, 2H, H3 & H3'), 3.34 (br m, 2H, H6), 3.71 (s, 3H, CH$_3$), 4.16 (br m, 2H, H5), 4.71 (m, 1H, H2 & H2' trans), 5.10 (br s, 1H, H2 & H2' cis), 5.40 (br s, 1H, NH), 5.58 (br m, 1H, H1 & H1' cis) and 5.88 (br m, 1H, H1 & H1' trans).

4b: R=Ethyl: $^1$H-NMR (300 MHz, CDCl$_3$): 1.24 (s, 3H, CH$_2$—CH$_3$), 1.42 (s, 9H, H9), 3.09 (br m, 2H, H3 & H3'), 3.34 (br m, 2H, H6), 4.16 (br m, 4H, CH$_2$—CH$_3$ and H5), 4.72 (br m, 1H, H2 & H2' trans), 5.10 (br m, 1H, H2 & H2' cis), 5.30 (br s, 1H, NH), 5.58 (br m, 1H, H1 & H1' cis), 5.88 (br m, 1H, H1 & H1' trans).

4c: R=Propyl: $^1$H-NMR (300 MHz, CDCl$_3$): 0.92 (m, 3H, CH$_2$—CH$_3$), 1.43 (s, 9H, H9), 1.62 (m, 2H, β-CH$_2$), 3.12 (br m, 2H, H3 & H3'), 3.34 (br m, 2H, H6), 4.10 (m, 4H, α-CH$_2$ and H5), 4.69 (br m, 1H, H2 & H2' trans), 5.12 (br m, 1H, H2 cis & H2'), 5.31 (br m, 1H, H1 & H1' cis), 5.59 (br s, 1H, NH), 5.88 (br m, 1H, H1 & H1' trans).

4d: R=Butyl: $^1$H-NMR (300 MHz, CDCl$_3$): 0.87 (m, 3H, CH$_2$—CH$_3$), 1.29 (m, 2H, γ-CH$_2$), 1.43 (s, 9H, H9), 1.59 (m, 2H, β-CH$_2$), 3.11 (br m, 2H, H3 & H3'), 3.37 (br m, 2H, H6), 4.10 (m, 4H, α-CH$_2$ and H5), 4.73 (br m, 1H, H2 & H2' trans), 5.11 (br m, 1H, H2 & H2' cis), 5.35 (br s, 1H, NH), 5.59 (br m, 1H, H1 & H1' cis), 5.88 (br m, 1H, H1 & H1' trans).

4e: R=iso-Pentyl: $^1$H-NMR (300 MHz, CDCl$_3$): 0.91 (m, 6H, CH—CH$_3$), 1.43 (s, 9H, H9), 1.52 (m, 1H, CH—CH$_3$), 1.62 (m, 2H, β-CH$_2$), 3.10 (br m, 2H, H3 & H3'), 3.35 (br m, 2H, H6), 4.15 (m, 4H, α-CH$_2$ and H5), 4.69 (br m, 1H, H2 & H2' trans), 5.11 (br m, 1H, H2 & H2' cis), 5.34 (br s, 1H, NH), 5.59 (br m, 1H, H1 & H1' cis), 5.88 (br m, 1H, H1 trans).

4f: R=Hexyl: $^1$H-NMR (300 MHz, CDCl$_3$): 0.88 (m, 3H, CH$_2$—CH$_3$), 1.29 (m, 2H, γ-ϵ-CH$_2$), 1.43 (s, 9H, H9), 1.56

TABLE 5

| | Experimental parameters for homopolymer synthesis | | | | | | | |
|---|---|---|---|---|---|---|---|---|
| Sample | Monomer | $N_{repeat}$ units | $M_n$ Target g mol$^{-1}$ | $M_{Monomer}$ g mol$^{-1}$ | $n_{Monomer}$ mmol | $m_{Monomer}$ mg | $M_{Catalyst}$ g mol$^{-1}$ | $n_{Catalyst}$ mmol | $m_{Catalyst}$ mg |
| Methyl_3k | Methyl | 9.7 | 3000 | 341 | 0.290 | 100 | 885 | 0.030 | 29.0 |
| Methyl_10k | Methyl | 29 | 10000 | 341 | 0.290 | 100 | 885 | 0.010 | 8.9 |
| Ethyl_3k | Ethyl | 8.6 | 3000 | 355 | 0.563 | 200 | 885 | 0.065 | 57.6 |
| Ethyl_10k | Ethyl | 28 | 10000 | 355 | 0.563 | 200 | 885 | 0.020 | 17.7 |
| Propyl_3k | Propyl | 8.4 | 3000 | 369 | 0.282 | 104 | 885 | 0.034 | 29.7 |
| Propyl_10k | Propyl | 29 | 1000 | 369 | 0.278 | 103 | 885 | 0.010 | 8.50 |
| Butyl_3k | Butyl | 7.2 | 3000 | 383 | 0.525 | 202 | 885 | 0.073 | 64.5 |
| Butyl_10k | Butyl | 27 | 1000 | 383 | 0.565 | 217 | 885 | 0.021 | 18.6 |
| Isopentyl_3k | Isopentyl | 7.9 | 3000 | 397 | 0.515 | 205 | 885 | 0.065 | 57.5 |
| Isopentyl_8k | Isopentyl | 20.1 | 8000 | 397 | 1.926 | 766 | 885 | 0.096 | 85.0 |
| Isopentyl_10 k | Isopentyl | 26 | 10000 | 397 | 0.508 | 202 | 885 | 0.020 | 17.5 |
| Hexyl_3k | Hexyl | 7.7 | 3000 | 412 | 0.516 | 212 | 885 | 0.067 | 59.0 |
| Hexyl_10k | Hexyl | 25 | 10000 | 412 | 0.493 | 203 | 885 | 0.020 | 17.7 |

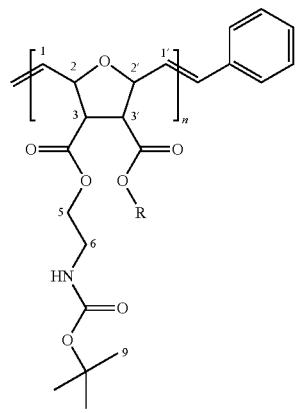

(m, 2H, β-CH$_2$), 3.10 (br m, 2H, H3 & H3'), 3.36 (br m, 2H, H6), 4.10 (m, 4H, α-CH$_2$ and H5), 4.70 (br m, 1H, H2 & H2' trans), 5.12 (br m, 1H, H2 & H2' cis), 5.38 (br s, 1H, NH), 5.58 (br m, 1H, H1 & H1' cis), 5.89 (br m, 1H, H1 & H1' trans).

(ii) The crude polymers were dissolved in 2 mL dichloromethane. An excess of TFA (2 mL, 2.97 g, 26.0 mmol) was added and the solution was stirred at room temperature over night. The excess acid was removed by azeotropic distillation with dichloromethane (2×15 mL) and methanol (1×15 mL) at the rotary evaporator. The samples were dried in vacuum over night and dissolved in 30 mL Milli-Q water or DMSO depending on solubility. The samples were dialyzed against Milli-Q water until the conductivity of the water was 0.1 μS after 12 h of dialysis (total dialysis time 4-7 days). The hydrolyzed polymers were then freeze dried.

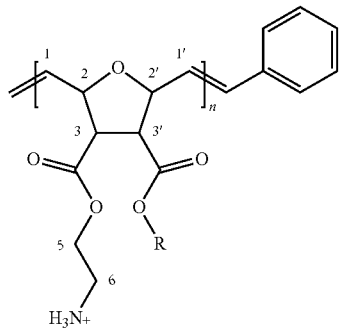

5a: R=Methyl: $^1$H-NMR (300 MHz, DMSO): 3.04 (br m, 2H, H3 & H3'), 3.30 (br m, 2H, H6), 3.59 (s, 31-1, CH$_3$), 4.16 (br m, 2H, H5), 4.57 (m, 1H, H2 & H2' trans), 4.91 (br m, 1H, H2 & H2' cis), 5.61 (br m, 1H, H1 & H1' cis), 5.82 (br m, 1H, H1 & H1' trans).

5b: R=Ethyl: $^1$H-NMR (300 MHz, D$_2$O): 1.28 (br s, 3H, CH$_2$—CH$_3$), 3.12 (br m, 2H, H3 & H3'), 3.32 (br m, 2H, H6), 3.49-3.81 (br m, 4H, CH$_2$—CH$_3$ and H5), 5.10-5.40 (br m, 2H, H2 & H2'), 5.30-5.90 (br m, 2H, H1 & H1').

5c: R=Propyl: $^1$H-NMR (300 MHz, D$_2$O): 0.94 (br m, 3H, CH$_2$—CH$_3$), 1.67 (br m, 2H, β-CH$_2$), 3.31 (br m, 2H, H3 & H3'), 3.50 (br m, 2H, H6), 4.12 (m, 4H, α-CH$_2$ and H5), 4.39 (br m, 1H, H2 & H2' trans), 5.12 (br m, 1H, H2 & H2' cis), 5.31 (br m, 1H, H1 & H1' cis), 5.88 (br m, 1H, H1 & H1' trans).

5d: R=Butyl: $^1$H-NMR (300 MHz, D$_2$O): 0.93 (m, 3H, CH$_2$—CH$_3$), 1.36 (m, 2H, γ-CH$_2$), 1.61 (m, 2H, β-CH$_2$), 3.10 (br m, 2H, H3 & H3'), 3.48 (br m, 2H, H6), 4.14 (m, 4H, α-CH$_2$ and H5), 4.38 (br m, 1H, H2 & H2' trans), 5.11 (br m, 1H, H2 & H2' cis), 5.35-6.20 (br m, 2H, H1 & H1').

5e: R=iso-Pentyl: $^1$H-NMR (300 MHz, DMSO): 0.91 (m, 6H, CH—CH$_3$), 1.55 (m, 1H, CH—CH$_3$), 1.69 (m, 2H, β-CH$_2$), 3.31 (br m, 2H, H3 & H3'), 3.48 (br m, 2H, H6), 4.15 and 4.40 (m, 4H, α-CH$_2$ and H5), 4.69 (br m, 1H, H2 & H2' trans), 5.11 (br m, 1H, H2 & H2' cis), 5.34 (br m, 1H, H1 & H1' cis), 5.88 (br m, 1H, H1 & H1' trans).

5f: R=Hexyl: $^1$H-NMR (300 MHz, D$_2$O): 0.90 (m, 3H, CH$_2$—CH$_3$), 1.31 (m, 2H, γ-ϵ-CH$_2$), 1.62 (m, 2H, β-CH$_2$), 3.30 (br m, 2H, H3 & H3'), 3.47 (br m, 2H, 1-16), 4.13 and 4.40 (m, 4H, α-CH$_2$ and H5), 4.70-5.12 (br m, 2H, H2 & H2'), 5.50-6.20 (br m, 2H, H1 & H1').

Copolymer Synthesis, Deprotection and Characterization:

Copolymers were synthesized and hydrolyzed using the same methods as for the homopolymers. Each comonomer was dissolved in 0.7 mL dichloromethane separately under argon. The monomer solutions were mixed, and the respective amount of G3 catalyst in 1 mL dichloromethane was added in one shot. Details are given in Table 6. The NMR spectroscopic data for each repeat unit proton matched the assignment of the analogous protons in the homopolymers. Where possible (no peak overlap), integration revealed that the copolymer composition matched the monomer feed ratio. Deprotection was performed as described for the homopolymers.

TABLE 6

Experimental parameters for copolymer synthesis: a) ethyl-propyl copolymers, b) methyl-ethyl copolymers, c) methyl-propyl copolymers.

a)

| Sample | Monomers | N$_{repeat\ units}$ | M$_{n\ Target}$ g mol$^{-1}$ | n$_{Ethyl}$ mmol | m$_{Ethyl}$ mg | n$_{Propyl}$ mmol | m$_{Propyl}$ mg | n$_{Catalyst}$ mmol | m$_{Catalyst}$ mg |
|---|---|---|---|---|---|---|---|---|---|
| E1:P9 | Ethyl:Propyl | 10 | 3500 | 0.06 | 20.2 | 0.54 | 192 | 0.060 | 53.1 |
| E1:P2 | Ethyl:Propyl | 10 | 3400 | 0.20 | 68.3 | 0.40 | 137 | 0.060 | 53.1 |
| E1:P1 | Ethyl:Propyl | 9 | 3000 | 0.14 | 48.0 | 0.14 | 51.4 | 0.037 | 32.2 |
| E2:P1 | Ethyl:Propyl | 10 | 3500 | 0.40 | 130 | 0.20 | 70.0 | 0.060 | 53.1 |
| E9:P1 | Ethyl:Propyl | 10 | 3400 | 0.54 | 183 | 0.06 | 20.1 | 0.060 | 53.1 | b)

| Sample | Monomers | N$_{repeat\ units}$ | M$_{n\ Target}$ g mol$^{-1}$ | n$_{Methyl}$ mmol | m$_{Methyl}$ mg | n$_{Ethyl}$ mmol | m$_{Ethyl}$ mg | n$_{Catalyst}$ mmol | m$_{Catalyst}$ mg |
|---|---|---|---|---|---|---|---|---|---|
| M1:E9 | Methyl-Ethyl | 10 | 3400 | 0.81 | 276.5 | 0.09 | 32.0 | 0.09 | 79.7 |
| M1:E1 | Methyl-Ethyl | 10 | 3500 | 0.45 | 153.6 | 0.45 | 159.9 | 0.09 | 79.7 |
| M9:E1 | Methyl-Ethyl | 10 | 3550 | 0.09 | 30.7 | 0.81 | 287.9 | 0.09 | 79.7 | c)

| Sample | Monomers | N$_{repeat\ units}$ | M$_{n\ Target}$ g mol$^{-1}$ | n$_{Methyl}$ mmol | m$_{Methyl}$ mg | n$_{Ethyl}$ mmol | m$_{Ethyl}$ mg | n$_{Catalyst}$ mmol | m$_{Catalyst}$ mg |
|---|---|---|---|---|---|---|---|---|---|
| M1:P9 | Methyl-Propyl | 10 | 3400 | 0.81 | 276.5 | 0.09 | 33.2 | 0.09 | 79.7 |
| M1:P1 | Methyl-Propyl | 10 | 3600 | 0.45 | 153.6 | 0.45 | 166.2 | 0.09 | 79.7 |
| M9:P1 | Methyl-Propyl | 10 | 3700 | 0.09 | 30.7 | 0.81 | 299.2 | 0.09 | 79.7 |

Propyl Oligomer Synthesis

Propyl Oligomers were synthesized and hydrolyzed using the same methods as for the homopolymers. Experimental data are included in Table 7. GPC traces and distribution functions obtained from the MALDI-TOF MS spectra of all oligomers are included in FIG. 6.

TABLE 7

Experimental parameters for oligomer synthesis

| Sample | Monomers | $N_{repeat\,units}$ | $M_{n\,Target}$ g mol$^{-1}$ | $n_{Propyl}$ mmol | $m_{Propyl}$ mg | $n_{Catalyst}$ mmol | $m_{Catalyst}$ mg |
|---|---|---|---|---|---|---|---|
| Oligo 1 | Propyl | 2 | 740 | 0.18 | 66.5 | 0.09 | 79.7 |
| Oligo 2 | Propyl | 3 | 1100 | 0.27 | 99.7 | 0.09 | 79.7 |
| Oligo 3 | Propyl | 4 | 1480 | 0.36 | 133.0 | 0.09 | 79.7 |
| Oligo 4 | Propyl | 5 | 1850 | 0.45 | 166.2 | 0.09 | 79.7 |
| Oligo 5 | Propyl | 6 | 2220 | 0.54 | 199.5 | 0.09 | 79.7 |
| Oligo 6 | Propyl | 7 | 2600 | 0.18 | 66.5 | 0.09 | 79.7 |

Biological Data

Representative curves for the determination of the $MIC_{90}$ as well as the $HC_{50}$ values are given here. (Rennie, et al., *J. Industr. Microbio. Biotech.* 2005, 32, 7, 296) The $MIC_{90}$ data was obtained from the plot of % growth vs. concentration. The concentration value below 10% growth was taken as the $MIC_{90}$. Controls with inactive polymers and polymers with known activity were included on each plate to ensure data reproducibility. Additionally, the data was collected in quadruplicate. Representative examples are given below (FIGS. 7-8). An example of the dose-response behavior for the different bacteria is shown in FIG. 7 *c*) and *d*). The shape of the dose-response curve is largely the same for both bacteria.

Hydrophobic polymers such as Propyl_3k sometimes appear to become less toxic at higher concentrations due to an artifact that comes from decreased solubility or aggregation at these concentrations. When the bacterial count is determined in these wells, there are zero remaining viable bacteria, or CFUs. Examples of typical $HC_{50}$ curves are shown in FIG. 9. The $HC_{50}$ value was taken as the average value of the data at 50% lysis.

To compare the differences between the reported $MIC_{90}$ (Tables 1b, 32b and 4b), and the value of $MIC_{100}$ which is sometime reported, Table 8 reports these $MIC_{100}$ values. When they differ from the $MIC_{90}$ values in the main text, they are highlighted in bold.

TABLE 8

Characterization of the antimicrobial homopolymers by biological assays: Inhibitory activity towards bacterial growth of *E. coli* and *S. aureus* bacteria. ($MIC_{100}$ = minimal inhibitory concentration preventing 100% bacterial growth) and hemolytic activity towards red blood cells ($HC_{50}$ = concentration lysing 50% of blood cells). a) Homopolymers, b) oligomers, and c) copolymers.

a)

| | $MIC_{100}$ µg mL$^{-1}$ | | | Selectivty | |
|---|---|---|---|---|---|
| Sample | *E. coli* | *S. aureus* | $HC_{50}$ µg mL$^{-1}$ | *E. coli* | *S. aureus* |
| Methyl_3k | >200 | >200 | 2000 | <10 | 10 |
| Ethyl_3k | 50 | 200 | 1400 | 28 | 7 |
| Propyl_3k | 6.25 | 25 | 50 | 8.0 | 2.0 |
| Butyl_3k | 15 | 25 | <50 | <3.3 | <2.0 |
| Isopentyl_3k | 12.5 | 50 | <50 | <4.0 | <1.0 |
| Hexyl_3k | >200 | >200 | <50 | <0.3 | <0.3 |
| Methyl_10k | >200 | >200 | 50 | <10 | <10 |
| Ethyl_10k | >200 | >200 | 1250 | <6.3 | <6.3 |
| Propyl_10k | 6.25 | >200 | <50 | <8.0 | <0.25 |
| Butyl_10k | 20 | >200 | <50 | <2.5 | <0.3 |
| Isopentyl_8k | 50 | >200 | <50 | <0.3 | <0.3 |
| Isopentyl_10k | 50 | 200 | <50 | <0.3 | <0.3 |
| Hexyl_10k | 100 | >200 | n.d. | n.d. | n.d. | b)

| | $MIC_{100}$ µg mL$^{-1}$ | | | Selectivty | |
|---|---|---|---|---|---|
| Sample | *E. coli* | *S. aureus* | $HC_{50}$ µg mL$^{-1}$ | *E. coli* | *S. aureus* |
| Monomer (3c, hydrolyzed) | >200 | >200 | n.d. | n.d. | n.d. |
| Oligo 1 | >200 | 6.25 | 1050 | 5.25 | 168 |
| Oligo 2 | 200 | 12.5 | 800 | 4.0 | 64 |
| Oligo 3 | 200 | 25 | 1250 | 6.3 | 50 |
| Oligo 4 | >200 | 50 | >2000 | >10 | 40 |
| Oligo 5 | 100 | >200 | 1000 | 10 | 5.0 |

TABLE 8-continued

Characterization of the antimicrobial homopolymers by biological assays: Inhibitory activity towards bacterial growth of E. coli and S. aureus bacteria. ($MIC_{100}$ = minimal inhibitory concentration preventing 100% bacterial growth) and hemolytic activity towards red blood cells ($HC_{50}$ = concentration lysing 50% of blood cells).
a) Homopolymers, b) oligomers, and c) copolymers.

| | | | | | |
|---|---|---|---|---|---|
| Oligo 6 | | 50 | 50 | 150 | 3.0 | 3.0 |
| Propyl_3k | | 6.25 | 25 | 50 | 8.3 | 2.0 |
| Propyl_10k | | 6.25 | >200 | <50 | <8.0 | <0.25 | c)

| Sample | Monomer | $MIC_{90}$ μg $mL^{-1}$ | | $HC_{50}$ μg $mL^{-1}$ | Selectivty | |
|---|---|---|---|---|---|---|
| | | E. coli | S. aureus | | E. coli | S. aureus |
| Propyl_3k | Propyl | 6.25 | 25 | 50 | 8.0 | 2.0 |
| E1:P9 | Ethyl:Propyl | 50 | 15 | <50 | <1.0 | <3.3 |
| E1:P2 | Ethyl:Propyl | 15 | 15 | <50 | <3.3 | <3.3 |
| E1:P1 | Ethyl:Propyl | 100 | 200 | 1000 | 10 | 5.0 |
| E2:P1 | Ethyl:Propyl | >200 | 200 | >2000 | 10 | >10 |
| E9:P1 | Ethyl:Propyl | >200 | 50 | 500 | <2.5 | 10 |
| Ethyl_3k | Ethyl | 50 | 200 | 1400 | 28 | 7 |
| Methyl_3k | Methyl | >200 | >200 | 2000 | <10 | <10 |
| M9:E1 | Methyl-Ethyl | >200 | 12.5 | 700 | <3.5 | 56 |
| M1:E1 | Methyl-Ethyl | >200 | 25 | 1200 | <6.0 | 48 |
| M1:E9 | Methyl-Ethyl | >200 | 12.5 | 1500 | <7 | 120 |
| Ethyl_3k | Ethyl | 50 | 200 | 1400 | 28 | 7 |
| Methyl_3k | Methyl | >200 | >200 | 2000 | 10 | <10 |
| M9:P1 | Methyl-Propyl | >200 | 3.75 | >2000 | 10 | 533 |
| M1:P1 | Methyl-Propyl | >200 | 3.75 | >2000 | 10 | 533 |
| M1:P9 | Methyl-Propyl | >200 | 3.75 | >2000 | 10 | 533 |
| Propyl_3k | Propyl | 6.25 | 25 | 50 | 8.3 | 2.0 | b. Doubly Selective Antimicrobial Polymers

The desirable properties of SMAMPs are a high antibacterial activity (a low $MIC_{90}$ value) and low red blood cell lysis (a high $HC_{50}$ value), leading to a high selectivity for bacteria over the mammalian host cells. SMAMPs that are equally active against Gram-positive bacteria (e.g. *S. aureus*) and Gram-negative bacteria (e.g. *E. coli*) are well described in the literature. (Gabriel, et al. *Mater. Sci. Eng., R: Rep.* 2007, 57, 28; Kuroda, et al., *J. Am. Chem. Soc.* 2005, 127, 4128; Sambhy, et al., *Angew. Chem. Inter. Ed.* 2008, 47, 1250; Mowery, et al., *J. Am. Chem. Soc.* 2007, 129, 15474.)

The morphological differences between Gram-negative and Gram-positive cells are significant. The Gram-negative cell (FIG. 10a) has an outer and a plasma membrane, with a thin layer of loosely cross-linked peptidoglycan in the periplasmic space between the two membranes. On the other hand, the Gram-positive bacteria cell (FIG. 10b) has a 20 to 80 nm thick, highly cross-linked peptidoglycan layer surrounding a single bilayer lipid membrane. Additionally, the membranes consist of different phospholipids. Generally, Gram-negative bacteria (and specifically *E. coli*) membranes mainly consists of phosphatidylethanolamine (PE) and phosphatidylglycerol (PG), while the membrane of *S. aureus*, like most other Gram-positive bacteria, is made predominantly from cardiolipin (CL). (Alberts, et al. *Molecular Biology of the Cell,* 4th Edition ed., Garland Science, New York, 2002; Som, et al, *J. Phys. Chem. B* 2008, 112, 3495.)

Recently, Kallenbach et al. reported a synthetic peptide with a selectivity of 4 for *E. coli* over *S. aureus* (which compares to the natural AMP gentamicin with a selectivity of about 40). (Liu, et al., *ChemBioChem* 2007, 8, 2063.) Muehle and Tam reported a design concept for the synthesis of AMPs with Gram-negative selectivity through binding to the lipopolysaccharide layer of Gram-negative bacteria. (Muhle, et al., *Biochemistry* 2001, 40, 5777.)

The molecular origin for the observed double selectivity could be the general structural difference, specifically the different lipid composition, of the plasma membranes. The additional peptidoglycan layer of *S. aureus* might be responsible for a molecular weight dependence seen in many SMAMPs, namely that antimicrobial activity is lost with increasing molecular weight. Using dye-leakage experiments on bacteria-mimicking model vesicles, the observed doubly selectivity of a model SMAMP (FIG. 11) are related to the morphological differences between these two bacterial types. (Lienkamp, et al, *Chem. Eur. J.* submitted.)

The SMAMP shown in FIG. 11 proved to be a suitable probe to test the above hypotheses, as it is doubly selective and has a molecular weight-dependent antimicrobial activity against *S. aureus*. It is generally accepted that SMAMPs, like AMPs, interact with bacteria membranes such that the membranes are corrupted (although other targets can exist). (Ikeda, et al., *Biochim. Biophys. Acta Biomembr.* 1990, 1021, 56.) Therefore, dye-leakage experiments on unilamellar model vesicles, which probe membrane activity, were performed. (Som, et al, *J. Phys. Chem. B* 2008, 112, 3495.) (FIG. 14a.)

In a first series of experiments, the model vesicles for *E. coli*, containing PE/PG lipid, and *S. aureus* bacteria, made from CL lipid, were exposed to the same concentration of the SMAMP. The dye-leakage data obtained showed that the SMAMP, regardless of its molecular weight, was membrane active against both model membranes (FIGS. 14b and 14c). As dye-leakage data obtained at a single polymer concentration is not necessarily the most quantitative measure of membrane activity, a concentration dependent leakage curve was obtained (FIG. 12a). Fitting this data to the Hill equation gave the polymer concentration that leads to 50% polymer-induced leakage, $EC_{50}$. (Som, et al, *J. Phys. Chem. B* 2008, 112, 3495.) For the PE/PG vesicles, $EC_{50}$ was 1.57 μg $mL^{-1}$ and for the CL vesicles 2.64 μg $mL^{-1}$; additionally, both vesicle types have the same maximum leakage. Therefore it is clear that the SMAMP is equally membrane-active against *S. aureus* and *E. coli* mimics, i.e. the different membrane composition is not responsible for the observed differences in antimicrobial activity, specifically the inactivity against *E. coli*.

Although vesicle studies are common in the (SM)AMP literature, these unilamellar vesicles are understood to be extremely simple models of the plasma membrane. They might be a reasonable model for *S. aureus*, with one membrane, but *E. coli* has a double membrane structure. This additional membrane effectively creates a gradient in SMAMP concentration (FIG. 10a). The outer membrane sees a concentration $c_1$ that causes membrane disintegration; however, the periplasmic space sees a significantly reduced concentration $c_2$, which is insufficient to damage the plasma membrane. As the experiments proved that the different nature of the lipids are not crucial for the observed double selectivity, the double membrane structure might be responsible for the inactivity of the SMAMP against *E. coli*, consistent with previous observations demonstrating that the mere loss of the outer membrane integrity was not sufficient to kill *E. coli* bacteria. (Shai, Biochim. Biophys. Acta Biomembr. 1999, 1462, 55.)

A second series of experiments were designed to study the peptidoglycan layer in *S. aureus* in connection with the observed loss of antimicrobial activity with increasing molecular weight. According to the dye-leakage data in FIG. 14c, for the *S. aureus*-like membranes, all SMAMPs were membrane-active regardless of their molecular weight $M_n$. It is proposed that the higher $M_n$ samples of the SMAMP cannot reach the plasma membrane of *S. aureus* due to the highly cross-linked peptidoglycan layer (FIG. 10b), which effectively reduces their concentration $c_2$ at the plasma membrane and renders them inactive in the $MIC_{90}$ experiments. The peptidoglycan layer consists of anionically charged, alternating copolymers of β-(1,4)-linked N-acetylmuramic acid and N-glucosamine, which are cross-linked by peptide chains. There are two possible $M_n$-dependent modes of interaction between this layer and SMAMPs. First, there may be SMAMP-peptidoglycan binding: Whatever the nature of this binding, whether it is charge-, polarity- or hydrophobicity-driven, the number of binding sites per chain will increase with $M_n$, making the binding gradually more irreversible. Second, the peptidoglycan may simply act as a sieve. Thus, the dimensions of the SMAMP can be crucial; the higher its $M_n$, the larger its hydrodynamic volume, which might prevent larger SMAMPs from passing through the peptidoglycan mesh.

As a mimic of this highly cross-linked peptidoglycan layer, peptidoglycan extract from *S. aureus* bacteria was used in the dye-leakage experiments. While this extract does not form a dense, uniform layer around the vesicle when added to a dye-leakage experiment and thus is not a perfect model for the sieving properties of the peptidoglycan layer of a real *S. aureus* cell, it is a very good model to investigate SMAMP-peptidoglycan binding.

The following experiments were designed to investigate the effect of peptidoglycan, and to differentiate between the two proposed modes of SMAMP-peptidoglycan interaction: (1) CL vesicles were incubated with the peptidoglycan extract for 10 min and 24 h, respectively, after which times the vesicles were exposed to the SMAMP. While the extract itself did not cause leakage, all molecular weights of the SMAMP were membrane-active in its presence for both incubation times. (2) CL vesicles were exposed to samples containing constant concentrations of the 3,000 g/mol polymer, which were previously incubated for 24 h with different amounts of peptidoglycan extract. Plotting the concentration of the peptidoglycan versus the induced leakage percentage, a peptidoglycan concentration-dependent curve was obtained (FIG. 12b). The data shows that the polymer-peptidoglycan ratio is critical for the amount of leakage reduction. At a sufficiently high peptidoglycan concentration, the leakage was near-quantitatively quenched, i.e. saturation was reached. (3) CL vesicles were mixed with SMAMP solutions that had been incubated with the previously determined saturation amount of peptidoglycan for 10 min and 24 h, respectively. In the case of short incubation time, all polymers were membrane active in the presence of the extract, meaning that no peptidoglycan-SMAMP complex formed. However after 24 h, as shown in FIG. 12c, the membrane activity of all samples was lost, indicating binding. The results of these experiments are illustrated in FIG. 13. SMAMP-peptidoglycan binding does occur, but it is a relatively slow process. On the timescale of an $MIC_{90}$ experiment, the loss of SMAMP activity with increasing $M_n$ due to binding is not responsible for the observed antimicrobial activity.

The results show that the CL model vesicles with non cross-linked peptidoglycan are not able to differentiate between different $M_n$ polymers because the added peptidoglycan does not form a uniform layer on the vesicle, which is why both the high and the low $M_n$ SMAMP are active when incubated for 10 min. In the parent bacteria, however, the peptidoglycan layer is thick, uniform and the pores have a finite size, meaning that only small molecules can diffuse through easily (FIG. 10b). Thus, the high molecular weight SMAMPs could only pass this layer by a repetition-like mode, meaning that the polymer coil would have to unravel. This process is so slow that, on the timescale of the MIC experiment, no antimicrobial activity is observed. This is consistent with the observation that only proteins with a diameter of up to 2 nm were able to pass cross-linked peptidoglycan layers that had been isolated from *E. coli* and *B. subtilis*. (Demchick, et al., J. Bacteriol. 1996, 178, 768.)

Experiments discussed herein give insight into the molecular origins of 'double selectivity' in SMAMPs: Lipid composition was shown not to be the decisive factor for losing antimicrobial activity against *E. coli*. It was further shown that the molecular weight dependence of the $MIC_{90}$ data for *S. aureus* is not due to binding to the peptidoglycan layer, but most likely a sieving effect.

EXAMPLES

General:

All chemicals were obtained as reagent grade from Aldrich, Fluka or Acros and used as received. $3^{rd}$ generation Grubbs catalyst (Dichloro-di(3-bromopyridino)-N,N'-Dimesitylenoimidazolino-Ru=CHPh; G3) was synthesized as described previously by Grubbs et al. (Klein, et al., Emerg. Infect. Dis. 2007, 13, 1840.) HPLC grade solvents N,N-dimethylformamide (DMF) were purchased from Aldrich, Fisher Scientific or Acros and used as received. THF (HPLC grade, Fisher Scientific) was distilled from sodium/benzophenone under nitrogen. Dichloromethane (HPLC grade, Fisher Scientific) was distilled from $CaH_2$ under nitrogen. Gel permeation chromatography (DMF/0.01 M LiCl, calibrated with polystyrene standards, toluene as flow marker, 50° C.) was measured on a PL50 GPC setup (Polymer Laboratories, Amherst, Mass.) with a PL Gel 5 μm pre-column and two 10 μm analytical Mixed-D columns (Polymer Laboratories, Amherst, Mass.). NMR spectra were recorded on a Bruker DPX300 spectrometer (Bruker, Madison, Wis.). High resolution mass spectra were obtained from a JEOL JMS 700 instrument (JEOL, Peabody, Mass.); Matrix Assisted Laser Desorption and Ionization Time of Flight Mass Spectra (MALDI- TOF MS) were measured on a Bruker Daltonics Reflex III (Bruker, Madison, Wis.). The biological activity of the polymer samples (the minimal concentration inhibiting 90% of bacterial growth (MIC$_{90}$) for *Escherichia coli* (D31) and *Staphylococcus aureus* (ATCC25923), and the concentration that lyses 50% of red blood cells (HC$_{50}$) were determined as reported previously. (Huang, *Biochemistry* 2000, 39, 8347.) Fluorescence measurements were performed on a Perkin-Elmer-LS55 luminescence spectrometer and Jobin Yvon Fluorolog-3. The phospholipids 1,1'-2,2'-tetraoleoyl cardiolipin sodium salt (CL), 1,2-dioleoyl-sn-glycero-3-phosphatidylethanolamine (PE) and 1,2-dioleoyl-sn-glycero-3-[phospho-rac-(1-glycerol)] (PG) were obtained as chloroform solutions from Avanti Polar Lipids, Inc. and used as received. Peptidoglycan extract from *S. aureus* was obtained from Fluka and used as received.

Polymer Synthesis:

The synthesis of the model SMAMP is shown in Scheme 3. (Brodgen, *Nature Rev. Microbiol.* 2005, 3, 238.) The characterization results are given in Table 9.

Dye-Leakage Experiments:

Vesicle Preparation:

Two buffers were prepared. Buffer A consisted of 1 mmol (142 mg) Na$_2$HPO$_4$ in 100 mL H$_2$O (c=10 mmol L$^{-1}$), which was then adjusted to pH=7.0 with 0.1 mol L$^{-1}$ NaOH. Buffer B was made from 10 mmol (1.42 g) Na$_2$HPO$_4$ in 1 L H$_2$O (c=10 mmol L$^{-1}$) and 90 mmol (5.26 g) NaCl (c=90 mmol L$^{-1}$). 0.4 mmol (249 mg) of calcein dye was dissolved in 10 mL buffer A. 0.1 mol NaOH was added dropwise until all calcein dissolved and the pH was 7.0, yielding a solution of 40 mmol L$^{-1}$.

The lipid solutions were added to thoroughly clean round bottom flask. For the CL vesicles, 600 μL (10 mmol) CL in chloroform was used, for the PE/PG 4:1 vesicles, 297 μL (8 mmol) PE and 159 μL (2 mmol) PG in chloroform were mixed. The solvent was evaporated to obtain a lipid film, which was hydrated with 1 mL of calcein solution in buffer. The suspension was stirred for 1 h and then subject to five freeze-thaw cycles (liquid nitrogen/water at room temperature). After that it was extruded ten times through a polycar- Scheme 3: Diamine polymer synthesis.

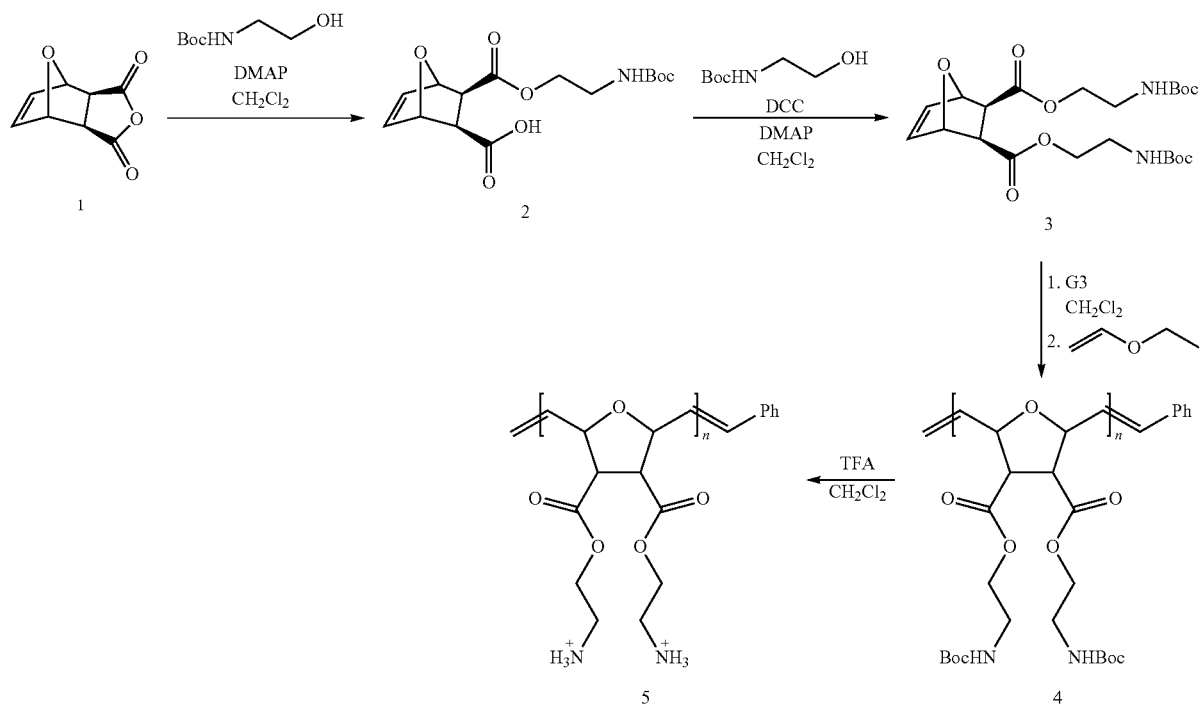

TABLE 9

Analytical results for the polymers.

| Sample | M$_{n, Target}$ g mol$^{-1}$ | GPC M$_n$ g mol$^{-1}$ | M$_w$/M$_n$ | MIC$_{90}$ μg mL$^{-1}$ | | HC$_{50}$ μg mL$^{-1}$ | Selectivity | |
|---|---|---|---|---|---|---|---|---|
| | | | | E. coli | S. aureus | | E. coli | S. aureus |
| Diamine_3k | 3000 | 8900 | 1.15 | >200 | 15 | 1000 | <5 | 67 |
| Diamine_5k | 5000 | 12900 | 1.08 | >200 | 25 | 1000 | <5 | 40 |
| Diamine_10k | 10000 | 22500 | 1.08 | >200 | 50 | 1000 | <5 | 20 |
| Diamine_50k | 50000 | 77000 | 1.07 | >200 | 200 | 2000 | <10 | 10 | bonate membrane with 400 nm pore diameter (Avanti Polar Lipids Mini-Extruder, Whatman membrane). The dye-filled vesicles were separated from the excess dye using an Sephadex G-50 and buffer B as an eluent. The vesicle fraction from the column was diluted by a factor of 20 for the dye-leakage experiments.

Fluorescence Measurement:

The polymer-induced leakage was monitored, as described previously, by recording the increase of calcein fluorescence intensity at a wavelength 515 nm (excitation wavelength=490 nm, slit width 3.0). (Som, et al., *J. Phys. Chem. B* 2008, 112, 3495.) To normalize the dye-leakage data, a base line of calcein fluorescence without polymer addition was observed for each sample. Also, after each measurement, 20 μL Triton X (20% in DMSO) was added to determine the fluorescence intensity corresponding to 100% leakage. With these data points, the measured fluorescence intensity was converted in % leakage (FIG. 14a). The polymer samples were dissolved in DMSO at various concentrations. Pure DMSO has been tested previously and was shown not to cause leakage. For the concentration-dependent $EC_{50}$ curves, the leakage percentage after 800 sec was plotted versus the concentration in a semi-logarithmic plot. The $EC_{50}$ concentration, which corresponds to 50% polymer-induced leakage, was determined using the Hill equation, $$y(c) = y_{max} + \frac{y_{min} - y_{max}}{1 + \left(\frac{c}{EC_{50}}\right)^n},$$

where y(c) is the leakage percentage at a given concentration c, $y_{min}$ is the leakage percentage corresponding to no polymer addition, $y_{max}$ is the leakage percentage at high polymer concentration (saturation), and n is a fit parameter, which may be interpreted as a measure for the number of molecules participating in the binding. The exact amounts of polymer and vesicles for each experiment is compiled in Tables 10 (experiments without peptidoglycan) and Tables 11 (experiments with peptidoglycan). All samples were filled up to a total volume of 2 mL with buffer B.

TABLE 10

| Vesicle type | Vesicle V | Polymer (in DMSO) | Polymer V |
|---|---|---|---|
| CL | 20 μL | Diamine_3k, 2 g/L | 20 μL |
| | | Diamine_5k, 2 g/L | |
| | | Diamine_10k, 2 g/L | |
| | | Diamine_50k, 2 g/L | |
| PE/PG | 10 μL | Diamine_3k, 2 g/L | 10 μL |
| | | Diamine_5k, 2 g/L | |
| | | Diamine_10k, 2 g/L | |
| | | Diamine_50k, 2 g/L | |
| CL | 20 μL | Diamine_3k, 4 g/L | 40 μL |
| | | | 20 μL |
| | | | 10 μL |
| | | | 5 μL |
| | | | 2.5 μL |
| | | | 1 μL |
| | | Diamine_3k, 0.25 g/L | 4 μL |
| | | | 1 μL |
| PE/PG | 10 μL | Diamine_3k, 4 g/L | 40 μL |
| | | | 20 μL |
| | | | 10 μL |
| | | | 5 μL |
| | | | 2.5 μL |
| | | | 1 μL |

TABLE 10-continued

| Vesicle type | Vesicle V | Polymer (in DMSO) | Polymer V |
|---|---|---|---|
| | | Diamine_3k, 0.25 g/L | 4 μL |
| | | | 1 μL |
| | | | 0.5 μL |

TABLE 11

| Vesicle Type | V | Polymer c (in DMSO) | Peptidoglycan V | | Incubation time |
|---|---|---|---|---|---|
| CL | 10 μL | Diamine_3k, 4 g/L | 10 μL | 400 μg | 24 h |
| | | | | 200 μg | |
| | | | | 100 μg | |
| | | | | 40 μg | |
| | | | | 20 μg | |
| | | | | 10 μg | |
| | | | | 5 μg | |
| | | | | 2.5 μg | |
| | | | | 0.5 μg | |
| CL | 20 μL | Diamine_3k, 2 g/L | 20 μL | 100 μg | 24 h |
| | | Diamine_5k, 2 g/L | | | |
| | | Diamine_10k, 2 g/L | | | |
| | | Diamine_50k, 2 g/L | | | |
| | | Diamine_3k, 4 g/L | | | |
| | | — | 0 μL | 100 μg | |
| CL | 20 μL | Diamine_3k, 2 g/L | 6 μL | 25 μg | 10 min |
| | | Diamine_50k, 2 g/L | | | |
| | | Diamine_3k, 2 g/L | | | 24 h |
| | | Diamine_50k, 2 g/L | | | | c. Manipulating Antimicrobial Properties by Organic Counterion and Charge Density Variation There have not been much literature on the effect of different counterions on the antimicrobial properties of a polymer has been essentially neglected in the SMAMP literature. (Ilker, et al., *Journal of the American Chemical Society* 2004, 126, 15870; Lienkamp, et al., *J Am Chem Soc* 2008, 130, 9836; Gabriel, et al., *Chemistry—A European Journal* 2009, 15, 433.) The few studies published so far investigate the effect of different inorganic counterions on polymer properties. Kanazawa et al. postulated an inverse correlation between the tightness of the ion pair of a polymer-counterion system and its antimicrobial properties ($Cl^- > BF_4^- > ClO_4^- > PF_6^-$). (Kanazawa, et al, *Journal of Polymer Science, Part A: Polymer Chemistry* 1993, 31, 1441.) Chen et al. saw higher activities for bromide than for chloride counterions with their polycationic dendrimers, while Panarin et al. did not see any significant differences between chloride, bromide, and iodide. (Chen, et al., *Biomacromolecules* 2000, 1, 473; Panarin, et al., *Makromol. Chem. Suppl.* 1985, 9, 25.) The ranking of 'activity' in these studies was based on relative bacterial survival rates in time-kill studies. However, none of these studies quantified antimicrobial activity in terms of MIC data. This makes it difficult to assess how much the antimicrobial activity is actually affected by the counterion exchange, and makes comparison between these studies even more difficult. While the previous examples focused on inorganic counterions, the effect of different organic counterions such as tosylate or hexanoate, to our knowledge, has not been studied.

Counterions of varying hydrophobicity may provide an easy and versatile tool to tune the hydrophobicity and thus the antimicrobial properties of the polymer. This approach of tuning the hydrophobicity requires much less synthetic effort than the covalent attachment of hydrophobic groups, both on the monomer and the polymer synthesis level. For example, replacing the trifluoroacetate counterions of a hydrophilic model SMAMP by hydrophobic organic counterions can influence the polymer's antimicrobial properties and its membrane activity.

The effect of molecular charge density may also be employed on the antimicrobial properties such as hydrophobicity. A series of polymers were made with gradually varied cationic charge, but with minimal changes to the overall polymer structure and hydrophobicity. A copolymer with a selectivity as high as 650 for *Staphylococcus aureus* over mammalian cells was discovered.

precursor polymer 4 was deprotected with trifluoroacetic acid (TFA) to yield the cationic SMAMP 5 (Scheme 4). To determine the optimum activity of polymer 5, a range of molecular weights was synthesized. The protected polymer 4 was characterized by gel permeation chromatography (GPC). All polymers had narrow polydispersities (1.07-1.15, Table 12); however polystyrene-calibrated GPC in DMF severely overestimated their molecular weights. This was confirmed by MALDI-TOF mass spectrometry, which showed that the molecular weights $M_n$ of those polymers were close to the targeted ones. When plotting $M_{n,Target}$ versus the molecular weights obtained from GPC, a straight line is obtained, indicating that the polymerization was controlled (FIG. 15).

Scheme 4: Synthesis and polymerization of the diamine monomer to yield SMAMP 5

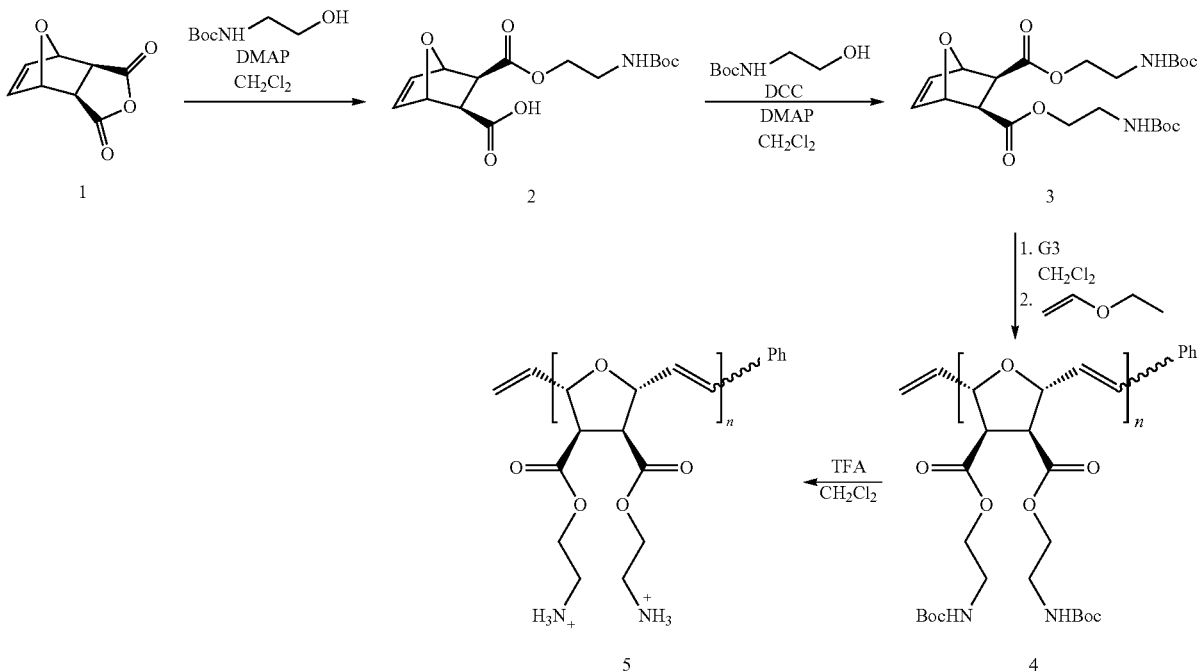

EXAMPLES

1. Diamine Homopolymer Synthesis.

A predominantly hydrophilic model polymer with two charges per repeat unit was synthesized (Scheme 4). Base-catalyzed ring-opening of the anhydride 1 with a Boc-protected amino ethanol gave the monoester 2. DCC coupling of 2 with a second equivalent of the alcohol yielded the diamine monomer 3, which was polymerized by ring-opening metathesis polymerization (ROMP) using Grubbs' third generation catalyst. (Jennifer, et al., *Angewandte Chemie International Edition* 2002, 41, 4035.) The obtained Boc-protected The biological activities, $MIC_{90}$ and $HC_{50}$, of the deprotected SMAMPs (5) were tested using standard procedures. (Rennie, et al., *Journal of Industrial Microbiology & Biotechnology* 2005, 32, 296.) The results are summarized in Table 12, where Diamine_3k refers to a sample of polymer 5 with a molecular weight of 3000 g/mol. The data shows that, while all polymers were inactive against *E. coli*, the antimicrobial activity against *S. aureus* was highest for the 3000 g/mol polymer, with an $MIC_{90}$ of 15 μg/mL. Upon increasing the molecular weight, the antimicrobial activity was lost, while the hemolytic activity $HC_{50}$ was about the same for all molecular weights.

TABLE 12

Characterization of SMAMP homopolymers.

| Sample | $M_{n,Target}$[a] g mol$^{-1}$ | GPC $M_n$[a] g mol$^{-1}$ | $M_w/M_n$[a] | $MIC_{90}$ μg mL$^{-1}$ [b] E. coli | S. aureus | $HC_{50}$[b] μg mL$^{-1}$ | Selectivity[b] E. coli | S. aureus |
|---|---|---|---|---|---|---|---|---|
| Diamine_3k | 3000 | 8900 | 1.15 | >200 | 15 | 1000 | <5 | 67 |
| Diamine_5k | 5000 | 12900 | 1.08 | >200 | 25 | 1000 | <5 | 40 |

TABLE 12-continued

Characterization of SMAMP homopolymers.

| Sample | $M_{n,\,Target}^{a)}$ g mol$^{-1}$ | GPC $M_n^{a)}$ g mol$^{-1}$ | $M_w/M_n^{a)}$ | MIC$_{90}$ μg mL$^{-1\,b)}$ E. coli | S. aureus | HC$_{50}^{b)}$ μg mL$^{-1}$ | Selectivity$^{b)}$ E. coli | S. aureus |
|---|---|---|---|---|---|---|---|---|
| Diamine_10k | 10000 | 22500 | 1.08 | >200 | 50 | 1000 | <5 | 20 |
| Diamine_50k | 50000 | 77000 | 1.07 | >200 | 200 | 2000 | <10 | 10 |

$^{a)}$GPC analysis was performed on the protected polymers 4 (in DMF, 0.01M LiCl, calibrated with polystyrene standards);
$^{b)}$Biological properties (minimum inhibitory concentration, hemolytic activity and selectivity) were determined for the corresponding deprotected polymers 5, with TFA counterions.

Effect of the Counterions.

As it was found that Diamine_3k was the most active polymer of the series, the ion exchange studies were performed with this sample. As a result of the deprotection conditions, the initial counterion of the polymer was TFA. By passing the polymer solution through an ion exchange column, TFA was exchanged for hydroxide. Immediately after the ion exchange, excess of the acid form of the target counterion (HX) was added. This neutralized the hydroxide before side reactions such as transamidation or base-catalyzed ester hydrolysis of the side chains could occur, and left X$^-$ as a counterion. Excess acid was removed by dialysis. Using this method, the hydrophobic organic counterions X$^-$=hexanoate, dodecanoate, benzoate and tosylate were introduced. $^1$H-NMR spectra of the freeze-dried polymers revealed that the counterion exchange was successful. These hydrophobic organic counterions were chosen because their distribution coefficient would be high. (In this context, the distribution coefficient is defined as the counterion concentration near the non-polar polymer backbone divided by the counterion concentration in the bulk polar buffer medium of the MIC experiment.) Thus, unlike more hydrophilic counterions such as TFA, they would not diffuse away from the polymer backbone and the effect of the counterion on the antimicrobial properties would be observed in the MIC experiment. The MIC$_{90}$ results for the series of ion exchanged polymers are summarized in Table 13. To investigate the effect of a covalently attached 'intramolecular counterion', which certainly would not be able to diffuse away from the polymer backbone, the monoester 2 was also polymerized, yielding polymer 6. After deprotection with TFA, the zwitterionic polymer 7 was obtained (Scheme 5). That MIC data is also included in Table 13. Here, the 3000 g/mol sample of polymer 7 will be referred to by Zwitterion_3k for convenience.

Scheme 5: Synthesis of the zwitterionic polymer 7

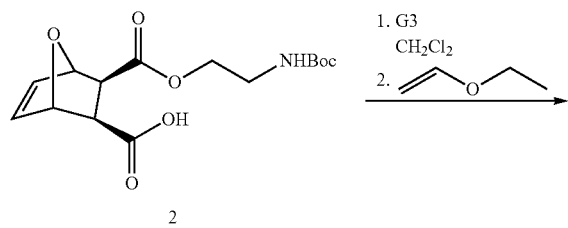

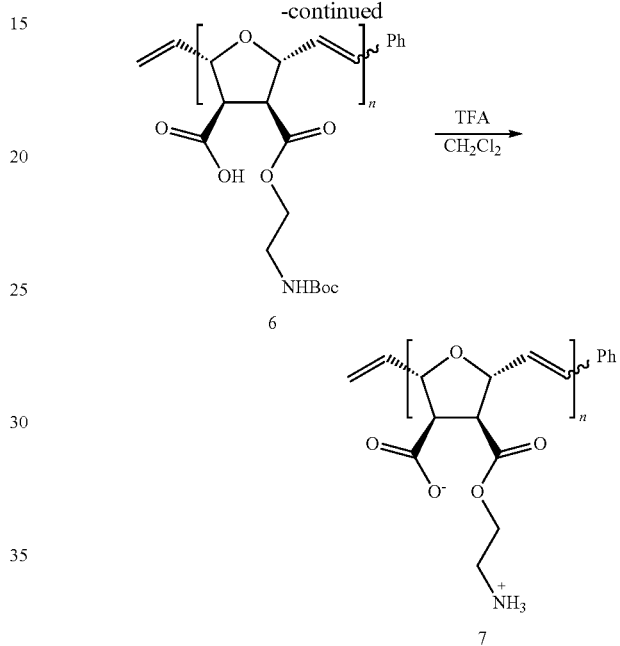

TABLE 13

Minimum inhibitory concentration of the zwitterionic and ion-exchanged polymers, determined for the deprotected polymers; ion exchanged polymers are referred to by their counterion, e.g. Tosylate_3k is the 3000 g/mol diamine polymer with a tosylate counterion. Diamine_3k has the original TFA counterion.

| | MIC$_{90}$ μg mL$^{-1}$ | |
|---|---|---|
| Sample | S. aureus | E. coli |
| Diamine_3k | 15 | >200 |
| Tosylate_3k | >200 | >200 |
| Benzoate_3k | >200 | >200 |
| Hexanoate_3k | >200 | >200 |
| Dodecanoate_3k | >200 | >200 |
| Zwitterion_3k | 50 | >200 |
| Zwitterion_10k | >200 | >200 |

Table 13 shows that the presence of the organic counterions influences the antimicrobial activity of the polymers: All polymers with hydrophobic counterions stayed inactive against E. coli and were significantly less active against S. aureus than Diamine_3k, although no discrimination between their relative activities within the range below 200 μg/mL could be made. Not only does this data confirm that the hydrophobic counterions stay close to the polymer backbone, but in fact they bind so strongly that they eliminate the antimicrobial activity.

There are two possible interpretations for this. First, the hydrophobic counterions could reduce the polymer solubility to such an extent that the SMAMP is unable to interact with the bacteria membrane and thus appears inactive in the MIC experiment. Second, the counterions could form such a tight ion pair with the ammonium groups that the overall positive charge of the polymer is effectively masked and the SMAMP is rendered inactive. One way to differentiate between these two possibilities is to perform dye-leakage experiments. (Abhigyan, et al., *J Phys Chem B* 2008, 112, 3495.) These experiments are designed to probe the membrane activity of a polymer. A polymer that is poorly soluble will still be active in dye-leakage experiments, because these studies are much more sensitive. An example of a polymer that is poorly soluble and therefore inactive in the MIC experiment, but retains significant membrane activity in the dye leakage experiment, is the previously reported Hexyl_3k. (Lienkamp, et al., *J Am Chem Soc* 2008, 130, 9836.) However, if the counterions of the ion exchanged polymers mask the positive charge of the polymer backbone, these polymers will be inactive both in the MIC and the dye-leakage experiments. Using standard procedures, dye-loaded unilamellar vesicles made from cardiolipin, the predominant component of the plasma membrane of *S. aureus* bacteria, were obtained. Leakage of the self-quenching dye from the vesicle led to fluorescence, which was monitored as a function of time. (Som, et al., *J Phys Chem B* 2008, 112, 3495.) The vesicles were exposed to a 20 µg/mL solution of the ion-exchanged polymers at t=100 sec. (The polymer concentration in the dye leakage experiments is 20 µg/mL. This makes the ratio of polymer to vesicles much higher than the ratio of polymer to bacteria in the MIC experiment. Although this polymer concentration is lower than in the MIC experiments, the much higher ratio of polymer to vesicle concentration would be expected to show leakage if the molecules are membrane disruptive. (Som, et al., *Biopolymers (Peptide Science)* 2008, 90, 83.) The resulting dye-leakage curves are plotted in FIG. 16 as % Leakage, normalized to the standard Triton X-100, versus time. The dye-leakage results from the *S. aureus*-mimicking vesicles closely follow the MIC trend against those bacteria: the polymers with hydrophobic counterions were membrane-inactive (<5% leakage), whereas the parent polymer Diamine_3k showed membrane activity (>50% leakage).

As illustrated in FIG. 17, the Hexanoate_3k and Hexyl_3k polymers are structurally similar, as each contains one hexyl chain per amine group, however Hexyl_3k ($MIC_{90}$>200 µg/mL) causes 38% leakage at 20 µg/mL, whereas Hexanoate_3k causes <5% leakage. This supports the second interpretation, that the hydrophobic counterions form tight ion pairs and thereby dramatically reduce the positive charge of the polymer, resulting in a loss of membrane activity and, consequently, of the antimicrobial activity.

Interestingly, the zwitterionic sample (Zwitterion_3k), with an MIC of 50 µg/mL, was more membrane active than the ion exchanged samples (FIG. 16), but less active than the Diamine_3k polymer. Whereas the other anions could diffuse freely to the positive charges on the polymer backbone, this is not possible for the build-in counterions of the zwitterionic sample. However, because the zwitterionic polymers are structurally irregular, this leads to an overall irregular charge distribution along the backbone, leading to local cationic and anionic patches, as illustrated in FIG. 18. Due to these residual charges, neither the antimicrobial activity nor membrane activity of Zwitterion_3k vanishes completely.

2. Charge Variation by Copolymerization.

The charge per repeat unit was diluted gradually from two to one by copolymerizing the diamine monomer 3 with structurally similar monoamine-alkyl monomers (FIG. 19). (Lienkamp, et al., *J Am Chem Soc* 2008, 130, 9836.)

Four series of copolymers were synthesized with R varying from Methyl to Butyl on the monoamine-alkyl monomer. The polymer characterization data of the protected copolymers, as well as the biological data of the deprotected copolymers, is summarized in Table 14 and FIG. 20. The data for certain homopolymers is included for comparison. (Lienkamp, et al., *J Am Chem Soc* 2008, 130, 9836.) M9:D1 refers to a copolymer with a molar ratio of methyl:diamine=9:1, while Methyl designates the monoamine-methyl homopolymer.

TABLE 14

Copolymer Characterization.

| Sample | Co-monomer | $M_{n,\,Target}$[a] g mol$^{-1}$ | GPC $M_n$[a] g mol$^{-1}$ | $M_w/M_n$[a] | $MIC_{90}$ µg mL$^{-1}$ [b] E. coli | S. aureus | $HC_{50}$[b] µg mL$^{-1}$ | Selectivity[b] E. coli | S. aureus |
|---|---|---|---|---|---|---|---|---|---|
| Diamine_3k | — | 3000 | 8900 | 1.15 | >200 | 15 | 1000 | 5 | 66 |
| M1:D9 | Methyl | 3500 | 17355 | 1.03 | >200 | 12.5 | 1400 | <7 | 112 |
| M1:D1 | | 4100 | 15400 | 1.07 | >200 | 6.25 | 1400 | <7 | 224 |
| M9:D1 | | 4600 | 17400 | 1.07 | >200 | 4 | 2600 | <13 | 650 |
| Methyl | — | 3000 | 11200 | 1.08 | 200 | 100 | 2000 | <10 | 20 |
| E1:D9 | Ethyl | 4600 | 13100 | 1.06 | >200 | 50 | 3100 | <15.5 | 62.0 |
| E1:D1 | | 4100 | 14700 | 1.08 | >200 | 15 | 1400 | <7.0 | 93.3 |
| Ethyl | — | 3000 | 9200 | 1.10 | 50 | 50 | 1400 | 28 | 28 |
| P1:D9 | Propyl | 4600 | 13700 | 1.06 | >200 | 15 | 4800 | <24.0 | 320.0 |
| P1:D1 | | 4200 | 13900 | 1.05 | >200 | 50 | 1400 | <7.0 | 28.0 |
| Propyl | — | 3000 | 9200 | 1.10 | 6.25 | 25 | 50 | 8.3 | 3.3 |
| B1:D9 | Butyl | 4600 | 14200 | 1.06 | >200 | 15 | 1200 | <6.0 | 80.0 |
| B1:D1 | | 4300 | 14700 | 1.07 | <15 | 25 | <50 | >3.3 | <2.0 |
| Butyl | — | 3000 | 11500 | 1.08 | 15 | 25 | <50 | <3.3 | <2.0 |

[a]GPC analysis was performed on the protected polymers (DMF, 0.01M LiCl, polystyrene standards);
[b]Biological properties (minimum inhibitory concentration, hemolysis and selectivity) were determined for the corresponding deprotected polymers.

As this data indicates, all the methyl and ethyl copolymers are non-hemolytic (FIGS. 20a and 20b) and inactive against *E. coli* bacteria, whereas the propyl and butyl copolymers become very hemolytic but at the same time more active against *E. coli* with increasing alkyl comonomer content (FIGS. 20c and 20d). This suggests that the properties of these polymers are dominated by the hydrophobicity of those R groups. Meanwhile, the methyl copolymers are obviously the least hydrophobic as observed by their limited activity against *E. coli* even for the methyl homopolymer, and their high $HC_{50}$ values. This lack of activity due to limited hydrophobicity is consistent with reverse phase thin layer chromatography results, and with the polymer solubilities in water and DMF, which showed that the polarity of the monoamine-methyl homopolymer closely resembled that of the diamine homopolymer, while the ethyl to butyl derivatives were significantly more hydrophobic.

These studies confirm that the methyl copolymers are the most appropriate model system to investigate the effect of charge density on biological activity.

Starting with Diamine_3k, which has an $HC_{50}$ of 1000 µg/mL, the hemolytic activity decreases across the series to M9:D1 with an $HC_{50}$ of 2600 µg/mL. This was paralleled by an increase in the antimicrobial activity from 15 to 4 µg/mL against S. aureus for the same polymers (see Table 14). When going further down in charge (M9:D1 to Methyl), there is a sudden jump in the MIC from 4 to 100 µg/mL, indicating that the optimum value for both the $HC_{50}$ and the $MIC_{90}$ against S. aureus is obtained for M9:D1.

An intriguing aside of this study is the finding that the methyl copolymers and Diamine_3k are not only selective for bacterial over mammalian cells, but also for Staphylococcus aureus over Escherichia coli (FIG. 20a). Further MIC experiments with M9:D1 and other bacteria revealed that this polymer has a Gram-selectivity: while inactive against Gram-negative E. coli, Pseudomonas aeruginosa and Klebsiella pneumoniae ($MIC_{90}$=100 µg/mL for the latter two organisms), it was found to be active against Gram-positive S. aureus, S. epidermis and even the multiresistant MRSA ($MIC_{90}$=12.5 µg/mL).

Disclosed here are several important parameters that influence the antimicrobial and hemolytic activity of SMAMPs were investigated. For example, exchanging the hydrophilic counterions of a ROMP-derived diamine polymer by hydrophobic organic counterions drastically reduced the antimicrobial properties of that polymer. It was shown by dye-leakage studies on model vesicles that this loss in antimicrobial activity was due to the loss of the positive charge of the polymer backbone by ion pair formation with the counterions. It is expected that by a partial exchange of the counterions, which would add hydrophobicity but at the same time retain the required minimum molecular charge, polymers with tunable properties—between those of the active Diamine 3k polymer and the inactive Hexanoate_3k polymer—could be obtained; this is however difficult to realize and quantify experimentally.

Copolymerization of two structurally similar monomers with one and two charges, respectively, led to a series of polymers with gradually decreased charge density but more or less constant hydrophobicity. These results indicate that, for a system of a given amphiphilicity, a minimum threshold of charge is required for obtaining favorable $HC_{50}$ values and activities. Above that threshold, the biological properties of the polymer are not affected by further charge increase. For the particular diamine-methyl copolymer system investigated here, this threshold is reached for M9:D1, with an average charge of 1.1 per repeat unit. In the process of optimizing the charge density of the copolymer system, a polymer with an impressive selectivity of 650 for S. aureus over human red blood cells was obtained. Additionally, this polymer was shown to be Gram-selective for all bacterial strains tested, including MRSA, which makes this SMAMP a promising candidate for materials applications.

EXAMPLES

General:

All chemicals were obtained as reagent grade from Aldrich, Fluka or Acros and used as received. $3^{rd}$ generation Grubbs catalyst (Dichloro-di(3-bromopyridino)-N,N'-Dimesitylenoimidazolino-Ru=CHPh; G3) was synthesized as described previously by Grubbs et al. (Love, et al, Angew. Chem. Internat. Ed. 2002, 41, 4035.) HPLC grade solvents were purchased from Aldrich, Fisher Scientific or Acros and used as received. THF (HPLC grade, Fisher Scientific) was distilled from sodium/benzophenone under nitrogen. Dichloromethane (HPLC grade, Fisher Scientific) was distilled from $CaH_2$ under nitrogen. Gel permeation chromatography (DMF/0.01 M LiCl and THF, each calibrated with polystyrene standards, toluene as flow marker, 50° C.) was measured on a PL50 GPC setup (Polymer Laboratories, Amherst, Mass.) with a PL Gel 5 µm pre-column and two 10 µm analytical Mixed-D columns (Polymer Laboratories, Amherst, Mass.). NMR spectra were recorded on a Bruker DPX300 spectrometer (Bruker, Madison, Wis.). High resolution mass spectra were obtained from a JEOL JMS 700 instrument (JEOL, Peabody, Mass.); Matrix Assisted Laser Desorption and Ionization Time of Flight Mass Spectra (MALDI-TOF MS) were measured on a Bruker Daltonics Reflex III (Bruker, Madison, Wis.). The biological activity of the polymer samples (the minimal concentration inhibiting 90% of bacterial growth ($MIC_{90}$) for Escherichia coli (D31) and Staphylococcus aureus (ATCC25923), and the concentration that lyses 50% of red blood cells ($HC_{50}$) were determined as reported previously. (Rennie, et al., Journal of Industrial Microbiology & Biotechnology 2005, 32, 296.) Amberlite IRA67 anion exchange resin (Aldrich) was used for counterion exchange. Dialysis was performed using Cellulose Ester dialysis tubes (SpectraPor6, SpectrumLabs) with a molecular weight cut-off of 1000 Da. Fluorescence measurements were performed on a Jobin Yvon Fluorolog-3. The phospholipid 1,1'-2,2'-tetraoleoyl cardiolipin sodium salt (CL), was obtained as chloroform solutions from Avanti Polar Lipids, Inc. and used as received.

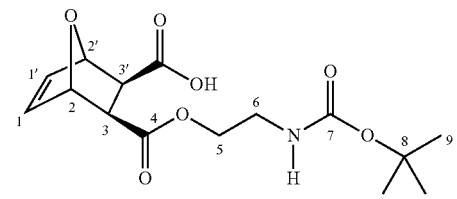

Monomers:

The monomer 2 was obtained from exo-7-oxabicyclo [2.2.1]hept-5-ene-2,3-dicarboxylic acid anhydride 1 (5 g, 30.0 mmol), which was dissolved in $CH_2Cl_2$. 1.1 eq of N-(tert-butoxycarbonyl)ethanolamine (5.32 g, 33 mmol) and 10 mol % 4-dimethylaminopyridine (DMAP) were added. After stirring over night, the solution was concentrated. Ether was added to precipitate DMAP salt, and the solution was filtered. This step was repeated until no more DMAP salts precipitated and the pure zwitterion was obtained. The isolated yield was 60-70%.

$^{1}$H-NMR (300 MHz, $CDCl_3$): δ=1.41 (s, 9H, H9), 2.83 (m, 2H, H3 & H3'), 3.37 (m, 2H, H6), 4.18 (m, 2H, H5), 5.24 &

5.32 (s, 2H, H2 & H2'), 6.46 (m, 2H, H1 & H1'), 7.5-8.2 (br s, 1H, OH). HR-MS (FAB): calc. 299.31 g/mol. found 272.1 g/mol (M-t-Butyl).

The diamine monomer 3 was obtained in a one pot-synthesis from exo-7-oxabicyclo[2.2.1]hept-5-ene-2,3-dicarboxylic acid anhydride 1 without isolating the intermediate 2:1 (5 g, 30.0 mmol) was dissolved in $CH_2Cl_2$. 1.1 eq of N-(tert-butoxycarbonyl)ethanolamine (5.32 g, 33 mmol) and 10 mol % 4-dimethylaminopyridine (DMAP) were added. After stirring over night at r.t., the solution was cooled to 0° C. 1.1 eq N-(tert-butoxycarbonyl)ethanolamine (5.32 g, 33 mmol) and 1.0 eq (6.19 g, 30 mmol) DCC(N,N'-dicyclohexylcarbodiimide) were added, and the mixture was stirred over night. The precipitate was filtered through a short alumina column (5 cm neutral $Al_2O_3$/dichlormethane) and a clear solution was obtained. The solvent was removed by vacuum evaporation and the crude product was chromatographed (15 cm silica gel, hexane:ethyl acetate gradient, 9:1 to 1:1). Evaporation of the solvent yielded the pure monomer. The isolated yield was 70 to 80%.

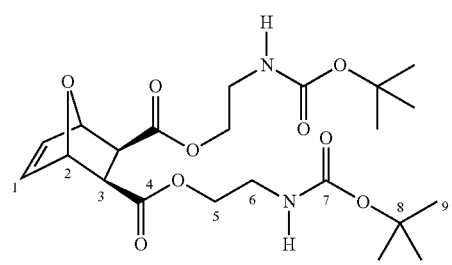

3

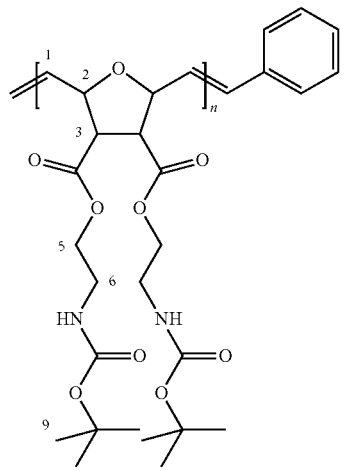

4

4: $^1$H-NMR (300 MHz, $CDCl_3$): 1.42 (s, 9H, H9), 3.15 (br m, 2H, H3), 3.36 (br m, 2H, H6), 4.16 (br m, 2H, H5), 4.72 (m, 1H, H2 trans), 5.10 (br s, 1H, H2 cis), 5.42 (br s, 1H, NH), 5.60 (br m, 1H, H1 cis) and 5.89 (br m, 1H, H1 trans). MALDI-TOF MS (for Diamine_3k): $M_n$=3409 g/mol, $M_w/M_n$=1.07, $M_{repeat\ unit}$=469.6 g/mol.

$^1$H-NMR (300 MHz, $CDCl_3$): δ=1.41 (s, 18H, H9), 2.81 (s, 2H, H3), 3.36 (m, 4H, H6), 4.17 (m, 4H, H5), 5.25 (s, 2H, H2), 6.44 (s, 2H, H1). $^{13}$C-NMR (75 MHz, $CDCl_3$): δ=28.39 (C9), 39.44 (C6), 47.03 (C3), 64.79 (C5), 80.55 (C2), 136.66 (C1). HR-MS (FAB): calc. 470.52 g/mol. found 471.23 g/mol.

Monoamine-Alkylmonomers:

Monomers for the copolymers M, E, P and B (R=Methyl, Ethyl, Propyl and Butyl) were synthesized and characterized. (Lienkamp, et al, *J. Am. Chem. Soc.* 2008, 130, 9836.)

Homopolymerization:

The monomers (2, 3 or 9) and the respective amount of G3-catalyst (see Table 15 for details) were dissolved in 1 mL dichloromethane each and subject to three freeze-thaw cycles. The catalyst was added in one shot to the vigorously stirring monomer solution at room temperature under $N_2$. After 30 min, the living polymer chain was end-capped with an excess of ethylvinyl ether (1 mL, 754 mg, 10.5 mmol). The solution was allowed to stir for 2 hours. After evaporation of the solvent and drying, an aliquot of each polymer was taken for GPC and NMR analysis. The product was a brown solid. GPC was performed in DMF (0.01 M LiCl, polystyrene standards) for polymers 4 and 10, and in THF (polystyrene standards) for polymers 6. NMR and MALDI-TOF data is given below.

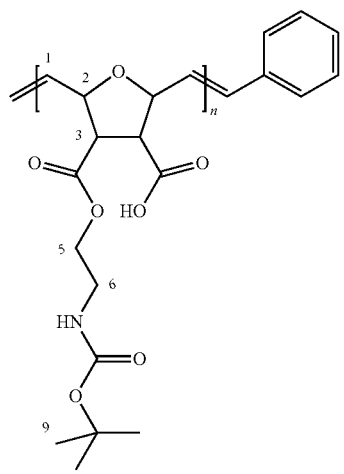

6

6: $^1$H-NMR (300 MHz, THF-$d_8$): 1.40 (s, 9H, H9), 3.10 (br m, 2H, H3 & H3'), 3.28 (br m, 2H, H6), 4.07 (br m, 2H, H5), 4.71 (m, 1H, H2 trans), 5.09 (br s, 1H, H2 cis), 5.59 (br s, 1H, NH), 5.91 (br m, 1H, H1 cis) and 6.12 (br m, 1H, H1 trans). MALDI-TOF MS: n.a.

TABLE 15

Experimental parameters for the homopolymer synthesis.

| Sample | Monomer | $N_{repeat\ units}$ | $M_{n\ Target}$ g $mol^{-1}$ | $M_{Monomer}$ g $mol^{-1}$ | $n_{Monomer}$ mmol | $m_{Monomer}$ mg | $M_{Catalyst}$ g $mol^{-1}$ | $n_{Catalyst}$ mmol | $m_{Catalyst}$ mg |
|---|---|---|---|---|---|---|---|---|---|
| Diamine_3k | 3 | 6.4 | 3000 | 470.5 | 0.425 | 200 | 885 | 0.067 | 59.0 |
| Diamine_5k | | 11 | 5000 | | | | | 0.040 | 35.4 |
| Diamine_10k | | 22 | 10000 | | | | | 0.020 | 17.7 |

TABLE 15-continued

Experimental parameters for the homopolymer synthesis.

| Sample | Monomer | $N_{repeat\ units}$ | $M_{n\ Target}$ g mol$^{-1}$ | $M_{Monomer}$ g mol$^{-1}$ | $n_{Monomer}$ mmol | $m_{Monomer}$ mg | $M_{Catalyst}$ g mol$^{-1}$ | $n_{Catalyst}$ mmol | $m_{Catalyst}$ mg |
|---|---|---|---|---|---|---|---|---|---|
| Diamine_50k  |   | 106  | 50000  |       |       |     |     | 0.004 | 3.5  |
| Diamine_100k |   | 213  | 100000 |       |       |     |     | 0.002 | 1.8  |
| Zwitterion_3k  | 2 | 10.0 | 3000   | 299.3 | 0.668 | 200 |     | 0.067 | 59.0 |
| Zwitterion_10k |   | 33.4 | 10000  |       |       |     |     | 0.020 | 17.7 |

Homopolymer Deprotection:

The crude polymers 4 and 6 respectively, were dissolved in 2 mL dichloromethane. An excess of TFA (2 mL, 2.97 g, 26.0 mmol) was added and the solution was stirred at room temperature over night. The excess acid was removed by azeotropic distillation with dichloromethane (2×15 mL) and methanol (1×15 mL) at the rotary evaporator. The samples were dried in vacuo over night and dissolved in 30 mL Milli-Q water or DMSO depending on solubility. They were dialyzed against Milli-Q water until the conductivity of the water was 0.1 µS after 12 h of dialysis (total dialysis time 4-7 days). The hydrolyzed polymers (5 and 7) were then freeze dried Copolymerization:

Copolymers were synthesized using the same methods as for the homopolymers. Specific reagent amounts are given in Table 16. Each comonomer was dissolved in 0.7 mL dichloromethane separately under argon. The monomer solutions were mixed, and the respective amount of G3 catalyst in 1 mL dichloromethane was added in one shot. The $^1$H-NMR spectroscopic data for each repeat unit proton matched the assignment of the analogous protons in the homopolymers. (Lienkamp, et al, *J. Am. Chem. Soc.* 2008, 130, 9836.) Where possible (no peak overlap), integration revealed that the copolymer composition matched the monomer feed ratio. For simplicity, the $^1$H-NMR peak positions are given for each repeat unit separately.

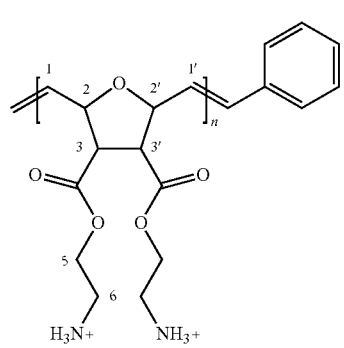

5: $^1$H-NMR (300 MHz, DMSO-d$_6$): 3.01 (br m, 2H, H3), 3.47 (br m, 4H, H6), 4.11 (br m, 4H, H5), 4.44 (br m, 1H, H2 trans), 4.99 (br m, 1H, H2 cis), 5.66 (br m, 1H, H1 cis), 5.84 (br

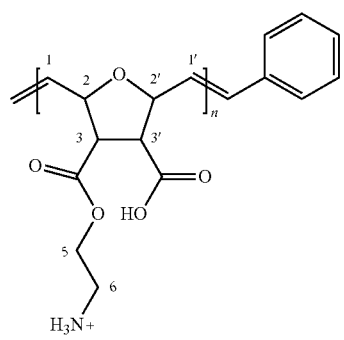

7: $^1$H-NMR (300 MHz, DMSO-d$_6$+D$_2$O): 3.02 (br m, 2H, H3 & H3'), 3.21 (br m, 2H, H6), 3.70 (br m, 2H, H5), 4.28 (m, 1H, H2 trans), 4.42 (br s, 1H, H2 cis), 5.60 (br m, 1H, H1 cis) and 5.83 (br m, 1H, H1 trans).

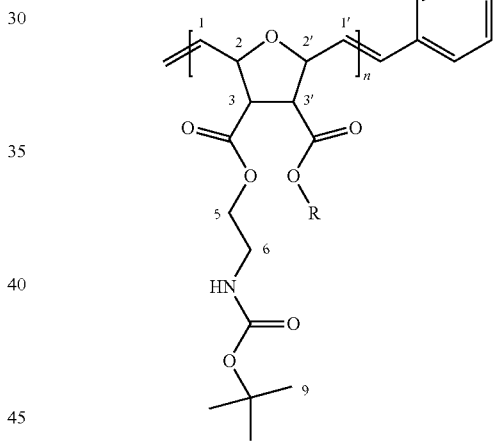

R=Amine: see above (Polymer 5)

R=Methyl: $^1$H-NMR (300 MHz, CDCl$_3$): 1.43 (s, 9H, H9), 3.12 (br m, 2H, H3 & H3'), 3.34 (br m, 2H, H6), 3.71 (s, 3H, CH$_3$), 4.16 (br m, 2H, H5), 4.71 (m, 1H, H2 & H2' trans), 5.10 (br s, 1H, H2 & H2' cis), 5.40 (br s, 1H, NH), 5.58 (br m, 1H, H1 & H1' cis) and 5.88 (br m, 1H, H1 & H1' trans).

R=Ethyl: $^1$H-NMR (300 MHz, CDCl$_3$): 1.24 (s, 3H, CH$_2$—CH$_3$), 1.42 (s, 9H, H9), 3.09 (br m, 2H, H3 & H3'), 3.34 (br m, 2H, H6), 4.16 (br m, 4H, CH$_2$—CH$_3$ and H5), 4.72 (br m, 1H, H2 & H2' trans), 5.10 (br m, 1H, H2 & H2' cis), 5.30 (br s, 1H, NH), 5.58 (br m, 1H, H1 & H1' cis), 5.88 (br m, 1H, H1 & H1' trans).

R=Propyl: $^1$H-NMR (300 MHz, CDCl$_3$): 0.92 (m, 3H, CH$_2$—CH$_3$), 1.43 (s, 9H, H9), 1.62 (m, 2H, β-CH$_2$), 3.12 (br m, 2H, H3 & H3'), 3.34 (br m, 2H, H6), 4.10 (m, 4H, α-CH$_2$ and H5), 4.69 (br m, 1H, H2 & H2' trans), 5.12 (br m, 1H, H2 cis & H2'), 5.31 (br m, 1H, H1 & H1' cis), 5.59 (br s, 1H, NH), 5.88 (br m, 1H, H1 & H1' trans).

R=Butyl: $^1$H-NMR (300 MHz, CDCl$_3$): 0.87 (m, 3H, CH$_2$—CH$_3$), 1.29 (m, 2H, γ-CH$_2$), 1.43 (s, 9H, H9), 1.59 (m, 2H, β-CH$_2$), 3.11 (br m, 2H, H3 & H3'), 3.37 (br m, 2H, H6), 4.10 (m, 4H, α-CH$_2$ and H5), 4.73 (br m, 1H, H2 & H2' trans), 5.11 (br m, 1H, H2 & H2' cis), 5.35 (br s, 1H, NH), 5.59 (br m, 1H, H1 & H1' cis), 5.88 (br m, 1H, H1 & H1' trans).

TABLE 16

Experimental parameters for copolymer synthesis

| Sample | Comonomer | N$_{repeat\ units}$ | M$_{n\ Target}$ g mol$^{-1}$ | n$_{Diamine}$ mmol | m$_{Diamine}$ mg | n$_{Comonomer}$ mmol | m$_{Comonomer}$ mg | n$_{Catalyst}$ mmol | m$_{Catalyst}$ mg |
|---|---|---|---|---|---|---|---|---|---|
| M1:D9 | Methyl | 10 | 4600 | 0.81 | 381 | 0.09 | 30.7 | 0.09 | 79.7 |
| M1:D1 | | | 4100 | 0.45 | 212 | 0.45 | 154 | | |
| M9:D1 | | | 3500 | 0.09 | 42.3 | 0.81 | 277 | | |
| E1:D9 | Ethyl | | 4600 | 0.81 | 381 | 0.09 | 32.0 | | |
| E1:D1 | | | 4100 | 0.45 | 212 | 0.45 | 160 | | |
| P1:D9 | Propyl | | 4600 | 0.81 | 381 | 0.09 | 33.2 | | |
| P1:D1 | | | 4200 | 0.45 | 212 | 0.45 | 166 | | |
| B1:D9 | Butyl | | 4600 | 0.81 | 381 | 0.09 | 34.5 | | |
| B1:D1 | | | 4300 | 0.45 | 212 | 0.45 | 173 | | |

Copolymer Deprotection:

The copolymers were deprotected using the same methods as for the homopolymers, and characterized by $^1$H-NMR. Again, the NMR peaks are given for each

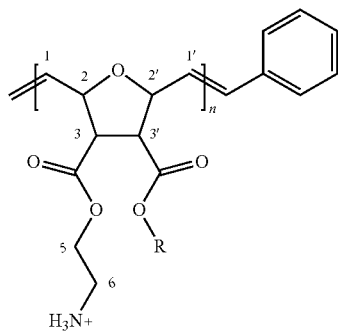

R=Diamine: see above (Polymer 6).

R=Methyl: $^1$H-NMR (300 MHz, DMSO-d$_6$): 3.04 (br m, 2H, H3 & H3'), 3.30 (br m, 2H, H6), 3.59 (s, 3H, CH$_3$), 4.16 (br m, 2H, H5), 4.57 (m, 1H, H2 & H2' trans), 4.91 (br m, 1H, H2 & H2' cis), 5.61 (br m, 1H, H1 & H1' cis), 5.82 (br m, 1H, H1 & H1' trans).

R=Ethyl: $^1$H-NMR (300 MHz, D$_2$O): 1.28 (br s, 3H, CH$_2$—CH$_3$), 3.12 (br m, 2H, H3 H3'), 3.32 (br m, 2H, H6), 3.49-3.81 (br m, 4H, CH$_2$—CH$_3$ and H5), 5.10-5.40 (br m, 2H, H2 & H2'), 5.30-5.90 (br m, 2H, H1 & H1').

R=Propyl: $^1$H-NMR (300 MHz, D$_2$O): 0.94 (br m, 3H, CH$_2$—CH$_3$), 1.67 (br m, 2H, β-CH$_2$), 3.31 (br m, 2H, H3 & H3'), 3.50 (br m, 2H, H6), 4.12 (m, 4H, α-CH$_2$ and H5), 4.39 (br m, 1H, H2 & H2' trans), 5.12 (br m, 1H, H2 & H2' cis), 5.31 (br m, 1H, H1 & H1' cis), 5.88 (br m, 1H, H1 & H1' trans).

R=Butyl: $^1$H-NMR (300 MHz, D$_2$O): 0.93 (m, 3H, CH$_2$—CH$_3$), 1.36 (m, 2H, γ-CH$_2$), 1.61 (m, 2H, β-CH$_2$), 3.10 (br m, 2H, H3 & H3'), 3.48 (br m, 2H, H6), 4.14 (m, 4H, α-CH$_2$ and H5), 4.38 (br m, 1H, H2 & H2' trans), 5.11 (br m, 1H, H2 & H2' cis), 5.35-6.20 (br m, 2H, H1 & H1').

Ion Exchange:

A 20 cm glass column was filled with Amberlite IRA resin and washed with 500 mL distilled water before use. The Diamine__3k polymer was dissolved in water (c=1 g/L), slowly passed through the column (1 drop/min), and washed down with 200 mL distilled water. Immediately after recovery, the solution containing the polymer with OH$^-$ counter ions was split into 4 parts. A ten fold excess of a DMSO solution of the respective counterion in its acid form (toluenesulfonic acid, benzoic acid, hexanoic acid and dodecanoic acid) was added. The mixture was dialyzed against 10 L distilled water until the conductivity of dialysis water was equal to that of fresh distilled water (0.1 µS). The polymer solution was then freeze dried. GPC data of the parent polymers of the ion-exchanged samples, together with their antimicrobial activities, is shown in Table 17. $^1$H-NMR revealed that ion exchange was successful (additional aromatic signals for tosylate and benzoate, and aliphatic signals for hexanoate and dodecanoate, respectively.

TABLE 17

| | | | | MIC$_{90}$ µg mL$^{-1}$ [b] | |
|---|---|---|---|---|---|
| Sample | M$_{n,\ Target}$ [a] g mol$^{-1}$ | GPC M$_n$ [a] g mol$^{-1}$ | M$_w$/M$_n$ [a] | S. aureus | E. coli |
| Diamine__3k [c] | 3000 | 8900 | 1.15 | 15 | >200 |
| Tosylate__3k | | | | >200 | >200 |
| Benzoate__3k | | | | >200 | >200 |
| Hexanoate__3k | | | | >200 | >200 |
| Dodecanoate__3k | | | | >200 | >200 |
| Zwitterion__3k | 3000 | 3100 | 1.21 | 50 | >200 |
| Zwitterion__10k | 10000 | 10700 | 1.16 | >200 | >200 |

[a] GPC data for the protected parent polymers,
[b] MIC data for the hydrolyzed, ion-exchanged polymers.

Vesicle Preparation:

Two buffers were prepared. Buffer A consisted of 1 mmol (142 mg) Na$_2$HPO$_4$ in 100 mL H$_2$O (c=10 mmol L$^{-1}$), which was then adjusted to pH=7.0 with 0.1° mol L$^{-1}$ NaOH. Buffer B was made from 10 mmol (1.42 g) Na$_2$HPO$_4$ in 1 L H$_2$O (c=10 mmol L$^{-1}$) and 90 mmol (5.26 g) NaCl (c=90 mmol L$^{-1}$). Calcein solution was prepared from 0.4 mmol (249 mg) of calcein dye in 10 mL buffer A. 0.1 mol L$^{-1}$ NaOH was added dropwise until all calcein dissolved and the pH was 7.0, yielding a solution of 40 mmol L$^{-1}$.

The CL lipid solution was added to thoroughly clean round bottom flask: 600 µL (10 mmol) CL in chloroform was used. The solvent was evaporated to obtain a lipid film, which was hydrated with 1 mL of calcein solution. The suspension was stirred for 1 h and then subject to five freeze-thaw cycles (liquid nitrogen/water at room temperature). After that it was extruded ten times through a polycarbonate membrane with 400 nm pore diameter (Avanti Polar Lipids Mini-Extruder, Whatman membrane). The dye-filled vesicles were separated from the excess dye using an Sephadex G-50 and buffer B as an eluent. The vesicle fraction from the column was diluted with buffer B by a factor of 20 for the dye-leakage experiments.

Dye-Leakage Experiments:

The polymer-induced leakage was monitored by recording the increase of calcein fluorescence intensity at a wavelength 515 nm (excitation wavelength=490 nm, slit width 3.0). (Eren, et al., *Macromol. Chem. Phys.* 2008, 209, 516.) To normalize the dye-leakage data, a base line of calcein fluorescence without polymer addition was observed for each sample. Also, after each measurement, 20 µL Triton X-100 (20% in DMSO) was added to determine the fluorescence intensity corresponding to 100% leakage. With these data points, the measured fluorescence intensity was converted into % leakage. The polymer samples were dissolved in DMSO at 2 g/L concentrations. Pure DMSO, as well as the acid form of the respective counterions, have been tested previously and was shown not to cause leakage. 20 µL of the 1/20 dilution of vesicles was added to 1980 µL buffer B. 20 µL polymer solution was added at t=100 sec, followed by the addition of Triton X at t=800 sec. This procedure is illustrated in FIG. 21.

d. Facially Amphiphilic Versus Segregated Monomers in Antibacterial Copolymers

Altering the amphiphilicity of antimicrobial polymers has been accomplished most commonly through two methods (FIG. 23). First is the copolymerization of "segregated" monomers, relatively non-polar monomers are polymerized with a masked cationic monomer (the cationic group is produced after polymerization) to produce cationic amphiphilic random copolymers. By using structurally different non-polar monomers having a range of hydrophobicities or by adjusting feed ratios, the amphiphilicities of the copolymers can be straightforwardly varied. This strategy is exemplified by DeGrado, Gellman, and Sen, independently, and by us in this report (structures A-D respectively, FIG. 23). (Kuroda, et al. *Journal of the American Chemical Society* 2005, 127, 4128-4129; Mowery, et al. *Journal of the American Chemical Society* 2007, 129, 15474-15476; Sambhy, et al. *Angewandie Chemie, International Edition* 2008, 47, 1250-1254.)

The second method using "facially amphiphilic" (FA) monomers is a strategy pioneered in our laboratories and involves the synthesis of monomers carrying both a masked cationic group and a non-polar group. (Ilker, et al. *J. Am. Chem. Soc.* 2004, 126, 15870-15875) Therefore every repeat unit of the resulting polymer has a cationic group and a tunable non-polar moiety. The spatial arrangement of polymer E (FIG. 23) or the linker flexibilities of polymer F allows the charged and non-polar moieties to be possibly positioned on opposite sides of the polymer backbone as it conforms to interact with the amphiphilic phospholipid bilayer of bacterial membranes. In effect the polymer itself can become FA. The study of a series of these types of polymers led to the discovery of several very selective polymers in which the compounds preferentially target specific bacteria and not mammalian red blood cells (FIG. 23).

One approach is that the membrane of the bacteria induces a globally amphiphilic conformation of the SMAMP without the benefit of a preorganized FA secondary structure in solution. (Arnt, et al. *Journal of Polymer Science Part A: Polymer Chemistry* 2004, 42, 3860-3864; Arnt, et al. *Langmuir* 2003, 19, 2404-2408; Arnt, et al. *Journal of the American Chemical Society* 2002, 124, 7664-7665; Mowery, et al. *Journal of the American Chemical Society* 2007, 129, 15474-15476.) In these cases it was hypothesized that the orientation of charged and non-polar groups does not necessarily have to conform to a defined secondary structure (helix or n-sheet for example) to exhibit potency. In other words, while AMPs such as human defensin and magainin from amphibians display a well-defined FA solution structure it has been shown that it is not a requirement for the activity of most SMAMPs. Several systems have thus shown that flexible polymers are presumably able to attain a globally FA conformation. (Schmitt, et al. *Journal of the American Chemical Society* 2007, 129, 417-428; Kuroda, et al. *Journal of the American Chemical Society* 2005, 127, 4128-4129; Arnt, et al. *Journal of Polymer Science Part A: Polymer Chemistry* 2004, 42, 3860-3864; Arnt, et al. *Langmuir* 2003, 19, 2404-2408; Arnt, et al. *Journal of the American Chemical Society* 2002, 124, 7664-7665.)

Second is the approach that the specific spatial arrangement of the charge and non-polar groups greatly influences the biological activity thoroughly demonstrated by Sen and coworkers. (Sambhy, et al. *Angewandte Chemie, International Edition* 2008, 47, 1250-1254.) They probed several series of pyridinium polymers that differ only in the spatial positioning of the positive charges and their non-polar alkyl tails (polymer C, FIG. 23). Some copolymers contained the cationic charge and various alkyl groups on the same pyridinium ring and in other copolymers these groups were positioned on different units. Most notably, their system is in contrast to many others which probe the effect of overall charge (and thus global amphiphilicity) and not the arrangement of charged and non-charged side groups locally along the polymer. (Sambhy, et al. *Angewandte Chemie, International Edition* 2008, 47, 1250-1254.)

The spatial arrangement is significant in determining a polymer's activity. Within a polynorbornene framework, this provides a direct comparison between polymers composed of FA monomers and polymers in which the charged and non-polar moieties are segregated on different monomers (FIG. 24). Overall, polyamine oxanorbornene (PAON) exhibited little antibacterial and hemolytic activity. New copolymers in which the amine and various alkyl chains reside on different monomers were designed to survey a wide range of amphiphilicities with the hope of attaining potent and selective polymers. This strategy of copolymerizing segregated monomers converted PAON into an active polymer, with some polymers with encouraging activity. No polymer though was found with selectivities superior to those constructed of very comparable FA monomers. Polymer-induced leakage studies using dye-filled liposomes corroborate a membrane-disruptive mechanism for the active copolymers while microscopy of stained cells in the presence of copolymer support membrane compromise, along with cell agglutination, as a key killing event.

EXAMPLES

Design and Synthesis.

Random copolymers with monomers splitting the charged and non-polar groups (FIG. 25) were synthesized. Instead of installing hydrophobicity early in the synthesis as was done in the previous system using FA monomers, a universal oxanorbornene imide precursor was used and derivatized with different alkyl chains (FIG. 30). One boc-protected amine oxanorbornene monomer and eleven monomers carrying various alkyl chains were synthesized. As a starting point 50/50 mol % random copolymers were targeted at two molecular weights using ring opening metathesis polymerization catalyzed by Grubbs' third generation catalyst. (Love, et al. *Angewandte Chemie, International Edition* 2002, 41, 4035-4037.) Gel permeation chromatography gave monomodal signals with narrow polydispersity indices (1.04-1.15). With this strategy, copolymers with a broad range of amphiphilicities, but with approximately the same number of amines and thus charges, can be easily obtained just by varying the feed ratio of comonomers.

Biological Assays.

MIC assays were used to evaluate the antibacterial properties of these polymers against Gram-negative Ec and Gram-positive Sa (Table 18). PAON was found to be inactive (MIC=400 µg/mL) against both bacteria while the MIC values of the low molecular weight copolymers against Ec showed a clear trend with the polymers of intermediate hydrophobicity (A4, A4', A5, and A5') having the most potent activities (MIC=50 µg/mL) (Table 18 and FIG. 26). The most hydrophilic copolymer A1 and the most hydrophobic copolymer A12 exhibited activities identical to PAON. A similar trend was seen against Sa although these copolymers performed slightly better against Gram-positive bacteria in general. Higher MW copolymers were, for the most part, fairly inactive compared to their lower MW analogues. In comparison, the previous polynorbornenes constructed of FA monomers identified a polymer with an MIC as low as 3.8 µg/mL.

activities (HC≦50 µg/mL) were measured for A4 and copolymers that were more hydrophobic than A4. The higher MW copolymers displayed undesirable hemolytic activities starting even sooner at A3. Finally, selectivity values (HC/MIC) greater than 10 (magainin has a selectivity of 10 for both Ec and S' a) were only observed for low MW A1 and A3 (Selectivity for Sa=20 for both copolymers). This value is far below that seen for the most selective polymers in the previous studies which were >100 (for the center polymer in FIG. 24) and >533 (for several polymers of structure F in FIG. 23).

The ability to adjust biological activities using the monomers that split the charged and non-polar moieties was

TABLE 18

Antibacterial and Hemolytic Activities.

| | PAO | A1 | A2 | A3 | A4 | A4' | A5 | A5' | A6 | A6' | A9 | A12 |
|---|---|---|---|---|---|---|---|---|---|---|---|---|
| Low MW polymers[a] | | | | | | | | | | | | |
| MIC (Ec) | 400 | 400 | 200 | 75 | 50 | 50 | 50 | 50 | 100 | 100 | 200 | 400 |
| MIC (Sa) | 400 | 100 | 50 | 25 | 50 | 50 | 75 | 50 | 100 | 50 | 125 | 100 |
| HC | 2000 | 200 | 250 | 500 | <50 | <50 | <50 | <50 | <50 | <50 | <50 | <50 |
| Selectivity | — | — | 1.3 | 6.7 | < | < | < | < | <05 | <05 | < | < |
| Selectivity | — | 20.0 | 5.0 | 20. | < | < | < | < | < | < | < | < |
| High MW polymers | | | | | | | | | | | | |
| MIC (Ec) | >400 | > | 200 | 50 | 100 | 200 | 400 | 400 | > | > | > | > |
| MIC (Sa) | 400 | 200 | 200 | 200 | 100 | 200 | 200 | 400 | 200 | 400 | 200 | 400 |
| HC | 2000 | 250 | 250 | 50 | <50 | <50 | <50 | <50 | <50 | <50 | <50 | <50 |
| Selectivity | — | — | 1.3 | 1.0 | < | < | — | — | — | — | — | — |
| Selectivity | — | 1.3 | 1.3 | 0.3 | < | < | < | — | < | — | < | — |

[a]MIC and HC values are reported in µg/mL.

Ec = *Escherichia coli*,

Sa = *Staphylococcus aureus*,

Selectivity = HC/MIC. Selectivity values are not given for inactive polymers (MIC ≧ 400 µg/mL).

Incorporating more hydrophobic groups onto the polyamine increased the copolymer's ability to lyse human red blood cells. A high hemolytic concentration (HC) is one measure of non-toxicity against mammalian cells and is important for polymers that may be used in the body as oppose to those developed for self-sterilizing surfaces and fixture. For the low MW copolymers, undesirable hemolytic encouraging. Feed ratios deviating from 50/50 were also explored. Analogues of low MW A1, which was inactive, and A5' which was active but not selective were tested (Table 19). The biological activities did not improve dramatically. In particular, incorporating more hydrophobicity to A1 hardly improved the activity much while adding more charge to A5' did not eliminate the copolymer's high hemolytic activity.

TABLE 19

Data for Non-50/50 Copolymers (Low MW).

| | A1 copolymers | | | | A5' copolymers | | | |
|---|---|---|---|---|---|---|---|---|
| | $A_.8 1_.2$ | $A_.6 1_.4$ | $A_.4 1_.6$ | $A_.2 1_.8$ | $A_.8 5'_.2$ | $A_.6 5'_.4$ | $A_.4 5'_.6$ | $A_.2 5'_.8$ |
| MIC (Ec) | 400 | 400 | 250 | 200 | 50 | 25 | 100 | 250 |
| MIC (Sa) | 200 | 100 | 200 | 250 | 50 | 50 | 100 | 250 |
| HC | 250 | 2000 | 2000 | 500 | <50 | <50 | <50 | <50 |
| Selectivity (Ec) | — | — | 8.0 | 2.5 | <1.0 | <2.0 | <0.5 | 0.6 |
| Selectivity (Sa) | 1.3 | 8.0 | 10.0 | 2.0 | <1.0 | <1.0 | <0.5 | 0.6 |

The inability to tune the biological properties was surprising. It was thought that adding hydrophobicity to A1 via increasing the ratio of the non-polar moiety should theoretically produce a copolymer nearing a similar amphiphilicity as the more hydrophobic copolymers A4 and A5 both of which are active (Table 18). In other words, if global amphiphilicity is a key determinant of activity then an A1 copolymer with a high enough ratio of non-polar groups (>50%) should approach a hydrophobicity (and therefore activity) of A4 or A5, both of which have a non-polar ratio of 50% and are modestly antibacterial. Similarly, making A5' more hydrophilic through feed ratio adjustments unpredictably did not decrease its hemolytic activity even though it was expected that a higher amine to non-polar monomer ratio could push the HC value of A5' closer to that of the relatively less hydrophobic A1 (HC=2000 µg/mL).

These unexpected results for the non-50/50 copolymers, when compared to the 50/50 copolymers and especially when compared to the polymers from FA monomers, support the finding that spatial arrangement of charge and non-polar groups is important and not just the overall amphiphilicity. In fact there may be profound advantageous effects in how a polymer made from FA monomers interacts with the phospholipid bilayer that copolymerization of segregated monomers cannot possibly attain.

It may be possible that due to the imperfect statistical nature of random copolymerization, there may exist runs of polar units and non-polar units, at least for some percentage of the polymer population (FIG. 27 B shows a run of three cationic groups as well as sections of adjacent non-polar units). This arrangement may not be optimum for disrupting the lipid membrane bilayer especially if the polymer loops in and out of the membrane at every repeat unit rather than having close contacts with the membrane as postulated here for the polymers of FA units (FIG. 275 A). With polymers from FA monomers, 100% of the polymer population has every monomer containing the identical ratio of cationic character to hydrophobic character. Because of these results it was not believed that antimicrobial activity and specificity in membrane-active polymers are a matter of overall global charge density. The series of copolymers presented here surveyed a wide range of overall global charge densities. The local charge density and the consistency of that density throughout the polymer may be extremely important.

Membrane Studies.

Two experiments were used to probe the membrane-disruption activity of these copolymers: vesicle dye leakage and fluorescence microscopy. Polymer-induced leakage studies on dye-filled liposomes composed of Ec lipid extracts were performed and showed that the most active copolymers caused the most dye release (FIG. 28). These Ec vesicles seem to model membranes quite well with the dye-leakage results tracking approximately with the MIC values. Still, they are not perfect mimics of Ec as can be seen when comparing the leakage abilities of PAON and A12. Both PAON and A12 have an MIC of 400 against Ec yet A12 caused much more dye release. Presumably, in the complex interactions between polyelectrolytes and vesicle membranes one has to consider that more hydrophobic polymers can interact better with the long alkyl lipid chains buried in the membrane bilayer. Still A12 does not cause as much leakage as the less hydrophobic but more antibacterial A4 and A5.

Additionally, live Ec bacteria were incubated with a two-component stain and treated with and without polymer (FIG. 29). The stain is made up of a green-emitting dye (SYTO9 from Invitrogen) which has the ability to stain all cells and a red-emitting propidium iodide dye that can only enter cells with compromised membranes. Fluorescence microscopy showed that PAON essentially has the same effect on Ec as the negative control. Antibacterial. A4 not only displayed more intense red-emission but also agglutination of the cells possibly due to the aggregation of patches of torn membrane.

Here, using a common copolymerization strategy (copolymerizing a masked amine monomer with different non-polar monomers and at different feed ratios), several antibacterial polyamine oxanorbornenes were identified. Another scheme using designed "facially amphiphilic" monomers, however, gave polymers with better activities and superior selectivities. An optimum hydrophobicity was observed for the most active 50/50 copolymers. Surprisingly, investigation of non-50/50 copolymers did not lead to improved activities or selectivities. This result supports that the balance of hydrophobic/hydrophilic areas at the local monomer level is much more critical to attain highly active and selective polymers rather than just the global amphiphilicity or overall charge density. FA monomers can be used for better control of biological properties.

Synthesis and Characterization

The synthesis of the non-polar oxanorbornene monomers, Monomer 1-12, involved the N-alkylation of a previously reported exo-Oxanorbornene imide (FIG. 30). Typically Oxanorbornene imide (1 eq.) is dissolved in $CH_3CN$ (Fisher Scientific) and the appropriate alkyl bromide (1.2 eq., Aldrich) and $K_2CO_3$ (2 eq., Fisher Scientific) are added, stirred vigorously, and refluxed for 4-8 h. The heterogeneous mixture is then filtered through a course fritted funnel and the $CH_3CN$ is evaporated. The residue is typically an oil which is dissolved in $Et_2O$ (Fisher Scientific) and washed with brine four times. The $Et_2O$ was dried with $Na_2SO_4$ (Fisher Scientific) and evaporated. The solid was then subjected to silica gel chromatography using a $CH_2Cl_2$/MeOH gradient which gave pure product in 55-82% yield depending on the monomer. NMR characterization of Monomer 1-12 follows below.

This monomers were copolymerized by ring-opening metathesis polymerization (ROMP) using Grubbs' 3rd generation catalyst, $[(H_2Imes)(3-Br-py)_2-(Cl)_2Ru=CHPh]$. The polymerization entailed adding to a test tube the appropriate monomers (100 mg total) plus catalyst. The test tube was capped with a septum and purged with $N_2$ for 5 min, then 1 mL dry $CH_2Cl_2$ (Acros, packed under $N_2$ and molecular sieves) was injected. The $N_2$ line was removed and the clear, brown solution was stirred at 28° C. for 30 min after which 0.4 mL ethyl vinyl ether was injected to terminate the polymer. After stirring for 15 min the solution was added dropwise to 300 mL of stirring pentane to precipitate the polymer. The pentane solution was stirred an additional 30 min and left standing undisturbed for an hour. The precipitate was then collected by a fine sinter funnel. The polymer was then redissolved in 1 mL of $CH_2Cl_2$, reprecipitated, collected, and then dried by vacuum for 8 h. NMR characterization of the Boc-protected PAON and A1-A12 follows below.

The Boc-protected polymers were deprotected by stirring 100 mg in 8 mL of 1:1 TFA:$CH_2Cl_2$ for 2 h. The solution was dried to an oil by rotary evaporator set at 40° C. and residual TFA was removed by sonicating the oil in more $CH_2Cl_2$ and evaporating the solvent again by rotary evaporator. The resulting solid was place under vacuum for 2 h. Finally, the solid was fully dissolved in 4 mL $H_2O$ and filtered through a polyethersulphone (PES) syringe filter (Whatman, 25 mm diameter, 0.45 µm pore) and freeze-dried for 48 h to give an eggshell colored soft solid. Final deprotected polymers were stored at −20° C.

Instrumentation.

Gel permeation chromatography (GPC) was performed on the Boc-protected polymers with a Polymer Lab LC1120 pump equipped with a Waters differential refractometer detector. The mobile phase was THF with a flow rate of 1.0 mL/min. Separations were performed with 105, 104, and 103 Å Polymer Lab columns and molecular weights were calibrated versus narrow molecular weight polystyrene standards. The Boc-protected polymers are THF soluble and GPC was used to approximate $M_n$ and polydispersity index (PDI). $^1$H-NMR and $^{13}$C-NMR spectra were obtained on a Bruker DPX-300 or Bruker Avance-400 NMR spectrometer.

Monomer 1.

$^1$H NMR (400 MHz, DMSO-$d_6$): δ=6.55 (2H, s) 5.12 (2H, s), 2.92 (2H, s), 2.81 (3H, s). $^{13}$C-NMR (100 MHz, CDCl$_3$): δ=176.3, 136.5, 80.8, 47.5, 24.9. HR-MS (FAB+): calc. 179.06. found 179.05.

Monomer 2.

$^1$H NMR (400 MHz, DMSO-$d_6$): δ=6.55 (2H, s), 5.13 (2H, s) 3.36 (2H, q, J=7.2 Hz), 2.91 (2H, s), 1.12 (3H, t, J=7.2 Hz). $^{13}$C-NMR (100 MHz, CDCl$_3$): δ=176.1, 136.6, 80.9, 47.4, 33.9, 13.0. HR-MS (FAB+): calc. 193.07. found 193.07.

Monomer 3.

$^1$H NMR (400 MHz, DMSO-$d_6$): δ 6.55 (2H, s), 5.13 (2H, s), 3.31 (2H, t, J=7.5 Hz), 2.92 (2H, s), 1.46 (2H, m), 0.78 (3H, t, J=7.3 Hz). $^{13}$C-NMR (100 MHz, CDCl$_3$): δ=176.4, 136.6, 81.0, 47.8, 40.5, 21.0, 11.1. HR-MS (FAB+): calc. 207.09. found 207.08.

Monomer 4.

$^1$H NMR (400 MHz, DMSO-$d_6$): δ=6.55 (2H, s), 5.12 (2H, S), 3.34 (2H, t, J=7.1 Hz), 2.92 (2H, s), 1.42 (2H, m), 1.21 (2H, m), 0.85 (3H, t, J=7.2 Hz). $^{13}$C-NMR (100 MHz, CDCl$_3$): δ=176.5, 136.5, 81.0, 47.3, 38.9, 28.6, 19.7, 13.7. HR-MS (FAB+): calc. 221.11. found 221.01.

Monomer 4'.

$^1$H NMR (400 MHz, DMSO-$d_6$): δ=6.55 (2H, s), 5.13 (2H, s), 3.16 (2H, d, 7.5 Hz), 2.92 (2H, s), 1.88 (1H, m), 0.79 (6H, d, J=6.6 Hz). $^{13}$C-NMR (100 MHz, CDCl$_3$): δ=176.5, 136.5, 81.0, 47.3, 46.2, 27.0, 19.9. HR-MS (FAB+): calc. 221.11. found 221.10.

Monomer 5.

$^1$H NMR (400 MHz, DMSO-$d_6$): δ=6.55 (2H, s), 5.12 (2H, s), 3.33 (2H, t, J=3.6 Hz), 2.91 (2H, s), 1.43 (2H, m), 1.23 (4H, m), 0.831 (3H, t, J=7.2 Hz). $^{13}$C-NMR (100 MHz, CDCl$_3$): δ=176.3, 136.6, 80.9, 47.4, 39.0, 28.8, 27.3, 22.2, 13.9. HR-MS (FAB+): calc. 235.12. found 235.12.

Monomer 5'.

$^1$H NMR (400 MHz, DMSO-$d_6$): δ=6.55 (2H, s), 5.12 (2H, s), 3.34 (2H, t, J=7.4 Hz), 2.91 (2H, s), 1.48 (1H, m), 1.31 (2H, q, 7.2 Hz), 0.86 (6H, d, J=6.9 Hz). $^{13}$C-NMR (100 MHz, CDCl$_3$): δ=176.3, 136.6, 80.9, 47.4, 37.5, 36.3, 25.9, 22.3. HR-MS (FAB+): calc. 235.12. found 235.10.

Monomer 6.

$^1$H NMR (400 MHz, DMSO-$d_6$): δ=6.55 (2H, s), 5.12 (2H, s), 3.33 (2H, t, J=7.1 Hz), 2.91 (2H, s), 1.43 (2H, s), 1.22 (6H, br), 0.84 (3H, t, J=6.6 Hz). $^{13}$C-NMR (100 MHz, CDCl$_3$): δ=176.3, 136.6, 80.9, 47.4, 39.0, 31.3, 27.6, 26.3, 22.5, 14.0. HR-MS (FAB+): calc. 249.14. found 249.12.

Monomer 6'.

$^1$H NMR (400 MHz, DMSO-$d_6$): δ=6.55 (2H, s), 5.12 (2H, s), 3.24 (2H, d, J=7.2 Hz), 2.92 (2H, s), 1.56 (1H, m), 1.20 (4H, m), 0.81 (6H, t, J=7.4 Hz). $^{13}$C-NMR (100 MHz, CDCl$_3$): δ=176.6, 136.5, 81.0, 47.3, 42.5, 38.6, 23.0, 10.3. HR-MS (FAB+): calc. 249.14. found 249.11.

Monomer 9.

$^1$H NMR (400 MHz, DMSO-$d_6$): δ=6.55 (2H, s), 5.11 (2H, s), 3.32 (2H, t, J=7.1 Hz), 2.91 (2H, s), 1.43 (1H, m), 1.22 (12H, br), 0.85 (3H, t, J=6.8 Hz). $^{13}$C-NMR (100 MHz, CDCl$_3$): δ=176.3, 136.6, 80.9, 47.4, 39.1, 31.8, 29.4, 29.2, 27.6, 26.7, 24.9, 22.7, 14.1. HR-MS (FAB+): calc. 291.18. found 291.18.

Monomer 12.

NMR (400 MHz, DMSO-$d_6$): δ=6.55 (2H, s), 5.11 (2H, s), 3.32 (2H, br), 2.91 (2H, s), 1.42 (2H, s), 1.23 (18H, br), 0.85 (3H, t, J=6.6 Hz). $^{13}$C-NMR (100 MHz, CDCl$_3$): δ=176.3, 136.6, 80.9, 47.4, 32.1, 31.9, 29.6, 29.5, 29.4, 29.3, 29.1, 27.6, 26.7, 22.7, 21.4, 14.1. HR-MS (FAB+): calc. 333.23. found 333.23.

Boc-Protected PAON, High MW.

$^1$H NMR (300 MHz, DMSO-$d_6$): δ=7.61 and 6.96 (1H total, br), 5.95 (trans) and 5.75 (cis) (2H total, br), 4.87 (cis) and 4.42 (trans) (2H total, br), 3.08 (4H, br), 1.35 (9H, s), cis:trans ratio=49:51 (For the lower MW homopolymer, cis:trans ratio=47:53).

PAON, High MW.

$^1$H NMR (300 MHz, DMSO-$d_6$): δ=8.04 (3H, br), 5.96 (1H, br), 5.76 (1H, br), 4.91 (1H, br), 4.48 (1H, br), 3.64 (2H, br), 3.00 (2H, br).

NMR Data for Copolymers.

For the determination of copolymer composition by NMR, the integrations of the t-butyl group(s) of the Boc-protected charged monomers were compared with the methyl signal(s) assigned to the non-polar monomers, to give a charged:non-polar monomer ratio. Proton signals in the 3.3 to 3.5 ppm range were obscured by a water signal in the samples. The following NMR data are for the higher MW but the cis:trans ratio and the charged:non-polar monomer ratio for the low MW analogues are given as well. NMR data for the deprotected copolymers (TFA-salt analogues), A1-A12, are given also.

Boc-Protected A1.

$^1$H NMR (300 MHz, DMSO-$d_6$): δ=6.91 (1H, br), 5.94 (2H, br), 5.74 (2H, br), 4.86 (2H, br), 4.42 (2H, br), 3.08 (2H, br), 2.82 (3H, br), 1.35 (9H, br), cis:trans ratio=54:46, A:1 mol ratio=51:49 (For the lower MW copolymer, cis:trans ratio=49:51, A:1 mol ratio=50:50).

A1.

$^1$H NMR (300 MHz, DMSO-$d_6$): δ=7.96 (3H, br), 5.96 (2H, br), 5.75 (2H, br), 4.89 (2H, br), 4.48 (2H, br), 3.64 (4H, br), 3.00 (2H, br), 2.85 (3H, br).

Boc-Protected A2.

$^1$H NMR (300 MHz, DMSO-$d_6$): δ=6.91 (1H, br), 5.95 (2H, br), 5.74 (2H, br), 4.86 (2H, br), 4.42 (2H, br), 3.08 (2H, br), 1.35 (9H, br), 1.06 (3H, br), cis:trans ratio=52:48, A:2 mol ratio=46:54 (For the lower MW copolymer, cis:trans ratio=47:53, A:2 mol ratio=44:56).

A2.

$^1$H NMR (300 MHz, DMSO-$d_6$): δ=7.94 (3H, br), 5.96 (2H, br), 5.75 (2H, br), 4.88 (2H, br), 4.45 (2H, br), 3.62 (br), 2.99 (2H, br), 1.06 (3H, br).

Boc-Protected A3.

$^1$H NMR (300 MHz, DMSO-$d_6$): δ=6.91 (1H, br), 5.95 (2H, br), 5.74 (2H, br), 4.86 (2H, br), 4.42 (2H, br), 3.08 (2H, br), 1.49 (2H, br), 1.35 (9H, br), 0.82 (3H, br), cis:trans ratio=50:50, A:3 mol ratio=47:53 (For the lower MW copolymer, cis:trans ratio=44:56, A:3 mol ratio=43:57).

A3.

$^1$H NMR (300 MHz, DMSO-$d_6$): δ=7.90 (3H, br), 5.96 (2H, br), 5.76 (2H, br), 4.88 (2H, br), 4.45 (2H, br), 3.62 (br), 2.99 (2H, br), 1.50 (2H, br), 0.82 (3H, br).

Boc-Protected A4.

$^1$H NMR (300 MHz, DMSO-$d_6$): δ=6.91 (1H, br), 5.95 (2H, br), 5.74 (2H, br), 4.86 (2H, br), 4.42 (2H, br), 3.08 (2H, br), 1.45 (2H, br), 1.35 (9H, br), 1.25 (2H, br), 0.87 (3H, br), cis:trans ratio=51:49, A:4 mol ratio=47:53 (For the lower MW copolymer, cis:trans ratio=48:52, A:4 mol ratio=44:56).

A4.

$^1$H NMR (300 MHz, DMSO-$d_6$): δ=7.92 (3H, br), 5.96 (2H, br), 5.76 (2H, br), 4.88 (2H, br), 4.42 (2H, br), 3.63 (br), 2.99 (2H, br), 1.46 (2H, br), 1.23 (2H, br), 0.87 (3H, br).

Boc-Protected A4'.

$^1$H NMR (300 MHz, DMSO-$d_6$): δ=6.90 (1H, br), 5.96 (2H, br), 5.75 (2H, br), 4.86 (2H, br), 4.42 (2H, br), 3.17 (2H, br), 3.08 (2H, br), 1.90 (1H, br), 1.35 (9H, br), 0.82 (6H, br), cis:trans ratio=51:49, A:4' mol ratio=50:50 (For the lower MW copolymer, cis:trans ratio=46:54, A:4' mol ratio=48:52).

A4'.

$^1$H NMR (300 MHz, DMSO-$d_6$): δ=7.93 (3H, br), 5.97 (2H, br), 5.76 (2H, br), 4.88 (2H, br), 4.42 (2H, br), 3.62 (br), 3.18 (2H, br), 2.99 (2H, br), 1.91 (1H, br), 0.83 (6H, br).

Boc-Protected A5.

$^1$H NMR (300 MHz, DMSO-$d_6$): δ=6.90 (1H, br), 5.95 (2H, br), 5.74 (2H, br), 4.86 (2H, br), 4.41 (2H, br), 3.08 (2H, br), 1.47 (2H, br), 1.35 (9H, br), 1.23 (4H, br), 0.84 (3H, br), cis:trans ratio=52:48, A:5 mol ratio=46:54 (For the lower MW copolymer, cis:trans ratio=47:53, A:5 mol ratio=43:57).

A5.

$^1$H NMR (300 MHz, DMSO-$d_6$): δ=7.93 (3H, br), 5.96 (2H, br), 5.76 (2H, br), 4.88 (2H, br), 4.42 (2H, br), 3.63 (br), 2.99 (2H, br), 1.48 (2H, br), 1.24 (4H, br), 0.85 (3H, br).

Boc-Protected A5'.

$^1$H NMR (300 MHz, DMSO-$d_6$): δ=6.90 (1H, br), 5.95 (21-1, br), 5.74 (2H, br), 4.86 (2H, br), 4.41 (2H, br), 3.08 (2H, br), 1.49 (3H, br), 1.35 (9H, br), 0.88 (6H, br), cis:trans ratio=53:47, A:5' mol ratio=49:51 (For the lower MW copolymer, cis:trans ratio=46:54, A:5' mol ratio=49:51).

A5'.

$^1$H NMR (300 MHz, DMSO-$d_6$): δ=7.93 (3H, br), 5.96 (2H, br), 5.76 (2H, br), 4.88 (2H, br), 4.42 (21-1, br), 3.62 (br), 2.99 (2H, br), 1.51 (1H, br), 1.37 (2H, br), 0.88 (6H, br).

Boc-Protected A6.

$^1$H NMR (300 MHz, DMSO-$d_6$): δ=6.90 (1H, br), 5.95 (2H, br), 5.74 (2H, br), 4.85 (2H, br), 4.41 (2H, br), 3.08 (2H, br), 1.46 (2H, br), 1.35 (9H, br), 1.23 (6H, br), 0.84 (3H, br), cis:trans ratio=49:51, A:6 mol ratio=47:53 (For the lower MW copolymer, cis:trans ratio=45:55, A:6 mol ratio=41:59).

A6.

$^1$H NMR (300 MHz, DMSO-$d_6$): δ=7.96 (3H, br), 5.96 (2H, br), 5.76 (2H, br), 4.88 (2H, br), 4.42 (2H, br), 3.63 (br), 2.99 (2H, br), 1.47 (2H, br), 1.24 (6H, br), 0.85 (3H, br).

Boc-Protected A6'.

$^1$H NMR (300 MHz, DMSO-$d_6$): δ=6.90 (1H, br), 5.96 (2H, br), 5.74 (2H, br), 4.85 (2H, br), 4.41 (2H, br), 3.08 (2H, br), 1.59 (1H, br), 1.35 (9H, br), 0.83 (6H, br), cis:trans ratio=52:48, A:6' mol ratio=49:51 (For the lower MW copolymer, cis:trans ratio=47:53, A:6' mol ratio=47:53).

A6'.

$^1$H NMR (300 MHz, DMSO-$d_6$): δ=7.92 (3H, br), 5.97 (2H, br), 5.76 (2H, br), 4.86 (2H, br), 4.42 (2H, br), 3.62 (br), 2.99 (2H, br), 1.59 (1H, br), 1.22 (4H, br), 0.83 (6H, br).

Boc-Protected A9.

$^1$H NMR (300 MHz, DMSO-$d_6$): δ=6.90 (1H, br), 5.95 (2H, br), 5.74 (2H, br), 4.86 (2H, br), 4.41 (2H, br), 3.08 (2H, br), 1.46 (2H, br), 1.35 (9H, br), 1.23 (12H, br), 0.84 (3H, br), cis:trans ratio=51:49, A9 mol ratio=41:59 (For the lower MW copolymer, cis:trans ratio=45:55, A:9 mol ratio=46:54).

A9.

$^1$H NMR (300 MHz, DMSO-$d_6$): δ=7.94 (3H, br), 5.96 (21-1, br), 5.76 (2H, br), 4.89 (2H, br), 4.42 (2H, br), 3.63 (br), 2.99 (2H, br), 1.47 (2H, br), 1.20 (12H, br), 0.85 (3H, br).

Boc-Protected A12.

$^1$H NMR (300 MHz, DMSO-$d_6$): δ=6.90 (1H, br), 5.95 (2H, br), 5.74 (2H, br), 4.86 (2H, br), 4.41 (2H, br), 3.08 (2H, br), 1.45 (2H, br), 1.34 (9H, br), 1.22 (18H, br), 0.84 (3H, br), cis:trans ratio=51:49, A12 mol ratio=44:56 (For the lower MW copolymer, cis:trans ratio=45:55, A:12 mol ratio=44:56).

A12.

$^1$H NMR (300 MHz, DMSO-$d_6$): δ=7.94 (3H, br), 5.96 (2H, br), 5.76 (2H, br), 4.87 (2H, br), 4.42 (2H, br), 3.63 (br), 2.99 (2H, br), 1.46 (2H, br), 1.19 (18H, br), 0.85 (3H, br).

Microbial and Hemolysis Assays

Bacteria suspensions of Ec, and Sa (*Escherichia coli* D31 and *Staphylococcus aureus* ATCC 25923) were grown in Mueller-Hinton Broth (MHB) overnight at 37° C., diluted with fresh MHB to an optical density of 0.001 at 600 nm ($OD_{600}$). This $OD_{600}$ gave an initial bacterial concentration of ~$10^5$ cells/mL. This suspension was mixed with different concentrations of freshly prepared polymer solutions dissolved in DMSO (40 mg/mL stock solution) by serial dilutions in a 96-well plate, and incubated for 6 h at 37° C. The $OD_{600}$ was measured for bacteria suspensions that were incubated in the presence of polymer solution or only MHB. Antibacterial activity was expressed as minimal inhibitory concentration (MIC), the concentration at which more than 90% inhibition of growth was observed after 6 h. All experiments were run in quadruplicate.

Hemolytic activity measurements were performed on all polymers. Freshly drawn human red blood cells (RBC, 30 μL), were suspended in 10 mL of Tris saline (10 mM Tris, 150 mM NaCl, pH 7.2, filtered through PES membrane with 0.22 μm pore size) and rinsed three times by centrifugation (5 min at 1500 rpm) and resuspended in Tris saline. Polymer solutions were prepared in DMSO at 40 mg/mL and further diluted as necessary. Freshly prepared polymer solutions with different concentrations were added to 100 μL of the above-prepared RBC suspension to reach a final volume of 200 μL on a 96-well plate. The resulting mixture was kept at 37° C. for 30 min on a stirring plate. Then the plate was centrifuged (IEC Centra-4B, 10 min at 1500 rpm), and the supernatant in each well was transferred to a new plate. Hemolysis was monitored by measuring the absorbance of the released hemoglobin at 414 nm. 100% Hemolysis was obtained by adding 10 μL of Triton-X (polyoxyethylene isooctylphenyl ether from Sigma-Aldrich) solution (20 vol % in DMSO), a strong surfactant, to the above-prepared HRBC suspension. The upper limit of polymer concentration that was required to cause 50% hemolysis is reported as $HC_{50}$, and the absorbance from Tris saline containing no polymer was used as 0% hemolysis. All experiments were run in quadruplicate.

Dye-Leakage from Large Unilamellar Vesicles

The following is a general procedure to make large unilamellar vesicles (LUV). Chloroform solutions of Cc lipids (25 mg, Avanti Polar Lipids, Inc.) were mixed in a 10 mL round bottom flask and the chloroform was removed at room temperature by rotary evaporator to form a uniform film. The flask was placed under vacuum for an additional 6 h. The dried film was hydrated with 1 mL of a 40 mM aqueous calcein (Sigma-Aldrich) solution in Tris buffer without added NaCl. The calcein dye solution was adjusted to pH=7 prior to adding it to the film. The solution was subjected through five freeze/thaw cycles using liquid nitrogen and warm water. The entire volume of 1 mL of solution was subjected to extrusion (a total of 15 passes) through two stacked 400 nm pore PC membranes (Avanti Polar Lipids, Inc.) at room temperature. Finally, the solution was pressurized through a small column packed with Sephadex-25 (Sigma-Aldrich) eluting with Tris-saline buffer to remove non-trapped calcein dye. Fractions (~5 drops each) were collected. The vesicle solution can be stored in a vial at 4° C. and diluted as needed for up to 4 days.

Diluted calcein-loaded vesicle fractions that afforded fluorescence intensities <80 a.u. without surfactant and >800 a.u. after addition of surfactant, were used (Ex.=490 nm used and Em.=515 nm monitored). 50 µL of 0.2% Triton-X was used as the strong surfactant which causes complete vesicle disruption and leakage. Typically, chosen vesicle fractions were diluted six-fold and 25 µL of this stock solution is added to 2 mL of Tris-saline buffer. A fluorescence intensity of <80 a.u. is verified to be stable over a minute before 25 µL of a polymer stock solution is added (2.5 µg/mL final concentration in cuvette), agitated briefly with the pipettor tip, then monitored at 515 nm. After 5 min Triton-X is added and the corresponding fluorescence was taken as 100% leakage.

Fluorescence Microscopy of Stained Bacteria Cells

An Olympus BX51 Reflected Fluorescence Microscope (Optical Analysis Corp. Nashua, N.H.) with a 100 W Mercury Lamp (Chin Technical Corp.) was used for fluorescence studies. A BacLight™ Kit L-7012 (Invitrogen Corp.) was used as the fluorescence dye in a mixture of 1:1 propidium iodide:SYTO9 to examine Sa in the presence of polymer. It is important to mention that an initial bacterial concentration of ~$10^8$ cells/mL was used for microscopy studies (three orders of magnitude higher than the MIC and bactericidal kinetics studies) for ease of visualization. The dye mixture was incubated with the bacteria at room temperature for 15 minutes before adding polymer solution (75 µg/mL final concentration). Solution of cells, dye, and polymer were allowed to sit for 30 min before 50 µL was placed on a slide, fitted with a coverslip, and visualized. Bacteria were viewed under a green filter (excitation/emission, 420-480 nm/520-800 nm) or a red filter (480-550 nm/590-800 nm).

e. A ROMP-Based Platform for SMAMPs

From AMPs Via Foldamers to Romp-Based SMAMPS—an Evolution

AMPs are host-defense peptides found in many organisms from invertebrates to humans. Their important feature is that they are facially amphiphilic molecules, as illustrated in FIG. 31. They contain a face with hydrophilic, positively charged groups (blue) and a hydrophobic face (green). (Boman, *Immunol. Rev.* 2000, 173, 5.) This segregation of the hydrophilic and hydrophobic side chains onto two opposite sides of the molecule results from the amino acid sequence of the peptide, which also dictates the conformation of the backbone and thus the secondary structure of the molecule. While most traditional antibiotics have specific cellular targets, AMPs use non-receptor interactions, including direct action against the bacteria's membranes, although intracellular targets have been identified in some cases. (Brodgen, *Nature Rev. Microbiol.* 2005, 3, 238.) Their facial amphiphilicity enables them to insert into cell membranes and locally change the membrane lipid organization, leading to pore formation, membrane rupture, or other interactions that impact the membrane elasticity so that cell viability is compromised. Several mechanisms have been proposed for trans-membrane pore formation by AMPs (carpet, barrel-stave and toroidal pore model). (Brodgen, *Nature Rev. Microbiol.* 2005, 3, 238; Yang, et al., *J. Am. Chem. Soc.* 2007, 127, 12141; Zasloff, *Nature* 2002, 415, 389; Boman, *Immunol. Rev.* 2000, 173, 5; Hancock, et al., *Trends Biotech.* 1998, 16, 82; Yeaman, et al., *Pharmacol. Rev.* 2003, 55, 27.) The careful balance between cationic hydrophilic and hydrophobic groups allows AMPs to differentiate between the neutral, phosphatylcholine and cholesterol rich surface of mammalian cells and the negatively charged cell surface of bacteria.

As AMP extraction from natural organisms or their production in multi-step syntheses is tedious and expensive, SMAMP research strived for a platform that yielded a library of molecules which retained the antibacterial activities of AMPs, but would be obtained in a few synthetic steps and in large quantities. As such, many substance classes have been used, including α- and β-amino acids, peptoids, aromatic oligomers, steroids, and synthetic polymers. (Mowery, et al., *J. Am. Chem. Soc.* 2007, 129, 15474; Kuroda, et al., *J. Am. Chem. Soc.* 2005, 127, 4128; Arnt, et *Polymer Sci. A-Polymer Chem.* 2004, 42, 3860; Tew, et al., *Proceed. Nat. Acad. Sci. USA* 2002, 99, 5110; Zasloff, *Proceed. Nat. Acad. Sci. USA* 1987, 84, 5449; Castro, et al., *Current Protein Peptide Sci.* 2006, 7, 473; Chen, et al., *J. Biol. Chem.* 2005, 280, 12316; Won, et al., *J. Biol. Chem.* 2004, 279, 14784; Hamuro, et al., *J. Am. Chem. Soc.* 1999, 121, 12200; Porter, et al., *Nature* 2000, 404, 565; Liu, et al., *J. Am. Chem. Soc.* 2001, 123, 7553; Epand, et al., *Biochemistry* 2004, 43, 9527; Patch, et al., *J. Am. Chem. Soc.* 2003, 125, 12092; Brouwer, et al., *Peptides* 2006, 27, 2585; Haynie, et al., *Antimicrob. Agents Chemother.* 1995, 39, 301; Liu, et al., *Angew. Chem. Internal. Ed.* 2004, 43, 1158; Tang, et al., *Chem. Comm.* 2005, 1537; Savage et al., *FEMS Microbio. Lett.* 2002, 217, 1; Mason et al., *Biophysical Journal* 2007, 93, 4289; Van et al. *Trends Pharmacol. Sci.* 2008, 29, 124; Ilker, et al., *J. Am. Chem. Soc.* 2004, 126, 15870; Arnt, et al., *J. Am. Chem. Soc.* 2002, 124, 7664; Arnt, et al., *Langmuir* 2003, 19, 2404.) Initially, it was believed that the helical rigidity of the AMP backbone (FIG. 31) was a prerequisite for biological activity. As a result, early work focused on emulating the amphiphilic α-helical arrangement of side chains observed in the natural structures, leading to a large number of potent and selective antimicrobial peptides based on the natural amino acids. The availability of β-peptides provided another avenue to test and further elucidate the features required for the construction of SMAMPs. $β^3$-peptides adopt "14-helices (14 residues within the repeating hydrogen-bonded rings), which have an approximate β-residue geometric repeat. Thus, if polar and apolar sidechains are arranged with precise three-residue periodicity in the sequence of an appropriately designed β-peptide, they will segregate to opposite sides of the helix. Indeed, repeating tripeptides composed of hAla, hLeu and/or hVal (the β-amino acids were $β^3$-substituted) were found to be have antimicrobial activity. Meanwhile, Gellman and coworkers described a potent and highly selective antimicrobial peptide based on cyclic β-amino acids. (Hamuro, et al., *J. Am. Chem. Soc.* 1999, 121, 12200; Porter, et al., *Nature* 2000, 404, 565; Liu, et al., *J. Am. Chem. Soc.* 2001, 123, 7553.) These studies, which were subsequently extended to a variety of different helical types formed by β-peptides, showed that charge, facial amphiphilicity, and an appropriate hydrophilic/hydrophobic balance were important to obtaining selective, non-toxic compounds.

All of these synthetic derivatives focused on helical secondary structures; however, the critical role of this secondary structural element was questioned early on as other folded forms of natural peptides were discovered. Within the synthetic analog community, early work on diastereomeric peptides containing D-amino acid substitutions believed to have little α-helix forming abilities but potent antibacterial activity supported this conclusion. (Shai, et al., *Peptides* 2001, 22, 1629; Hong, et al., *Biochemistry* 1999, 38, 16963; Oren, et al. *Biochemistry* 1997, 36, 1826.) Further support for the overall amphiphilicity being more important than a specific folded structure comes from recent work on scrambled sequence α/β-peptides which are selective antimicrobial agents without the ability to adopt globally amphiphilic helices.

(Schmitt, et al., *J. Am. Chem. Soc.* 2007, 417.) Thus, it appears that there is no unique requirement for a rigid conformation so long the composition of that sequence is conducive for binding to the target membrane.

It is questionable whether this general approach could be extended to design much simpler oligomers and polymers that capture the essential biological and physiochemical properties of AMPs. In particular, one can consider two design strategies: On the one hand, the amphiphilic secondary and tertiary structures of natural AMPs can be mimicked by placing hydrophilic and hydrophobic groups on an appropriate framework. In this case, a preorganized backbone would help minimize the unfavorable conformational entropy of binding leading to good potency. On the other hand, if a rigid conformation is not an absolute requirement for activity, far more flexible (co)polymers might be expected to be active as they would be able to adopt the necessary conformations. In either case, it is important to optimize the structures for maximal activity by careful consideration of the molecular weight, charge and hydrophilic/lipophilic balance.

Probably the most (r)evolutionary step in SMAMP design simplification was to completely, dispense with the helical motif in favor of a less complicated but rigid aromatic molecular scaffold. DeGrado and Tew developed aryl amide-based oligomeric SMAMPs with facially amphiphilic repeat units. (Tew, et al., *Proceed. Nat. Acad. Sci. USA* 2002, 99, 5110; Liu, et al., *Angew. Chem. Internat. Ed.* 2004, 43, 1158; Breitenkamp, et al., *Polymers Adv. Technol.* 2005, 16, 189.) These molecules were still potently antibacterial, and while they did not have the confinement of the helical secondary structure, the rigidity of the aryl amide backbone and hydrogen bonding between their functional groups ensured that one side of the molecule contained the hydrophobic groups and the opposite side the charged hydrophilic groups. This work clearly demonstrated that a helical backbone is not necessary. By synthesizing molecules with a phenylene ethynylene backbone, it was tested whether the configuration constraints of the backbone could be further relaxed. These molecules still possessed the rigidity of an aromatic backbone, but had no intramolecular hydrogen bonds. (Tew, et al., *Biochim. Biophys. Acta-Biomembranes* 2006, 1758, 1387; Arnt, et al., *J. Polymer Sci.A-Polymer Chem.* 2004, 42, 3860; Arnt, et al. *J. Phys. Chem. B* 2006, 110, 3527; Arnt, et al., *Langmuir* 2003, 19, 2404; Breitenkamp, et al., *Polymers Adv. Technol.* 2005; 16, 189; Arnt, et al., *Macromolecules* 2004, 37, 1283.) While the aromatic backbone ensured an overall linear conformation, the repeat units were free to rotate around their single bonds. This allowed their functional groups to orient themselves to a facially amphiphilic conformation upon contact with a cell membrane or a similar hydrophilic-hydrophobic interface. The phenylene ethynylene polymers had the desired antibacterial activities; by small-angle X-ray scattering, it was shown that even phenylene ethynylene trimers were able to form pores when exposed to model membranes. (Yang, et al., *J. Am. Chem. Soc.* 2007, 127, 12141.)

The final move in SMAMP design was to get rid of the rigid aromatic backbone altogether and to equip synthetic polymers with hydrophobic and hydrophilic repeat units, hoping they would self-orient their functional groups to be facially amphiphilic and membrane active upon contact with cells. Several polymers were synthesised based on this idea, and it was demonstrated that, if the functional groups were adequately balanced and positioned, even this last constraint could be given up while the polymers still had superb antibacterial properties. (Sambhy, et al., *Angew. Chem. Int. Ed.* 2008, 47, 1250; Mowery, et al., *J. Am. Chem. Soc.* 2007, 129, 15474; Ilker, et al., *J. Am. Chem. Soc.* 2004, 126, 15870; Gabriel, et al., *Chem. Eur. J.* 2009, 15, 433; Lienkamp, et al., *J. Am. Chem. Soc.* 2008, 130, 9836.)

ROMP-Based Synthetic Mimics of Antibacterial Peptides

Over the last five years, a large number of ROMP-based SMAMPs were synthesized, and both their biological properties and mechanism of interaction with membranes were studied. The structures of these compounds are summarized in FIG. 34. This figure illustrates how, by gradual structural variation, a library of polymers with tunable antibacterial and hemolytic properties was obtained, and how the investigation of structure-property relationships of those polymers helped to elucidate key factors of SMAMP design.

ROMP was chosen as a synthetic platform as it is a living polymerization technique, yields molecules with low polydispersity over a wide range of molecular weights and is highly functional group tolerant. (Kiessling, et al., Vol. 3, Wiley-VCH, Weinheim, 2003; Trnka, et al., *Acc. Chem. Res.* 2001, 34, 18; Buchmeiser, *Chemical Rev.* 2000, 1565.) The variety of molecules, especially bioactive ones, that were accessible through ROMP has been reviewed elsewhere. (Smith, et al., *Polymer Rev.* 2007, 47, 419.)

The field of ROMP-based SMAMPs was pioneered by Ilker et al. (Ilker, et al., *J. Am. Chem. Soc.* 2004, 126, 15870.) They reported a series of poly(norbornene) derivatives with facially amphiphilic repeat units (poly1 to poly4, series 1 in FIG. 34). In this polymer series, the ratio of hydrophobic and hydrophilic moieties per repeat unit was gradually varied, and the effect of this variation on the antibacterial and hemolytic activities of these polymers was studied where a backbone-modification strategy was used to obtain the desired gradient in hydrophobicity across the polymer series, in which the different hydrophobic groups are attached in the first step of monomer synthesis (FIG. 33*a*).

These polymers are large molecular weight SMAMP-derivatives with good selectivity (>100). Also, this parent series with its norbornene-imide structure inspired many further modifications that allowed property fine tuning or more detailed investigations of certain design parameters, as illustrated in FIG. 34.

Unlike the imide-based series, whose polymers are more difficult to synthesize because the backbone modification comes in an early step (FIG. 33*a*), and thus each monomer requires different precursors to be prepared, ester-based monomers (2 in FIG. 34) can be obtained from the same precursor and the critical modification leading to installation of the different hydrophilic or hydrophobic groups is introduced independently and in either order in the last synthetic steps (FIG. 33*b*). Thus, a large variety of monomers can be obtained from the same precursors, which is why this ester-based platform is termed a 'molecular construction kit'. (See Section a above; Lienkamp, et al., *J. Am. Chem. Soc.* 2008, 130, 9836.)

Structural Modifications and their Effects on SMAMP Activity

Increasing Hydrophobicity in a Series of Facially Amphiphilic Homopolymers

Three series of polymers with facially amphiphilic repeat units and gradually increasing hydrophobicity have been synthesized. (Ilker, et al., *J. Am. Chem. Soc.* 2004, 126, 15870; Lienkamp, et al., *J. Am. Chem. Soc.* 2008, 130, 9836; Eren, et al., *Macromolecular Chem. Phys.* 2008, 209, 516.) The already mentioned poly(norbornene) imide series is shown as 1 in FIG. 34. In this series of molecules, the hydrophilic, cationic ammonium group was kept constant, and the hydrophobic group attached to the backbone was modified. The result of this structural modification on the biological properties is summarized in FIG. 35*a*. (Ilker, et al., *J. Am. Chem.*

Soc. 2004, 126, 15870.) Eren et al. synthesized a series of poly(oxanorbornene) derivatives similar to poly1, the most hydrophilic polymer of series 1. They obtained different hydrophobicities by alkylation of the imide with side chains of different length containing quaternary pyridinium groups. (Eren, et al., *Macromolecular Chem. Phys.* 2008, 209, 516.) This yielded series 3, with R=ethyl to dodecyl, and R=phenylethyl. The biological data for these molecules are shown in FIG. 35*b*. Using the ester-based platform (Series 2 in FIG. 34), a systematic change of the hydrophobic group from R=methyl to hexyl led to a third series of hydrophobically modified polymers. The $MIC_{90}$ and $HC_{50}$ values for this series are shown in FIG. 35*c*. When comparing FIG. 35*a* to *c*, overall the same trends are observed in the antibacterial and hemolytic activities of these polymers. The $HC_{50}$ values are highest for the most hydrophilic polymers and then decrease significantly as the polymers become more hydrophobic, which means that adding hydrophobicity makes the SMAMPs increasingly more hemolytic. The $MIC_{90}$ values start off high for more hydrophilic polymers, meaning that those are inactive, and then go through a minimum for all three series, with poly3 (FIG. 35*a*), the octyl imide (FIG. 35*b*), and the propyl ester (FIG. 35*c*) being the most active structures in each series, respectively. At one point, however, the solubility of the SMAMP decreases so much that it severely aggregates and consequently becomes unavailable to interact with the bacteria membrane; therefore the $MIC_{90}$ value goes up again. The overlapping trend of increasing activity and decreasing solubility then lead to the observed minimum in the $MIC_{90}$ data for all three series of polymers. Thus, with increasing hydrophobicity the polymers become toxic to both bacteria and mammalian cells.

Copolymers—Facially Amphiphilic Versus Segregated Monomers

Since poly3 in Series 1 had the lowest $MIC_{90}$, and poly2 the highest $HC_{50}$, Ilker et al. attempted to increase the therapeutic window of these polymers by copolymerizing the corresponding two monomers at different ratios, and tested their activities. (Ilker, et al., *J. Am. Chem. Soc.* 2004, 126, 15870.) The biological data thus obtained is summarized in FIG. 36*a*. As can be seen from this data, for monomer feed ratios from 2:1 to 9:1, the resulting copolymers stayed non-hemolytic but became active even when the molar ratio the 'antimicrobial' component was 10%. This led to selectivities as high as 100 against both *E. coli* and *S. aureus* bacteria. Similar results were obtained when monomers of the ester series (2) were copolymerized. While the ethyl homopolymers of that series were the ones with the highest selectivity, the methyl polymers were the least hemolytic and the propyl polymers the most active. Thus, a systematic property variation was expected by copolymerization of these monomers. Three copolymer series (Series 4 in FIG. 34, with R1/R2=methyl/ethyl, methyl/propyl and ethyl/propyl) were thus obtained. The biological data from these series is summarized in FIG. 36*b-d*. Copolymerization of the ethyl with the methyl copolymer gave little improvement in the antimicrobial properties, and no significant difference in the $HC_{50}$ data. Likewise, while incorporation of ethyl into the propyl copolymers made those less toxic, at the same time they lost their activity. The methyl-propyl copolymers, on the other hand, show the same trend as the poly2-poly3 copolymers, and can therefore be considered as the direct analogue to that series. From a feed ratio of 1:9 to 9:1, these polymers became more active against *S. aureus* bacteria, and at the same time less hemolytic. The selectivities of those polymers were >533. However, unexpectedly, these polymers lost their activity against *E. coli* and were therefore termed 'doubly selective' SMAMPs because they were active against bacteria, but did not lyse mammalian cells, and they preferentially killed one kind of bacteria over another.

The common structural feature of both the poly2-poly3 copolymers and the ester-based copolymers (4) is that both comonomers were facially amphiphilic. While successive structural simplification in going from AMPs via foldamers to SMAMPs showed that many design features, such as the rigid nature of the backbone and the presence of aromatic groups, were not essential for obtaining high selectivities for bacteria over mammalian cells, it was found by Gabriel et al. that the facial amphiphilicity on the monomer level was critical. (Gabriel, et al., *Chem. Eur. J.* 2009, 15, 433.) To obtain a polymer series with tunable antimicrobial properties without the need to go through the tedious synthetic procedures of the poly1-4 series (FIG. 34), SMAMP copolymers from one hydrophilic unit (the poly1 monomer) and comonomers that carried the hydrophobic group were made, with a feed ratio of 1:1 (Series 5 in FIG. 34). Due to the high structural similarity between these polymers and the poly1-4 series, one could expect that this approach would lead to polymers with similarly tunable properties. However, while these new polymers (series 5) followed the general trends that had been found before (a minimum value for the $MIC_{90}$ and $HC_{50}$ values that decreased with increasing hydrophobicity), the overall selectivities of these polymers remained much lower, with a maximum selectivity of 20 (FIG. 37*a*). Deviation from the 1:1 monomer feed ratio did not improve the selectivities. This was thought to be a result of the segregation of the functional groups onto two different monomers, which leads to runs of hydrophobic and hydrophilic groups in the statistical copolymer (FIG. 37*b*, top). Thus, the local hydrophobicity of these polymers was not uniform, whereas the polymers from facially amphiphilic monomers have a well-defined local hydrophobicity (FIG. 37*b*, bottom). This led to the reduced activity of the segregated SMAMPs when interacting with the bacterial membrane (FIG. 37*b*).

Adding Hydrophilicity

The observation that the least hydrophobic polymers of series 1, 2 and 3 were usually also the least hemolytic (FIG. 35) led to the idea that the hemolytic activity of an active but toxic polymer could be reduced by copolymerizing the respective monomer with a hydrophilic comonomer. poly3, the most active and hemolytic polymer in series 1, was modified by incorporating non-ionic and zwitterionic hydrophilic repeat units. (Colak, et al., 2009, *Biomacromolecules*, 10, 353.) This strategy is different from the above approach, where hydrophobicity is modified by varying R groups in a series of facially amphiphilic monomers: the hydrophilic moieties used are not facially amphiphilic, each carries a lot of functionalities that impart hydrophilicity, and as a result they are structurally very dissimilar to the previously used inactive comonomers. Also, these comonomers all had the same charge, while the hydrophilic repeat units used by Colak et al. were overall neutral. The hydrophilic moieties chosen were a sugar residue, a zwitterionic side chain, and a short poly(ethylene glycol) chain (Series 6 in FIG. 34). The activities of these polymers are shown in FIG. 38*a-c*, respectively. The data indeed shows that gradually making poly3 more hydrophilic systematically reduced its hemolytic activity; however the dilution of the active component, the ammonium group, also rendered these molecules increasingly inactive, and therefore the selectivities of these polymers remained low.

The Effect of Charge

Two series with systematic charge variation were investigated, one of them imide-based (Series 7 in FIG. 34), and the other ester-based (Series 8 in FIG. 34). (Al-Badri, et al., *Biomacromolecules* 2008, 9, 2805; Lienkamp, et al., *J. Am. Chem. Soc.* 2008, 130, 9836) For the imide-based series, poly1 and poly3, respectively, were taken as a starting point. Structurally alike polymers carrying two and three charges per repeat unit were made (Series 7 in FIG. 34), and their biological properties were compared to their parent compounds. (Al-Badri, et al., *Biomacromolecules* 2008, 9, 2805.) The data for these polymers is reported in FIG. 39. The hydrophobic poly3, which is active and toxic, became drastically less hemolytic and more active against *E. coli* as the charge doubled. However, further addition of charge did not improve the biological properties. On the other hand, the hemolytic activity of the already hydrophilic poly1 did not improve upon addition of more charge, yet the polymer became more active against *S. aureus* bacteria.

Charge and hydrophilicity are two parameters that are difficult to separate. When increasing the charge across a polymer series, the hydrophilicity is automatically altered also. The effect this has on the biological properties depends on the overall hydrophobicity of the polymer series. In an already hydrophilic polymer like poly1, adding charge does not alter the hydrophilicity dramatically, thus the overall properties of the polymer change minimally. However, as seen by the drastic jump in hemolytic activity the poly3, adding charge here drastically influences the overall hydrophilicity of the molecule. Thus the poly1 series is probably the better model to isolate the effect of charge on the biological properties.

Taking these considerations into account, the ester-platform was used to obtain four series of copolymers from a doubly charged and a singly charged repeat unit carrying a variable R group (R=methyl to butyl). The thus obtained polymer series had different overall hydrophobicities between each series. Additionally, different monomer feed ratios allowed the charge density to be continuously varied across the series in contrast to the 'step-function' (one, two, or three charges per repeat unit). The biological properties of those polymers are summarized in FIG. 40.

As this data indicates, all the methyl and ethyl copolymers are non-hemolytic, whereas the propyl and butyl copolymers become more hemolytic with high propyl and butyl comonomer content, respectively. Thus, the properties of those two series are dominated by the hydrophobicity of those R groups. It was found with complementary methods that the hydrophobicity of the monoamine-methyl homopolymer closely resembled that of the diamine homopolymer, while the ethyl to butyl homopolymers were significantly more hydrophobic. Thus, the methyl copolymers were found to be a suitable model system of polymers to study the effect of increasing charge density. Indeed, the properties of this polymer series (FIG. 40a) are very similar to those of the poly1 derivatives (FIG. 39): With increasing charge, the hemolytic activity is slightly affected; however the activity against *S. aureus* dramatically improves. When going down in charge in the methyl-diamine series (from M9:D1 to Methyl in FIG. 40a), there is a sudden jump in the MIC from 4 to 100 µg/mL. The same is found in the poly1 derivatives when going from one to two charges per repeat unit. These findings, together with AMP literature data led to the postulation that there is a specific charge threshold that needs to be exceeded to obtain decent activities against *S. aureus*. (Pasupuleti, et al., *Biochemistry* 2008, 47, 9057.) Rather than a certain number of charges per repeat unit, this charge threshold is to be understood as a minimum charge density, or charge per unit volume, and the exact threshold number of charges per repeat unit will be slightly different for each SMAMP series depending on the molecular volume of the repeat units. On the molecular level, this postulated charge threshold translates into a minimum charge density that is necessary to trigger successful attachment of the SMAMP to the bacterial membrane. Once enough charge is present to enable this attachment, the hydrophobicity of the molecule will then determine to what extent the SMAMP is active. For *S. aureus*, the methyl-propyl copolymers 8 are active, for *E. coli*, apparently they are not hydrophobic enough, as no activity is seen against these bacteria. Preliminary evidence indicates these molecules bind to *E. coli*, meaning that the interpretation that these molecules have not reached the charge threshold for *E. coli* interactions, is unlikely.

Counterion Effects

To further probe the interaction between charge and hydrophobicity, the effect of counterion exchange on the biological properties of the series 2 polymers was studied. The hydrophilic counterions of the most hydrophilic ester-based polymer (polymer 9 in FIG. 34) were exchanged by hydrophobic organic counterions (e.g. hexanoate and tosylate). While the original idea was that exchanging these counterions would impart hydrophobicity onto the polymer and make it more active, it was found ion-exchanging these polymers completely eliminated the antibacterial activities (FIG. 41). Using dye-leakage studies, it was found that, while the parent polymer 9 was membrane active, the ion-exchanged polymers were not, meaning that the ammonium group of these polymers and the organic counterions formed such a tight ion pair that the overall positive charge of the polymer was masked.

The Effect of Molecular Weight

Ilker et al. found a weak molecular weight dependence for their poly3 compound, which at that time did not seem significant (FIG. 42a). (Ilker, et al., *J. Am. Chem. Soc.* 2004, 126, 15870.) In the case of the poly2 and poly4 series, no trend was observed as those polymers were in the inactive regime. Eren's low and high molecular weight polymers ($M_n$~3000 g/mol and 10000 g/mol, respectively) all had similar antibacterial and hemolytic activities, whether they were in the active or inactive regime. (Eren, et al., *Macromolecular Chem. Phys.* 2008, 209, 516.) For the 'segregated' copolymers, Gabriel found that the high molecular weight polymers ($M_n$~10,000 g/mol) were less active than the low molecular weight polymers ($M_n$~3000 g/mol) by a factor of 2-8. (Gabriel, et al., *Chem. Eur. J.* 2009, 15, 433.) Some of them were also slightly more hemolytic. The same general trend was found by Lienkamp et al. for the higher molecular weight ester-based polymers (Series 2 in FIG. 34, $M_n$~10,000 g/mol, biological data in FIG. 42b). Compared to their $M_n$~3000 g/mol analogues (FIG. 35c), these polymers were less active against *E. coli*, with the exception of the Propyl_10k polymer which was surprisingly active against that bacterial type. More notably, they were all inactive against *S. aureus*. (Lienkamp, et al., *J. Am. Chem. Soc.* 2008, 130, 9836.) Similarly, the diamine homopolymers (polymer 9 with TFA counterions in FIG. 34, biological data in FIG. 42c) showed a systematic decrease in activity against *S. aureus* with molecular weight, together with inactivity against *E. coli* at all molecular weights. This lead to the hypothesis that, at higher molecular weights, these particular polymers get stuck in the peptidoglycan layer of Gram-positive bacteria, as will be discussed in more detail below.

To investigate the molecular weight effect in more detail, especially in the low molecular weight region, a series of oligomers from the propyl polymer series 2 was prepared (FIG. 42d). As this data shows, the molecular weight dependence for both the hemolytic and antibacterial activities is highly nonlinear and different for each bacterial species involved. In the case presented here, Oligo 1 is selective for *S. aureus* over *E. coli*, while Propyl_3k shows the opposite tendency.

Mechanistic Studies of ROMP-Based SMAMPs

Vesicle Experiments and Fluorescence Microscopy

In the field of SMAMPs, the most popular method to probe the SMAMP-membrane interaction is the dye-leakage experiment. In this experiment, dye-filled lipid vesicles that are simplified models for bacteria and mammalian cell membranes are used. These vesicles capture the key features of cellular plasma membranes, and although they lack cell features such as the peptidoglycan cell wall of Gram-positive organisms, the double-membrane structure of Gram-negative bacteria, or the many proteins found in cell membranes, they are well-accepted methods to investigate the interaction of membranes with polymers or proteins, and can be used to correlate the membrane-disrupting properties of a compound to its biological activity. (Tew, et. al., *Proceed. Nat. Acad. Sci. USA* 2002, 99, 5110; Liu, et al., *J. Am. Chem. Soc.* 2001, 123, 7553; Oren, *Biochemistry* 1997, 36, 1826.) The lipid composition of these model vesicles was chosen to closely match the cell type they are supposed to mimic; consequently the primary lipid(s) that make up the plasma membrane of that cell type was used to match properties like surface charge, fluidity, and lipid curvature as closely as possible within these simple models. For example, pure cardiolipin vesicles are most commonly used to mimic *S. aureus* bacteria, whereas a mixture of phosphatidylethanolamine (PE) and phosphatidylglycerol (PG) is used to mimic *E. coli*, and phosphatidylcholine (PC) is used to mimic human red blood cells. (Som, et al., *J. Phys. Chem. B* 2008, 112, 3495.) Alternatively, a full lipid extract from the respective bacteria can also be used. Leakage of the self-quenching dye from the vesicle upon exposure to the SMAMPs leads to fluorescence, which is monitored as a function of time, or the leakage percentage upon SMAMP exposure can be plotted versus SMAMP concentration. (Som, et al., *J. Phys. Chem. B* 2008, 112, 3495.)

Ilker et al. investigated the lysis of neutral cholesterol:PC vesicles (as a mimic for erythrocytes) and of negatively charged phosphatidyserine:PC vesicles. They found that the lysing properties of poly2, poly3 and the poly2-3 copolymers were in good agreement with their antibacterial activities, poly2 being inactive and the other two polymers showing marked dye leakage. (Ilker, et al., *Macromolecules* 2004, 37, 694.) Gabriel et al. also studied the poly1 to poly3 series using *E. coli* mimicking PE:PG vesicles and found that their lysis behavior followed the $MIC_{90}$ trend exactly. Eren et al. studied the effect of exposing their polymers to PC vesicles (erythrocyte mimics) and *E. coli* extract, and found a good correlation between the membrane disruptive properties of these polymers and their $HC_{50}$ and $MIC_{90}$ data, respectively. (Eren, et al., *Macromolecular Chem. Phys.* 2008, 209, 516.) However, in this special case the activity towards PE:PG vesicles did not correlate with the $MIC_{90}$ data. Al-Badri et al. also found good agreement of the leakage from PC vesicles with the hemolysis data of his polymers. (Al-Badri, et al., *Biomacromolecules* 2008, 9, 2805.) Their samples also followed the general trend for both PE:PG and CL vesicles, i.e. that the poly3-derived samples were more membrane disruptive than the poly1-derived ones. For the segregated copolymers it was found that their activity against *E. coli* matched their membrane-disruptive potency towards vesicles made from *E. coli* lipid extracts.[57] (Gabriel, et al., *Chem. Eur. J.* 2009, 15, 433) Lienkamp et al. studied their polymers on *S. aureus* mimicking CL vesicles. They found a good correlation between the $MIC_{90}$ for *S. aureus* and the vesicle leakage for the methyl to butyl homopolymers. (Lienkamp, et al., *Chemistry Eur. J.* 2009, submitted.) As this body of data shows, overall there is a good correlation between dye-leakage activity of a SMAMP and the corresponding biological activity. This led to the conclusion that the mechanism of antibacterial activity for all those polymers is by disruption of the plasma membrane of the bacteria, which then causes a breakdown of the membrane potential, leakage of the cell content, and, eventually, cell death.

When dye-leakage studies fail to model cell-SMAMP interactions, this can indicate that other components of the cell structure are important which are not adequately modeled by the simple bilayer membrane, such as the peptidoglycan cell wall of Gram-positive bacteria. Lienkamp et al. studied the behavior of their diamine homopolymers (polymer 9 with trifluoroacetate counterions in FIG. 34, $M_n$~3000 g/mol), towards both cardiolipin (*S. aureus* mimic) and PE:PG (*E. coli* mimic) vesicles. (Lienkamp, et al., *Chemistry Eur. J.* 2009, submitted.) These polymers had previously been found to be 'doubly selective' first for bacteria over mammalian cells, and for *S. aureus* ($MIC_{90}$=15 µg/mL over *E. coli* ($MIC_{90}$>200 µg/mL). (Lienkamp, et al., *Chemistry Eur. J.* 2009, submitted.) Surprisingly, although the $MIC_{90}$s of the 3000 g/mol sample of polymer 9 were dramatically different for *E. coli* and *S. aureus*, this polymer had almost identical lysis percentages against both vesicle types (FIG. 43). This demonstrated that the differences in lipid composition of the two bacteria were not responsible for the observed differences in $MIC_{90}$; it was therefore postulated that the cell selectivity was due to the double membrane structure of *E. coli*, while *S. aureus* only has one plasma membrane. Since it was observed that the 3000 g/mol polymer was active against *S. aureus*, but that the 50,000 g/mol polymer was inactive, it was considered that the peptidoglycan cell wall found in Gram-positive organisms was an impenetrable barrier for large SMAMPs. This could be due to binding or due to steric hindrance.

In other cases, the cause for discrepancies between dye-leakage experiments and biological data might not have to do with the experiment at all, but with the SMAMP solubility. It was found that the two most hydrophobic polymers of series 5, with R=dodecyl, and series 2, with R=hexyl, did not follow the $MIC_{90}$-dye leakage correlation,[57,80] while the other molecules in both series were perfectly well-behaved. In both cases, a hydrophilic polymer of the same series with the same $MIC_{90}$ as the 'odd' polymer caused much less dye leakage than the corresponding hydrophobic polymer. (Gabriel, et al., *Chem. Eur. J.* 2009, 15, 433; Lienkamp, et al., *Chemistry Eur. J.* 2009, submitted.) The reason for this is the low solubility of the hydrophobic polymer at the comparatively high concentrations of the MIC experiment. The SMAMP concentration in the dye leakage experiments is usually lower than in the MIC experiments, as these experiments are understood to be much more sensitive, and even at these lower polymer concentrations, the ratio of polymer to vesicles is much higher than the ratio of polymer to bacteria in the MIC experiment. (Som, et al., *Biopolymers* 2008, 90, 83.) If a polymer has poor solubility in aqueous media, it will seem less active in the MIC experiment, but it will still be active in the dye-leakage experiment, causing a discrepancy in the results from the two methods.

Another method to probe the membrane-polymer interaction is the so called 'live-dead' stain. This somewhat misleading name refers to an experiment in which the bacteria are incubated with a dye mixture of SYTO 9, giving green fluorescence, and propidium iodide, a red fluorescent dye. While SYTO 9 can diffuse through the membranes of both intact and membrane-compromised cells, propidium iodide can only enter the cells with damaged plasma membranes and competes with the green dye for binding sites. Thus, a 'live' cell will appear green when using the green filter of the fluorescence microscope, and not red under the red filter, whereas a membrane-compromised, 'dead' cell will appear red when the red filter is applied, and may or may not appear green under the green filter depending on the dye stoichiometry. Using fluorescence microscopy, it was shown that the antibacterially active butyl polymer of series 5 caused red fluorescence and severe aggregation in E. coli bacteria, whereas the inactive poly1 did neither (FIG. 44). (Gabriel, et al., Chem. Eur. J. 2009, 15, 433.) This demonstrates again that active SMAMPs compromise the bacteria cell membranes. Using the same method, when comparing different molecular weights of polymer 9 it was discovered that there is a correlation between SMAMP concentration and bacteria aggregation, as well as between SMAMP molecular weight and bacteria aggregation. At the same concentration, higher molecular weight SMAMPs cause more cell aggregation than lower molecular weight ones. Also, the higher the SMAMP concentration, the more cell aggregation was observed.

Other Techniques

In the most detailed physical study on ROMP-based SMAMPs to date, HPLC, dye-leakage studies, light-scattering, isothermal calorimetry and fluorescence microscopy were combined to investigate the mechanism of polymer-membrane interactions of the poly1 to poly4 series.[83] The combination of these methods allowed Gabriel et al. to elucidate the mechanism of SMAMP-bacteria interaction in unprecedented detail. As expected, they found a linear correlation between HPLC elution times and the alkyl side chain length of the polymers from poly1 to poly4, which proved the intuitive assumption that the hydrophobicity increases from poly1 to poly4. As mentioned above, they also demonstrated that the dye-leakage data of these polymers follows their MIC trend, i.e. the inactive poly1 does not lyse vesicles, whereas poly2 and poly3 are increasingly membrane active. (Gabriel, et al., Langmuir 2008, 24, 12489.) Dynamic light scattering was used to monitor the effect of SMAMP addition on the hydrodynamic radius of the vesicles a function of time. While the radii of vesicles exposed to poly1 remained unaltered, those exposed to poly2 and poly3 grew significantly over time (FIG. 45).

This is another indication that poly1 is not membrane-active, whereas poly2 and poly3 clearly are, although the light scattering studies do not capture the significant difference in the $MIC_{90}$s of those polymers (200 vs. 25 µg/mL). It is also not clear whether the vesicle growth is due to aggregation or vesicle fusion. Consequently, this effect was further studies by fluorescence microscopy on dye-labeled vesicles and stained bacteria cells. (Gabriel, et al., Langmuir 2008, 24, 12489.) In the case of vesicles, giant fluorescent vesicles appeared upon exposure with poly3, while the E. coli bacteria aggregate, as has been observed with other SMAMPs. (Gabriel, et al., Chem. Eur. J. 2009, 15, 433.) These aggregation phenomena highlight that SMAMPs are not just a very complicated detergent. When added to vesicles, detergents would just dissolve the membranes, instead of causing vesicle fusion or aggregation. Also, detergents do not have the ability to differentiate between cells. The membrane-SMAMP interactions were further studies with isothermal calorimetry. These studies revealed that, while no binding interaction between the vesicles and poly1 or poly4, respectively, was observed, there was a strong binding event between the vesicles and both poly2 and poly3. (Gabriel, et al., Langmuir 2008, 24, 12489.) Fitting the data with modeling software revealed that the binding between the vesicle and the SMAMP is entropically favorable, and the overall free enthalpy of binding was about the same for both poly2 and poly3. However, marked differences were observed in the binding stoichiometry—the ratio of vesicle lipids to ammonium groups of the polymer was 0.4 for poly2, and 1.06 for the more active poly3.

Beyond SMAMPs—Cell Penetrating Peptides

Recently, an unusual SMAMP has been discovered (polymer 10 in FIG. 34). While all the previously discussed ROMP-based SMAMPS had amine groups as the positively charged moiety, this polymer contained guanidinium groups and had broad-spectrum antibacterial activity against both Gram-negative (E. coli and S. marcescens, $MIC_{90}$=6 µg/mL and 50 µg/mL, respectively) and Gram-positive (S. aureus and B. subtilis, $MIC_{90}$=12 µg/mL for both) bacteria. Together with a remarkably low hemolytic activity ($HC_{50}$=1500 µg/mL), this yields a selectivity for E. coli over red blood cells of 250, which is the highest selectivity so far observed for a broad-spectrum SMAMP, as the polymers of series 4 and 8 were only active against Gram-positive bacteria. Using bactericidal kinetics studies (also known as time-kill assays), it was shown that this polymer caused a 5 log reduction in less than 60 minutes at 4× the $MIC_{90}$, meaning that the polymer is indeed bactericidal and not just bacteriostatic. (Gabriel, et al., Biomacromolecules 2008, 9, 2980.) Comparative dye-leakage studies with poly1, poly3 and polymer 10 showed that, in spite of its low $MIC_{90}$ value, this polymer did not lyse model membranes (FIG. 46a). Similarly, while the active poly3 caused membrane damage and cell aggregation, as observed in fluorescence microscopy experiments (FIG. 46b, panel C and D), the red fluorescence caused by polymer 10 (FIG. 46b, panel E and F) was undistinguishable from that of the membrane-inactive poly1 (FIG. 46b, panel A and B). These indicate that the antimicrobial activity of this polymer is not due to membrane damage, leakage of cell content, and resulting cell death, as it is the case for the other SMAMPs. The guanidinium groups contained in this SMAMP are also found in poly(arginine) and other cell-penetrating peptides, and such cell-penetrating peptides are known to be able to cross membranes, transport cargo into cells and bind DNA. (Miyatake, et al., J. Am. Chem. Soc. 2006, 128, 12420; Henriques, et al., Biochemical J. 2006, 399, 1; Rothbard, et al., J. Med. Chem. 2002, 45, 3612; Futaki, et al., J. Biol. Chem. 2001, 276, 5836; Mitchell, et al., J. Peptide. Res. 2000, 56, 318; Sakai, et al., Soft Matter 2006, 2, 636; Pantos, et al., Biochim. Biophys. Acta 2008, 1778, 811; Schroeder, et al., J. Med. Chem. 2008, 51, 376; Deglane, et al., ChemBioChem 2006, 7, 684; Fillon, et al., J. Am. Chem. Soc. 2005, 127, 11798; Funhoff, et al., Bioconjugate Chem. 2004, 15, 1212.) In the light of this body of literature and the above results, it was postulated that polymer 10 may be antibacterially active by first penetrating the cell membrane without causing damage, and then interacting with an intracellular target, potentially the bacteria DNA, which leads to the cell's death. (Gabriel, et al., Biomacromolecules 2008, 9, 2980.)

Using ring-opening metathesis polymerization as a synthesis platform, a large variety of synthetic mimics of antimicrobial peptides (SMAMPs) was obtained. By carefully tuning the overall hydrophobicity and charge density of these molecules, polymers with tailor-made properties, from inactive/non-hemolytic via active/non-hemolytic to active/toxic, were obtained.

f. Hydrophilic Modifications and Hemolytic Activity

Here is disclosed an approach to fine-tune the properties of this interesting polymer, Poly3, by incorporating hydrophilic, biocompatible functionalities including sugar, zwitterionic, and polyethylene glycol (PEG) moieties (FIG. 47). Carbohydrate based sugars, in addition to being used as solubilizing agents, play an important role in application areas of biomolecular chemistry. (Dwek, Chemical Reviews 1996, 96, 683-720; Goto, et al. *Journal of Controlled Release* 1994, 28, 223-33.) PEG and various zwitterions have been widely used for improving the water-solubility of compounds. (Travert-Branger, et al. *Langmuir* 2008, 24, 3016-3019; Guillemet, et al. *Langmuir* 2006, 22, 1875-1879.) Having similar properties, all these groups have been routinely employed in conjunction with each other as solubilizing agents in many biological systems, where they were found to be non-toxic, thus making them good candidates for this study. (Travert-Branger, et al. *Langmuir* 2008, 24, 3016-3019; Narain, et al. *Journal of Polymer Science, Part A: Polymer Chemistry* 2006, 44, 6558-6568; Yasugi, et al. *Macromolecules* 1999, 32, 8024-8032.) The importance of repeat unit level facial amphiphilicity, rather than globally (or the entire molecule), on the selectivity of SMAMPs was recently emphasized by Lienkamp et al. (Lienkamp, et al. *Journal of the American Chemical Society* 2008, 130, 9836-9843.) Easily synthesizable structures that contain both hydrophobic and hydrophilic units on the same monomer allowed successful tuning of the SMAMPs' selectivities. Gabriel et al. also emphasized the advantages of the facial amphiphilicity approach at the repeat unit level versus random copolymers of hydrophilic and hydrophobic monomers. (Gabriel, et al. *Biomacromolecules* 2008, 9, 2980.)

Here, facially amphiphilic monomers having the same hydrophobic backbone, but various hydrophilic pendant groups, were incorporated into Poly3 via ROMP (FIG. 47). The resulting effects on the overall biological activities of these polymers were studied via determination of MICs coupled with hemolytic activity ($HC_{50}$) studies.

EXAMPLES

Materials and Instrumentation

Polyethylene glycol) methylether acrylate (PEG-acrylate) (99%), triphenylphosphine ($Ph_3P$) (99%), diisopropylazodicarboxylate (DIAD) (94%), $2^{nd}$ generation Grubbs' catalyst, and 3-bromopyridine (99%) were purchased from Sigma-Aldrich and used as received. Maleimide (98%) was obtained from Alfa Aesar and used as received. 1,2:3,4-Di-O-isopropylidene-D-galactopyranose (97%), N,N-dimethylethanolamine (99%), and ethylvinyl ether (EVE) (99%) were purchased from Acros Organics and used without further purification. 4-Bromobutanoic acid tert-butyl ester (95%) was purchased from Astatech, Inc. and used as is. Ethyl acetate, hexane, anhydrous diethyl ether, methanol, sodium bicarbonate ($NaHCO_3$), citric acid, and trifluoroacetic acid (TFA) were purchased from Fisher Scientific and used as received. Tetrahydrofuran (THF) was obtained from Fisher Scientific and was distilled form sodium/benzophenone under nitrogen before use. Dichloromethane (DCM) (Fisher Scientific) was distilled from $CaH_2$, under nitrogen. $3^{rd}$ generation Grubbs' catalyst (G3) (dichloro-di(3-bromopyridino)-N,N'-dimethylenoimidazolino-Ru=CHPh) was synthesized according to a previously published procedure. (Love, et al. *Angewandte Chemie, International Edition* 2002, 41, 4035-4037.)

$^1$H NMR and $^{13}$C NMR spectra were recorded on a Bruker DPX300 spectrometer (Bruker, Madison, Wis.). Gel permeation chromatography (GPC) was performed using a Polymer Laboratories PL-GPC50 (Amherst, Mass.) instrument equipped with a PL Gel 5 μm pre-column and two 5 μm Mixed D columns. The mobile phase was THF with a flow rate of 1 mL/min and toluene was used as a flow marker. The instrument was calibrated with narrow molecular weight polystyrene standards using a Knauer RI detector. High resolution mass spectra were obtained on a JEOL JMS 700 instrument (JEOL, Peabody, Mass.).

Synthesis of M1

Isopropylfulvene (7.0 g, 58.3 mmol) and maleimide (4.7 g, 48.6 mmol) were charged in a Schlenk flask and dissolved in toluene (100 mL). (Ilker, et al. *Macromolecules* 2004, 37, 694-700.) The reaction mixture was placed in an oil bath at 135° C., stirred for 12 h, then cooled to room temperature. Excess toluene was removed under reduced pressure to yield a mixture of exo/endo (9/1 by $^1$H NMR) product. The pure exo product 1 was isolated by crystallization from diethyl ether as a colorless solid. Yield: 60%. $^1$H NMR (300 MHz, $CDCl_3$, ppm) δ: 0.87 (q, J=6.6 Hz, 6H), 2.3 (m, 1H), 2.77 (m, 2H), 3.37 (s, 1H), 3.74 (s, 1H), 4.76 (d, J=9.6 Hz, 1H), 6.4 (m, 2H), 8.24 (s, 1H). $^{13}$C NMR (75 MHz, $CDCl_3$, ppm) δ: 22.97, 23.47, 28.10, 44.53, 48.61, 49.04, 120.90, 136.99, 137.54, 143.62, 178.10, 178.21.

Compound 1 (2.0 g, 9.2 mmol), $Ph_3P$ (2.4 g, 9.2 mmol), and 1,2:3,4-Di-O-isopropylidene-D-galactopyranose (2.4 g, 9.2 mmol) were dissolved in dry THF (50 mL) in a 250 mL round bottom flask, under $N_2$ atmosphere. The solution was then cooled to 0° C. in an ice bath. DIAD (1.8 g, 1.8 mL, 9.2 mmol) was added drop wise to the cooled reaction mixture. After addition was complete, the ice bath was removed and the solution was stirred at room temperature for 24 h. Excess THF was removed under reduced pressure to yield a yellow, oily product, which was recrystallized from toluene. After discarding the white precipitate the excess toluene from the filtrate was removed under reduced pressure to yield an oily product. The pure M1 was isolated by crystallization from cold diethyl ether to afford a colorless solid. Yield: 50%. $^1$H NMR (300 MHz, $CDCl_3$) δ: 0.77 (q, J=4.14 Hz, 3H), 0.85 (d, J=6.59 Hz, 3H), 1.29 (d, J=17.7 Hz, 6H), 1.45 (d, J=9.2 Hz, 6H), 2.23 (m, 1H), 2.76 (m, 2H), 3.27 (d, J=2.6 Hz, 1H), 3.34 (d, J=2.6 Hz, 1H), 3.69 (d, J=3.0 Hz, 1H), 3.95 (m, 1H), 4.17 (d, J=8.3 Hz, 2H), 4.26 (q, J=2.4 Hz, 1H), 4.58 (d, J=2.5 Hz, 1H), 4.65 (d, J=9.6 Hz, 1H), 5.43 (d, J=5.1 Hz, 1H), 6.38 (m, 2H). $^{13}$C NMR (75 MHz, $CDCl_3$) δ: 23.82, 24.45, 25.33, 25.79, 26.54, 26.73, 28.89, 39.76, 45.24, 48.32, 48.64, 49.71, 64.87, 71.17, 71.64, 72.23, 97.05, 109.54, 110.56, 121.43, 137.80, 138.65, 144.81, 177.67, 178.69. HR-MS (FAB): calculated 459.53. found 460.20.

Synthesis of M2

Compound 1 (4.0 g, 18.4 mmol), $Ph_3P$ (4.8 g, 18.4 mmol), and N,N-dimethylethanolamine (1.6 g, 1.8 mL, 18.4 mmol) were dissolved in dry THF (150 mL) in a 250 mL round-bottom flask, under $N_2$ atmosphere. The solution was then cooled to 0° C. in an ice bath. DIAD (3.7 g, 3.6 mL, 18.4 mmol) was added drop-wise to the cooled reaction mixture. After addition was complete, the ice bath was removed and the solution was stirred at room temperature for 24 h. Excess THF was removed under reduced pressure. The remaining product was extracted from ethyl acetate into citric acid solution (pH=4.0), pH of the solution was adjusted to 13.0 by the addition of saturated $NaHCO_3$ solution. Compound 2 was then extracted with hexane/diethyl ether mixture. The excess solvent was removed under reduced pressure to yield a colorless powder. Yield=70%. $^1$H NMR (300 MHz, $CD_3OD$) δ: 0.86 (q, J=6.8 Hz, 6H), 2.27 (m, 7H), 2.5 (t, J=6.7 Hz, 2H), 2.81 (dd, J=7.2 Hz, 2H), 3.26 & 3.66 (s, 2H), 3.53 (t, J=6.7 Hz, 2H), 4.63 (d, J=9.4 Hz, 1H), 6.46 (m, 2H). $^{13}$C NMR (75 MHz, $CD_3OD$) δ: 23.49 & 24.01, 29.21, 36.93, 45.46 & 45.53, 49.07 & 49.13, 50.08, 57.06, 120.9, 138.22 & 138.95, 146.44, 179.39 & 179.52.

Compound 2 (2.0 g, 6.9 mmol) was dissolved in 50 mL of dry THF. To the solution 4-bromobutanoic acid ten-butyl ester (3.1 g, 13.8 mmol) was added and the reaction mixture was stirred at 50° C. for 36 h. The product was filtered, washed with excess dry THF, and dried under vacuum to yield M2 as a colorless powder. Yield=65%. $^1$H NMR (300 MHz, CD$_3$OD) δ: =0.88 (q, J=6.7 Hz, 6H), 1.48 (s, 9H), 2.04 (m, 2), 2.29 (m, 1H), 2.43 (t, J=6.6 Hz, 2H), 2.9 (m, 2H), 3.19 (m, 6H), 3.45 (m, 4H), 3.72 (m, 2H), 3.91 (t, J=7.2 Hz, 2H), 4.67 (d, J=9.2 Hz, 1H), 6.48 (m, 2H). $^{13}$C NMR (75 MHz, CD$_3$OD) δ: 19.8, 24.3, 25.2, 29.2, 30.1, 32.8, 33.7, 46.4, 52.8, 61.5, 65.3, 83.0, 121.9, 139.1, 139.8, 147.1, 173.8 (ester, —C=O), 179.7 (imide, —C=O). HR-MS (FAB): calculated $\overline{431.59}$. found 431.29.

Homo- and Copolymer Synthesis and Deprotection

Homopolymerization of M1 and M2:

All the monomers were polymerized using 3$^{rd}$ generation Grubbs' catalyst as an initiator. The same procedures were followed for the homopolymerization of M1 and M2 and the deprotection of the corresponding polymers. In a typical experiment, M1 (0.4 g, 0.8 mmol) and G3 (0.013 g, 0.014 mmol) were weighed in separate reaction flasks and purged with N$_2$ gas. The monomer was dissolved in 1 mL and the catalyst was dissolved in 0.5 mL of THF. In the homopolymerization of M2, the monomer was dissolved in 1 mL of methanol due to its insolubility in THF. Both solutions were degassed by three freeze-pump-thaw cycles. After warming the solutions to room temperature, the monomer solution was cannulated into the catalyst solution. The reaction mixture was stirred at 60° C. for 2 h. The reaction was cooled in an ice bath and terminated by the addition of EVE (0.3 g, 0.6 mL, 6.3 mmol). The reaction mixture was further stirred for 1 h. The resultant homopolymers, Poly1 and Poly2, were precipitated from excess diethyl ether to yield dark brown powders. Yield=95%.

Poly1:

$^1$H NMR (300 MHz, CDCl$_3$) δ: 0.92 (br m, 6H), 1.27 (br m, 3H), 1.33 (br m, 3H), 1.48 (br in, 3H), 1.59 (br m, 3H), 2.41 (br m, 1H), 3.04 (br in, 2H), 3.37 (br in, 2H), 3.77 (br m, 1H), 3.99 (br m, 1H), 4.18 (br m, 2H), 4.27 (br m, 1H), 4.59 (br m, 1H), 5.16 (br in, 1H), 5.42 (br m, 2H), 5.61 (br m, 1H). Poly2: $^1$H NMR (300 MHz, DMSO-d$_6$) δ: 0.89 (br m, 6H), 1.42 (br m, 9H), 1.91 (br m, 2H), 2.32 (br m, 3H), 2.82 (br m, 2H), 3.15 (br m, 6H), 3.43 (br m, 4H), 3.64 (br m, 2H), 3.8 (br m, 2H), 4.6 (d, 1H), 5.18 (br m, 2H, cis), 5.33 (br in, 2H, trans).

Deprotection of Poly1 and Poly2:

The deprotection reactions of all the polymers were done as follows: in a typical procedure, 0.25 g of Poly1 was dissolved in 3 mL of neat TFA and stirred at room temperature for 24 h. The deprotected polymer was precipitated from diethyl ether. The deprotected Poly1 was dried under vacuum for 24 h, then dissolved in 5 mL methanol and 25 mL RO water, and freeze-dried to remove all organic solvents. Yield=85%.

Deprotected Poly1:

$^1$H NMR (300 MHz, DMSO-d$_6$) δ: 0.87 (br m, 6H), 3.21 (br m, 2H), 3.49 (br m, 4H, —OH), 4.09 (br m, 1H), 4.84 (br m, 1H), 4.99 (br m, 1H), 5.14 (br$\overline{m}$, 1H), 5.35 (br m, 1H), 5.58 (br m, 1H), 7.32 (br m, 2H, aromatic), 7.41 (br m, 3H, aromatic). Deprotected Poly2: $^1$H NMR (300 MHz, DMSO-d$_6$) δ: 0.88 (br m, 6H), 1.92 (br m, 2H), 2.33 (br m, 3H), 2.81 (br m, 2H), 3.12 (br m, 6H), 3.4 (br m, 4H), 3.7 (br m, 4H), 5.2 (br m, 2H, cis), 5.3 (br m, 2H, trans).

Copolymerizations of M1 and M2 with M3:

The same procedure described above for the homopolymerization of Poly1 and Poly2 was used for the synthesis of all Poly3-co-Poly1 and Poly3-co-Poly2 series. Corresponding monomers were mixed in the same reaction vessel prior to reacting with the catalyst. Copolymers with varying compositions were synthesized by adjusting the molar amounts of the monomers at the desired ratios.

The monomer composition of the copolymers was quantified by $^1$H NMR analysis. For the Poly3-co-Poly1 samples copolymer composition was determined by comparing the integration value of methyl protons (6H, at 0.92 ppm) at the backbone to the —NH$_3$ (3H, at 7.88 ppm) protons of M3, after deprotection. In the case of Poly3-co-Poly2 copolymer composition was determined from the comparison of the integration value of methyl protons (6H, at 0.92 ppm) at the backbone to the methyl protons (9H, at 1.39 ppm) of the tert-butyl group of the M2.

Poly3-co-Poly1 (50:50):

$^1$H NMR (300 MHz, CDCl$_3$) δ: 0.92 (br m, 6H), 1.27 (br m, 3H), 1.33 (br m, 3H), 1.41 (br m, 9H), 1.47 (br m, 6H), 2.41 (br m, 1H), 3.04 (br m, 2H), 3.29 (br m, 21-1), 3.61 (br m, 2H), 3.78 (br m, 1H), 3.98 (br m, 1H), 4.17 (br m, 2H), 4.27 (br m, 1H), 4.60 (br m, 1H), 5.17 (br m, 2H), 5.42 (br m, 1H), 5.62 (br m, 1H). Deprotected Poly3-co-Poly1 (50:50): $^1$H NMR (300 MHz, DMSO-d$_6$) δ: 0.88 (br m, 6H), 2.95 (br m, 2H), 3.21 (br m, 2H), 3.43 (br m, 4H, —OH), 3.61 (br m, 2H), 3.87 (br m, 1H), 4.07 (br m, 1H), 4.85 (br$\overline{m}$, 1H), 5.02 (br m, 1H), 5.16 (br m, 1H), 5.29 (br m, 2H), 5.46 (br in, 1H), 5.59 (br m, 1H), 7.32 (br in, 2H, aromatic), 7.40 (br m, 3H, aromatic), 7.88 (br m, 3H, —NH$_3^+$).

Poly3-co-Poly2 ($\overline{50}$:50):

$^1$H NMR (300 MHz, CD$_3$OD) δ: 0.92 (br m, 6H), 1.39 (br m, 9H), 1.44 (br m, 9H), 2.03 (br m, 1H), 2.39 (br m, 2H), 3.19 (br m, 2H), 3.29 (br m, 6H), 3.52 (br m, 2H), 3.95 (br m, 2H), 5.54 (br m, 1H), 5.71 (br m, 1H), 7.28 (br m, 2H), 7.38 br m, 2H). Deprotected Poly3-co-Poly2 (50:50): $^1$H NMR (300 MHz, DMSO-d$_6$) δ: 0.87 (br m, 6H), 1.91 (br m, 1H), 2.33 (br m, 2H), 3.09 (br m, 2H), 3.39 (br m, 6H), 3.61 (br m, 2H), 3.91 (br m, 2H), 5.54 (br m, 1H), 5.62 (br m, 1H), 7.5 (br m, 5H), 8.04 (br m, 3H).

Synthesis of Poly3-co-PolyP:

A post-functionalization approach was utilized for the synthesis of Poly3-co-PolyP copolymer. Poly3 was synthesized and deprotected according to a previous literature procedure. The repeat unit determination was done by GPC analysis. In a typical reaction, deprotected Poly3 (0.15 g, 0.4 mmol) was dissolved in 10 mL DMSO. Triethyl amine (0.02 g, 0.20 mmol) was added to the reaction mixture and stirred for 30 min followed by the addition of PEG-acrylate (0.15 g, 0.3 mmol). The reaction mixture was stirred at room temperature for 24 hours. The pure polymer was isolated by crystallization three times from cold diethyl ether affording a light brown solid. Yield: 70%.

Copolymer composition was determined by the ratio of the integration values of methyl protons of the backbone (6H) appearing at 0.75 ppm to the methylene peaks next to the ester linkage of the PEG-acrylate (2H) appearing at 4.07 ppm. $^1$H NMR (300 MHz, D$_2$O) δ: 0.85 (br m, 6H), 2.42 (br m, 1H), 2.84 (br m, 2H), 3.05 (br m, 2H), 3.15 (br m, 3H, —CH$_3$ of PEG), 3.46 (br m, 32H), 3.55 (br m, 2H), 4.07 (br $\overline{m,}$ 2H, —COOCH$_2$—), 5.18 (br m, 1H), 5.48 (br m, 1H), 7.10 (br m, 5H, aromatic).

Polymer Synthesis and Characterization

Facial amphiphilicity at the repeat unit level has an important effect on the overall selectivity of the SMAMPs compared to random copolymers of hydrophobic and hydrophilic monomers, yielding an amphiphilic structure. (Ilker, et al. *J. Am. Chem. Soc.* 2004, 126, 15870-15875; Lienkamp, et al. *J. Am. Chem. Soc.* 2008, 130, 9836-9843; Gabriel, et al. *Biomacromolecules* 2008, 9, 29808).; Sambhy, et al. *Angew. Che-* mie, Int'l Ed. 2008, 47, 1250-1254.) Selectivity values can be improved by fine tuning of these systems by copolymerization. Monomers composed of hydrophobic backbone and varying biocompatible hydrophilic pendant moieties were designed and synthesized (FIG. 47).

ROMP has been successfully used to polymerize norbornene based monomers bearing various functionalities to obtain well-defined systems. (Eren, et al. *Macromolecular Chemistry and Physics* 2008, 209, 516-524; Ilker, et al. *Macromolecules* 2004, 37, 694-700; Alfred, et al. *Journal of Polymer Science, Part A: Polymer Chemistry* 2008, 46, 2640-2648.) However, it has been also reported that the presence of particular additives such as pyridine, secondary amines, thiols, or benzoic acid, can significantly slow or shut down the kinetics of ROMP. (Slugovc, *Macromolecular Rapid Communications* 2004, 25, 1283-1297; Colak, et al. *Macromolecules* 2008, 41, 8436) Therefore, to prevent these retardation effects and to be able to successfully perform ROMP, a protecting group approach was utilized to synthesize the highly functionalized monomers (M1-M3). In addition to facilitating the polymerization process, the protective group approach also provided ease in the later polymer characterization by gel permeation chromatography (GPC) and nuclear magnetic resonance (NMR). Upon complete polymerization, the protective groups were removed to yield the corresponding antimicrobially active polymers.

The first step of the monomer synthesis is the Diels-Alder reaction of maleimide with isopropylfulvene to yield product 1. M1, the sugar functional norbornene based monomer, was synthesized via Misunobu coupling of 1 with the corresponding alcohol (Scheme 6). (Mitsunobu, *Synthesis* 1981, 1, 10-28.) The same reaction conditions were employed to obtain 2, which was further alkylated with 4-bromobutanoic acid ten-butyl ester to yield the positively charged M2 as the quaternary ammonium salt, leading to the zwitterionic functionality upon deprotection (Scheme 6). (Colak, et al. *Macromolecules* 2008, 41, 8436.) M3 was synthesized according to a previously published procedure. (Ilker, et al. *Macromolecules* 2004, 37, 694-700.) All monomers were characterized using NMR techniques. FIGS. 48 and 49 show the resulting $^1$H NMR spectra of M1 and M2, respectively.

Scheme 6. Synthesis of M1 and M2.

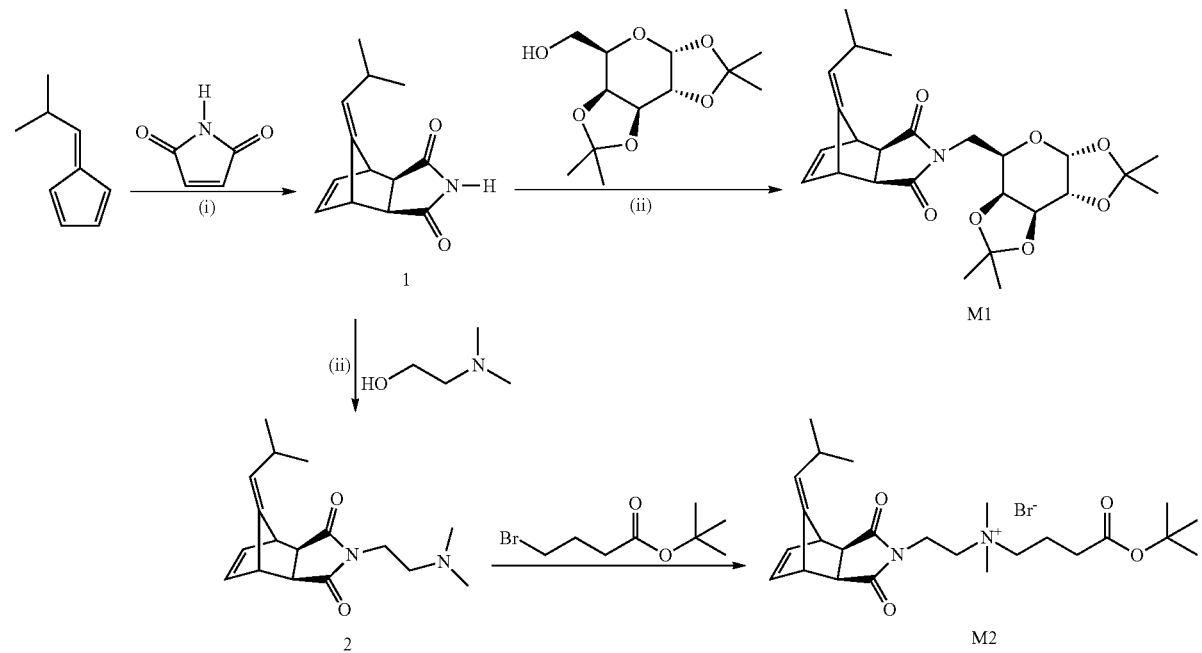

(i) Toluene, at 135° C. for 12 h. (ii) THF, Ph$_3$P, DIAD, at RT for 24 h. (iii) THF, at 50° C. for 36 h.

All homopolymers (Poly1, Poly2, and Poly3) and copolymers (Poly3$_n$-co-Poly1$_m$, Poly3$_n$-co-Poly2$_m$, and Poly3$_n$-co-PolyP$_m$, where n indicates the mol fraction of M3 and m indicates the mol fraction of M1, M2, or MP (PEG functionality) in the copolymer composition) were synthesized using $3^{rd}$ generation Grubbs' catalyst as an initiator. Upon reaction completion, the polymerizations were terminated via addition of excess ethyl vinyl ether. ROMP yielded polymers with approximate molecular weights of 3 kDa and narrow polydispersity indices ranging from 1.08 to 1.15, as determined by GPC (See Table 20). All polymers were deprotected using trifluoroacetic acid to obtain the antimicrobially active polymers.

Syntheses of Poly3$_n$-co-Poly1$_m$ (sugar functional) and Poly3$_n$-co-Poly2$_m$ (zwitterionic functional) copolymers were done via random copolymerization of the corresponding facially amphiphilic monomers. To vary the amphiphilicity of the resulting polymers, different molar ratios of the monomers were used in the copolymerization reactions (Table 20). Depending on the solubility of the monomers and the catalyst, different solvent systems were used to provide homogeneous reaction media for all polymerizations. Poly3$_n$-co-Poly1$_m$ was synthesized using only THF, whereas Poly3$_n$-co-Poly2$_m$ was synthesized in a THF-methanol solvent mixture (Scheme 7). The copolymerization kinetics were studied via $^1$H NMR analysis by recording spectra every 30 minutes, until the reaction was completed within 2 h. The constant decrease in the intensity of the broad peak at 6.5 ppm, corresponding to the alkene functionalities of both norbornene monomers, indicated successful copolymer formation. The complete disappearance of the same peak and the simultaneous appearance of two new peaks at approximately 5.4 and 5.6 ppm, corresponding to the cis and trans conformations of double bonds of the polymer backbone, indicated complete conversion.

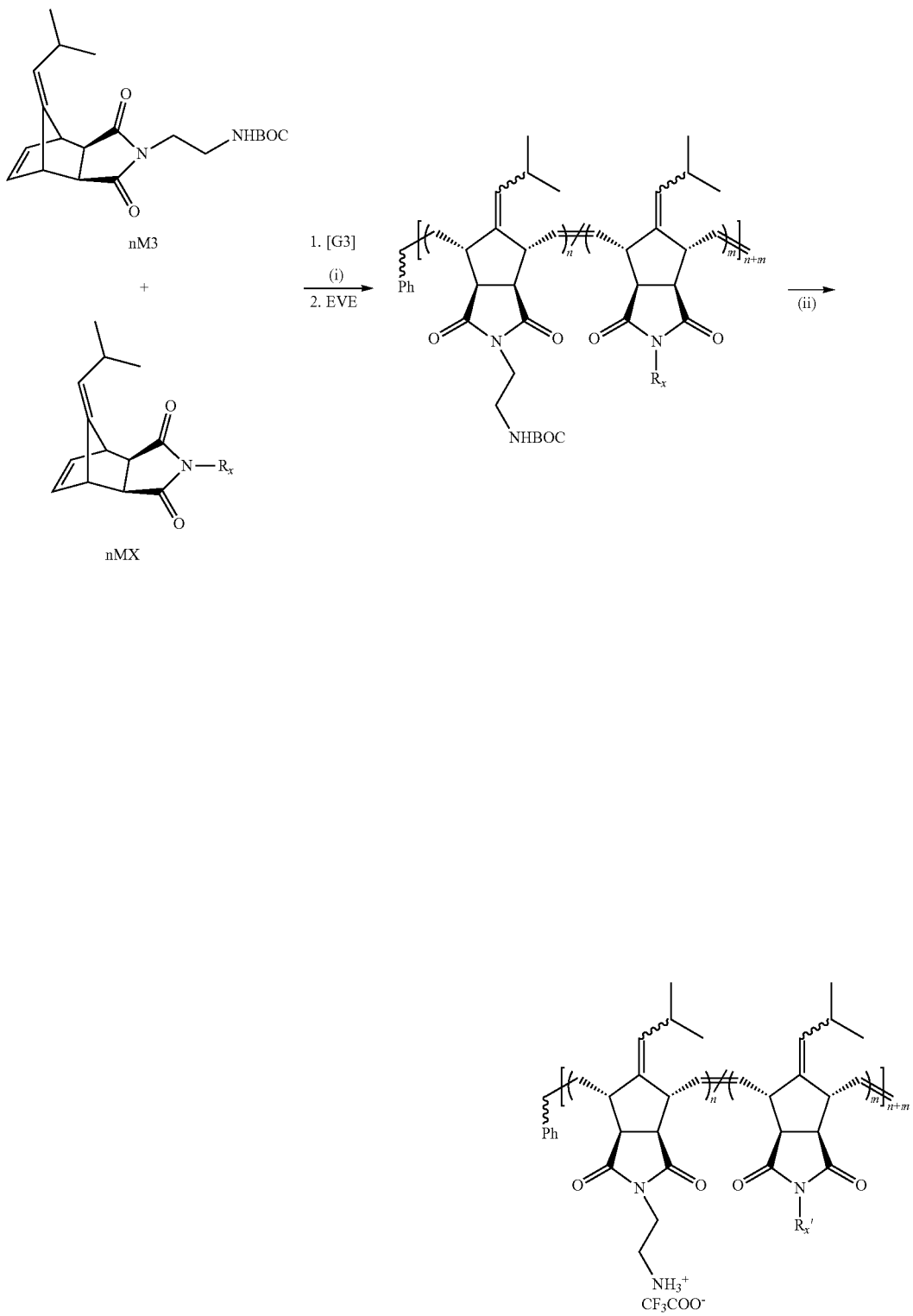

Scheme 7. Copolymerizartion of M1 and M2 with M3 and deprotection of the resulting polymers.

-continued

| X | $R_x$ | $R_x'$ |
|---|---|---|
| 1 | 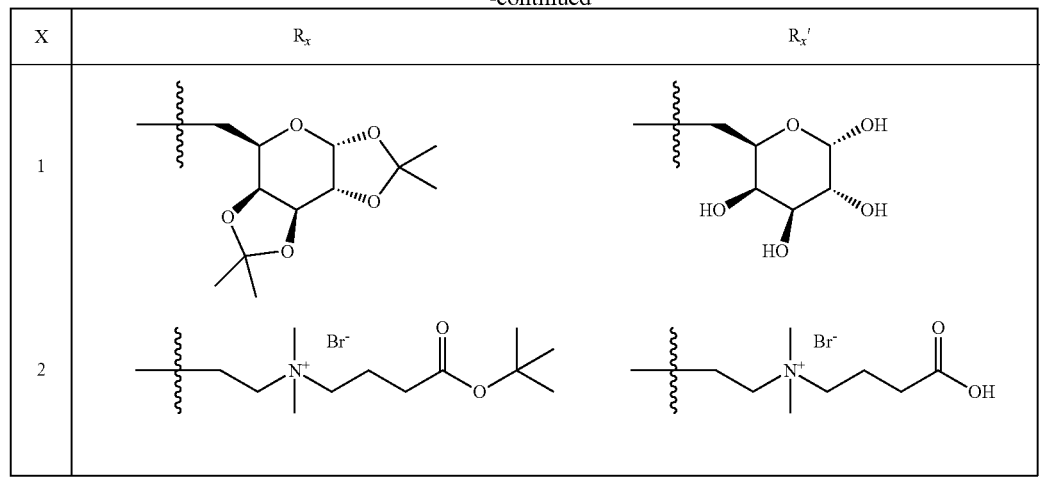 | |
| 2 | | |

(i) X = 1: THF, 60° C., 2 h; X = 2: THF, CH₃OH, 60° C., 2 h. (ii) X = 1: TFA, RT, 24 h; X = 2: TFA/H₂O (9/1), RT, 24 h.

Molecular weight characterization of Poly3$_n$-co-Poly1$_m$ was done by gel permeation chromatography (GPC) with THF as the eluent, and calibration was done against polystyrene standards. The experimental molecular weights were in accordance with the theoretical (calculated) values (Table 20). Representative GPC traces of Poly1 (homopolymer of M1) and the copolymer, Poly3$_{0.5}$-co-Poly1$_{0.5}$, are shown in FIG. 50.

It is well known that GPC of charged polymers is challenging due to formation of ionic aggregation or interactions with the stationary phase of the chromatography column. (Volet, et al. *Journal of Liquid Chromatography* 1994, 17, 559-577.) Therefore, instead of performing GPC analysis on the charged polymers, ¹H NMR end group analysis was used for the molecular weight determination of Poly3$_n$-co-Poly2$_m$ copolymers. The ratio of the phenyl end group integral value to the methyl protons of the isopropylfulvene backbone yielded the degree of polymerizations, which was used to calculate the total molecular weight of the polymers.

Prior to any functionalization, M3 was polymerized to yield Boc-protected Poly3 which was then deprotected with TFA to yield the antimicrobially active polymer according to the previously published procedure. (Ilker, et al. *Macromolecules* 2004, 37, 694-700.) Positively charged ammonium groups were neutralized to yield the amine functionalities, which were then used to react with the acrylate end functionalized PEG via Michael-addition (Scheme 8). (Colak, et al. *Journal of Applied Polymer Science* 2007, 104, 2244-2253.) In the ¹H NMR spectra of the purified polymers no residual acrylate peaks were observed and the appearance of a peak at 4.07 ppm corresponding to the methylene peaks next to the ester linkage of the PEG-acrylate indicated the successful addition.

Scheme 8. Synthesis of Poly 3$_n$-co-PolyP$_m$ copolymers.

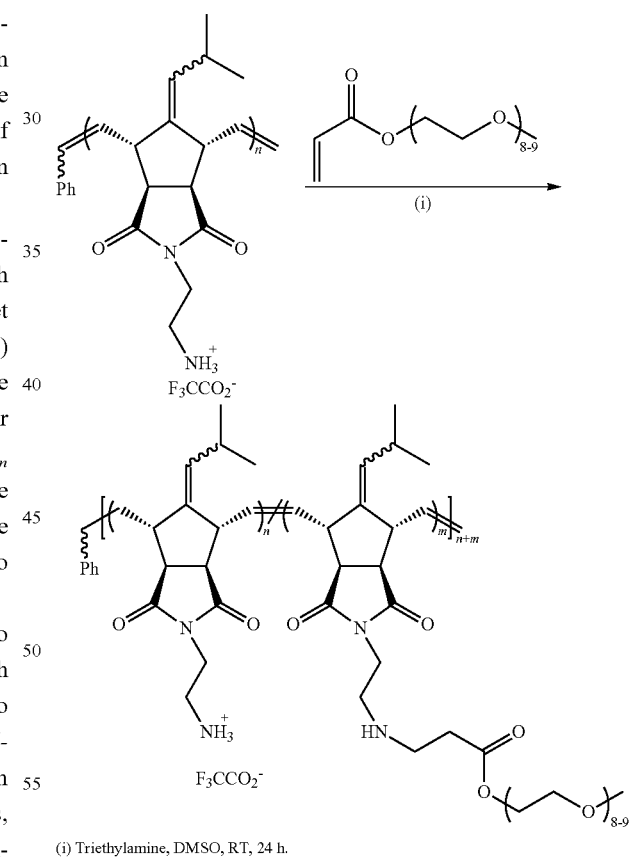

(i) Triethylamine, DMSO, RT, 24 h.

Antimicrobial and Hemolytic Activity Analyses

To assess the biological activities of the polymers, the minimum inhibitory concentrations (MIC) against *Escherichia coli* (*E. coli*) and *Staphylococcus aureus* (*S. aureus*) and hemolytic activity (HC$_{50}$) were determined according to standard procedures. (Rennie, et al. *Journal of Industrial Microbiology & Biotechnology* 2005, 32, 296-300.) All of the analyses were performed using the deprotected polymer samples. FIG. 51 shows the results of the Poly3$_n$-co-Poly1$_m$ series. As the sugar content of the copolymer was increased from 0% to 100% (referring to the Poly1 homopolymer), a linear decrease in the biological activity was observed; MIC values increased from 50 to 200 µg/mL. This loss of activity might be attributed to the fact that, as the number of repeat units containing sugar residues is increased, the overall positive charge of the polymer is being reduced. It should also be noted that the sugar functional homopolymer, Poly1, is inactive towards bacteria. However, due to its biocompatible nature and overall neutral charge, its toxicity toward mammalian cells, HC$_{50}$=2000 µg/mL, is much lower than that of Poly3, HC$_{50}$<1 µg/mL. Thus, while increasing the sugar content of the Poly3$_n$-co-Poly1$_m$ copolymers improved their hemolytic properties, it caused a reduction of the antibacterial activities.

The same behavior was observed for the Poly3$_n$-co-Poly2$_m$ copolymer series until equal co-monomer composition was reached (Poly3$_{0.5}$-co-Poly2$_{0.5}$) (FIG. 52). As the number of zwitterionic residues was further increased, loss of antimicrobial activity along with higher hemolytic activity was observed. A possible explanation for the loss of activity with higher zwitterionic content could be the increased possibility of forming intra- or interchain associations, causing significant conformational changes in the polymer backbone, thus affecting overall facial amphiphilicity.

The highest biological activity was observed for Poly3$_n$-co-PolyP$_m$ samples (FIG. 53). Upon incorporation of PEG groups up to 30%, lower MIC values were obtained compared to Poly3, accompanied with a slight improvement in the hemolytic activities. Compared to the sugar or zwitterionic functionalized copolymers, the presence of an amine (primary or secondary) on every repeat unit in the Poly3$_n$-co-PolyP$_m$ structures, indicate that the overall charge remained constant even as PEG content increased. However, after 50% functionalization the same loss of activity was observed as for the other polymers.

Table 20 summarizes the resulting MIC and HC$_{50}$ values of all the studied SMAMPs, as well as the selectivity values, calculated taking the ratio of HC$_{50}$ and MIC. When the results are compared to that of Poly3, generally the same behavior is observed for all the samples; with increasing hydrophilicity, biological activity is reduced. However, due to the biocompatible nature of these hydrophilic groups, improvements of the hemolytic activities were observed (from <0.02 up to 7.5 µg/mL for Poly3$_{0.5}$-co-Poly2$_{0.5}$), thus higher selectivities were obtained.

TABLE 20

Biological activity data of Poly3$_n$-co-Poly1$_m$ copolymers.

| Copolymer Ratio (n/m) | M$_n$ (kDa) | PDI | MIC [µg/mL] E. coli | MIC [µg/mL] S. aureus | HC$_{50}$ [µg/mL] | Selectivity (HC$_{50}$/MIC) E. coli | Selectivity (HC$_{50}$/MIC) S. aureus |
|---|---|---|---|---|---|---|---|
| Poly3 | 2.8[a] | 1.15 | <50 | <50 | <1 | <0.02 | <0.02 |
| Poly3$_{0.7}$-co-Poly1$_{0.3}$ | 2.9[a] | 1.10 | 100 | 100 | 50 | 0.2 | 0.2 |
| Poly3$_{0.5}$-co-Poly1$_{0.5}$ | 2.9[a] | 1.10 | 200 | 200 | 100 | 0.5 | 0.5 |
| Poly3$_{0.3}$-co-Poly1$_{0.7}$ | 3.0[a] | 1.09 | >200 | >200 | 400 | <2.0 | 2.0 |
| Poly1 | 3.0[a] | 1.08 | >200 | >200 | 2000 | <10.0 | <10.0 |
| Poly3$_{0.7}$-co-Poly2$_{0.3}$ | 3.6[b] | n.d. | 100 | 100 | 250 | 2.5 | 2.5 |
| Poly3$_{0.5}$-co-Poly2$_{0.5}$ | 4.1[b] | n.d. | 150 | 200 | 1500 | 10.0 | 7.5 |
| Poly3$_{0.3}$-co-Poly2$_{0.7}$ | 4.3[b] | n.d. | >200 | >200 | 750 | <3.8 | <3.8 |
| Poly2 | 4.0[b] | n.d. | >400 | >400 | 750 | <1.9 | <1.9 |
| Poly3$_{0.8}$-co-PolyP$_{0.2}$ | 3.3[d] | 1.15 | 15 | 25 | <50 | <3.3 | <2 |
| Poly3$_{0.7}$-co-PolyP$_{0.3}$ | 3.6[d] | 1.15 | 20 | 100 | <50 | <2.5 | <0.2 |
| Poly3$_{0.5}$-co-PolyP$_{0.5}$ | 4.1[d] | 1.15 | >200 | >200 | 1000 | <5 | <5 |

[a] M$_n$ determined by GPC of the protected polymers.
[b] M$_n$ determined by $^1$H NMR of the deprotected polymers.
[c] M$_n$ reported after subtracting the corresponding weights of the protecting groups.
[d] M$_n$ includes the molecular weight of the PEG chains.

TABLE 21

Summary of M/I ratios of all the Poly3-co-Poly1 and Poly3-co-Poly2 copolymer series and their corresponding homopolymers.

| Sample | Monomer Concentrations (mmol/mL) M3 | Monomer Concentrations (mmol/mL) MX[a] | Initiator Concentrations (mmol/mL) | Degree of Polymerization (DP) = [M]/[I] | M$_{n\ theoretical}$ (kDa) | M$_{n\ experimental}$ (kDa) |
|---|---|---|---|---|---|---|
| Poly3 | 0.37 | — | 0.044 | 8.22 | 2.9 | 2.8[b] |
| Poly3$_{0.7}$-co-Poly1$_{0.3}$ | 0.14 | 0.06 | 0.027 | 7.40 | 2.9 | 2.9[b] |

TABLE 21-continued

Summary of M/I ratios of all the Poly3-co-Poly1 and Poly3-co-Poly2 copolymer series and their corresponding homopolymers.

| Sample | Monomer Concentrations (mmol/mL) M3 | Monomer Concentrations (mmol/mL) MX$^a$ | Initiator Concentrations (mmol/mL) | Degree of Polymerization (DP) = [M]/[I] | $M_{n\ theoretical}$ (kDa) | $M_{n\ experimental}$ (kDa) |
|---|---|---|---|---|---|---|
| Poly3$_{0.5}$-co-Poly1$_{0.5}$ | 0.11 | 0.11 | 0.030 | 7.33 | 3.0 | 2.9$^b$ |
| Poly3$_{0.3}$-co-Poly1$_{0.7}$ | 0.08 | 0.12 | 0.027 | 7.40 | 3.1 | 3.0$^b$ |
| Poly1 | — | 0.22 | 0.033 | 6.53 | 3.0 | 3.0$^b$ |
| Poly3$_{0.7}$-co-Poly2$_{0.3}$ | 0.17 | 0.072 | 0.026 | 9.3 | 3.5 | 3.6$^c$ |
| Poly3$_{0.5}$-co-Poly2$_{0.5}$ | 0.11 | 0.12 | 0.021 | 10.9 | 4.2 | 4.1$^c$ |
| Poly3$_{0.3}$-co-Poly2$_{0.7}$ | 0.062 | 0.14 | 0.019 | 10.6 | 4.2 | 4.3$^c$ |
| Poly2 | — | 0.23 | 0.033 | 6.95 | 3.0 | 4.0$^c$ |

$^a$X = 1 for Poly1, 2 for Poly2.
$^b$M$_n$ determined by GPC of the protected polymers.
$^c$M$_n$ determined by $^1$H NMR of the deprotected polymers.

g. Charge Density and Hemolytic Activity

A series of norbornene monomers were designed that carry one, two, and three amine groups (FIG. 55). ROMP of the Boc protected monomers, followed by deprotection, resulted in SMAMPs with multiple amine groups on each repeat unit (FIG. 56).

The syntheses of A$_1$ and B$_1$ were previously reported in the literature (FIG. 55). (Ilker, et al. *J. Am. Chem. Soc.* 2004, 126, 15870-15875.) The other monomers were prepared by Mitsunobu coupling of norbornene derivates with the corresponding alcohols. The Boc-protected polyA$_{1-3}$ and polyB$_{1-3}$ series (FIG. 56) were prepared via ROMP using Grubbs' 3$^{rd}$ generation catalyst. The number average molecular weights (M$_n$) of all polymers were approximately 3 kDa and the polydispersity indices (PDI) were 1.1 as measured by GPC. The amine protecting groups were then removed by treating the polymers with trifluoroacetic acid to afford the cationic polyA$_{1-3}$ and polyB$_{1-3}$ series. The synthesis and characterization of these monomers and polymers are reported in the supporting information.

Hemolytic and Antibacterial Activities

The biological activity of polyA$_1$ indicates that it is non-selectively active, meaning it disrupts both mammalian and bacterial cell membranes. (Ilker, M. F.; Nusslein, K.; Tew, G. N.; Coughlin, E. B. *J. Am. Chem. Soc.* 2004, 126, 15870-15875.) The toxicity of polyA$_1$ was attributed to its hydrophobic nature; the polymer backbone contains the isobutenyl functionality which increased the overall hydrophobicity of the polymer. The effect of doubling and tripling the number of amine groups per monomer on the biological activity of polyA$_{1-3}$ was investigated.

The results show that increasing the number of amine groups significantly reduces the hemolytic behavior of polyA$_1$ (FIG. 57A). The hemolytic activities were tested against human red blood cells (RBCs) and reported as HC$_{50}$ values. (HC$_{50}$: Is the concentration required to lyse 50% of human red blood cells.) PolyA$_1$ is very hemolytic (<1 µg/mL). Upon doubling and tripling number of amine groups the polymers become non-hemolytic with HC$_{50}$ values of 700 and 500 µg/mL for polyA$_2$ and polyA$_3$, respectively. Meanwhile, the antimicrobial activities of polyA$_{1-3}$, reported as the minimum inhibitory concentration required to restrain 90% of bacterial growth (MIC$_{90}$), were tested against Gram-negative (*E. coli*) and Gram-positive (*S. aureus*) bacteria (FIGS. 57B and 573C). The MIC$_{90}$s show no significant change in the antimicrobial activity upon doubling or tripling number of amine groups.

The above results show that increasing the number of amine groups, while keeping the hydrophobic moieties the same has a favorable impact on the hemolysis but little influence on the antimicrobial activities of polyA$_{1-3}$. This observation highlights the significance of optimizing the balance between the hydrophobic and hydrophilic components of the polymer. Because polyA$_2$ and polyA$_3$ were much less hemolytic while retaining their antimicrobial activity, the influence of increasing the number of amine groups on a non-active polymer, polyB$_1$, was investigated. The results show no significant change in the hemolytic behavior of the polyB$_{1-3}$ series and they remain inactive against RBCs, as expected, due to the overall hydrophilic nature of these polymers (FIG. 57A). The antimicrobial activities of these new polyB derivatives remain inactive against *E. coli* (FIG. 57B); however, polyB$_2$ and polyB$_3$ become active against *S. aureus* as the number of amine groups is doubled or tripled. This was manifested by the decrease in the MIC$_{90}$ values from >200 µg/mL for polyB$_1$ to 25 and 15 µg/mL for polyB$_2$ and polyB$_3$, respectively.

Model Membrane Studies

Understanding the interactions between SMAMPs and different cell membranes is of important scientific concern, although a complicated, multi-component problem. (Som, et al. *Biopolymers* 2008, 90, 83-93.) Apart from the differences in intracellular components and membrane proteins, bacterial cell walls and mammalian cell membranes are also very distinct with respect to their phospholipid compositions. (Som, et al. *J. Phys. Chem. B* 2008, 112, 3495-3502.) The outer surface of RBC membranes is devoid of anionic lipids and composed predominantly of zwitterionic phosphatidylcholine (PC). On the other hand, Gram-positive bacterial (e.g., *S. aureus*) membranes are mainly composed of anionic phospholipids (phosphatidylglycerol (PG) and cardiolipin (CL)), while the membranes of most Gram-negative bacteria are rich in zwitterionic lipid phosphatidylethanolamine (PE). For example the plasma membrane of *E. coli* is composed of ~80% PE and ~20% PG. (Gabriel, et al. *Mater. Sci. Eng., R* 2007, 57, 28-64.) The specific role of PE in SMAMP induced pore formation was recently reported. (Yang, et al. *J. Am. Chem. Soc.* 2007, 129, 12141-12147.)

To investigate the membrane activity of these new SMAMPs, polymer induced leakage from three different calcein dye loaded vesicles were examined: (i) 100% PC vesicles $V_1$ to mimic RBC outer leaflets, (ii) 20/80 PG/PE vesicles $V_2$ to mimic *E. coli* lipid membranes, and (iii) 100% CL vesicles $V_3$ to mimic *S. aureus* lipid membranes. Membrane activity of these polymers against PC vesicles $V_1$ (RBC mimic) was monitored and is shown in FIG. 58. The hemolytic $polyA_1$ is highly membrane active against PC vesicles; however, the leakage activity is significantly reduced upon doubling ($polyA_2$) or tripling ($polyA_3$) the number of amine groups. The entire non-hemolytic $polyB_{1-3}$ series remains inactive against PC vesicles. All of these experiments correlate with the hemolytic activities of the $polyA_{1-3}$ and $polyB_{1-3}$ series.

To understand the interactions of these SMAMPs with bacterial membrane mimics, calcein dye leakage from PG/PE vesicles ($V_2$) and CL vesicles ($V_3$) was studied. $PolyA_1$ showed 80% leakage activity against both $V_2$ and $V_3$; doubling the number the of amine groups ($polyA_2$) slightly reduces the leakage activity by 15% and 5% for $V_2$ and $V_3$, respectively (FIGS. 59A and 59B). Upon tripling the number of amine groups ($polyA_3$) the leakage activity against $V_2$ is similar to $polyA_2$; however, the leakage activity against $V_3$ is much less (FIGS. 59A and 59B). In contrast, $polyB_1$ remains inactive against both $V_2$ and $V_3$, whereas $polyB_2$ and $polyB_3$ show increasing leakage activity from these vesicles with $polyB_2$ being the most active (FIGS. 59C and 59D).

If membrane activity was predominantly based on hydrophobicity, $polyA_1$ would be active and $polyB_1$ would be inactive against RBCs. By doubling or tripling the number of amine groups in the $polyA_{1-3}$ series, the activity against PC vesicles is reduced, consistent with the observed $HC_{50}$ values. In contrast, due to the hydrophilic nature of $polyB_1$, the polymer shows no affinity towards RBCs or PC membranes and remains non-hemolytic upon increasing the number of amine groups.

While antimicrobial activity of the $polyA_{1-3}$ series remains unchanged upon increasing charge density, the $polyB_{1-3}$ series shows no activity against *E. coli* but enhanced activity against *S. aureus* (FIGS. 57B and 57C). This phenomenon could be due to the difference in the structural makeup of their cell membranes. Most Gram-positive bacteria are rich in negatively charged lipids. It is also possible that these highly hydrophilic cationic polymers ($polyA_3$ and $polyB_{2-3}$) interact with the outer murein layer which is composed of negatively charged peptidoglycans. (Navarre, et al. *J. Biol. Chem.* 1999, 274, 15847-15856.) The model membrane activities generally correlate with the biological activity of these SMAMPs. The unusual decrease in membrane activity for $polyA_3$ and $polyB_{2-3}$ against anionic CL vesicles (FIGS. 59B and 59D) indicate that $polyA_3$ and $polyB_{2-3}$ may not be membrane-lipid dependent, but rather interact with other extra-cellular and/or intra-cellular targets.

In order to increase the selectivity of SMAMPs there has to be a balance between the hydrophobic and hydrophilic moieties. In the case of $polyA_{1-3}$, non-toxic polymers are obtained by doubling or tripling the number of amine group. The hemolysis of $polyA_1$ was improved from <1 µg/mL to 700 µg/mL for $polyA_2$. The $polyB_{1-3}$ series remains non-hemolytic as expected; however, $polyB_2$ and $polyB_3$ show enhanced activity against Gram-positive bacteria. This enhanced antimicrobial activity of $polyB_2$ and $polyB_3$ coupled to their lack of hemolysis and membrane activity in the vesicle studies suggest that these SMAMPs may have other cell targets besides the membrane.

EXAMPLES

Instrumentation.

NMR spectra were recorded on Bruker DPX-300 MHz ($^1$H NMR; $^{13}$C NMR, 75 MHz) spectrometer. Chemical shifts are reported in δ (ppm), referenced to the $^1$H (of residual protons) and $^{13}$C signals of deuterated solvents. Molecular weights and polydispersity indices (PDIs) were measured by GPC in THF relative to polystyrene standards on systems equipped with two-column sets (Polymer Laboratories) and refractive-index detectors (HP 1047A) at 40° C. with a flow rate of 1 mL/min. Fluorescence measurements were performed on a Jobin Yvon Fluorolog-3.

Materials.

All reagents were purchased either from Acros Organics, Aldrich, or Strem and used without further purification. Phospholipids, 1,2-dioleoyl-sn-glycero-3-phosphatidylcholine (DOPC), 1,2-dioleoyl-sn-glycero-3-phosphatidyl ethanolamine (DOPE), 1,2-dioleoyl-sn-glycero-3-[phospho-rac-(1-glycerol)] (DOPG); 1,1'2,2'-tetraoleoyl cardiolipin (TOCL) were purchased from Avanti Polar Lipids Inc. Calcein was purchased from Sigma, all salts and buffers of the best grade were available from Sigma-Aldrich, and used as received. Dichloromethane and THF were dried over $CaH_2$ and sodium benzophenone ketyl, respectively. Compounds 3, 5, 7, and $3^{rd}$ generation Grubbs' catalyst were synthesized according to the literature. Monomers $A_{1-2}$ and $B_{2-3}$ were synthesized according to Scheme 9. (Davis, et al. *Bioorg. Med. Chem.* 1999, 7, 2303; Stone, et al. *J. Org. Chem.* 1984, 49, 1849; Kwart, et al. *J. Am. Chem. Soc.* 1952, 74, 3094; Louie, et al. *Angew. Chem. Int. Ed.* 2001, 40, 247.)

Boc-Protected Bisamino Alcohol 2.

A solution of bis-amine 1 (3.00 g, 33.3 mmol) was dissolved in a minimal amount of water (1 mL) and added to a solution of di-tert-butyl dicarbonate (16.0 g, 73.3 mmol) in dioxane (400 mL). The reaction mixture was stirred for 24 hours at room temperature under nitrogen. The solvent was removed under reduced pressure. The resulting solid was dissolved in dichloromethane (300 mL), washed with water (300 mL), dried over $MgSO_4$, and filtered. The solvent was removed under reduced pressure to afford a white solid. The white solid was washed with ether and filtered (9.18 g, 98%). $^1$H NMR ($CDCl_3$): δ 5.34-5.30 (br, 2NH, 2H), 4.03 (s, 1H, OH), 3.73-3.68 (m, 1H, CH), 3.18-3.14 (m, 4H, $2CH_2$,), 1.39 (s, 18H, $6CH_3$). $^{13}$C NMR ($CDCl_3$): δ 157.2, 79.71, 70.67, 43.46, 28.39.

Boc-Protected Trisamino Alcohol 4.

A solution of tris-amine salt 3 (3 g, 12.37 mmol) dissolved in a minimal amount of water (1 mL) was added to a solution of triethylamine (5.7 mL, 40.81 mmol), and di-tert-butyl dicarbonate (8.9 g, 40.81 mmol) in dioxane (200 mL). The reaction mixture was stirred for 24 hours at room temperature under nitrogen. The solvent was removed under reduced pressure. The resulting solid was dissolved in dichloromethane (250 mL), washed with water (250 mL), dried over $MgSO_4$, and filtered. The solvent was removed under reduced pressure to afford a white solid. The white solid was washed with ether and filtered (5.07 g, 95%). NMR ($CDCl_3$): δ 5.83 (t, J=6.6 Hz, 3H, 3NH), 4.34 (t, J=7.5 Hz, 1H, OH), 3.10 (d, J=7.5 Hz, 2H, $CH_2$), 2.78 (d, J=6.6 Hz, 6H, $3CH_2$,), 1.41 (s, 27H, $9CH_3$). $^{13}$C NMR ($CDCl_3$): δ 157.8, 79.59, 60.24, 46.10, 38.98, 28.33.

Functionalized Norbornene 6.

A solution of 5 (6.81 g, 56.66 mmol) and maleimide (5 g, 51.5 mmol) in toluene (200 mL) was heated to 130° C. in a sealed tube for 24 hours. After removal of toluene under reduced pressure, the resulting solid was dissolved in a minimal amount of ether. Successive recrystallizations afforded the pure exo isomer 6 (3.6 g, 32%). $^1$H NMR (CDCl$_3$): 8.97 (s, NH, 1H), 6.36 (s, 2H, CH$_2$), 4.71 (d, J=9.6 Hz, 1H, CH), 3.69 (s, 1H, CH), 3.32 (s, 1H, CH), 2.73 (s, 2H, CH$_2$), 2.29-2.22 (m, 1H CH), 0.85 (d, J=6.6 Hz, 3H, CH$_3$), 0.80 (d, J=6.6 Hz, 3H, CH$_3$). $^{13}$C NMR (CDCl$_3$): δ 178.2, 143.6, 137.5, 137.0, 120.9, 49.04, 48.61, 44.53, 28.10, 23.47, 22.97.

General Synthesis Procedure for Monomers $A_{2-3}$ and $B_{2-3}$.

To a round bottom flask charged with compound 7 or 8, alcohol derivatives 2 or 4, and 1.1 equivalent of triphenylphosphine, THF was added. The solution mixture was then immersed in an ice bath and 1.1 equivalent of diisopropyl azodicarboxylate (DIAD) was added drop wise. After the addition of DIAD, the ice bath was removed and the reaction was allowed to stir at room temperature for 24 h. The solvent was removed under reduced pressure and the crude product was dissolved in toluene and kept at −20° C. for 24 h. The byproducts (white crystals) were removed by filtration and the mother liquor was concentrated. The product was crystalized from cold anhydrous diethyl ether (−20° C.). The mother liquor was concentrated and the remaining product was isolated by column chromatography.

Monomer $A_2$.

Norbornene 8 (2.37 g, 10.9 mmol), alcohol 2 (5.44 g, 12.0 mmol), triphenylphosphine (3.15 g, 12.0 mmol) DIAD (2.33 mL, 12.0 mmol). The product was purified by flash chromatography (Silica, 120 g ISCO column, 50:50 ethyl acetate/hexane). Yield; 2.88 g, 54%. $^1$H NMR (CDCl$_3$): δ 6.43-6.35 (m, 2H, CH$_2$), 5.07 (br, 2H, 2NH), 4.70 (d, J=9.6 Hz, 1H, CH), 4.15 (br, 1H, CH), 3.70-3.32 (m, 6H, 2CH, 2CH$_2$,), 2.74-2.64 (m, 2H, CH$_2$), 2.33-2.21 (m, 1H, CH), 1.38 (s, 18H, 6CH$_3$), 0.87-0.82 (m, 6H, 2CH$_3$). $^{13}$C NMR (CDCl$_3$): δ 177.9, 156.0, 145.0, 138.4, 137.1, 119.9, 79.41, 52.53, 48.84, 47.47, 44.30, 39.56, 28.24, 28.01, 23.21.

Monomer $A_3$.

Norbornene 8 (1.00 g, 4.60 mmol), alcohol 4 (2.19 g, 5.06 mmol), triphenylphosphine (1.33 g, 5.06 mmol), DIAD (0.98 mL, 5.06 mmol). The product was purified by flash chromatography (Silica, 120 g ISCO column, 10:90 acetonitrile/dichloromethane). Yield; 1.75 g, 60%. $^1$H NMR (CDCl$_3$): δ 6.39 (s, 2H, CH$_2$), 5.78 (br, 3H, 3NH), 4.64 (d, J=9.6 Hz, 1H, CH), 3.67 (s, 1H, CH), 3.33 (s, 1H, CH$_2$), 3.24 (s, 2H, CH$_2$), 2.90-2.80 (m, 8H, 4CH$_2$), 1.41 (s, 27H, 9CH$_3$), 0.84 (d, J=6.6, 3H, CH$_3$), 0.76 (d, J=6.6, 3H, CH$_3$). $^{13}$C NMR (CDCl$_3$): δ 178.7, 156.8, 144.0, 137.8, 137.2, 120.6, 79.27, 48.84, 47.73, 44.42, 41.42, 39.53, 28.39, 27.98, 23.56, 23.03.

Monomer $B_2$.

Oxanorbornene 7 (4.00 g, 24.2 mmol), alcohol 2 (7.73 g, 26.6 mmol), triphenylphosphine (6.99 g, 26.6 mmol), DIAD (5.17 mL, 26.6 mmol). The product was purified by flash chromatography (Silica, 120 g ISCO column, 10:90 acetone/dichloromethane). Yield; 6.32 g, 60%. $^1$H NMR (CDCl$_3$): δ 6.48 (s, 2H, $C_{1-12}$), 5.20 (s, 2H, CH$_2$), 4.97 (br, 2H, 2NH), 4.26 (br, 1H, CH), 3.51-3.38 (m, 2H, 2CH$_2$), 2.79 (s, 2H, CH$_2$), 1.36 (s, 18H, 6CH$_3$). $^{13}$C NMR (CDCl$_3$): δ 176.7, 155.9, 136.4, 81.16, 79.33, 52.88, 47.06, 39.09, 28.24.

Monomer $B_3$.

Oxanorbornene 7 (2.73 g, 16.5 mmol), alcohol 4 (7.87 g, 18.2 mmol), triphenylphosphine (4.78 g, 18.2 mmol) in dry THF (300 mL), DIAD (3.54 mL, 18.2 mmol). The product was purified by flash chromatography (Silica, 120 g ISCO column, 20:80 acetone/dichloromethane) Yield; 6.89 g, 70%. $^1$H NMR (CDCl$_3$): δ 6.48 (s, 2H, CH$_2$), 5.82 (br, 3H, 3NH), 5.23 (s, 2H, CH$_2$), 3.36 (s, 2H, CH$_2$), 2.88-2.87 (m, 8H, 4CH$_2$), 2.84 (s, 2H, CH$_2$), 1.40 (s, 27H, 6CH$_3$). $^{13}$C NMR (CDCl$_3$): δ 177.2, 156.9, 136.4, 80.93, 79.24, 47.30, 45.09, 41.22, 40.08, 28.33.

General Polymerization Procedure.

The polymerization for monomers $A_{2-3}$ and $B_{2-3}$ were conducted in anhydrous THF and CH$_2$Cl$_2$, respectively (Scheme 10). A known amount of monomer was weighed into a Schlenk flask, placed under an atmosphere of nitrogen, and dissolved in anhydrous CH$_2$Cl$_2$ or THF (1 mL per 100 mg of monomer). Into a separate Schlenk flask, a desired amount of $3^{rd}$ generation Grubbs' catalyst was added, flushed with nitrogen, and dissolved in a minimum amount of anhydrous CH$_2$Cl$_2$ or THF. Both flasks were degassed three times by freeze-pump-thaw cycles. The monomer was transferred to the flask containing the catalyst via a cannula. The reaction was allowed to stir until the polymerization is complete (as monitored by NMR and GPC). The polymerization for $A_{2-3}$ series was conducted at 60° C. for 30 min, whereas for $B_{2-3}$ series, the polymerization was conducted at room temperature for 10 min. The polymerization reaction was quenched with ethyl vinyl ether (0.2 mL). An aliquot was taken for GPC analysis. For poly$A_{2-3}$, the solvent, THF, was first removed under reduced pressure. The polymers were then redissolved in CH$_2$Cl$_2$ and passed through a short silica plug. For poly$B_{2-3}$, the polymer solutions were passed through a short silica plug to remove the catalyst. The solvent, CH$_2$Cl$_2$, was then removed under reduced pressure.

Poly$A_2$.

Monomer:catalyst ratio=6:1; monomer $A_2$ (0.10 g, 0.20 mmol), Grubbs' $3^{rd}$ generation catalyst (0.030 g, 0.033 mmol). Yield; 75%. $^1$H NMR (CDCl$_3$): δ broad signals 5.61, 5.45, 5.12, 4.25, 3.76, 3.55, 3.38, 3.00, 2.53, 1.38, 0.92. $^{13}$C NMR (CDCl$_3$): δ 178.8, 155.6, 138.8, 136.0, 131.5, 128.1, 125.9, 79.79, 78.92, 52.30, 51.02, 49.91, 49.36, 46.42, 38.86, 27.86, 22.77. $M_n$=3 kDa, PDI=1.10.

Poly$A_3$.

Monomer:catalyst ratio=5:1; monomer $A_3$ (0.10 g, 0.16 mmol), Grubbs' $3^{rd}$ generation catalyst (0.028 g, 0.032 mmol). Yield; 80%. $^1$H NMR (CDCl$_3$): δ broad signals 5.84, 5.59, 5.42, 3.79, 3.33, 2.87, 2.43, 1.40, 0.88. $^{13}$C NMR (CDCl$_3$): δ 179.2, 156.6, 136.7, 134.9, 129.7, 128.4, 126.1, 79.09, 51.46, 50.03, 46.69, 44.82, 41.19, 39.70, 28.18, 22.77. $M_n$=3 kDa, PDI=1.10.

Poly$B_2$.

Monomer:catalyst ratio=7:1; monomer $B_2$ (0.10 g, 0.22 mmol), Grubbs' $3^{rd}$ generation catalyst (0.028 g, 0.031 mmole). Yield; 90%. $^1$H NMR (CDCl$_3$): δ 6.01, 5.74, br 5.50-4.55, 4.49, 4.20, br 3.55-3.48, 3.27, 1.39. $^{13}$C NMR (CDCl$_3$): δ 176.2, 156.07, 130.9, 80.69, 79.50, 52.04, 39.12, 28.27. $M_n$=3 kDa, PDI=1.09.

Poly$B_3$.

Monomer:catalyst ratio=5:1; monomer $B_3$ (0.10 g, 0.17 mmol), Grubbs' $3^{rd}$ generation catalyst (0.030 g, 0.034 mmol). Yield; 85%. $^1$H NMR (CDCl$_3$): δ 6.06, 5.83, br 5.750, br 5.00, 4.43, 3.34, 2.87, 1.39. $^{13}$C NMR (CDCl$_3$): δ 176.6, 156.9, 131.9, 130.7, 80.58, 79.36, 52.24, 45.14, 41.22, 28.33. $M_n$=3 kDa, PDI=1.10.

General Deprotection Procedure.

All polymers were dissolved in a minimal amount of CH$_2$Cl and excess amount of trifluoroacetic acid (TFA) was added. The solution was allowed to stir at room temperature for 6 h. TFA was removed under reduced pressure and the polymers were dissolved in distilled water, passed through a short silica plug, and freeze dried for 48 h.

Liposome Preparation.

The following buffers were used: Buffer A, 40 mM calcein, 10 mM $Na_2HPO_4$ pH 7.0; buffer B, 10 mM $Na_2HPO_4$, 90 mM NaCl, pH 7.0. Homogeneous large unilamellar vesicles (LUVs) were prepared by the extrusion method. (Som, et al. J. Phys. Chem. B 2008, 112, 3495-3502.) Vesicle abbreviations with the corresponding lipid compositions, inside and outside buffer are listed in Table 22.

General Procedure for Vesicle Preparation:

Appropriate volume of lipid stock solution (25 mg/mL $CHCl_3$) were taken in 2 mL $CHCl_3$ and evaporated slowly at reduced pressure and then placed under vacuum >2 h to prepare a thin film. The thin film was then hydrated for 1 h with 1 mL buffer A. The resulting suspension was subjected to five freeze-thaw cycles (using liquid nitrogen to freeze and warm water bath to thaw) and extruded >10 times using a mini-extruder through a polycarbonate membrane (Whatman, pore size 400 nm), stacked between two pairs of membrane supports. The external calcein was removed by gel filtration (Sephadex G-50) using buffer B and the resulting 1.0 mL vesicle solution was diluted with buffer B to 20 mL to give calcein loaded LUVs stock solution, having final lipid concentration of 0.5 mM. Following the general vesicle preparation procedure vesicles $V_1$-$V_3$ were prepared using appropriate lipid ratios.

Dye Leakage Assays.

Calcein loaded LUVs (20 µL) were added to 1.98 mL buffer B in a fluorescence cuvette (final lipid concentration in the cuvette 5.0 µM). Fluorescence emission intensity $I_t$ ($\lambda_{em}$=510 nm, $\lambda_{ex}$=450 nm) was monitored as a function of time (i) during addition of 20 µL DMSO solution of polymer and 50 µL of 20% Triton X-100. Control experiments were performed adding only 20 µL DMSO. Flux curves were normalized to percentage leakage activity Y, where Y=[($I_t$-$I_0$)/($I_\infty$-$I_0$)]*100. $I_0$, is $I_t$ before addition of samples (polyA$_{1-3}$ or polyB$_{1-3}$), and $I_\infty$ is $I_t$ after addition of 20% Triton-X.

Antimicrobial Studies.

The antimicrobial activities of polyA$_{1-3}$ and polyB$_{1-3}$ were evaluated using standard methods. (Hamuro, et al. J. Am. Chem. Soc. 1999, 121, 12200-12201.) Stock solutions of polymers were made in DMSO and then diluted into 96-well plates with Mueller Hinton (MH) medium to a constant volume. All bacteria (used cell lines: Escherichia coli D31 and Staphylococcus aureus ATCC25923) were taken from MH glycerol solutions or from a frozen stock, diluted into MH medium, and grown overnight at 37° C. Sub-samples of these cultures were grown for 3 h, the $OD_{600}$ was measured and then the cells were diluted to 0.001 $OD_{600}$. The diluted cell solutions (approximately $10^5$ cells/mL) were then added to the 96-well plate and incubated at 37° C. for 6 h. The $MIC_{90}$ values reported are the minimum concentration necessary to inhibit 90% of the cell growth. Experiments were run in duplicate. The results are shown in Table 23.

Hemolysis Studies.

Fresh human erythrocytes were obtained by centrifuging whole blood (3000 rpm, 10 min) to remove plasma and white blood cells. The RBCs (1 mL) were diluted with 9 mL of TBS buffer (10 mM Tris buffer, pH=7.0, 150 mM NaCl), and the suspension was further diluted by a factor of 40 to give a RBC stock suspension (0.25% blood cells). This RBC stock (120 µL), TBS buffer (15 µL), and the polymer stock solutions (15 µL) (or control solutions) were added to a 200 µL centrifugation tube and incubated at 37° C. for 1 h. The tube was centrifuged at 4000 rpm for 5 min. Supernatant (30 µL) was diluted with TBS buffer (100 µL), and $OD_{414}$ of the solution was measured as hemoglobin concentration. A control solution containing only DMSO was used as a reference for 0% hemolysis. Complete hemolysis was measured by adding 1% Triton X-100 to the RBCs and measuring $OD_{414}$. Nonlinear exponential curve-fitting plots of $OD_{414}$ vs the concentration of polyA$_{1-3}$ and polyB$_{1-3}$ series determined the $HC_{50}$, the hemolytic dose required to lyse 50% of the RBCs. The results are shown in Table 23.

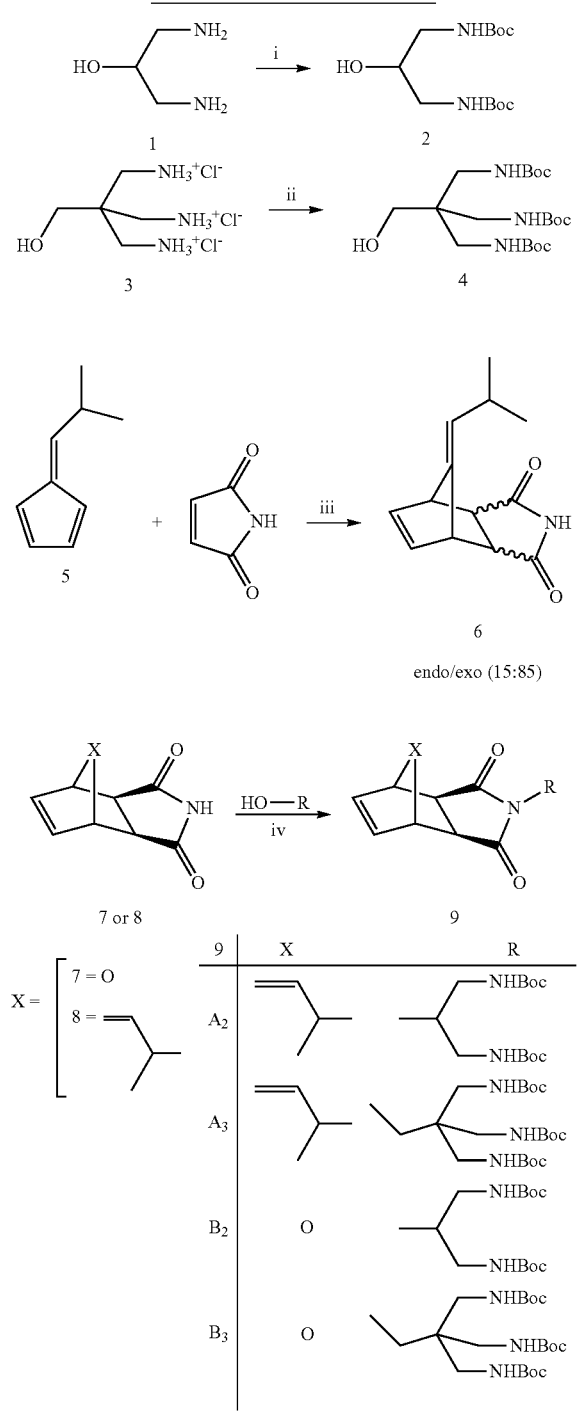

Scheme 9. Synthesis of A$_{2-3}$ and B$_{2-3}$;

i = $H_2O$, di-tert-butyl dicarbonate, dioxane, 24 h, rt; ii = $H_2O$, TEA, di-tert-butyl dicarbonate, dioxane; iii = 130° C. for 24 h; iv = THF, $Ph_3P$, DIAD, -10° C.-rt.

Scheme 10. Synthesis of polyA$_{2-3}$ and polyB$_{2-3}$.

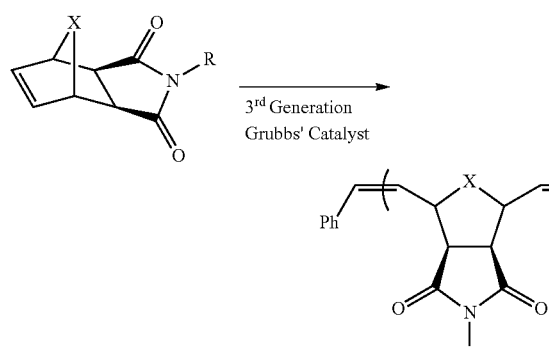

| Monomers | X | R |
|---|---|---|
| A$_2$ | =⟨ | —NHBoc, —NHBoc |
| A$_3$ | =⟨ | —NHBoc, —NHBoc, —NHBoc |
| B$_2$ | O | —NHBoc, —NHBoc |
| B$_3$ | O | —NHBoc, —NHBoc, —NHBoc |

| Monomers | X | R |
|---|---|---|
| polyA$_2$ | =⟨ | —NHBoc, —NHBoc |
| polyA$_3$ | =⟨ | —NHBoc, —NHBoc, —NHBoc |
| polyB$_2$ | O | —NHBoc, —NHBoc |
| polyB$_3$ | O | —NHBoc, —NHBoc, —NHBoc |

The polymerizations were conducted using 3$^{rd}$ generation Grubbs' catalyst; polyA$_{2-3}$ series were conducted in THF at 60° C.; polyB$_{2-3}$ series were conducted at rt in CH$_2$Cl$_2$.

TABLE 22

Vesicles composition

| Vesicles | Lipid Composition | Buffer inside | Buffer outside |
|---|---|---|---|
| V$_1$ | DOPC 100% | A | B |
| V$_2$ | DOPG/DOPE 20/80 | A | B |
| V$_3$ | TOCL 100% | A | B |

TABLE 23

Antimicrobial and hemolytic activity.

| | MIC$_{90}$ (µg/mL) | | |
|---|---|---|---|
| Polymers | E. coli | S. aureus | HC$_{50}$ (µg/mL) |
| polyA$_1$ | 25 | 50 | <1 |
| polyA$_2$ | 6 | 50 | 700 |
| polyA$_3$ | 25 | 25 | 500 |
| polyB$_1$ | >400 | >200 | >2150 |
| polyB$_2$ | 200 | 25 | 1400 |
| polyB$_3$ | 200 | 15 | 1200 |

INCORPORATION BY REFERENCE

References and citations to other documents, such as patents, patent applications, patent publications, journals, books, papers, web contents, have been made in this disclosure. All such documents are hereby incorporated herein by reference in their entirety for all purposes.

EQUIVALENTS

The representative examples are intended to help illustrate the invention, and are not intended to, nor should they be construed to, limit the scope of the invention. Indeed, various modifications of the invention and many further embodiments thereof, in addition to those shown and described herein, will become apparent to those skilled in the art from the full contents of this document, including the examples herein and the references to the scientific and patent literature cited herein. The examples contain important additional information, exemplification and guidance which can be adapted to the practice of this invention in its various embodiments and equivalents thereof.

What is claimed is:

1. A method for reducing or eliminating bacterial microorganisms comprising treating an object with a composition comprising an antimicrobial effective amount of a polymer, wherein the polymer comprises a monomer unit having the structure of:

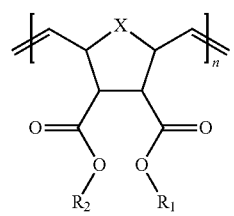

(II)

wherein one of R$_1$ and R$_2$ comprises a hydrophobic group and the other one of R$_1$ and R$_2$ comprises a hydrophilic group; and X is C=R$_3$, O or S, wherein R$_3$ is a C$_1$-C$_{12}$ alkyl or alkoxy group.

2. The method of claim 1, wherein the hydrophobic group comprises a substituted or unsubstituted alkyl group.

3. The method of claim 1, wherein the hydrophilic group comprises a group selected from ammonium ions, sulfonium ions, guanidinium ions, phosphonium ions, and mono- and di-alkyl substituted amino groups.

4. The method of claim 1, wherein the hydrophilic group is a guanidinium ion.

5. The method of claim 1, wherein X is O; $R_1$ is a linear or branched $C_1$-$C_{12}$ alkyl group; and $R_2$ is $^+H_3N\!\!-\!\!(\ )_p\!\!-\!\!$ or a guanidinium ion, wherein p is an integer from about 1 to about 10.

6. The method of claim 1, wherein both —C(=O)O— groups in (II) occupy the exo-stereo position.

7. The method of claim 5, wherein $R_1$ is a linear or branched $C_1$-$C_6$ alkyl group; and p is an integer from about 1 to about 5.

8. The method of claim 1, wherein X is C=$R_3$; $R_1$ is a linear or branched $C_1$-$C_{12}$ alkyl group; $R_2$ is $^+H_3N\!\!-\!\!(\ )_p\!\!-\!\!$ or a guanidinium ion, wherein p is an integer from 1-10.

9. The method of claim 8, wherein $R_3$ is a $C_1$-$C_{12}$ alkyl.

10. The method of claim 1, wherein n is an integer from about 1 to about 1,000.

11. The method of claim 1, wherein the polymer is a co-polymer.

12. The method of claim 11, wherein the co-polymer comprises the structural monomer units of:

(III)

and (IV)

wherein each of X' and X" is C=$R_3$, O or S, wherein $R_3$ is a $C_1$-$C_{12}$ alkyl or alkoxy group;

each of $R_1'$ and $R_1''$ is a hydrophobic group and each of $R_2'$ and $R_2''$ is a hydrophilic group, provided that $R_1'$ and $R_1''$ are not the same, $R_2'$ and $R_2''$ are the same, or X' and X" are not the same; and each of m and n is an integer from about 1 to about 1,000.

13. The method of claim 12, wherein the hydrophilic group comprises a group selected from ammonium ions, sulfonium ions, guanidinium ions, phosphonium ions, and mono- and di-alkyl substituted amino groups.

14. The method of claim 12, wherein all —C(=O)O— groups in (III) and (IV) occupy the exo-stereo position.

15. The method of claim 12, wherein each of $R_1'$ and $R_1''$ is independently a linear or branched $C_1$-$C_{12}$ alkyl group; and each of $R_2'$ and $R_2''$ is independently $^+H_3N\!\!-\!\!(\ )_p\!\!-\!\!$ or a guanidinium ion, wherein p is an integer from 1-10.

\* \* \* \* \*